US005635477A

United States Patent [19]

Degrado et al.

[11] Patent Number: 5,635,477
[45] Date of Patent: Jun. 3, 1997

[54] CYCLIC COMPOUNDS USEFUL AS INHIBITORS OF PLATELET GLYCOPROTEIN IIB/IIIA

[75] Inventors: William F. Degrado, Moylan; Sharon A. Jackson, Chadds Ford; Shaker A. Mousa, Lincoln University, all of Pa.; Anju Parthasarathy, New Castle, Del.; Michael Sworin, Newark, Del.; Maria Rafalski, Wilmington, Del.

[73] Assignee: The DuPont Merck Pharmaceutical Company, Wilmington, Del.

[21] Appl. No.: 461,611

[22] Filed: Jun. 5, 1995

Related U.S. Application Data

[63] Continuation of Ser. No. 38,448, Mar. 29, 1993, abandoned, which is a continuation-in-part of Ser. No. 949,285, Sep. 9, 1992, abandoned, which is a continuation-in-part of Ser. No. 767,848, Sep. 30, 1991, abandoned.

[51] Int. Cl.$^6$ .................................................. A61K 38/12
[52] U.S. Cl. ................................... 514/11; 514/9; 514/2; 530/317
[58] Field of Search ............................ 514/9, 11, 2, 802; 530/317

[56] References Cited

U.S. PATENT DOCUMENTS

| | | | |
|---|---|---|---|
| 4,578,079 | 3/1986 | Ruoslahti et al. | 514/2 |
| 4,614,517 | 9/1986 | Ruoslahti et al. | 530/330 |
| 4,857,508 | 8/1989 | Adams et al. | 514/18 |
| 4,952,562 | 8/1990 | Klein et al. | 514/18 |
| 5,041,380 | 8/1991 | Ruoslahti et al. | 514/18 |
| 5,041,430 | 8/1991 | Addicks et al. | 514/161 |

FOREIGN PATENT DOCUMENTS

| | | |
|---|---|---|
| 0293881 | 12/1988 | European Pat. Off. . |
| 0406428 | 3/1990 | European Pat. Off. . |
| 0422937 | 10/1990 | European Pat. Off. . |
| 0422938 | 10/1990 | European Pat. Off. . |
| 0410541 | 1/1991 | European Pat. Off. . |
| 425212 | 5/1991 | European Pat. Off. . |
| 0425212 | 5/1991 | European Pat. Off. . |
| 0478362 | 4/1992 | European Pat. Off. . |
| 478328A1 | 4/1992 | European Pat. Off. . |
| 0341915 | 11/1992 | European Pat. Off. . |
| 8907609 | 8/1989 | WIPO . |
| 900275 | 3/1990 | WIPO . |
| 910133 | 2/1991 | WIPO . |
| 9104247 | 4/1991 | WIPO . |
| 9200995 | 1/1992 | WIPO . |
| 9207568 | 5/1992 | WIPO . |
| 9207870 | 5/1992 | WIPO . |
| 9307170 | 4/1993 | WIPO . |

OTHER PUBLICATIONS

Cadroy et al., *J. Clin. Invest.* vol. 84, 939–944 (1989).
Alig et al., *J. Med. Chem.* vol. 35, 4393–4407 (1992).
Editors: Smith et al. "Peptides—Proceedings of 12th American Peptide Symposium, Jun. 1991, Cambridge, USA" 1992, Escom, Leiden, Holland & Burner et al. Small cyclic RGD containing peptides as potent inhibitors of platelet aggregation, pp. 755–756.

Ibid, Nutt et al. "Development of Novel, highly selective fibrinogen receptor antagonists as potentially useful anti-thrombic agents"; pp. 914–916.
Editors: Giralt et al. "Peptides 1990—Proceedings of the 21st European Peptide Symposium, Sep. 1990, Platja D'Aro, Spain" 1991, Escom, Leiden, Holland & Nutt et al. Structure–and conformation–activity studies leading to potent fibrinogen receptor antagonists containing Arg–Gly–Asp; pp. 784–786.
Biochemical and Biophysical Research Communications, vol. 177(1), May 1991, pp. 74–82; Kumagai et al. pp. 80–81.
Fuster et al., *The New England Journal of Medicine*, vol. 320, No. 6, pp. 392–394 (1989).
Lewis et al., *The New England Journal of Medicine*, vol. 309, No. 7, pp. 396–403 (1983).
Cairns et al., *The New England Journal of Medicine*, vol. 313, No. 22, pp. 1369–1375 (1985).
Fuster et al., *Perspective*, vol. 77, No. 6, 1213–1220 (1988).
Schafer et al., *J. Clin. Invest.*, vol. 75, pp. 456–461 (1985).
Schafer et al., *J. Clin. Invest.*, vol. 78, pp. 73–79 (1986).
Fitzgerald et al., *Circulation*, vol. 77, No. 1, pp. 142–150 (1988).
Yasuda et al., *J. Clin. Invest.*, vol. 81, pp. 1284–1291 (1988).
Gold et al., *Circulation*, vol. 77(3), pp. 670–677 (1988).
Shebuski, *J. Biological Chem.*, vol. 264(36), pp. 21550–21556 (1989).
Stamler et al., *Circulation Research*, vol. 65, pp. 796–804 (1989).
Lam et al., *J. Pharmacology and Experimental Therapeutics*, vol. 259(3), pp. 1371–1378 (1991).
Collen et al., *Annu. Rev. Med.*, vol. 39, pp. 405–423 (1988).
Simons et al., *Annu. Rev. Med.*, vol. 40, pp. 181–200 (1989).
Davidson et al., *Circ.* vol. 85, pp. 124 & 492 (1991).
Gold et al., *Circ.*, vol. 84, pp. 124 & 496 (1991).
Haskel et al., *Thrombosis Research*, vol. 56, pp. 687–695 (1989).
Phillips et al., *Cell*, vol. 65, pp. 359–362 (1991).

*Primary Examiner*—Howard E. Schain
*Assistant Examiner*—Anish Gupta
*Attorney, Agent, or Firm*—Blair Q. Ferguson

[57] ABSTRACT

This invention relates to novel cyclic compounds containing carbocyclic ring systems useful as antagonists of the platelet glycoprotein IIb/IIIa complex, to pharmaceutical compositions containing such cyclic compounds, with or without other therapeutic agents, and to methods of using these compounds, with or without other therapeutic agents, for the inhibition of platelet aggregation, as thrombolytics, and/or for the treatment of other thromboembolic disorders. This invention also relates to methods of using the cyclic compounds of the invention in combination with anti-coagulants such as warfarin or heparin, or additional anti-platelet agents such as aspirin, piroxicam or ticlopidine, or thrombin inhibitors such as boropeptides, hirudin or argatroban, or thrombolytic agents such as tissue plasminogen activator, anistreplase, urokinase or streptokinase, or combinations thereof, for the treatment of thromboembolic disorders. A representative compound of the invention is cyclo(D-Val-($^\alpha$N-methyl Arg)-Gly-Asp-(3-aminomethylbenzoic acid).

22 Claims, 9 Drawing Sheets

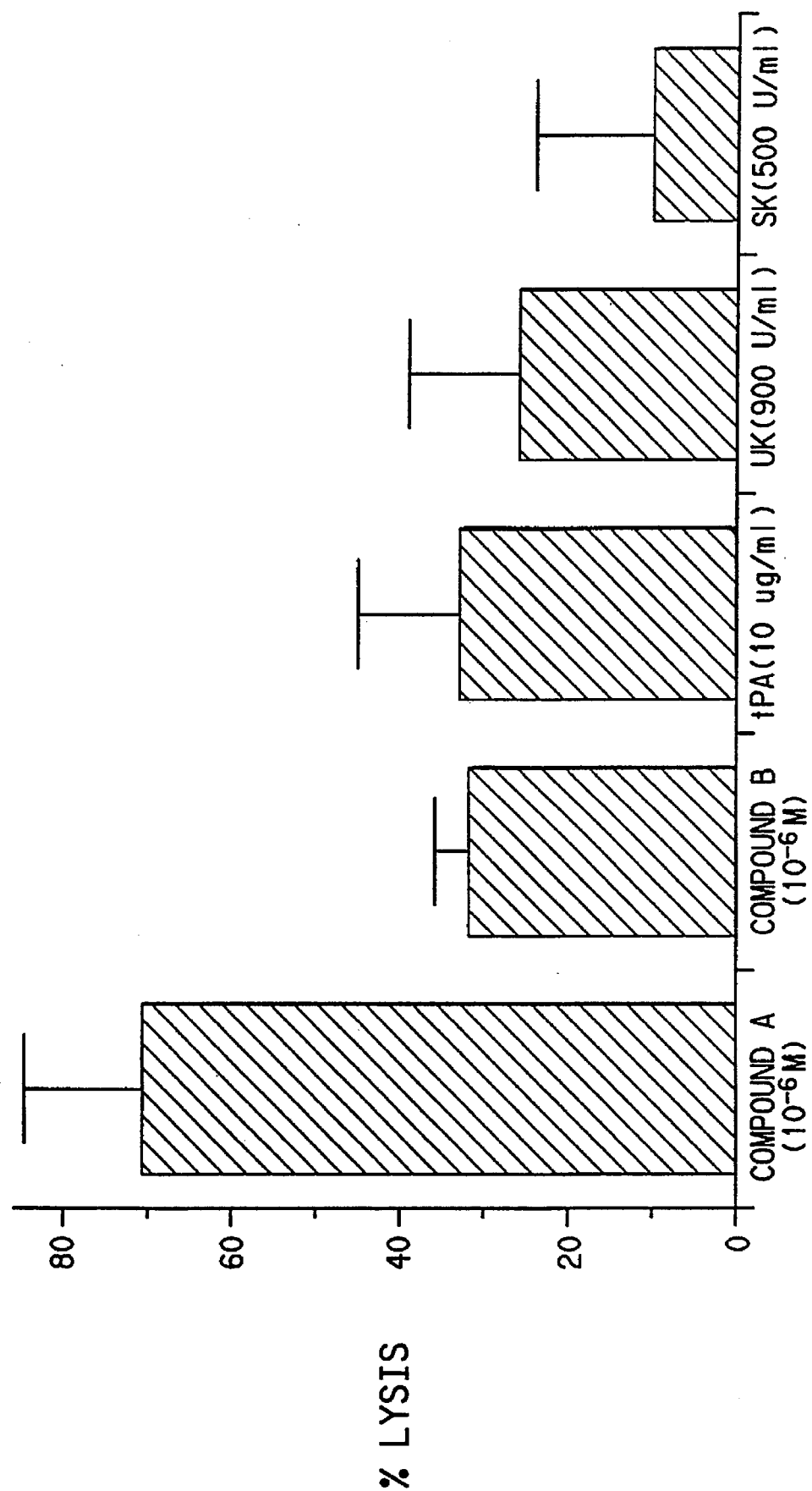

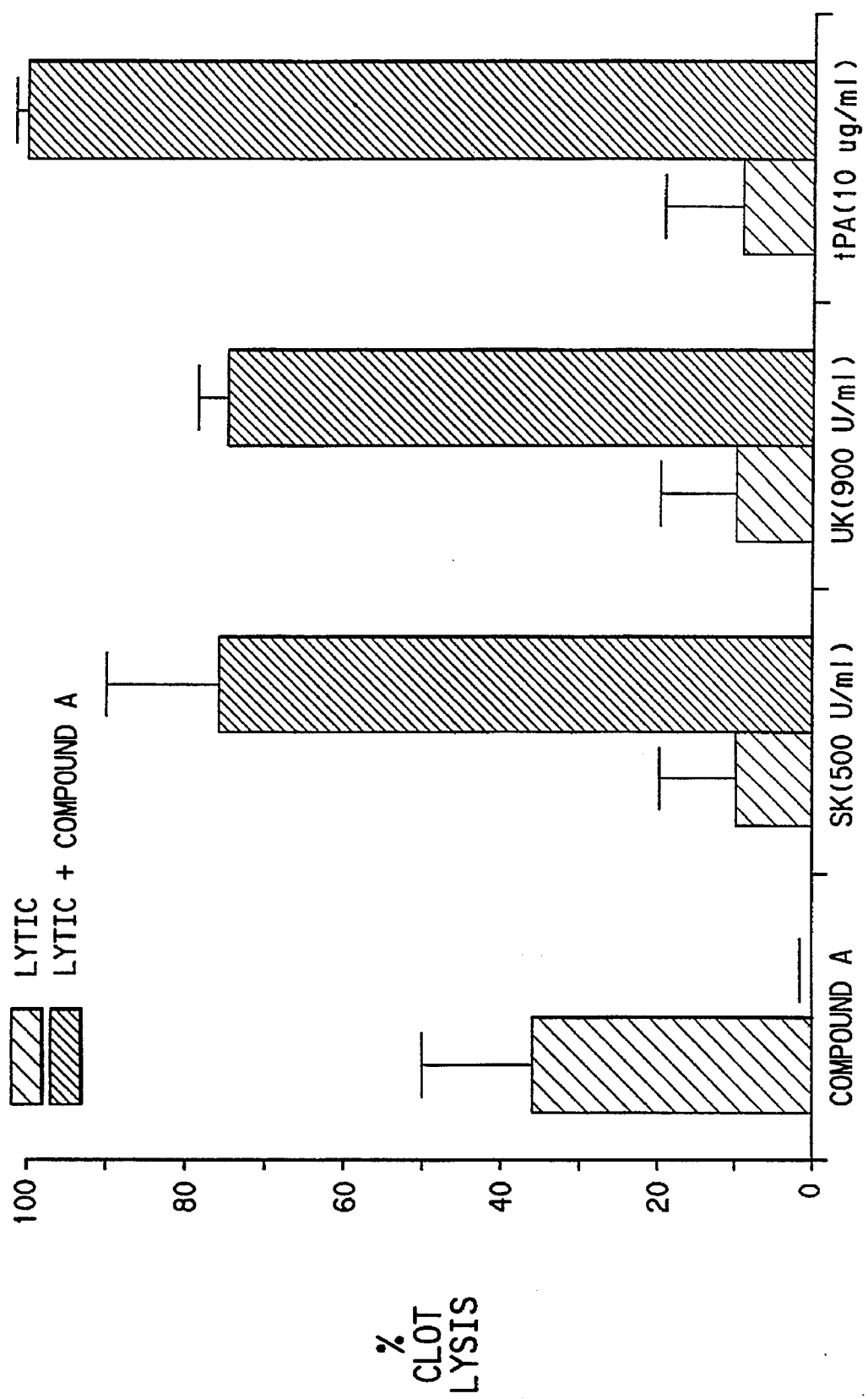

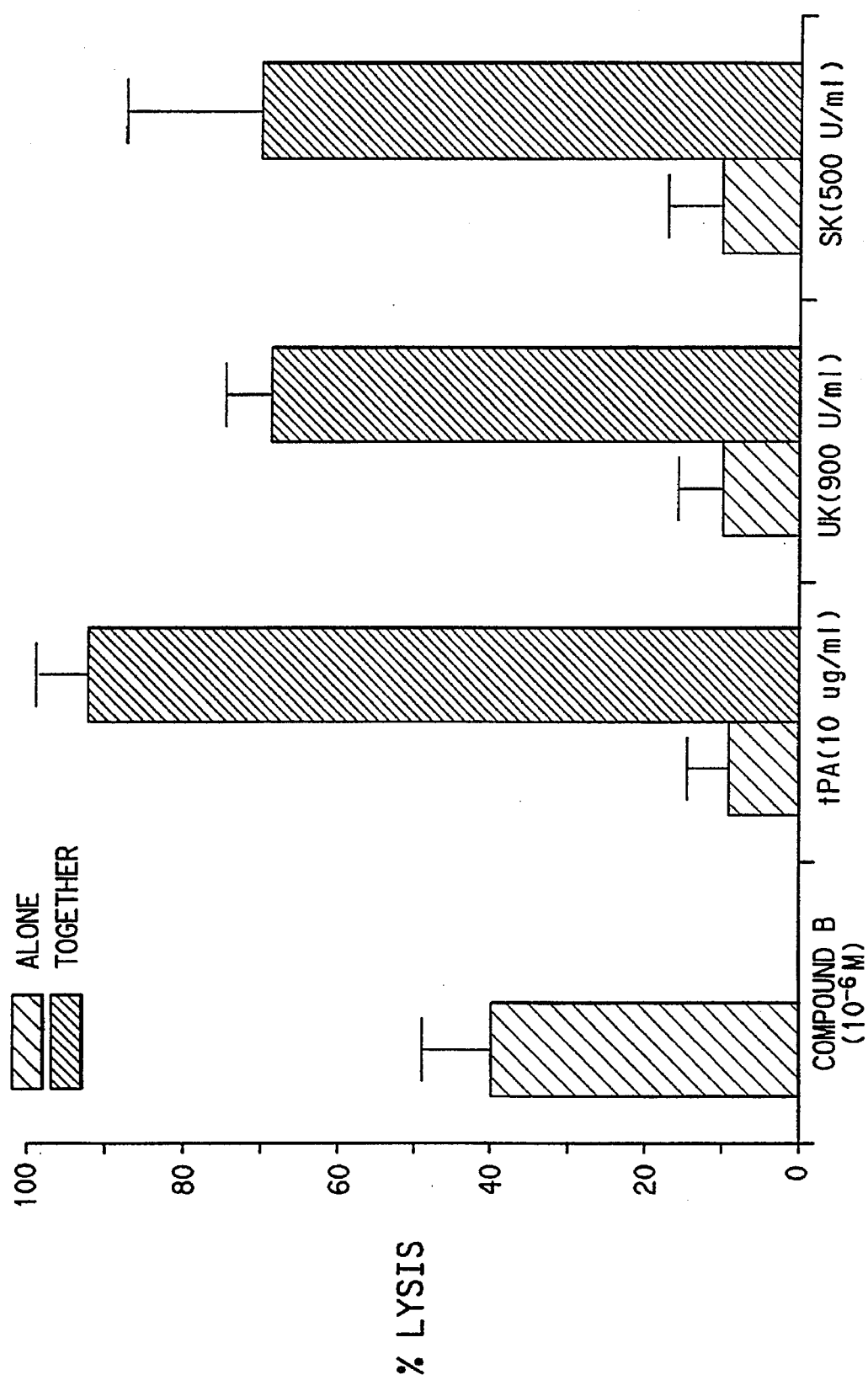

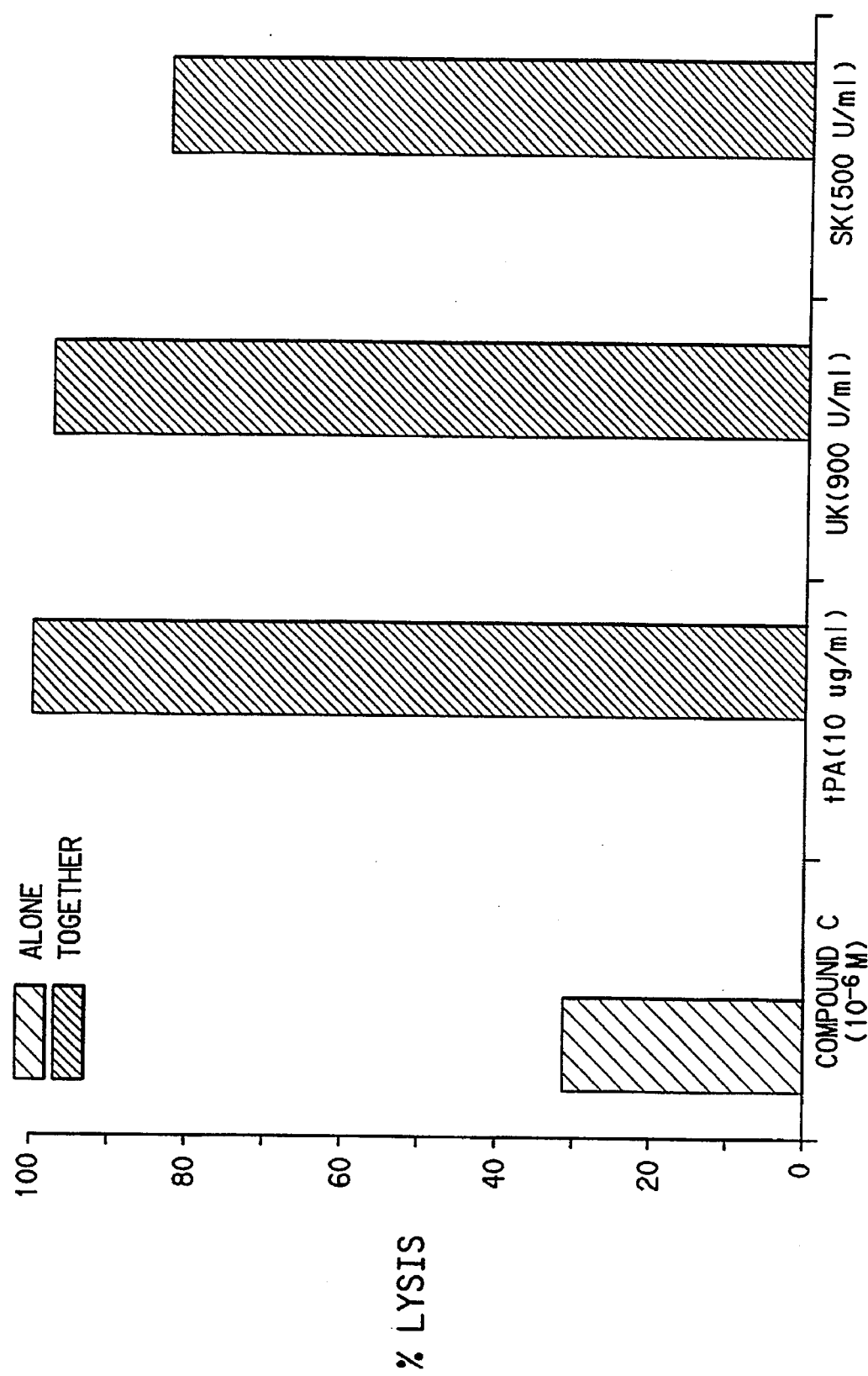

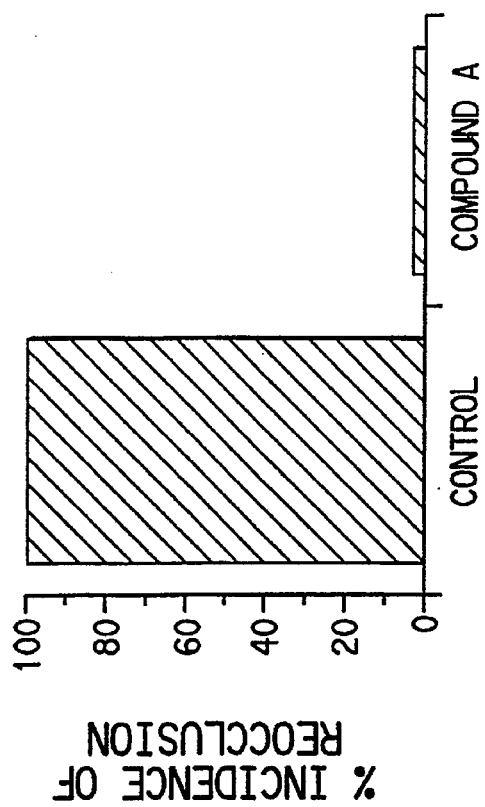
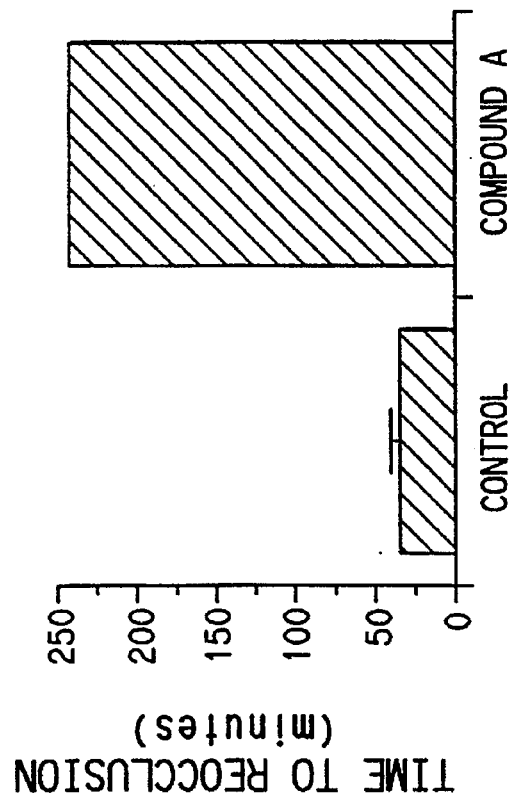

1

CYCLIC COMPOUNDS USEFUL AS INHIBITORS OF PLATELET GLYCOPROTEIN IIB/IIIA

CROSS-REFERENCE TO RELATED APPLICATIONS

This is a continuation of application Ser. No. 08/038,448 filed Mar. 29, 1993, now abandoned which is a continuation-in-part application of U.S. Ser. No. 07/949,285, filed Sep. 9, 1992, abandonded which in turn is a continuation-in-part application of U.S. Ser. No. 07/767,848, filed Sep. 30, 1991, abandonded the disclosures of each of which are hereby incorporated herein by reference, in their entirety.

FIELD OF THE INVENTION

This invention relates to novel cyclic compounds containing carbocyclic ring systems useful as antagonists of the platelet glycoprotein IIb/IIIa complex, to pharmaceutical compositions containing such cyclic compounds, with or without other therapeutic agents, and to methods of using these compounds, with or without other therapeutic agents, for the inhibition of platelet aggregation, as thrombolytics, and/or for the treatment of other thromboembolic disorders.

BACKGROUND OF THE INVENTION

Activation of platelets and the resulting platelet aggregation and secretion of factors by the platelets has been associated with different pathophysiological conditions including cardiovascular and cerebrovascular thromboembolic disorders, for example, the thromboembolic disorders associated with unstable angina, myocardial infarction, transient ischemic attack, stroke, atherosclerosis and diabetes. The contribution of platelets to these disease processes stems from their ability to form aggregates, or platelet thrombi, especially in the arterial wall following injury or plaque rupture.

Platelets are known to play an essential role in the maintenance of hemostasis and in the pathogenesis of arterial thrombosis. Platelet activation has been shown to be enhanced during coronary thrombolysis which can lead to delayed reperfusion and reocclusion. Clinical studies with aspirin, ticlopidine and a monoclonal antibody for platelet glycoprotein IIb/IIIa provide biochemical evidence for platelet involvement in unstable angina, early stage of acute myocardial infarction, transient ischemic attack, cerebral ischemia, and stroke.

Platelets are activated by a wide variety of agonists resulting in platelet shape change, secretion of granular contents and aggregation. Aggregation of platelets serves to further focus clot formation by concentrating activated clotting factors in one site. Several endogenous agonists including adenosine diphosphate (ADP), serotonin, arachidonic acid, thrombin, and collagen, have been identified. Because of the involvement of several endogenous agonists in activating platelet function and aggregation, an inhibitor which acts against all agonists would represent a more efficacious antiplatelet agent than currently available antiplatelet drugs, which are agonist-specific.

Current antiplatelet drugs are effective against only one type of agonist; these include aspirin, which acts against arachidonic acid; ticlopidine, which acts against ADP; thromboxane $A_2$ synthetase inhibitors or receptor antagonists, which act against thromboxane $A_2$; and hirudin, which acts against thrombin.

Recently, a common pathway for all known agonists has been identified, namely platelet glycoprotein IIb/IIIa complex (GPIIb/IIIa), which is the membrane protein mediating platelet aggregation. A recent review of GPIIb/IIIa is provided by Phillips et al. (1991) Cell 65: 359–362. The development of a GPIIb/IIIa antagonist represents a promising new approach for antiplatelet therapy. Recent studies in man with a monoclonal antibody for GPIIb/IIIa indicate the antithrombotic benefit of a GPIIb/IIIa antagonist.

There is presently a need for a GPIIb/IIIa-specific antiplatelet agent which inhibits the activation and aggregation of platelets in response to any agonist. Such an agent should represent a more efficacious antiplatelet therapy than the currently available agonist-specific platelet inhibitors.

GPIIb/IIIa does not bind soluble proteins on unstimulated platelets, but GPIIb/IIIa in activated platelets is known to bind four soluble adhesive proteins, namely fibrinogen, von Willebrand factor, fibronectin, and vitronectin. The binding of fibrinogen and von Willebrand factor to GPIIb/IIIa causes platelets to aggregate. The binding of fibrinogen is mediated in part by the Arg-Gly-Asp (RGD) recognition sequence which is common to the adhesive proteins that bind GPIIb/IIIa.

Several RGD-containing peptides and related compounds have been reported which block fibrinogen binding and prevent the formation of platelet thrombi. For example, see Cadroy et al. (1989) J. Clin. Invest. 84: 939–944; Klein et al. U.S. Pat. No. 4,952,562, issued Aug. 28, 1990; European Patent Application EP 0319506 A; European Patent Application EP 0422938 A1; European Patent Application EP 0422937 A1; European Patent Application EP 0341915 A2; PCT Patent Application WO 89/07609; PCT Patent Application WO 90/02751; PCT Patent Application WO 91/04247; and European Patent Application EP 0343085 A1.

In the present invention we use conformationally-constraining carbocyclic ring systems as templates for cyclizing peptides such that they have high affinity and selectivity for GPIIb/IIIa.

SUMMARY OF THE INVENTION

This invention provides novel cyclic compounds containing carbocyclic ring systems useful as antagonists of the platelet glycoprotein IIb/IIIa complex, pharmaceutical compositions containing such cyclic compounds, and methods of using these compounds for the inhibition of platelet aggregation, as thrombolytics, and/or for the treatment of thromboembolic disorders.

This invention also relates to combination products, that is, pharmaceutical compositions containing the novel cyclic compounds of the invention in combination with anticoagulants such as warfarin or heparin, or anti-platelet agents such as aspirin, piroxicam or ticlopidine, or thrombin inhibitors such as boropeptides, hirudin or argatroban, or thrombolytic agents such as tissue plasminogen activator, anistreplase, urokinase or streptokinase, or combinations thereof, to pharmaceutical kits containing these combination products, and to methods of using these combination products for the inhibition of platelet aggregation, as thrombolytics, and/or for the treatment of thromboembolic disorders.

BRIEF DESCRIPTION OF THE FIGURES

FIG. I. FIG. I shows the platelet deaggregatory and thrombolytic effects of the cyclic IIb/IIIa antagonist compounds cyclo-(D-AbuNMeArg-Gly-Asp-Mamb) (Compound A) and cyclo-(D-Val-NMeArgGly-Asp-Mamb) (Compound B) at varying concentrations on an already formed platelet-rich clot. The clot was formed by incubating the platelets with agonists for 30 minutes. The cyclic compounds of the present invention had a significant lytic effect on the clot, with an IC$_{50}$ of about 0.0005 mM for Compound A. By comparison, the linear peptide RGDS was much less effective as a thrombolytic, even at substantially higher concentrations.

FIG. II. FIG. II shows the thrombolytic effect of the cyclic IIb/IIIa antagonist compounds cyclo-(D-AbuNMeArg-Gly-Asp-Mamb) (Compound A) and cyclo-(D-Val-NMeArgGly-Asp-Mamb) (Compound B), and the standard thrombolytics tissue plasminogen activator (tPA), urokinase (UK) and streptokinase (SK) on an already formed platelet-rich clot. The clot was formed by incubating the platelets with agonists for 30 minutes. Both Compounds A and B showed a significant thrombolytic effect as compared to the standard thrombolytics tissue plasminogen activator, urokinase, and streptokinase.

Figure 1A:
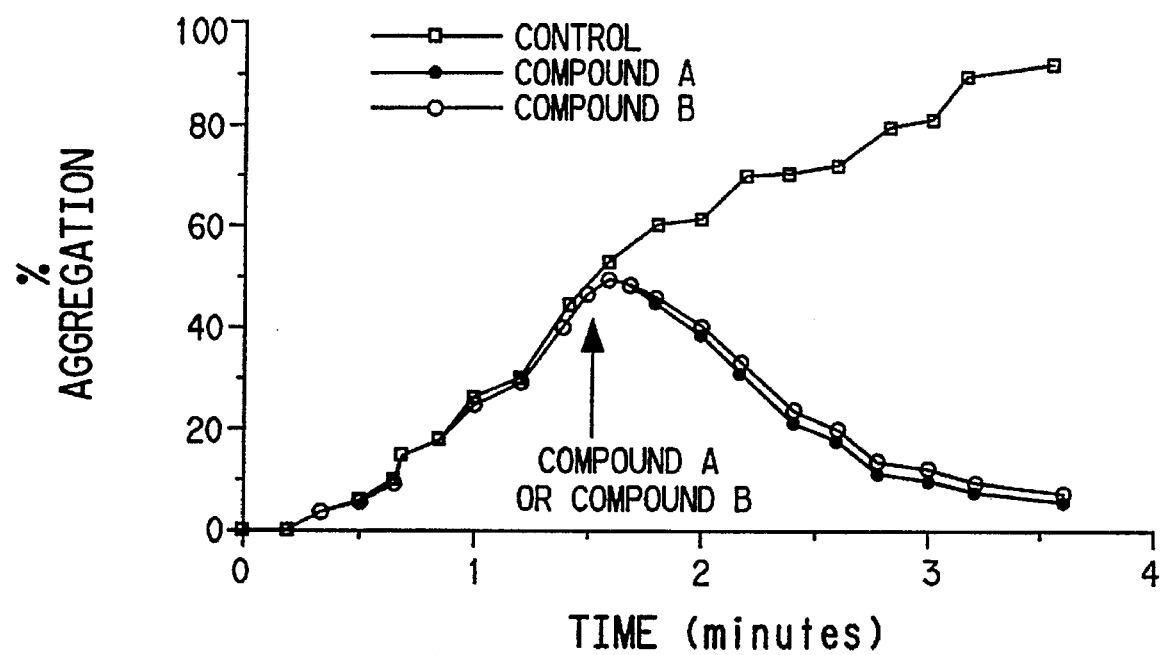

FIG. III FIG. III shows the thrombolytic effect of the cyclic compound cyclo-(D-AbuNMeArg-Gly-Asp-Mamb) (Compound A) and the standard thrombolytics tissue plasminogen activator (tPA), urokinase (UK), and streptokinase (SK), both alone and in combination, on an already formed platelet-rich clot. The clot was formed by incubating the platelets with agonists for 30 minutes. Compound A showed a significant thrombolytic effect, providing significant clot lysis at 1.0 uM. Moreover, Compound A in combination with tissue plasminogen activator, urokinase, or streptokinase was significantly better than Compound A alone, and significantly better than the additive effects of both agents administered alone.

FIG. IV. FIG. IV shows the thrombolytic effect of the cyclic IIb/IIIa antagonist compound cyclo-(D-Val-NMeArg-Gly-Asp-Mamb) (Compound B) and the standard thrombolytics tissue plasminogen activator (tPA), urokinase (UK) and streptokinase (SK), both alone and in combination, on an already formed platelet-rich clot. The clot was formed by incubating the platelets with agonists for 30 minutes. Compound B showed a significant thrombolytic effect, providing significantly better clot lysis than tissue plasminogen activator, urokinase or streptokinase. Moreover, Compound B in combination with tissue plasminogen activator, urokinase or streptokinase was significantly better than Compound B alone, and significantly better than the additive effects of both agents.

FIG. V. FIG. V shows the thrombolytic effect of the cyclic compound cyclo-(DVal-NMeArg-Gly-Asp-MeMamb) (isomer 1; the compound of Example 68) (Compound C) alone and in combination with the standard thrombolytics tissue plasminogen activator (tPA), urokinase (UK) and streptokinase (SK) on an already formed platelet-rich clot. The clot was formed by incubating the platelets with agonists for 30 minutes. Compound C alone showed a significant thrombolytic effect. In combination with tissue plasminogen activator, urokinase or streptokinase, a thrombolytic effect was achieved which was greater than the additive effect of the agents when administered alone.

FIG. VI. FIG. VI shows the thrombolytic effect of the cyclic compound cyclo-(D-Val-NMeArg-Gly-Asp-MeMamb) MeMamb) (isomer 2; the compound of Example 68a) (Compound D) alone and in combination with the standard thrombolytics tissue plasminogen activator (tPA), urokinase (UK) and streptokinase (SK) on an already formed plateletrich clot. The clot was formed by incubating the platelets with agonists for 30 minutes. Compound D alone showed a significant thrombolytic effect. In combination with tissue plasminogen activator, urokinase or streptokinase, a thrombolytic effect was achieved which was greater than the additive effect of the agents when administered alone.

FIG. VII. FIG. VII shows the in vivo thrombolytic and anti-thrombotic effect of the cyclic glycoprotein IIb/IIIa compound cyclo-(D-Abu-NMeArg-Gly-Asp-Mamb) (Compound A), alone or in combination with the standard thrombolytic streptokinase (SK). The experiments were carried out using an arterial thrombosis animal model. FIG. VII shows the results of initial administration as a percentage of clot lysis. Compound A alone showed good in vivo thrombolytic efficacy, and the use of Compound A with streptokinase resulted in an increase in in vivo thrombolytic efficacy while allowing a significantly lower dose of streptokinase. This study demonstrated significant reduction in the dose of streptokinase required to achieve 100% lysis in vivo when Compound A is administered along with streptokinase.

FIG. VIII. FIG. VIII a–d shows the results of administration of Compound A or saline following streptokinase (SK) or tissue plasminogen activator (t-PA) thrombolysis, with the results reported as time to reocclusion and percentage of reocclusion. The saline control showed 100% reocclusion, whereas administration of Compound A resulted in virtually no reocclusion.

DETAILED DESCRIPTION OF THE INVENTION

[1] This invention is directed to novel compounds of the formula (I):

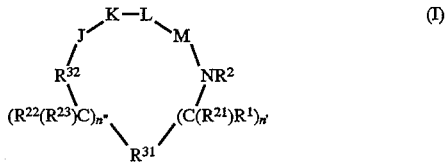

or a pharmaceutically acceptable salt or prodrug form thereof wherein:

$R^{31}$ is a $C_6$–$C_{14}$ saturated, partially saturated, or aromatic carbocyclic ring system substituted with 0–4 $R^{10}$ or $R^{10a}$;

$R^{32}$ is selected from:
—C(=O)—;
—C(=S)—
—S(=O)$_2$—;
—S(=O)—;
—P(=Z) (ZR$^{13}$)—;

Z is S or O;

n" and n' are independently 0–2;

$R^1$ and $R^{22}$ are independently selected from the following groups:
hydrogen,
$C_1$–$C_8$ alkyl substituted with 0–2 $R^{11}$;
$C_2$–$C_8$ alkenyl substituted with 0–2 $R^{11}$;
$C_2$–$C_8$ alkynyl substituted with 0–2 $R^{11}$;
$C_3$–$C_{10}$ cycloalkyl substituted with 0–2 $R^{11}$;
aryl substituted with 0–2 $R^{12}$;
a 5–10-membered heterocyclic ring system containing 1–4 heteroatoms independently selected from N, S, and O, said heterocyclic ring being substituted with 0–2 $R^{12}$;
=O, F, Cl, Br, I, —CF$_3$, —CN, —CO$_2$R$^{13}$, —C(=O)R$^{13}$, —C(=O)N(R$^{13}$)$_2$, —CHO, —CH$_2$OR$^{13}$, —OC(=O)R$^{13}$, —OC(=O)OR$^{13a}$, —OR$^{13}$, —OC(=O)

$N(R^{13})_2$, $-NR^{13}C(=O)R^{13}$, $-NR^{14}C(=O)OR^{13a}$, $-NR^{13}C(=O)N(R^{13})_2$, $-NR^{14}SO_2N(R^{13})_2$, $-NR^{14}SO_2R^{13a}$, $-SO_3H$, $-SO_2R^{13a}$, $-SR^{13}$, $-S(=O)R^{13a}$, $-SO_2N(R^{13})_2$, $-N(R^{13})_2$, $-NHC(=NH)NHR^{13}$, $-C(=NH)NHR^{13}$, $=NOR^{13}$, $NO_2$, $-C(=O)NHOR^{13}$, $-C(=O)NHNR^{13}R^{13a}$, $-OCH_2CO_2H$, 2-(1-morpholino)ethoxy;

$R^1$ and $R^{21}$ can alternatively join to form a 3–7 membered carbocyclic ring substituted with 0–2 $R^{12}$;

when n' is 2, $R^1$ or $R^{21}$ can alternatively be taken together with $R^1$ or $R^{21}$ on an adjacent carbon atom to form a direct bond, thereby to form a double or triple bond between said carbon atoms;

$R^{22}$ and $R^{23}$ can alternatively join to form a 3–7 membered carbocyclic ring substituted with 0–2 $R^{12}$;

when n" is 2, $R^{22}$ or $R^{23}$ can alternatively be taken together with $R^{22}$ or $R^{23}$ on an adjacent carbon atom to form a direct bond, thereby to form a double or triple bond between the adjacent carbon atoms;

$R^1$ and $R^2$, where $R^{21}$ is H, can alternatively join to form a 5–8 membered carbocyclic ring substituted with 0–2 $R^{12}$;

$R^{11}$ is selected from one or more of the following:

$=O$, F, Cl, Br, I, $-CF_3$, $-CN$, $-CO_2R^{13}$, $-C(=O)R^{13}$, $-C(=O)N(R^{13})_2$, $-CHO$, $-CH_2OR^{13}$, $-OC(=O)R^{13}$, $-OC(=O)OR^{13a}$, $-OR^{13}$, $-OC(=O)N(R^{13})_2$, $-NR^{13}C(=O)R^{13}$, $-NR^{14}C(=O)OR^{13a}$, $-NR^{13}C(=O)N(R^{13})_2$, $-NR^{14}SO_2N(R^{13})_2$, $-NR^{14}SO_2R^{13a}$, $-SO_3H$, $-SO_2R^{13a}$, $-SR^{13}$, $-S(=O)R^{13a}$, $-SO_2N(R^{13})_2$, $-N(R^{13})_2$, $-NHC(=NH)NHR^{13}$, $-C(=NH)NHR^{13}$, $=NOR^{13}$, $NO_2$, $-C(=O)NHOR^{13}$, $-C(=O)NHNR^{13}R^{13a}$, $-OCH_2CO_2H$, 2-(1-morpholino)ethoxy, $C_1$-$C_5$ alkyl, $C_2$-$C_4$ alkenyl, $C_3$-$C_6$ cycloalkyl, $C_3$-$C_6$ cycloalkylmethyl, $C_2$-$C_6$ alkoxyalkyl, $C_3$-$C_6$ cycloalkoxy, $C_1$-$C_4$ alkyl (alkyl being substituted with 1–5 groups selected independently from: $-NR^{13}R^{14}$, $-CF_3$, $NO_2$, $-SO_2R^{13a}$, or $-S(=O)R^{13a}$), aryl substituted with 0–2 $R^{12}$, a 5–10-membered heterocyclic ring system containing 1–4 heteroatoms independently selected from N, S, and O, said heterocyclic ring being substituted with 0–2 $R^{12}$;

$R^{12}$ is selected from one or more of the following:

phenyl, benzyl, phenethyl, phenoxy, benzyloxy, halogen, hydroxy, nitro, cyano, $C_1$-$C_5$ alkyl, $C_3$-$C_6$ cycloalkyl, $C_3$-$C_6$ cycloalkylmethyl, $C_7$-$C_{10}$ arylalkyl, $C_1$-$C_5$ alkoxy, $-CO_2R^{13}$, $-C(=O)NHOR^{13a}$, $-C(=O)NHN(R^{13})_2$, $=NOR^{13}$, $-B(R^{34})(R^{35})$, $C_3$-$C_6$ cycloalkoxy, $-OC(=O)R^{13}$, $-C(=O)R^{13}$, $-OC(=O)OR^{13a}$, $-OR^{13}$, $-(C_1$-$C_4$ alkyl$)-OR^{13}$, $-N(R^{13})_2$, $-OC(=O)N(R^{13})_2$, $-NR^{13}C(=O)R^{13}$, $-NR^{13}C(=O)OR^{13a}$, $-NR^{13}C(=O)N(R^{13})_2$, $-NR^{13}SO_2N(R^{13})_2$, $-NR^{13}SO_2R^{13a}$, $-SO_3H$, $-SO_2R^{13a}$, $-S(=O)R^{13a}$, $-SR^{13}$, $-SO_2N(R^{13})_2$, $C_2$-$C_6$ alkoxyalkyl, methylenedioxy, ethylenedioxy, $C_1$-$C_4$ haloalkyl, $C_1$-$C_4$ haloalkoxy, $C_1$-$C_4$ alkylcarbonyloxy, $C_1$-$C_4$ alkylcarbonyl, $C_1$-$C_4$ alkylcarbonylamino, $-OCH_2CO_2H$, 2-(1-morpholino)ethoxy, $C_1$-$C_4$ alkyl (alkyl being substituted with $-N(R^{13})_2$, $CF_3$, $NO_2$, or $-S(=O)R^{13a}$);

$R^{13}$ is selected independently from: H, $C_1$-$C_{10}$ alkyl, $C_3$-$C_{10}$ cycloalkyl, $C_4$-$C_{12}$ alkylcycloalkyl, aryl, $-(C_1$-$C_{10}$ alkyl)aryl, or $C_3$-$C_{10}$ alkoxyalkyl;

$R^{13a}$ is $C_1$-$C_{10}$ alkyl, $C_3$-$C_{10}$ cycloalkyl, $C_4$-$C_{12}$ alkylcycloalkyl, aryl, $-(C_1$-$C_{10}$ alkyl)aryl, or $C_3$-$C_{10}$ alkoxyalkyl;

when two $R^{13}$ groups are bonded to a single N, said $R^{13}$ groups may alternatively be taken together to form $-(CH_2)_{2-5}-$ or $-(CH_2)O(CH_2)-$;

$R^{14}$ is OH, H, $C_1$-$C_4$ alkyl, or benzyl;

$R^{21}$ and $R^{23}$ are independently selected from:
hydrogen;
$C_1$-$C_4$ alkyl, optionally substituted with 1–6 halogen;
benzyl;

$R^2$ is H or $C_1$-$C_8$ alkyl;

$R^{10}$ and $R^{10a}$ are selected independently from one or more of the following:

phenyl, benzyl, phenethyl, phenoxy, benzyloxy, halogen, hydroxy, nitro, cyano, $C_1$-$C_5$ alkyl, $C_3$-$C_6$ cycloalkyl, $C_3$-$C_6$ cycloalkylmethyl, $C_7$-$C_{10}$ arylalkyl, $C_1$-$C_5$ alkoxy, $-CO_2R^{13}$, $-C(=O)N(R^{13})_2$, $-C(=O)NHOR^{13a}$, $-C(=O)NHN(R^{13})_2$, $=NOR^{13}$, $-B(R^{34})(R^{35})$, $C_3$-$C_6$ cycloalkoxy, $-OC(=O)R^{13}$, $-C(=O)R^{13}$, $-OC(=O)OR^{13a}$, $-OR^{13}$, $-(C_1$-$C_4$ alkyl$)-OR^{13}$, $-N(R^{13})_2$, $-OC(=O)N(R^{13})_2$, $-NR^{13}C(=O)R^{13}$, $-NR^{13}C(=O)OR^{13a}$, $-NR^{13}C(=O)N(R^{13})_2$, $-NR^{13}SO_2N(R^{13})$, $-NR^{13}SO_2R^{13a}$, $-SO_3H$, $-SO_2R^{13a}$, $-S(=O)R^{13a}$, $-SR^{13}$, $-SO_2N(R^{13})_2$, $C_2$-$C_6$ alkoxyalkyl, methylenedioxy, ethylenedioxy, $C_1$-$C_4$ haloalkyl (including $-C_vF_w$ where v=1 to 3 and w=1 to (2v+1)), $C_1$-$C_4$ haloalkoxy, $C_1$-$C_4$ alkylcarbonyloxy, $C_1$-$C_4$ alkylcarbonyl, $C_1$-$C_4$ alkylcarbonylamino, $-OCH_2CO_2H$, 2-(1-morpholino)ethoxy, $C_1$-$C_4$ alkyl (alkyl being substituted with $-N(R^{13})_2$, $-CF_3$, $NO_2$, or $-S(=O)R^{13a}$);

J is β-Ala or an L-isomer or D-isomer amino acid of structure $-N(R^3)C(R^4)(R^5)C(=O)-$, wherein:

$R^3$ is H or $C_1$-$C_8$ alkyl;

$R^4$ is H or $C_1$-$C_3$ alkyl;

$R^5$ is selected from:
hydrogen;
$C_1$-$C_8$ alkyl substituted with 0–2 $R^{11}$;
$C_2$-$C_8$ alkenyl substituted with 0–2 $R^{11}$;
$C_2$-$C_8$ alkynyl substituted with 0–2 $R^{11}$;
$C_3$-$C_{10}$ cycloalkyl substituted with 0–2 $R^{11}$;
aryl substituted with 0–2 $R^{12}$;
a 5–10-membered heterocyclic ring system containing 1–4 heteroatoms independently selected from N, S, or O, said heterocyclic ring being substituted with 0–2 $R^{12}$;

$=O$, F, Cl, Br, I, $-CF_3$, $-CN$, $-CO_2R^{13}$, $-C(=O)R^{13}$, $-C(=O)N(R^{13})_2$, $-CHO$, $-CH_2OR^{13}$, $-OC(=O)R^{13}$, $-OC(=O)OR^{13a}$, $-OR^{13}$, $-OC(=O)N(R^{13})_2$, $-NR^{13}C(=O)R^{13}$, $-NR^{14}C(=O)OR^{13a}$, $-NR^{13}C(=O)N(R^{13})_2$, $-NR^{14}SO_2N(R^{13})_2$, $NR^{14}SO_2R^{13a}$, $-SO_3H$, $-SO_2R^{13a}$, $-SR^{13}$, $-S(=O)R^{13a}$, $-SO_2N(R^{13})_2$, $-N(R^{13})_2$, $-NHC(=NH)NHR^{13}$, $-C(=NH)NHR^{13}$, $=NOR^{13}$, $NO_2$, $-C(=O)NHOR^{13}$, $-C(=O)NHNR^{13}R^{13a}$, $=NOR^{13}$, $-B(R^{34})(R^{35})$, $-OCH_2CO_2H$, 2-(1-morpholino)ethoxy, $-SC(=NH)NHR^{13}$, $N_3$, $-Si(CH_3)_3$, $(C_{1-C5}$ alkyl)$NHR^{16}$;

—($C_0$-$C_6$ alkyl)X;

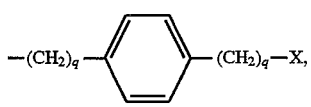

where q is independently 0,1;

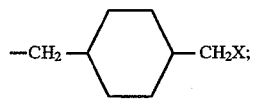

—$(CH_2)_mS(O)_{p'}(CH_2)_2X$, where m=1,2 and p'=0–2; wherein X is defined below; and $R^3$ and $R^4$ may also be taken together to form

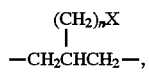

where
n=0,1 and X is

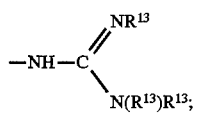

$R^3$ and $R^5$ can alternatively be taken together to form —$(CH_2)_t$— or —$CH_2S(O)_pC(CH_3)_2$—, where t=2–4 and p'=0–2; or $R^4$ and $R^5$ can alternatively be taken together to form —$(CH_2)_u$—, where u=2–5;

$R^{16}$ is selected from:
an amine protecting group;
1–2 amino acids;
1–2 amino acids substituted with an amine protecting group;

K is a D-isomer or L-isomer amino acid of structure —$N(R^6)CH(R^7)C(=O)$—, wherein:

$R^6$ is H or $C_1$-$C_8$ alkyl;
$R^7$ is selected from:
—($C_1$-$C_7$ alkyl)X;

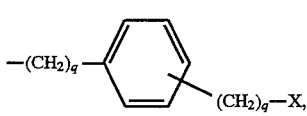

wherein each q is independently 0–2 and substitution on the phenyl is at the 3 or 4 position;

wherein each q is independently 0–2 and substitution on the cyclohexyl is at the 3 or 4 position;

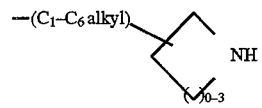

—$(CH_2)_mO$—($C_1$-$C_4$ alkyl)—X, where m=1 or 2;
—$(CH_2)_mS(O)_{p'}$—($C_1$-$C_4$ alkyl)—X, where m=1 or 2 and p'=0–2; and X is selected from:

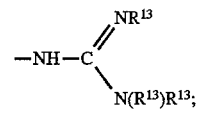

$N(R^{13})R^{13}$; —C(=NH)($NH_2$); —SC(=NH)—$NH_2$;
—NH—C(=NH)(NHCN); —NH—C(=NCN)($NH_2$); —NH—C(=N—$OR^{13}$)($NH_2$);

$R^6$ and $R^7$ can alternatively be taken together to form

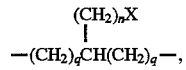

wherein each q is independently 1 or 2 and wherein n=0 or 1 and X is —$NH_2$ or

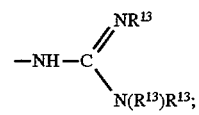

L is —Y$(CH_2)_vC(=O)$—, wherein:
Y is NH, N($C_1$-$C_3$ alkyl), O, or S; and v=1 or 2;
M is a D-isomer or L-isomer amino acid of structure

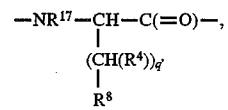

wherein:
q' is 0–2;
$R^{17}$ is H, $C_1$-$C_3$ alkyl;
$R^8$ is selected from:
—$CO_2R^{13}$, —$SO_3R^{13}$, —$SO_2NHR^{14}$, —B($R^{34}$)($R^{35}$), —$NHSO_2CF_3$, —$CONHNHSO_2CF_3$, —PO($OR^{13}$)$_2$, —PO($OR^{13}$)$R^{13}$, —$SO_2$NH-heteroaryl (said heteroaryl being 5–10-membered and having 1–4 heteroatoms selected independently from N, S, or O), —$SO_2$NH-heteroaryl (said heteroaryl being 5–10-membered and having 1–4 heteroatoms selected independently from N, S, or O), —$SO_2NHCOR^{13}$, —$CONHSO_2R^{13a}$, —$CH_2CONHSO_2R^{13a}$, —$NHSO_2NHCOR^{13a}$, —$NHCONHSO_2R^{13a}$, —$SO_2NHCONHR^{13}$, —$CO_2R^{13b}$;

$R^{34}$ and $R^{35}$ are independently selected from:
—OH,
—F,
—N($R^{13}$)$_2$, or
$C_1$-$C_8$-alkoxy;

$R^{34}$ and $R^{35}$ can alternatively be taken together form:
a cyclic boron ester where said chain or ring contains from 2 to 20 carbon atoms and, optionally, 1–4 heteroatoms independently selected from N, S, or O;

a divalent cyclic boron amide where said chain or ring contains from 2 to 20 carbon atoms and, optionally, 1–4 heteroatoms independently selected from N, S, or O;

a cyclic boron amide-ester where said chain or ring contains from 2 to 20 carbon atoms and, optionally, 1–4 heteroatoms independently selected from N, S, or O;

$R^{13b}$ is selected from:
(a) $C_1$–$C_8$ alkyl;
(b) $C_2$–$C_8$ alkenyl;
(c) $C_2$–$C_8$ alkynyl;
(d) $C_3$–$C_8$ cycloalkyl;
(e) $C_1$–$C_8$ alkyl substituted with
  (i) aryl, optionally substituted with 1–2 substituents independently selected from halogen, phenyl, $C_1$–$C_5$ alkyl, $C_1$–$C_5$ alkoxy, $NO_2$, —$S(O)_{0-2}$($C_1$–$C_5$ alkyl), OH, $N(R^{13})_2$, $CO_2R^{13}$, $CON(R^{13})_2$ or —$C_vF_w$, where v=1 to 3 and w=1 to (2v+1);
  (ii) $C_3$–$C_8$ cycloalkyl;

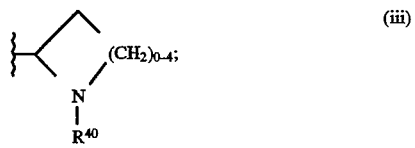 (iii)

(f) aryl, optionally substituted with 1–2 substituents independently selected from halogen, phenyl, $C_1$–$C_5$ alkyl, $C_1$–$C_5$ alkoxy, $NO_2$, —$S(O)_{0-2}$($C_1$–$C_5$ alkyl), OH, $N(R^{13})_2$, $CO_2R^{13}$, $CON(R^{13})_2$ or —$C_vF_w$ where v=1 to 3 and w=1 to (2v+1);
(g) $C_2$–$C_8$ alkyl, alkenyl or alkynyl; substituted with 1–2 substituents independently selected from $C_1$–$C_4$ alkyl, $C_3$–$C_8$ cycloalkyl, $C_1$–$C_5$ alkoxy, phenoxy, benzyloxy, halogen, $NO_2$, CN, $CO_2R^{13}$, $CON(R^{13})_2$, $N(R^{36})COR^{36}$, morpholino, 2-(1-morpholino)ethoxy, $N(R^{13})_2$, $N^+(R^{13})_3$, $OCOCH_3$, $CF_3$, $S(O)_{0-2}R^{13a}$;
(h) $CH(R^{36})OR^{38}$;
(i) $CH(R^{36})OC(=O)R^{37}$;
(j) $CH(R^{36})OC(=O)OR^{38}$;
(k) $CH(R^{36})OC(=O)N(R^{37})_2$;
(l) $CH(R^{36})N(R^{36})C(=O)R^{36}$;
(m) $CH(R^{36})CO_2R^{37}$;
(n) $CH(R^{36})CON(R^{13})_2$;
(o) $CH(R^{36})N(R^{13})_2$;

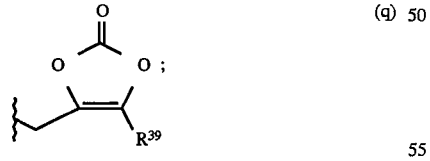 (q)

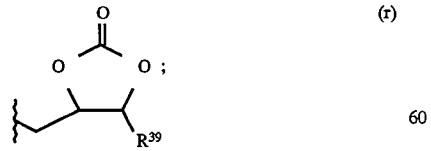 (r)

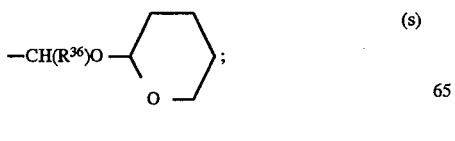 (s)

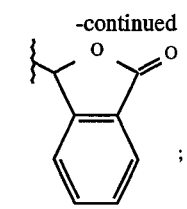 (t)

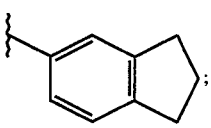 (u)

$R^{36}$ is selected independently from: H, $C_1$–$C_8$ alkyl, $C_3$–$C_{10}$ cycloalkyl, phenyl, or benzyl;

$R^{37}$ is selected from:
(a) H;
(b) $C_1$–$C_8$ alkyl or $C_3$–$C_8$ cycloalkyl, said alkyl or cycloalkyl being substituted with 1–2 groups independently selected from:
  (i) $C_1$–$C_4$ alkyl;
  (ii) $C_3$–$C_8$ cycloalkyl;
  (iii) $C_1$–$C_5$ alkoxy;
  (iv) aryl substituted with 0–2 groups independently selected from: halogen, phenyl, $C_1$–$C_6$ alkyl, $C_1$–$C_6$ alkoxy, $NO_2$, —$S(C_1$–$C_5$alkyl), —SO($C_1$–$C_5$ alkyl), —$SO_2(C_1$–$C_5$ alkyl), —OH, —$N(R^{13})_2$, —$CO_2R^{13}$, —$C(=O)N(R^{13})_2$, or —$C_vF_w$, where v=1 to 3 and w=1 to (2v+1);
(c) aryl substituted with 0–2 groups independently selected from: halogen, phenyl, $C_1$–$C_6$ alkyl, $C_1$–$C_6$ alkoxy, $NO_2$, —$S(C_1$–$C_5$ alkyl), —$SO(C_1$–$C_5$ alkyl), —$SO_2(C_1$–$C_5$ alkyl), —OH, —$N(R^{13})_2$, —$CO_2R^{13}$, —$C(=O)N(R^{13})_2$, or —$C_vF_w$ where v=1 to 3 and w=1 to (2v+1);

$R^{38}$ is selected from:
(a) $C_1$–$C_8$ alkyl or $C_3$–$C_8$ cycloalkyl, said alkyl or cycloalkyl being substituted with 1–2 groups independently selected from:
  (i) $C_1$–$C_4$ alkyl;
  (ii) $C_3$–$C_8$ cycloalkyl;
  (iii) $C_1$–$C_5$ alkoxy;
  (iv) aryl substituted with 0–2 groups independently selected from: halogen, phenyl, $C_1$–$C_6$ alkyl, $C_1$–$C_6$ alkoxy, $NO_2$, —$S(C_1$–$C_5$ alkyl), —SO($C_1$–$C_5$ alkyl), —$SO_2(C_1$–$C_5$ alkyl), —OH, —$N(R^{13})_2$, —$CO_2R^{13}$, —$C(=O)N(R^{13})_2$, or —$C_vF_w$ where v=1 to 3 and w=1 to (2v+1);
(b) aryl substituted with 0–2 groups independently selected from: halogen, phenyl, $C_1$–$C_6$ alkyl, $C_1$–$C_6$ alkoxy, $NO_2$, —$S(C_1$–$C_5$ alkyl), —$SO(C_1$–$C_5$ alkyl), —$SO_2(C_1$–$C_5$ alkyl), —OH, —$N(R^{13})_2$, —$CO_2R^{13}$, —$C(=O)N(R^{13})_2$, or —$C_vF_w$ where v=1 to 3 and w=1 to (2v+1);

$R^{39}$ is selected from:
(a) H
(b) $C_1$–$C_8$ alkyl or $C_3$–$C_8$ cycloalkyl, said alkyl or cycloalkyl being substituted with 1–2 groups independently selected from:
  (i) $C_1$–$C_6$ alkyl;
  (ii) $C_1$–$C_6$ alkoxy;
  (iii) aryl substituted with 0–2 groups independently selected from: halogen, phenyl, $C_1$—$C_6$ alkyl, $C_1$–$C_6$ alkoxy, $NO_2$, —$S(C_1$–$C_5$ alkyl), —SO($C_1$–$C_5$ alkyl), —$SO_2(C_1$–$C_5$ alkyl), —OH, —$N(R^{13})_2$, —$CO_2R^{13}$, —$C(=O)N(R^{13})_2$, or —$C_vF_w$ where v=1 to 3 and w=1 to (2v+1);
(c) aryl substituted with 0–2 groups independently selected from: halogen, phenyl, $C_1$–$C_6$ alkyl, $C_1$–$C_6$ alkoxy, $NO_2$, —S($C_1$–$C_5$ alkyl), —SO($C_1$–$C_5$ alkyl), —$SO_2$($C_1$–$C_5$ alkyl), —OH, —N($R^{13}$)$_2$, —$CO_2R^{13}$, —C(=O)N($R^{13}$)$_2$, or —$C_vF_w$ where v=1 to 3 and w=1 to (2v+1);

$R^{40}$ is selected from: H, $C_1$–$C_5$ alkyl, or benzyl.

[2] The present invention includes those compounds above wherein:
$R^{31}$ is bonded to (C($R^{23}$)$R^{22}$)$_{n''}$ and (C($R^{21}$)$R^1$)$_{n'}$ at 2 different atoms on said carbocyclic ring.

[3] Included in the present invention are those compounds above, wherein:
n" is 0 and n' is 0;
n" is 0 and n' is 1;
n" is 0 and n' is 2;
n" is 1 and n' is 0;
n" is 1 and n' is 1;
n" is 1 and n' is 2;
n" is 2 and n' is 0;
n" is 2 and n' is 1; or
n" is 2 and n' is 2.

[4] Included in the present invention are those compounds of formula (I) above wherein $R^6$ is methyl, ethyl, or propyl.

[5] This invention includes those compounds above of the formula:

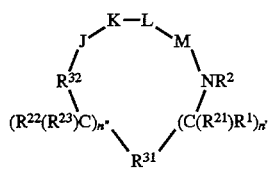

or a pharmaceutically acceptable salt or prodrug form thereof wherein:

is a $C_6$–$C_{14}$ saturated, partially saturated, or aromatic carbocyclic ring system substituted with 0–4 $R^{10}$ or $R^{10a}$;

$R^{32}$ is selected from:
—C(=O)—;
—C(=S)—
—S(=O)$_2$—;

Z is S or O;

n" and n' are independently 0–2;

$R^1$ and $R^{22}$ are independently selected from the following groups:
hydrogen,
$C_1$–$C_8$ alkyl substituted with 0–2 $R^{11}$,
$C_2$–$C_8$ alkenyl substituted with 0–2 $R^{11}$,
$C_2$–$C_8$ alkynyl substituted with 0–2 $R^{11}$,
$C_3$–$C_8$ cycloalkyl substituted with 0–2 $R^{11}$,
$C_6$–$C_{10}$ bicycloalkyl substituted with 0–2 $R^{11}$,
aryl substituted with 0–2 $R^{12}$,
a 5–10-membered heterocyclic ring system containing 1–4 heteroatoms independently selected from N, S, or O, said heterocyclic ring being substituted with 0–2 $R^{12}$;
=O, F, Cl, Br, I, —$CF_3$, —CN, —$CO_2R^{13}$, —C(=O)$R^{13}$, —C(=O)N($R^{13}$)$_2$, —CHO, —$CH_2OR^{13}$, —OC(=O)$R^{13}$, —OC(=O)O$R^{13a}$, —O$R^{13}$, —OC(=O)N($R^{13}$)$_2$, —$NR^{13}$C(=O)$R^{13}$, —$NR^{14}$C(=O)O$R^{13a}$, —$NR^{13}$C(=O)N($R^{13}$)$_2$, —$NR^{14}SO_2$N($R^{13}$)$_2$, —$NR^{14}SO_2R^{13a}$, —$SO_3H$, —$SO_2R^{13a}$, —$SR^{13}$, —S(=O)$R^{13a}$, —$SO_2$N($R^{13}$)$_2$, —$CH_2$N($R^{13}$)$_2$, —N($R^{13}$)$_2$, —NHC(=NH)NH$R^{13}$, —C(=NH)NH$R^{13}$, $NO_2$;

$R^1$ and $R^{21}$ can alternatively join to form a 5–7 membered carbocyclic ring substituted with 0–2 $R^{12}$;

when n' is 2, $R^1$ or $R^{21}$ can alternatively be taken together with $R^1$ or $R^{21}$ on an adjacent carbon atom to form a direct bond, thereby to form a double or triple bond between said carbon atoms;

$R^{22}$ and $R^{23}$ can alternatively join to form a 3–7 membered carbocyclic ring substituted with 0–2 $R^{12}$;

when n" is 2, $R^{22}$ or $R^{23}$ can alternatively be taken together with $R^{22}$ or $R^{23}$ on an adjacent carbon atom to form a direct bond, thereby to form a double or triple bond between said carbon atoms;

$R^1$ and $R^2$, where $R^{21}$ is H, can alternatively join to form a 5–8 membered carbocyclic ring substituted with 0–2 $R^{12}$;

$R^{11}$ is selected from one or more of the following:
=O, F, Cl, Br, I, —$CF_3$, —CN, —$CO_2R^{13}$, —C(=O)$R^{13}$, —C(=O)N($R^{13}$)$_2$, —CHO, —$CH_2OR^{13}$, —OC(=O)$R^{13}$, —OC(=O)O$R^{13a}$, —O$R^{13}$, —OC(=O)N($R^{13}$)$_2$, —$NR^{13}$C(=O)$R^{13}$, —$NR^{14}$C(=O)O$R^{13a}$, —$NR^{13}$C(=O)N($R^{13}$)$_2$, —$NR^{14}SO_2$N($R^{13}$)$_2$, —$NR^{14}SO_2R^{13a}$, —$SO_3H$, —$SO_2R^{13a}$, —$SR^{13}$, —S(=O)$R^{13a}$, —$SO_2$N($R^{13}$)$_2$, —$CH_2$N($R^{13}$)$_2$, —N($R^{13}$)$_2$, —NHC(=NH)NH$R^{13}$, —C(=NH)NH$R^{13}$, =NO$R^{13}$, $NO_2$;
$C_1$–$C_5$ alkyl, $C_2$–$C_4$ alkenyl, $C_3$–$C_6$ cycloalkyl, $C_3$–$C_6$ cycloalkylmethyl, $C_2$–$C_6$ alkoxyalkyl, $C_1$–$C_4$ alkyl (substituted with —$NR^{13}R^{14}$, —$CF_3$, $NO_2$, —$SO_2R^{13}$, or —S(=O)$R^{13a}$)
aryl substituted with 0–2 $R^{12}$,
a 5–10-membered heterocyclic ring system containing 1–4 heteroatoms independently selected from N, S, or O, said heterocyclic ring being substituted with 0–2 $R^{12}$;

$R^{12}$ is selected from one or more of the following:
phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_5$ alkoxy, —$CO_2R^{13}$, —C(=O)NHO$R^{13a}$, —C(=O)NH($R^{13}$)$_2$, =NO$R^{13}$, —B($R^{34}$)($R^{35}$), $C_3$–$C_6$ cycloalkoxy, —OC(=O)$R^{13}$, —C(=O)$R^{13}$, —OC(=O)O$R^{13a}$, —O$R^{13}$, —($C_1$–$C_4$ alkyl)—O$R^{13}$, —N($R^{13}$)$_2$, —OC(=O)N($R^{13}$)$_2$, $NR^{13}$C(=O)$R^{13}$, —$NR^{13}$C(=O)O$R^{13a}$, —$NR^{13}$C(=O)N($R^{13}$)$_2$, —$NR^{13}SO_2$N($R^{13}$)$_2$, —$NR^{13}SO_2R^{13a}$, —$SO_3H$, —$SO_2R^{13a}$, —S(=O)$R^{13a}$, —$SR^{13}$, —$SO_2$N($R^{13}$)$_2$, $C_2$–$C_6$ alkoxyalkyl, methylenedioxy, ethylenedioxy, $C_1$–$C_4$ haloalkyl, $C_1$–$C_4$ haloalkoxy, $C_1$–$C_4$ alkylcarbonyloxy, $C_1$–$C_4$ alkylcarbonyl, $C_1$–$C_4$ alkylcarbonylamino, —OCH$_2$CO$_2$H, 2-(1-morpholino)ethoxy, $C_1$–$C_4$ alkyl (alkyl being substituted with —N($R^{13}$)$_2$, —$CF_3$, $NO_2$, or —S(=O)$R^{13a}$);

$R^{13}$ is selected independently from: H, $C_1$–$C_{10}$ alkyl, $C_3$–$C_{10}$ cycloalkyl, $C_4$–$C_{12}$ alkylcycloalkyl, aryl, —($C_1$–$C_{10}$ alkyl)aryl, or $C_3$–$C_{10}$ alkoxyalkyl;

$R^{13a}$ is $C_1$–$C_{10}$ alkyl, $C_3$–$C_{10}$ cycloalkyl, $C_4$–$C_{12}$ alkylcycloalkyl, aryl, —($C_1$–$C_{10}$ alkyl)aryl, or $C_3$–$C_{10}$ alkoxyalkyl;

when two $R^{13}$ groups are bonded to a single N, said $R^{13}$ groups may alternatively be taken together to form —(CH$_2$)$_{2-5}$— or —(CH$_2$)O(CH$_2$)—;

$R^{14}$ is OH, H, $C_1$–$C_4$ alkyl, or benzyl;

$R^{21}$ and $R^{23}$ are independently selected from:
hydrogen;
$C_1$–$C_4$ alkyl, optionally substituted with 1–6 halogen;
benzyl;

$R^2$ is H or $C_1$–$C_8$ alkyl;

$R^{10}$ and $R^{10a}$ are selected independently from one or more of the following:
phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_5$ alkoxy, —$CO_2R^{13}$, —C(=O)NHOR$^{13a}$, —C(=O)NHN(R$^{13}$)$_2$, =NOR$^{13}$, —B(R$^{34}$)(R$^{35}$), $C_3$–$C_6$ cycloalkoxy, —OC(=O)R$^{13}$, —C(=O)R$^{13}$, —OC(=O)OR$^{13a}$, —OR$^{13}$, —($C_1$–$C_4$ alkyl)—OR$^{13}$, —N(R$^{13}$)$_2$, —OC(=O)N(R$^{13}$)$_2$, —NR$^{13}$C(=O)R$^{13}$, —NR$^{13}$C(=O)OR$^{13a}$, —NR$^{13}$C(=O)N(R$^{13}$)$_2$, —NR$^{13}$SO$_2$N(R$^{13}$)$_2$, —NR$^{13}$SO$_2$R$^{13a}$, —SO$_3$H, —SO$_2$R$^{13a}$, —S(=O)R$^{13a}$, —SR$^{13}$, —SO$_2$N(R$^{13}$)$_2$, $C_2$–$C_6$ alkoxyalkyl, methylenedioxy, ethylenedioxy, $C_1$–$C_4$ haloalkyl, $C_1$–$C_4$ haloalkoxy, $C_1$–$C_4$ alkylcarbonyloxy, $C_1$–$C_4$ alkylcarbonyl, $C_1$–$C_4$ alkylcarbonylamino, —OCH$_2$CO$_2$H, 2-(1-morpholino)ethoxy, $C_1$–$C_4$ alkyl (alkyl being substituted with —N(R$^{13}$)$_2$, —CF$_3$, NO$_2$, or —S(=O)R$^{13a}$);

J is β-Ala or an L-isomer or D-isomer amino acid of structure —N(R$^3$)C(R$^4$)(R$^5$)C(=O)—, wherein:

$R^3$ is H or CH$_3$;

$R^4$ is H or $C_1$–$C_3$ alkyl;

$R^5$ is H, $C_1$–$C_8$ alkyl, $C_3$–$C_6$ cycloalkyl, $C_3$–$C_6$ cycloalkylmethyl, $C_1$–$C_6$ cycloalkylethyl, phenyl, phenylmethyl, CH$_2$OH, CH$_2$SH, CH$_2$OCH$_3$, CH$_2$SCH$_3$, CH$_2$CH$_2$SCH$_3$, (CH$_2$)$_s$NH$_2$, (CH$_2$)$_s$NHC(=NH)(NH$_2$), (CH$_2$)$_s$NHR$^{16}$, where s=3–5;

$R^3$ and $R^5$ can alternatively be taken together to form —(CH$_2$)$_t$— (t=2–4) or —CH$_2$SC(CH$_3$)$_2$—; or $R^4$ and $R^5$ can alternatively be taken together to form —(CH$_2$)$_u$—, where u=2–5;

$R^{16}$ is selected from:
an amine protecting group;
1–2 amino acids;
1–2 amino acids substituted with an amine protecting group;

K is a D-isomer or L-isomer amino acid of structure —N(R$^6$)CH(R$^7$)C(=O)—, wherein:

$R^6$ is H or $C_1$–$C_8$ alkyl;

$R^7$ is selected from:
—($C_1$–$C_7$ alkyl)X;

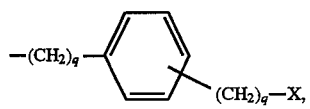

wherein each q is independently 0–2 and substitution on the phenyl is at the 3 or 4 position;

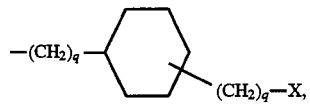

wherein each q is independently 0–2 and substitution on the cyclohexyl is at the 3 or 4 position;

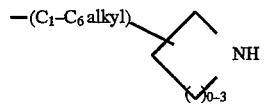

—(CH$_2$)$_m$O—($C_1$–$C_4$ alkyl)—X, where m=1 or 2;
—(CH$_2$)$_m$S—($C_1$–$C_4$ alkyl)—X, where m=1 or 2; and X is selected from:
—NH—C(=NH)(NH$_2$), 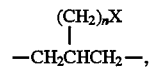, —C(=NH)(NH$_2$), —SC(NH)—NH$_2$;

$R^6$ and $R^7$ can alternatively be taken together to form

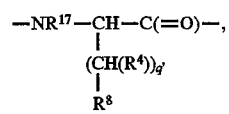

where
n=0 or 1 and X is —NH$_2$ or —NH—C(=NH)(NH$_2$);

L is —Y(CH$_2$)$_v$C(=O)—, wherein:

Y is NH, N($C_1$–$C_3$ alkyl), O, or S; and v=1 or 2;

M is a D-isomer or L-isomer amino acid of structure $$-NR^{17}-CH-C(=O)-,$$
$$\phantom{-NR^{17}-}\overset{|}{(CH(R^4))_{q'}}$$
$$\phantom{-NR^{17}-CH}\overset{|}{R^8}$$

wherein:
q' is 0–2;

$R^{17}$ is H, $C_1$–$C_3$ alkyl;

$R^8$ is selected from:
—CO$_2$R$^{13}$, —SO$_3$R$^{13}$, —SO$_2$NHR$^{14}$, —B(R$^{34}$)(R$^{35}$), —NHSO$_2$CF$_3$, —CONHNHSO$_2$CF$_3$, —PO(OR$^{13}$)$_2$, —PO(OR$^{13}$)R$^{13}$, —SO$_2$NH-heteroaryl (said heteroaryl being 5–10-membered and having 1–4 heteroatoms selected independently from N, S, or O), —SO$_2$NH-heteroaryl (said heteroaryl being 5–10-membered and having 1–4 heteroatoms selected independently from N, S, or O), —SO$_2$NHCOR$^{13}$, —CONHSO$_2$R$^{13a}$, —CH$_2$CONHSO$_2$R$^{13a}$, —NHSO$_2$NHCOR$^{13a}$, —NHCONHSO$_2$R$^{13a}$, —SO$_2$NHCONHR$^{13}$, —CO$_2$R$^{13b}$;

$R^{34}$ and $R^{35}$ are independently selected from:
—OH,
—F,
—NR$^{13}$R$^{14}$, or
$C_1$–$C_8$-alkoxy;

$R^{34}$ and $R^{35}$ can alternatively be taken together form:
a cyclic boron ester where said chain or ring contains from 2 to 20 carbon atoms and, optionally, 1–4 heteroatoms independently selected from N, S, or O;
a divalent cyclic boron amide where said chain or ring contains from 2 to 20 carbon atoms and, optionally, 1–4 heteroatoms independently selected from N, S, or O;
a cyclic boron amide-ester where said chain or ring contains from 2 to 20 carbon atoms and, optionally, 1–4 heteroatoms independently selected from N, S, or O;

$R^{13b}$ is selected from:
(a) $C_1$–$C_8$ alkyl;
(b) $C_2$–$C_8$ alkenyl;
(c) $C_2$–$C_8$ alkynyl;
(d) $C_3$–$C_8$ cycloalkyl;

(e) $C_1$–$C_8$ alkyl substituted with
  (i) aryl, optionally substituted with 1–2 substituents independently selected from halogen, phenyl, $C_1$–$C_5$ alkyl, $C_1$–$C_5$ alkoxy, $NO_2$, —$S(O)_{0-2}$($C_1$–$C_5$ alkyl), OH, N($R^{13}$)$_2$, $CO_2R^{13}$, $CON(R^{13})_2$ or —$C_vF_w$ where v=1 to 3 and w=1 to (2v+1);
  (ii) $C_3$–$C_8$ cycloalkyl;

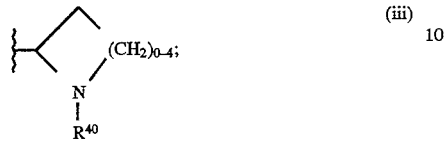
(iii)

(f) aryl, optionally substituted with 1–2 substituents independently selected from halogen, phenyl, $C_1$–$C_5$ alkyl, $C_1$–$C_5$ alkoxy, $NO_2$, —$S(O)_{0-2}$($C_1$–$C_5$ alkyl), OH, N($R^{13}$)$_2$, $CO_2R^{13}$, $CON(R^{13})_2$ or —$C_vF_w$ where v=1 to 3 and w=1 to (2v+1);

(g) $C_2$–$C_8$ alkyl, alkenyl or alkynyl; substituted with 1–2 substituents independently selected from $C_1$–$C_4$ alkyl, $C_3$–$C_8$ cycloalkyl, $C_1$–$C_5$ alkoxy, phenoxy, benzyloxy, halogen, $NO_2$, CN, $CO_2R^{13}$, $CON(R^{13})_2$, $N(R^{36})COR^{36}$, morpholino, 2-(1-morpholino) ethoxy, $N(R^{13})_2$, $N^+(R^{13})_3$, $OCOCH3$, $CF_3$, $S(O)_{0-2}R^{13a}$;

(h) $CH(R^{36})OR^{38}$;
(i) $CH(R^{36})OC(=O)R^{37}$;
(j) $CH(R^{36})OC(=O)OR^{38}$;
(k) $CH(R^{36})OC(=O)N(R^{37})_2$;
(l) $CH(R^{36})N(R^{36})C(=O)R^{36}$;
(m) $CH(R^{36})CO_2R^{37}$;
(n) $CH(R^{36})CON(R^{13})_2$;
(o) $CH(R^{36})N(R^{13})_2$;

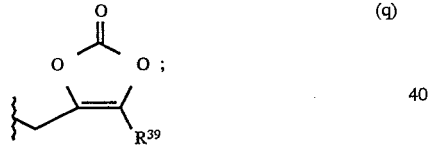
(q)

(r)

(s)

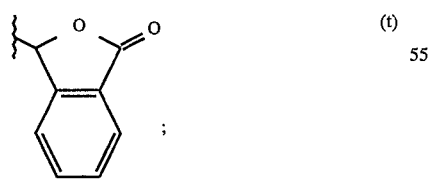
(t)

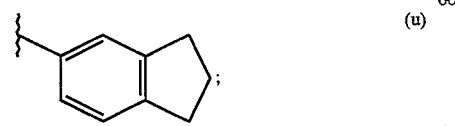
(u)

$R^{36}$ is selected independently from: H, $C_1$–$C_8$ alkyl, $C_3$–$C_{10}$ cycloalkyl, phenyl, or benzyl;

$R^{37}$ is selected from:
  (a) H;
  (b) $C_1$–$C_8$ alkyl or $C_3$–$C_8$ cycloalkyl, said alkyl or cycloalkyl being substituted with 1–2 groups independently selected from:
    (i) $C_1$–$C_4$ alkyl;
    (ii) $C_3$–$C_8$ cycloalkyl;
    (iii) $C_1$–$C_5$ alkoxy;
    (iv) aryl substituted with 0–2 groups independently selected from: halogen, phenyl, $C_1$–$C_6$ alkyl, $C_1$–$C_6$ alkoxy, $NO_2$, —$S(C_1$–$C_5$alkyl), —SO($C_1$–$C_5$ alkyl), —$SO_2(C_1$–$C_5$ alkyl), —OH, —$N(R^{13})_2$, —$CO_2R^{13}$, —$C(=O)N(R^{13})_2$, or —$C_vF_w$ where v=1 to 3 and w=1 to (2v+1);
  (c) aryl substituted with 0–2 groups independently selected from: halogen, phenyl, $C_1$–$C_6$ alkyl, $C_1$–$C_6$ alkoxy, $NO_2$, —$S(C_1$–$C_5$ alkyl), —SO($C_1$–$C_5$ alkyl), —$SO_2(C_1$–$C_5$ alkyl), —OH, —N ($R^{13}$)$_2$, —$CO_2R^{13}$, —$C(=O)N(R^{13})_2$, or —$C_vF_w$ where v=1 to 3 and w=1 to (2v+1);

$R^{38}$ is selected from:
  (a) $C_1$–$C_8$ alkyl or $C_3$–$C_8$ cycloalkyl, said alkyl or cycloalkyl being substituted with 1–2 groups independently selected from:
    (i) $C_1$–$C_4$ alkyl;
    (ii) $C_3$–$C_8$ cycloalkyl;
    (iii) $C_1$–$C_5$ alkoxy;
    (iv) aryl substituted with 0–2 groups independently selected from: halogen, phenyl, $C_1$–$C_6$ alkyl, $C_1$–$C_6$ alkoxy, $NO_2$, —$S(C_1$–$C_5$ alkyl), —SO($C_1$–$C_5$ alkyl), —$SO_2(C_1$–$C_5$ alkyl), —OH, —$N(R^{13})_2$, —$CO_2R^{13}$, —$C(=O)N(R^{13})_2$, or —$C_vF_w$ where v=1 to 3 and w=1 to (2v+1);
  (b) aryl substituted with 0–2 groups independently selected from: halogen, phenyl, $C_1$–$C_6$ alkyl, $C_1$–$C_6$ alkoxy, $NO_2$, —$S(C_1$–$C_5$ alkyl), —$SO(C_1$–$C_5$ alkyl), —$SO_2(C_1$–$C_5$ alkyl), —OH, —$N(R^{13})_2$, —$CO_2R^{13}$, —$C(=O)N(R^{13})_2$, or —$C_vF_w$ where v=1 to 3 and w=1 to (2v+1);

$R^{39}$ is selected from:
  (a) H
  (b) $C_1$–$C_8$ alkyl or $C_3$–$C_8$ cycloalkyl, said alkyl or cycloalkyl being substituted with 1–2 groups independently selected from:
    (i) $C_1$–$C_6$ alkyl;
    (ii) $C_1$–$C_6$ alkoxy;
    (iii) aryl substituted with 0–2 groups independently selected from: halogen, phenyl, $C_1$–$C_6$ alkyl, $C_1$–$C_6$ alkoxy, $NO_2$, —$S(C_1$–$C_5$ alkyl), —SO ($C_1$–$C_5$ alkyl), —$SO_2(C_1$–$C_5$ alkyl), —OH, —N ($R^{13}$)$_2$, —$CO_2R^{13}$, —$C(=O)N(R^{13})_2$, or —$C_vF_w$ where v=1 to 3 and w=1 to (2v+1);
  (c) aryl substituted with 0–2 groups independently selected from: halogen, phenyl, $C_1$–$C_6$ alkyl, $C_1$–$C_6$ alkoxy, $NO_2$, —$S(C_1$–$C_5$ alkyl), —$SO(C_1$–$C_5$ alkyl), —$SO_2(C_1$–$C_5$ alkyl), —OH, —$N(R^{13})_2$, —$CO_2R^{13}$, —$C(=O)N(R^{13})_2$, or —$C_vF_w$ where v=1 to 3 and w=1 to (2v+1);

$R^{40}$ is selected from: H, $C_1$–$C_5$ alkyl, or benzyl.

[6] Included in the present invention are compounds above, wherein:

$R^{31}$ is selected from the group consisting of:
  (a) a 6 membered saturated, partially saturated or aromatic carbocyclic ring substituted with 0–3 $R^{10}$ or $R^{10a}$;
  (b) a 8–11 membered saturated, partially saturated, or aromatic fused bicyclic carbocyclic ring substituted with 0–4 $R^{10}$ or $R^{10a}$; or (c) a 14 membered saturated, partially saturated, or aromatic fused tricyclic carbocyclic ring substituted with 0–4 $R^{10}$ or $R^{10a}$.

[7] The present invention includes compounds of formula (I) above wherein:

$R^{31}$ is selected from the group consisting of:

(a) a 6 membered saturated, partially saturated, or aromatic carbocyclic ring of formula:

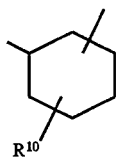

wherein any of the bonds forming the carbocyclic ring may be a single or double bond, and wherein said carbocyclic ring is substituted independently with 0–4 $R^{10}$;

(b) a 10 membered saturated, partially saturated, or aromatic bicyclic carbocyclic ring of formula:

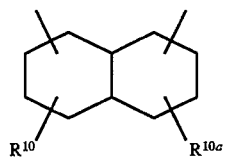

wherein any of the bonds forming the carbocyclic ring may be a single or double bond, and wherein said carbocyclic ring is substituted independently with 0–4 $R^{10}$ or $R^{10a}$;

(c) a 9 membered saturated, partially saturated, or aromatic bicyclic carbocyclic ring of formula:

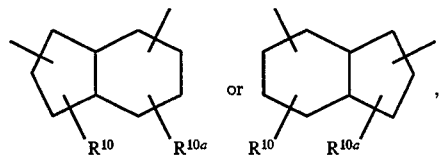

wherein any of the bonds forming the carbocyclic ring may be a single or double bond, and wherein said carbocyclic ring is substituted independently with 0–4 $R^{10}$ or $R^{10a}$.

[8] This invention includes compounds of formula (I) wherein:

$R^{31}$ is selected from (the dashed bond may be a single or double bond):

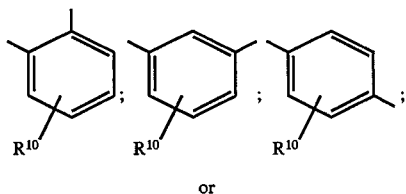

or

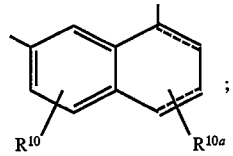

wherein $R^{31}$ may be substituted independently with 0–3 $R^{10}$ or $R^{10a}$;

n" is 0 or 1;

n' is 0–2.

[9] The present invention includes compounds of formula (I) above wherein:

$R^1$ and $R^{22}$ are independently selected from:

phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_5$ alkoxy, —$CO_2R^{13}$, —C(=O) $NHOR^{13a}$, —C(=O)$NHN(R^{13})_2$, =$NOR^{13}$, —B($R^{34}$)($R^{35}$), $C_3$–$C_6$ cycloalkoxy, —OC(=O)$R^{13}$, —C(=O)$R^{13}$, —OC(=O)O$R^{13a}$, —O$R^{13}$, —($C_1$–$C_4$ alkyl)—O$R^{13}$, —N($R^{13})_2$, —OC(=O)N ($R^{13})_2$, $NR^{13}$C(=O)$R^{13}$, —$NR^{13}$C(=O)O$R^{13a}$, —$NR^{13}$C(=O)N($R^{13})_2$, —$NR^{13}$SO$_2$N($R^{13})_2$, —$NR^{13}$SO$_2R^{13a}$, —SO$_3$H, —SO$_2R^{13a}$, —S(=O) $R^{13a}$, —$SR^{13}$, —SO$_2$N($R^{13})_2$, $C_2$–$C_6$ alkoxyalkyl, methylenedioxy, ethylenedioxy, $C_1$–$C_4$ haloalkyl, $C_1$–$C_4$ haloalkoxy, $C_1$–$C_4$ alkylcarbonyloxy, $C_1$–$C_4$ alkylcarbonyl, $C_1$–$C_4$ alkylcarbonylamino, —OCH$_2$CO$_2$H, 2-(1-morpholino)ethoxy, $C_1$–$C_4$ alkyl (alkyl being substituted with —N($R^{13})_2$, —CF$_3$, NO$_2$, or —S(=O)$R^{13a}$).

[10] The present invention includes compounds of formula (I), or a pharmaceutically acceptable salt or prodrug form thereof wherein:

$R^{31}$ is selected from:

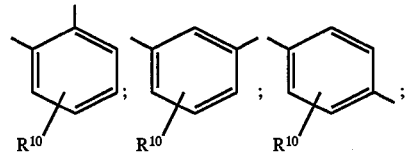

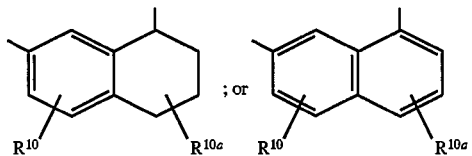

wherein $R^{31}$ may be substituted independently with 0–3 $R^{10}$ or $R^{10a}$;

$R^{32}$ is —C(=O)— n" is 0 or 1;

n' is 0–2;

$R^1$ and $R^{22}$ are independently selected from H, $C_1$–$C_4$ alkyl; phenyl, benzyl, phenyl-($C_2$–$C_4$)alkyl, $C_1$–$C_4$ alkoxy;

$R^{21}$ and $R^{23}$ are independently H or $C_1$–$C_4$ alkyl;

$R^2$ is H or $C_1$–$C_8$ alkyl;

$R^{13}$ is selected independently from: H, $C_1$–$C_{10}$ alkyl, $C_3$–$C_{10}$ cycloalkyl, $C_4$–$C_{12}$ alkylcycloalkyl, aryl, —($C_1$–$C_{10}$ alkyl)aryl, or $C_3$–$C_{10}$ alkoxyalkyl;

$R^{13a}$ is $C_1$–$C_{10}$ alkyl, $C_3$–$C_{10}$ cycloalkyl, $C_4$–$C_{12}$ alkylcycloalkyl, aryl, —($C_1$–$C_{10}$ alkyl)aryl, or $C_3$–$C_{10}$ alkoxyalkyl;

when two $R^{13}$ groups are bonded to a single N, said $R^{13}$ groups may alternatively be taken together to form —$(CH_2)_{2-5}$— or —$(CH_2)O(CH_2)$—;

$R^{14}$ is OH, H, $C_1$–$C_4$ alkyl, or benzyl;

$R^{10}$ and $R^{10a}$ are selected independently from: H, $C_1$–$C_8$ alkyl, phenyl, halogen, or $C_1$–$C_4$ alkoxy;

J is β-Ala or an L-isomer or D-isomer amino acid of structure —$N(R^3)C(R^4)(R^5)C(=O)$—, wherein:
$R^3$ is H or $CH_3$;
$R^4$ is H or $C_1$–$C_3$ alkyl;
$R^5$ is H, $C_1$–$C_8$ alkyl, $C_3$–$C_6$ cycloalkyl, $C_3$–$C_6$ cycloalkylmethyl, $C_1$–$C_6$ cycloalkylethyl, phenyl, phenylmethyl, $CH_2OH$, $CH_2SH$, $CH_2OCH_3$, $CH_2SCH_3$, $CH_2CH_2SCH_3$, $(CH_2)_sNH_2$, —$(CH_2)_sNHC(=NH)(NH_2)$, —$(CH_2)_sNHR^{16}$, where s=3–5; or
$R^{16}$ is selected from:
an amine protecting group;
1–2 amino acids; or
1–2 amino acids substituted with an amine protecting group;
$R^3$ and $R^5$ can alternatively be taken together to form —$(CH_2)_t$— (t=2–4) or —$CH_2SC(CH_3)_2$—; or
$R^4$ and $R^5$ can alternatively be taken together to form —$(CH_2)_u$—, where u=2–5;

K is an L-isomer amino acid of structure —$N(R^6)CH(R^7)C(=O)$—, wherein:
$R^6$ is H or $C_1$–$C_8$ alkyl;
$R^7$ is

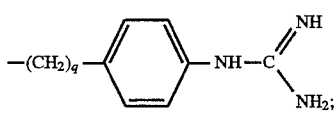

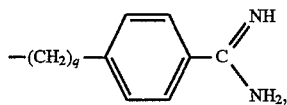

—$(CH_2)_rX$, where r=3–6;

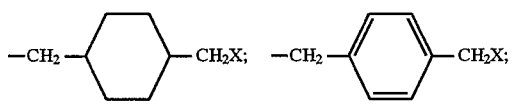

—$(CH_2)_2X$, where m=1 or 2;
—$(C_3$–$C_7$ alkyl)—NH—$(C_1$–$C_6$ alkyl)

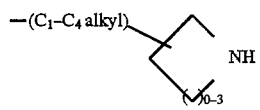

—$(CH_2)_m$—O—$(C_1$–$C_4$ alkyl)—NH—$(C_1$–$C_6$ alkyl), where m=1 or 2;
—$(CH_2)_m$—S—$(C_1$–$C_4$ alkyl)—NH—$(C_1$–$C_6$ alkyl), where m=1 or 2; and X is —$NH_2$ or —$NHC(=NH)(NH_2)$; or $R^6$ and $R^7$ can alternatively be taken together to form

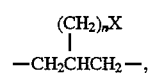

where n=0 or 1 and X is —$NH_2$ or —$NHC(=NH)(NH_2)$;

L is —$Y(CH_2)_vC(=O)$—, wherein:
Y is NH, O, or S; and v=1 or 2;

M is a D-isomer or L-isomer amino acid of structure

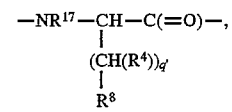

wherein:
q' is 0–2;

$R^{17}$ is H, $C_1$–$C_3$ alkyl;

$R^8$ is selected from:
—$CO_2R^{13}$, —$SO_3R^{13}$, —$SO_2NHR^{14}$, —$B(R^{34})(R^{35})$, —$NHSO_2CF_3$, —$CONHNHSO_2CF_3$, —$PO(OR^{13})_2$, —$PO(OR^{13})R^{13}$, —$SO_2NH$-heteroaryl (said heteroaryl being 5–10-membered and having 1–4 heteroatoms selected independently from N, S, or O), —$SO_2NH$-heteroaryl (said heteroaryl being 5–10-membered and having 1–4 heteroatoms selected independently from N, S, or O), —$SO_2NHCOR^{13}$, —$CONHSO_2R^{13a}$, —$CH_2CONHSO_2R^{13a}$, —$NHSO_2NHCOR^{13a}$, —$NHCONHSO_2R^{13a}$, —$SO_2NHCONHR^{13}$, —$CO_2R^{13b}$;

$R^{13b}$ is selected from:
(a) $C_1$–$C_8$ alkyl;
(b) $C_2$–$C_8$ alkenyl;
(c) $C_2$–$C_8$ alkynyl;
(d) $C_3$–$C_8$ cycloalkyl;
(e) $C_1$–$C_8$ alkyl substituted with
(i) aryl, optionally substituted with 1–2 substituents independently selected from halogen, phenyl, $C_1$–$C_5$ alkyl, $C_1$–$C_5$ alkoxy, $NO_2$, —$S(O)_{0-2}(C_1$–$C_5$ alkyl), OH, $N(R^{13})_2$, $CO_2R^{13}$, $CON(R^{13})_2$ or —$C_vF_w$ where v=1 to 3 and w=1 to (2v+1);
(ii) $C_3$–$C_8$ cycloalkyl;

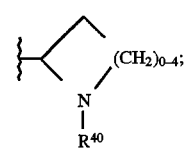

(f) aryl, optionally substituted with 1–2 substituents independently selected from halogen, phenyl, $C_1$–$C_5$ alkyl, $C_1$–$C_5$ alkoxy, $NO_2$, —$S(O)_{0-2}(C_1$–$C_5$ alkyl), OH, $N(R^{13})_2$, $CO_2R^{13}$, $CON(R^{13})_2$ or —$C_vF_w$ where v=1 to 3 and w=1 to (2v+1);

(g) $C_2$–$C_8$ alkyl, alkenyl or alkynyl; substituted with 1–2 substituents independently selected from $C_1$–$C_4$ alkyl, $C_3$–$C_8$ cycloalkyl, $C_1$–$C_5$ alkoxy, phenoxy, benzyloxy, halogen, $NO_2$, CN, $CO_2R^{13}$, $CON(R^{13})_2$, $N(R^{36})COR^{36}$, morpholino, 2-(1-morpholino) ethoxy, $N(R^{13})_2$, $N^+(R^{13})_3$, $OCOCH3$, $CF_3$, $S(O)_{0-2}R^{13a}$;

(h) $CH(R^{36})OR^{38}$;
(i) $CH(R^{36})OC(=O)R^{37}$;
(j) $CH(R^{36})OC(=O)OR^{38}$;
(k) $CH(R^{36})OC(=O)N(R^{37})_2$;
(l) $CH(R^{36})N(R^{36})C(=O)R^{36}$;
(m) $CH(R^{36})CO_2R^{37}$;

(n) CH(R$^{36}$)CON(R$^{13}$)$_2$;
(o) CH(R$^{36}$)N(R$^{13}$)$_2$;

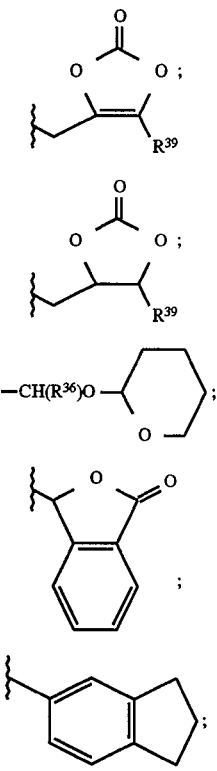

(q)

(r)

(s)

(t)

(u)

$R^{36}$ is selected independently from: H, $C_1$–$C_8$ alkyl, $C_3$–$C_{10}$ cycloalkyl, phenyl, or benzyl;

$R^{37}$ is selected from:
(a) H;
(b) $C_1$–$C_8$ alkyl or $C_3$–$C_8$ cycloalkyl, said alkyl or cycloalkyl being substituted with 1–2 groups independently selected from:
 (i) $C_1$–$C_4$ alkyl;
 (ii) $C_3$–$C_8$ cycloalkyl;
 (iii) $C_1$–$C_5$ alkoxy;
 (iv) aryl substituted with 0–2 groups independently selected from: halogen, phenyl, $C_1$–$C_6$ alkyl, $C_1$–$C_6$ alkoxy, $NO_2$, —S($C_1$–$C_5$ alkyl), —SO ($C_1$–$C_5$ alkyl), —SO$_2$($C_1$–$C_5$ alkyl), —OH, —N($R^{13}$)$_2$, —CO$_2R^{13}$, —C(=O)N($R^{13}$)$_2$, or —C$_v$F$_w$ where v=1 to 3 and w=1 to (2v+1);
(c) aryl substituted with 0–2 groups independently selected from: halogen, phenyl, $C_1$–$C_6$ alkyl, $C_1$–$C_6$ alkoxy, $NO_2$, —S($C_1$–$C_5$ alkyl), —SO($C_1$–$C_5$ alkyl), —SO$_2$($C_1$–$C_5$ alkyl), —OH, —N($R^{13}$)$_2$, —CO$_2R^{13}$, —C(=O)N($R^{13}$)$_2$, or —C$_v$F$_w$ where v=1 to 3 and w=1 to (2v+1);

$R^{38}$ is selected from:
(a) $C_1$–$C_8$ alkyl or $C_3$–$C_8$ cycloalkyl, said alkyl or cycloalkyl being substituted with 1–2 groups independently selected from:
 (i) $C_1$–$C_4$ alkyl;
 (ii) $C_3$–$C_8$ cycloalkyl;
 (iii) $C_1$–$C_5$ alkoxy;
 (iv) aryl substituted with 0–2 groups independently selected from: halogen, phenyl, $C_1$–$C_6$ alkyl, $C_1$–$C_6$ alkoxy, $NO_2$, —S($C_1$–$C_5$alkyl), —SO ($C_1$–$C_5$ alkyl), —SO$_2$($C_1$–$C_5$ alkyl), —OH, —N($R^{13}$)$_2$, —CO$_2R^{13}$, —C(=O)N($R^{13}$)$_2$, or —C$_v$F$_w$ where v=1 to 3 and w=1 to (2v+1);

(b) aryl substituted with 0–2 groups independently selected from: halogen, phenyl, $C_1$–$C_6$ alkyl, $C_1$–$C_6$ alkoxy, $NO_2$, —S($C_1$–$C_5$ alkyl), —SO($C_1$–$C_5$ alkyl), —SO$_2$($C_1$–$C_5$ alkyl), —OH, —N($R^{13}$)$_2$, —CO$_2R^{13}$, —C(=O)N($R^{13}$)$_2$, or —C$_v$F$_w$ where v=1 to 3 and w=1 to (2v+1);

$R^{39}$ is selected from:
(a) H
(b) $C_1$–$C_8$ alkyl or $C_3$–$C_8$ cycloalkyl, said alkyl or cycloalkyl being substituted with 1–2 groups independently selected from:
 (i) $C_1$–$C_6$ alkyl;
 (ii) $C_1$–$C_6$ alkoxy;
 (iii) aryl substituted with 0–2 groups independently selected from: halogen, phenyl, $C_1$–$C_6$ alkyl, $C_1$–$C_6$ alkoxy, $NO_2$, —S($C_1$–$C_5$ alkyl), —SO ($C_1$–$C_5$ alkyl), —SO$_2$($C_1$–$C_5$ alkyl), —OH, —N($R^{13}$)$_2$, —CO$_2R^{13}$, —C(=O)N($R^{13}$)$_2$, or —C$_v$F$_w$ where v=1 to 3 and w=1 to (2v+1);
(c) aryl substituted with 0–2 groups independently selected from: halogen, phenyl, $C_1$–$C_6$ alkyl, $C_1$–$C_6$ alkoxy, $NO_2$, —S($C_1$–$C_5$ alkyl), —SO($C_1$–$C_5$ alkyl), —SO$_2$($C_1$–$C_5$ alkyl), —OH, —N($R^{13}$)$_2$, —CO$_2R^{13}$, —C(=O)N($R^{13}$)$_2$, or —C$_v$F$_w$ where v=1 to 3 and w=1 to (2v+1);

$R^{40}$ is selected from: H, $C_1$–$C_5$ alkyl, or benzyl.

[11] Preferred compounds of the invention are 1,3-disubstituted phenyl compounds of the formula (II):

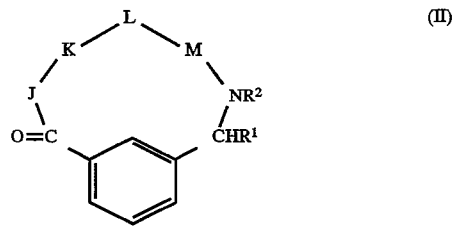

(II)

wherein:
the phenyl ring in formula (II) may be further substituted with 0–3 $R^{10}$;

$R^{10}$ is selected independently from: H, $C_1$–$C_8$ alkyl, phenyl, halogen, or $C_1$–$C_4$ alkoxy;

$R^1$ is H, $C_1$–$C_4$ alkyl, phenyl, benzyl, or phenyl-($C_1$–$C_4$) alkyl;

$R^2$ is H or methyl;

$R^{13}$ is selected independently from: H, $C_1$–$C_{10}$ alkyl, $C_3$–$C_{10}$ cycloalkyl, $C_4$–$C_{12}$ alkylcycloalkyl, aryl, —($C_1$–$C_{10}$ alkyl)aryl, or $C_3$–$C_{10}$ alkoxyalkyl;

$R^{13a}$ is $C_1$–$C_{10}$ alkyl, $C_3$–$C_{10}$ cycloalkyl, $C_4$–$C_{12}$ alkylcycloalkyl, aryl, —($C_1$–$C_{10}$ alkyl)aryl, or $C_3$–$C_{10}$ alkoxyalkyl;

when two $R^{13}$ groups are bonded to a single N, said $R^{13}$groups may alternatively be taken together to form —(CH$_2$)$_{2-5}$— or —(CH$_2$)O(CH$_2$)—;

$R^{14}$ is OH, H, $C_1$–$C_4$ alkyl, or benzyl;

J is β-Ala or an L-isomer or D-isomer amino acid of structure —N($R^3$)C($R^4$)($R^5$)C(=O)—, wherein:
 $R^3$ is H or CH$_3$;
 $R^4$ is H or $C_1$–$C_3$ alkyl;
 $R^5$ is H, $C_1$–$C_8$ alkyl, $C_3$–$C_6$ cycloalkyl, $C_3$–$C_6$ cycloalkylmethyl, $C_1$–$C_6$ cycloalkylethyl, phenyl, phenylmethyl, CH$_2$OH, CH$_2$SH, CH$_2$OCH$_3$, CH$_2$SCH$_3$, CH$_2$CH$_2$SCH$_3$, (CH$_2$)$_s$NH$_2$, —(CH$_2$)$_s$NHC(=NH)(NH$_2$), —(CH$_2$)$_s$NHR$^{16}$, where s=3–5; or $R^{16}$ is selected from:
  an amine protecting group;
  1–2 amino acids; or
  1–2 amino acids substituted with an amine protecting group;
$R^3$ and $R^5$ can alternatively be taken together to form —CH$_2$CH$_2$CH$_2$—; or
$R^4$ and $R^5$ can alternatively be taken together to form —(CH$_2$)$_u$—, where u=2–5;
K is an L-isomer amino acid of structure —N(R$^6$)CH(R$^7$)C(=O)—, wherein:
  $R^6$ is H or C$_1$–C$_8$ alkyl;
  $R^7$ is:

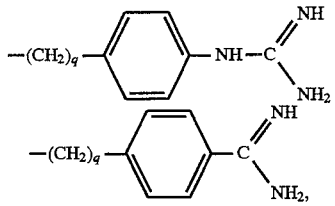

where q=0 or 1;
—(CH$_2$)$_r$X, where r=3–6;

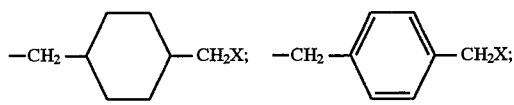

—(CH$_2$)$_m$S(CH$_2$)$_2$X, where m=1 or 2;
—(C$_3$–C$_7$ alkyl)—NH—(C$_1$–C$_6$ alkyl)

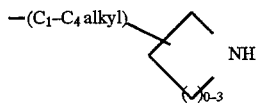

—(CH$_2$)$_m$—O—(C$_1$–C$_4$ alkyl)—NH—(C$_1$–C$_6$ alkyl), where m=1 or 2;
—(CH$_2$)$_m$—S—(C$_1$–C$_4$ alkyl)—NH—(C$_1$–C$_6$ alkyl), where m=1 or 2; and
X is —NH$_2$ or —NHC(=NH)(NH$_2$), provided that X is not —NH$_2$ when r=4; or
$R^6$ and $R^7$ are alternatively be taken together to form

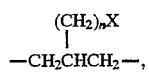

where n=0,1 and X is —NH$_2$ or —NHC(=NH)(NH$_2$);
L is —Y(CH$_2$)$_v$C(=O)—, wherein:
  Y is NH, O, or S; and v=1,2;
M is a D-isomer or L-isomer amino acid of structure

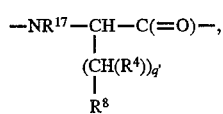

wherein:
q' is 0–2;
$R^{17}$ is H, C$_1$–C$_3$ alkyl;
$R^8$ is selected from:
  —CO$_2$R$^{13}$, —SO$_3$R$^{13}$, —SO$_2$NHR$^{14}$, —B(R$^{34}$)(R$^{35}$), —NHSO$_2$CF$_3$, —CONHNHSO$_2$CF$_3$, —PO(OR$^{13}$)$_2$, —PO(OR$^{13}$)R$^{13}$, —SO$_2$NH-heteroaryl (said heteroaryl being 5–10-membered and having 1–4 heteroatoms selected independently from N, S, or O), —SO$_2$NH-heteroaryl (said heteroaryl being 5–10-membered and having 1–4 heteroatoms selected independently from N, S, or O), —SO$_2$NHCOR$^{13}$, —CONHSO$_2$R$^{13a}$, —CH$_2$CONHSO$_2$R$^{13a}$, —NHSO$_2$NHCOR$^{13a}$, —NHCONHSO$_2$R$^{13a}$, —SO$_2$NHCONHR$^{13}$, —CO$_2$R$^{13b}$;

$R^{13b}$ is selected from:
  (a) C$_1$–C$_8$ alkyl;
  (b) C$_2$–C$_8$ alkenyl;
  (c) C$_2$–C$_8$ alkynyl;
  (d) C$_3$–C$_8$ cycloalkyl;
  (e) C$_1$–C$_8$ alkyl substituted with
    (i) aryl, optionally substituted with 1–2 substituents independently selected from halogen, phenyl, C$_1$–C$_5$ alkyl, C$_1$–C$_5$ alkoxy, NO$_2$, —S(O)$_{0-2}$(C$_1$–C$_5$ alkyl), OH, N(R$^{13}$)$_2$, CO$_2$R$^{13}$, CON(R$^{13}$)$_2$ or —C$_v$F$_w$, where v=1 to 3 and w=1 to (2v+1);
    (ii) C$_3$–C$_8$ cycloalkyl;

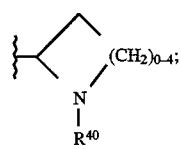

(f) aryl, optionally substituted with 1–2 substituents independently selected from halogen, phenyl, C$_1$–C$_5$ alkyl, C$_1$–C$_5$ alkoxy, NO$_2$, —S(O)$_{0-2}$(C$_1$–C$_5$ alkyl), OH, N(R$^{13}$)$_2$, CO$_2$R$^{13}$, CON(R$^{13}$)$_2$ or —C$_v$F$_w$ where v=1 to 3 and w=1 to (2v+1);
  (g) C$_2$–C$_8$ alkyl, alkenyl or alkynyl; substituted with 1–2 substituents independently selected from C$_1$–C$_4$ alkyl, C$_3$–C$_8$ cycloalkyl, C$_1$–C$_5$ alkoxy, phenoxy, benzyloxy, halogen, NO$_2$, CN, CO$_2$R$^{13}$, CON(R$^{13}$)$_2$, N(R$^{36}$)COR$^{36}$, morpholino, 2-(1-morpholino)ethoxy, N(R$^{13}$)$_2$, N$^+$(R$^{13}$)$_3$, OCOCH3, CF$_3$, S(O)$_{0-2}$R$^{13a}$;
  (h) CH(R$^{36}$)OR$^{38}$;
  (i) CH(R$^{36}$)OC(=O)R$^{37}$;
  (j) CH(R$^{36}$)OC(=O)OR$^{38}$;
  (k) CH(R$^{36}$)OC(=O)N(R$^{37}$)$_2$;
  (m) CH(R$^{36}$)CO$_2$R$^{37}$;

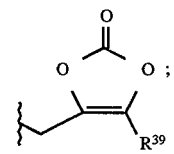

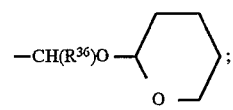

$R^{36}$ is selected independently from: H, C$_1$–C$_8$ alkyl, C$_3$–C$_{10}$ cycloalkyl, phenyl, or benzyl;
$R^{37}$ is selected from:
  (a) H;
  (b) C$_1$–C$_8$ alkyl or C$_3$–C$_8$ cycloalkyl, said alkyl or cycloalkyl being substituted with 1–2 groups independently selected from:
    (i) C$_1$–C$_4$ alkyl;
    (ii) C$_3$–C$_8$ cycloalkyl;
    (iii) C$_1$–C$_5$ alkoxy;

(iv) aryl substituted with 0–2 groups independently selected from: halogen, phenyl, $C_1$–$C_6$ alkyl, $C_1$–$C_6$ alkoxy, $NO_2$, —S($C_1$–$C_5$ alkyl), —SO($C_1$–$C_5$ alkyl), —$SO_2$($C_1$–$C_5$ alkyl), —OH, —N($R^{13}$)$_2$, —$CO_2R^{13}$, —C(=O)N($R^{13}$)$_2$, or —$C_vF_w$ where v=1 to 3 and w=1 to (2v+1);

(c) aryl substituted with 0–2 groups independently selected from: halogen, phenyl, $C_1$–$C_6$ alkyl, $C_1$–$C_6$ alkoxy, $NO_2$, —S($C_1$–$C_5$ alkyl), —SO($C_1$–$C_5$ alkyl), —$SO_2$($C_1$–$C_5$ alkyl), —OH, —N($R^{13}$)$_2$, —$CO_2R^{13}$, —C(=O)N($R^{13}$)$_2$, or —$C_vF_w$ where v=1 to 3 and w=1 to (2v+1);

(a) $C_1$–$C_8$ alkyl or $C_3$–$C_8$ cycloalkyl, said alkyl or cycloalkyl being substituted with 1–2 groups independently selected from:
(i) $C_1$–$C_4$ alkyl;
(ii) $C_3$–$C_8$ cycloalkyl;
(iii) $C_1$–$C_5$ alkoxy;
(iv) aryl substituted with 0–2 groups independently selected from: halogen, phenyl, $C_1$–$C_6$ alkyl, $C_1$–$C_6$ alkoxy, $NO_2$, —S($C_1$–$C_5$ alkyl), —SO($C_1$–$C_5$ alkyl), —$SO_2$($C_1$–$C_5$ alkyl), —OH, —N($R^{13}$)$_2$, —$CO_2R^{13}$, —C(=O)N($R^{13}$)$_2$, or —$C_vF_w$ where v=1 to 3 and w=1 to (2v+1);

(b) aryl substituted with 0–2 groups independently selected from: halogen, phenyl, $C_1$–$C_6$ alkyl, $C_1$–$C_6$ alkoxy, $NO_2$, —S($C_1$–$C_5$ alkyl), —SO($C_1$–$C_5$ alkyl), —$SO_2$($C_1$–$C_5$ alkyl), —OH, —N($R^{13}$)$_2$, —$CO_2R^{13}$, —C(=O)N($R^{13}$)$_2$, or —$C_vF_w$ where v=1 to 3 and w=1 to (2v+1);

$R^{39}$ is selected from:
(a) H
(b) $C_1$–$C_8$ alkyl or $C_3$–$C_8$ cycloalkyl, said alkyl or cycloalkyl being substituted with 1–2 groups independently selected from:
(i) $C_1$–$C_6$ alkyl;
(ii) $C_1$–$C_6$ alkoxy;
(iii) aryl substituted with 0–2 groups independently selected from: halogen, phenyl, $C_1$–$C_6$ alkyl, $C_1$–$C_6$ alkoxy, $NO_2$, —S($C_1$–$C_5$ alkyl), —SO($C_1$–$C_5$ alkyl), —$SO_2$($C_1$–$C_5$ alkyl), —OH, —N($R^{13}$)$_2$, —$CO_2R^{13}$, —C(=O)N($R^{13}$)$_2$, or —$C_vF_w$ where v=1 to 3 and w=1 to (2v+1);
(c) aryl substituted with 0–2 groups independently selected from: halogen, phenyl, $C_1$–$C_6$ alkyl, $C_1$–$C_6$ alkoxy, $NO_2$, —S($C_1$–$C_5$ alkyl), —SO($C_1$–$C_5$ alkyl), —$SO_2$($C_1$–$C_5$ alkyl), —OH, —N($R^{13}$)$_2$, —$CO_2R^{13}$, —C(=O)N($R^{13}$)$_2$, or —$C_vF_w$ where v=1 to 3 and w=1 to (2v+1);

$R^{40}$ is selected from: H, $C_1$–$C_5$ alkyl, or benzyl.

[12] Further preferred compounds of the invention are 1,3-disubstituted phenyl compounds of the formula (II):

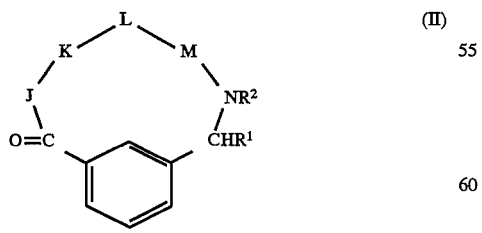

(II)

wherein:
the phenyl ring in formula (II) may be further substituted with 0–3 $R^{10}$ or $R^{10a}$;
$R^{10}$ or $R^{10a}$ are selected independently from: H, $C_1$–$C_8$ alkyl, phenyl, halogen, or $C_1$–$C_4$ alkoxy;

$R^1$ is H, $C_1$–$C_4$ alkyl, phenyl, benzyl, or phenyl-($C_2$–$C_4$) alkyl;

$R^2$ is H or methyl;

$R^{13}$ is selected independently from: H, $C_1$–$C_{10}$ alkyl, $C_3$–$C_{10}$ cycloalkyl, $C_4$–$C_{12}$ alkylcycloalkyl, aryl, —($C_1$–$C_{10}$ alkyl)aryl, or $C_3$–$C_{10}$ alkoxyalkyl;

when two $R^{13}$ groups are bonded to a single N, said $R^{13}$ groups may alternatively be taken together to form —($CH_2$)$_{2-5}$— or —($CH_2$)O($CH_2$)—;

$R^{13a}$ is $C_1$–$C_{10}$ alkyl, $C_3$–$C_{10}$ cycloalkyl, $C_4$–$C_{12}$ alkylcycloalkyl, aryl, —($C_1$–$C_{10}$ alkyl)aryl, or $C_3$–$C_{10}$ alkoxyalkyl;

$R^{14}$ is OH, H, $C_1$–$C_4$ alkyl, or benzyl;

J is β-Ala or an L-isomer or D-isomer amino acid of structure —N($R^3$)C($R^4$)($R^5$)C(=O)—, wherein:
$R^3$ is H or $CH_3$;
$R^4$ is H;
$R^5$ is H, $C_1$–$C_8$ alkyl, $C_3$–$C_6$ cycloalkyl, $C_3$–$C_6$cycloalkylmethyl, $C_1$–$C_6$ cycloalkylethyl, phenyl, phenylmethyl, $CH_2OH$, $CH_2SH$, $CH_2OCH_3$, $CH_2SCH_3$, $CH_2CH_2SCH_3$, ($CH_2$)$_s$$NH_2$, ($CH_2$)$_s$NHC(=NH)($NH_2$), ($CH_2$)$_s$$R^{16}$, where s=3–5;

$R^3$ and $R^5$ can alternatively be taken together to form —$CH_2CH_2CH_2$—;

$R^{16}$ is selected from:
an amine protecting group;
1–2 amino acids;
1–2 amino acids substituted with an amine protecting group;

K is an L-isomer amino acid of structure —N($R^6$)CH($R^7$)C(=O)—, wherein:
$R^6$ is H or $C_3$–$C_8$ alkyl;
$R^7$ is

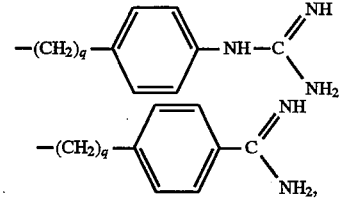

q=0 or 1;
—($CH_2$)$_r$X, where r=3–6;

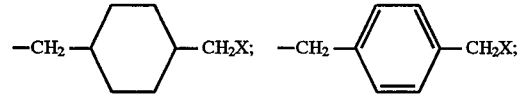

—($CH_2$)$_m$S($CH_2$)$_2$X, where m=1 or 2;
—($C_4$–$C_7$alkyl)—NH—($C_1$–$C_6$ alkyl)

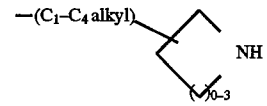

—($CH_2$)$_m$—O—($C_1$–$C_4$ alkyl)—NH—($C_1$–$C_6$ alkyl), where m=1 or 2;
—($CH_2$)$_m$—S—($C_1$–$C_4$ alkyl)—NH—($C_1$–$C_6$ alkyl), where m=1 or 2; and X is —$NH_2$ or —NHC(=NH)($NH_2$), provided that X is not —$NH_2$ when r=4; or L is —$YCH_2$C(=O)—, wherein:

Y is NH or O;

M is a D-isomer or L-isomer amino acid of structure

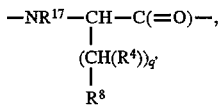

wherein:

q' is 1;

$R^{17}$ is H, $C_1$-$C_3$ alkyl;

$R^8$ is selected from: —$CO_2H$, —$SO_3R^{13}$, —$CO_2R^{13b}$;

$R^{13b}$ is selected independently from:
—CH($R^{36}$)OC(=O)$R^{37}$;
—CH($R^{36}$)OC(=O)O$R^{38}$;
—$CH_2$OC(=O)N($R^{37}$)$_2$;
—$CH_2CH_2$N($R^{13}$)$_2$;
—CH($R^{36}$)$CO_2R^{37}$;

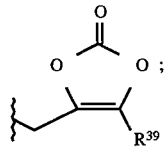

$R^{36}$ is selected independently from: H, $C_1$-$C_8$ alkyl, phenyl, or benzyl;

$R^{37}$ is selected from:
(a) H;
(b) $C_1$-$C_8$ alkyl or $C_3$-$C_8$ cycloalkyl, said alkyl or cycloalkyl being substituted with 1–2 groups independently selected from:
  (i) $C_1$-$C_4$ alkyl;
  (ii) $C_3$-$C_8$ cycloalkyl;
  (iii) $C_1$-$C_5$ alkoxy;
  (iv) aryl substituted with 0–2 groups independently selected from: halogen, phenyl, $C_1$-$C_6$ alkyl, $C_1$-$C_6$ alkoxy, $NO_2$, —S($C_1$-$C_5$alkyl), —SO($C_1$-$C_5$ alkyl), —$SO_2$($C_1$-$C_5$ alkyl), —OH, —N($R^{13}$)$_2$, —$CO_2R^{13}$, —C(=O)N($R^{13}$)$_2$, or —$C_vF_w$ where v=1 to 3 and w=1 to (2v+1);
(c) aryl substituted with 0–2 groups independently selected from: halogen, phenyl, $C_1$-$C_6$ alkyl, $C_1$-$C_6$ alkoxy, $NO_2$, —S($C_1$-$C_5$ alkyl), —SO($C_1$-$C_5$ alkyl), —$SO_2$($C_1$-$C_5$ alkyl), —OH, —N($R^{13}$)$_2$, —$CO_2R^{13}$, —C(=O)N($R^{13}$)$_2$, or —$C_vF_w$ where v=1 to 3 and w=1 to (2v+1);

$R^{38}$ is selected from:
(a) $C_1$-$C_8$ alkyl or $C_3$-$C_8$ cycloalkyl, said alkyl or cycloalkyl being substituted with 1–2 groups independently selected from:
  (i) $C_1$-$C_4$ alkyl;
  (ii) $C_3$-$C_8$ cycloalkyl;
  (iii) $C_1$-$C_5$ alkoxy;
  (iv) aryl substituted with 0–2 groups independently selected from: halogen, phenyl, $C_1$-$C_6$ alkyl, $C_1$-$C_6$ alkoxy, $NO_2$, —S($C_1$-$C_5$ alkyl), —SO($C_1$-$C_5$ alkyl), —$SO_2$($C_1$-$C_5$ alkyl), —OH, —N($R^{13}$)$_2$, —$CO_2R^{13}$, —C(=O)N($R^{13}$)$_2$, or —$C_vF_w$ where v=1 to 3 and w=1 to (2v+1);
(b) aryl substituted with 0–2 groups independently selected from: halogen, phenyl, $C_1$-$C_6$ alkyl, $C_1$-$C_6$ alkoxy, $NO_2$, —S($C_1$-$C_5$ alkyl), —SO($C_1$-$C_5$ alkyl), —$SO_2$($C_1$-$C_5$ alkyl), —OH, —N($R^{13}$)$_2$, —$CO_2R^{13}$, —C(=O)N($R^{13}$)$_2$, or —$C_vF_w$ where v=1 to 3 and w=1 to (2v+1);

$R^{39}$ is selected from: $C_1$-$C_5$ alkyl, benzyl or phenyl.

[13] Preferred compounds of the present invention are compounds of formula (II) above, wherein:

the phenyl ring in formula (II) may be further substituted with 0–2 $R^{10}$ or $R^{10a}$;

$R^{10}$ or $R^{10a}$ are selected independently from: H, $C_1$-$C_8$alkyl, phenyl, halogen, or $C_1$-$C_4$ alkoxy;

$R^1$ is H;

$R^2$ is H;

$R^{13}$ is selected independently from: H, $C_1$-$C_{10}$ alkyl, $C_3$-$C_{10}$ cycloalkyl, $C_4$-$C_{12}$ alkylcycloalkyl, aryl, —($C_1$-$C_{10}$ alkyl)aryl, or $C_3$-$C_{10}$ alkoxyalkyl;

$R^{13a}$ is $C_1$-$C_{10}$ alkyl, $C_3$-$C_{10}$ cycloalkyl, $C_4$-$C_{12}$ alkylcycloalkyl, aryl, —($C_1$-$C_{10}$ alkyl)aryl, or $C_3$-$C_{10}$ alkoxyalkyl;

when two $R^{13}$ groups are bonded to a single N, said $R^{13}$ groups may alternatively be taken together to form —($CH_2$)$_{2-5}$— or —($CH_2$)O($CH_2$)—;

$R^{14}$ is OH, H, $C_1$-$C_4$ alkyl, or benzyl;

J is β-Ala or an L-isomer or D-isomer amino acid of formula —N($R^3$)CH($R^5$)C(=O)—, wherein:
$R^3$ is H and $R^5$ is H, $CH_3$, $CH_2CH_3$, CH($CH_3$)$_2$, CH($CH_3$)$CH_2CH_3$, $CH_2CH_2CH_3$, $CH_2CH_2CH_2CH_3$, $CH_2CH_2SCH_3$, $CH_2$CH($CH_3$)$_2$, ($CH_2$)$_4NH_2$, ($C_3$-$C_5$ alkyl)$NHR^{16}$; or
$R^3$ is $CH_3$ and $R^5$ is H; or
$R^3$ and $R^5$ can alternatively be taken together to form —$CH_2CH_2CH_2$—;

$R^{16}$ is selected from:
an amine protecting group;
1–2 amino acids;
1–2 amino acids substituted with an amine protecting group;

K is an L-isomer amino acid of formula —N($CH_3$)CH($R^7$)C(=O)—, wherein:
$R^7$ is —($CH_2$)$_3$NHC(=NH)($NH_2$);

L is —$NHCH_2$C(=O)—; and

M is a D-isomer or L-isomer amino acid of structure

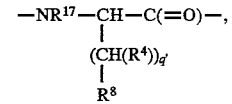

wherein:
q' is 1;
$R^4$ is H or $CH_3$;
$R^{17}$ is H;
$R^8$ is
—$CO_2H$;
—$SO_3H$;
—$CO_2R^{13b}$;

$R^{13b}$ is selected independently from:
—CH($R^{36}$)OC(=O)$R^{37}$;
—CH($R^{36}$)OC(=O)O$R^{38}$;

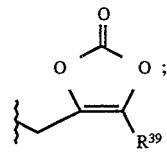

$R^{36}$ is $C_1$-$C_4$ linear alkyl or H;

$R^{37}$ is selected from:
(a) H;
(b) $C_1$–$C_8$ alkyl or $C_3$–$C_8$ cycloalkyl, said alkyl or cycloalkyl being substituted with 1–2 groups independently selected from:
  (i) $C_1$–$C_4$ alkyl;
  (ii) $C_3$–$C_8$ cycloalkyl;
  (iii) $C_1$–$C_5$ alkoxy;
  (iv) aryl substituted with 0–2 groups independently selected from: halogen, phenyl, $C_1$–$C_6$ alkyl, $C_1$–$C_6$ alkoxy, $NO_2$, —S($C_1$–$C_5$alkyl), —SO($C_1$–$C_5$ alkyl), —$SO_2$($C_1$–$C_5$ alkyl), —OH, —N($R^{13}$)$_2$, —$CO_2R^{13}$, —C(=O)N($R^{13}$)$_2$, or —$C_vF_w$ where v=1 to 3 and w=1 to (2v+1);
(c) aryl substituted with 0–2 groups independently selected from: halogen, phenyl, $C_1$–$C_6$ alkyl, $C_1$–$C_6$ alkoxy, $NO_2$, —S($C_1$–$C_5$ alkyl), —SO($C_1$–$C_5$ alkyl), —$SO_2$($C_1$–$C_5$ alkyl), —OH, —N($R^{13}$)$_2$, —$CO_2R^{13}$, —C(=O)N($R^{13}$)$_2$, or —$C_vF_w$ where v=1 to 3 and w=1 to (2v+1);

$R^{38}$ is selected from:
(a) $C_1$–$C_8$ alkyl or $C_3$–$C_8$ cycloalkyl, said alkyl or cycloalkyl being substituted with 1–2 groups independently selected from:
  (i) $C_1$–$C_4$ alkyl;
  (ii) $C_3$–$C_8$ cycloalkyl;
  (iii) $C_1$–$C_5$ alkoxy;
  (iv) aryl substituted with 0–2 groups independently selected from: halogen, phenyl, $C_1$–$C_6$ alkyl, $C_1$–$C_6$ alkoxy, $NO_2$, —S($C_1$–$C_5$ alkyl), —SO($C_1$–$C_5$ alkyl), —$SO_2$($C_1$–$C_5$ alkyl), —OH, —N($R^{13}$)$_2$, —$CO_2R^{13}$, —C(=O)N($R^{13}$)$_2$, or —$C_vF_w$ where v=1 to 3 and w=1 to (2v+1);
(b) aryl substituted with 0–2 groups independently selected from: halogen, phenyl, $C_1$–$C_6$ alkyl, $C_1$–$C_6$ alkoxy, $NO_2$, —S($C_1$–$C_5$ alkyl), —SO($C_1$–$C_5$ alkyl), —$SO_2$($C_1$–$C_5$ alkyl), —OH, —N($R^{13}$)$_2$, —$CO_2R^{13}$, —C(=O)N($R^{13}$)$_2$, or —$C_vF_w$ where v=1 to 3 and w=1 to (2v+1);

$R^{39}$ is $C_1$–$C_4$ alkyl, benzyl, or phenyl.

[14] Preferred compounds of the present invention are compounds of formula (II), or a pharmaceutically acceptable salt thereof, wherein:

$R^1$ and $R^2$ are independently selected from H, methyl;

J is selected from D-Val, D-2-aminobutyric acid, D-Leu, D-Ala, Gly, D-Pro, D-Ser, D-Lys, β-Ala, Pro, Phe, NMeGly, D-Nle, D-Phg, D-Ile, D-Phe, D-Tyr, Ala, N$^ε$-p-azidobenzoyl-D-Lys, N$^ε$-p-benzoylbenzoyl-D-Lys, N$^ε$-tryptophanyl-D-Lys, N$^ε$-o-benzylbenzoyl-D-Lys, N$^ε$-p-acetylbenzoyl-D-Lys, N$^ε$-dansyl-D-Lys, N$^ε$-glycyl-D-Lys, N$^ε$-glycyl-p-benzoylbenzoyl-D-Lys, N$^ε$-p-phenylbenzoyl-D-Lys, N$^ε$-m-benzoylbenzoyl-D-Lys, N$^ε$-o-benzoylbenzoyl-D-Lys;

K is selected from NMeArg, Arg;

L is selected from Gly, β-Ala, Ala;

M is selected from Asp; αMeAsp; βMeAsp; NMeAsp; D-Asp;
Asp-(methylcarbonyloxymethyl ester);
Asp-(ethylcarbonyloxymethyl ester);
Asp-(t-butylcarbonyloxymethyl ester);
Asp-(cyclohexylcarbonyloxymethyl ester);
Asp-(1-(methylcarbonyloxy)ethyl ester);
Asp-(1-(ethylcarbonyloxy)ethyl ester);
Asp-(1-(t-butylcarbonyloxy)ethyl ester);
Asp-(1-(cyclohexylcarbonyloxy)ethyl ester);
Asp-(i-propyloxycarbonyloxymethyl ester);
Asp-(cyclohexylcarbonyloxymethyl ester);
Asp-(t-butyloxycarbonyloxymethyl ester);
Asp-(1-(i-propyloxycarbonyloxy)ethyl ester);
Asp-(1-(cyclohexyloxycarbonyloxy)ethyl ester);
Asp-(1-(t-butyloxycarbonyloxy) ethyl ester);
Asp-(dimethylaminoethyl ester);
Asp-(diethylaminoethyl ester);
Asp-((1,3-dioxa-5-methyl-cyclopenten-2-one-4-yl) methyl ester);
Asp-((5-(t-butyl)-1,3-dioxa-cyclopenten-2-one-4-yl) methyl ester);
Asp-((1,3-dioxa-5-phenyl-cyclopenten-2-one-4-yl) methyl ester);
Asp-(1-(2-(2-methoxypropyl)carbonyloxy)ethyl ester).

[15] Preferred compounds of the present invention are compounds of formula (II), or a pharmaceutically acceptable salt thereof, wherein:

$R^1$ and $R^2$ are independently selected from H, methyl;

J is selected from: D-Val, D-2-aminobutyric acid, D-Leu, D-Ala, Gly, D-Pro, D-Ser, D-Lys, β-Ala, Pro, Phe, NMeGly, D-Nle, D-Phg, D-Ile, D-Phe, D-Tyr, Ala;

K is selected from NMeArg;

L is Gly;

M is selected from Asp; αMeAsp; βMeAsp; NMeAsp; D-Asp;
Asp-(methylcarbonyloxymethyl ester);
Asp-(ethylcarbonyloxymethyl ester);
Asp-(t-butylcarbonyloxymethyl ester);
Asp-(cyclohexylcarbonyloxymethyl ester);
Asp-(1-(methylcarbonyloxy)ethyl ester);
Asp-(1-(ethylcarbonyloxy)ethyl ester);
Asp-(1-(t-butylcarbonyloxy)ethyl ester);
Asp-(1-(cyclohexylcarbonyloxy)ethyl ester);
Asp-(i-propyloxycarbonyloxymethyl ester);
Asp-(cyclohexylcarbonyloxymethyl ester);
Asp-(t-butyloxycarbonyloxymethyl ester);
Asp-(1-(i-propyloxycarbonyloxy)ethyl ester);
Asp-(1-(cyclohexyloxycarbonyloxy)ethyl ester);
Asp-(1-(t-butyloxycarbonyloxy)ethyl ester);
Asp-(dimethylaminoethyl ester);
Asp-(diethylaminoethyl ester);
Asp-((1,3-dioxa-5-methyl-cyclopenten-2-one-4-yl) methyl ester);
Asp-((5-(t-butyl)-1,3-dioxa-cyclopenten-2-one-4-yl) methyl ester);
Asp-((1,3-dioxa-5-phenyl-cyclopenten-2-one-4-yl) methyl ester);
Asp-(1-(2-(2-methoxypropyl)carbonyloxy)ethyl ester).

[16] Specifically preferred compounds of the present invention are the following compounds and pharmaceutically acceptable salts thereof:

The compound of formula (II) wherein $R^1$ and $R^2$ are H; J is D-Val; K is NMeArg; L is Gly; and M is Asp-(methylcarbonyloxymethyl ester).

The compound of formula (II) wherein $R^1$ and $R^2$ are H; J is D-Val; K is NMeArg; L is Gly; and M is Asp-(ethylcarbonyloxymethyl ester).

The compound of formula (II) wherein $R^1$ and $R^2$ are H; J is D-Val; K is NMeArg; L is Gly; and M is Asp-(t-butylcarbonyloxymethyl ester).

The compound of formula (II) wherein $R^1$ and $R^2$ are H; J is D-Val; K is NMeArg; L is Gly; and M is Asp-(cyclohexylcarbonyloxymethyl ester).

The compound of formula (II) wherein $R^1$ and $R^2$ are H; J is D-Val; K is NMeArg; L is Gly; and M is Asp-(1-(methylcarbonyloxy)ethyl ester).

The compound of formula (II) wherein $R^1$ and $R^2$ are H; J is D-Val; K is NMeArg; L is Gly; and M is Asp-(1-(ethylcarbonyloxy)ethyl ester).

The compound of formula (II) wherein $R^1$ and $R^2$ are H; J is D-Val; K is NMeArg; L is Gly; and M is Asp-(1-(t-butylcarbonyloxy)ethyl ester).

The compound of formula (II) wherein $R^1$ and $R^2$ are H; J is D-Val; K is NMeArg; L is Gly; and M is Asp-(1-cyclohexylcarbonyloxy)ethyl ester).

The compound of formula (II) wherein $R^1$ and $R^2$ are H; J is D-Val; K is NMeArg; L is Gly; and M is Asp-(i-propyloxycarbonyloxymethyl ester).

The compound of formula (II) wherein $R^1$ and $R^2$ are H; J is D-Val; K is NMeArg; L is Gly; and M is Asp-(cyclohexylcarbonyloxymethyl ester).

The compound of formula (II) wherein $R^1$ and $R^2$ are H; J is D-Val; K is NMeArg; L is Gly; and M is Asp-(t-butyloxycarbonyloxymethyl ester).

The compound of formula (II) wherein $R^1$ and $R^2$ are H; J is D-Val; K is NMeArg; L is Gly; and M is Asp-(1-(i-propyloxycarbonyloxy)ethyl ester).

The compound of formula (II) wherein $R^1$ and $R^2$ are H; J is D-Val; K is NMeArg; L is Gly; and M is Asp-(1-(cyclohexyloxycarbonyloxy)ethyl ester).

The compound of formula (II) wherein $R^1$ and $R^2$ are H; J is D-Val; K iS NMeArg; L is Gly; and M is Asp-(1-(t-butyloxycarbonyloxy)ethyl ester).

The compound of formula (II) wherein $R^1$ and $R^2$ are H; J is D-Val; K is NMeArg; L is Gly; and M is Asp-(dimethylaminoethyl ester).

The compound of formula (II) wherein $R^1$ and $R^2$ are H; J is D-Val; K is NMeArg; L is Gty; and M is Asp-(diethylaminoethyl ester).

The compound of formula (II) wherein $R^1$ and $R^2$ are H; J is D-Val; K is NMeArg; L is Gly; and M is Asp-((1,3-dioxa-5-methyl-cyclopenten-2-one-4-yl)methyl ester).

The compound of formula (II) wherein $R^1$ and $R^2$ are H; J is D-Val; K is NMeArg; L is Gly; and M is Asp-((5-(t-butyl)-1,3-dioxa-cyclopenten-2-one-4-yl)methyl ester).

The compound of formula (II) wherein $R^1$ and $R^2$ are H; J is D-Val; K is NMeArg; L is Gly; and M is Asp-((1,3-dioxa-5-phenyl-cyclopenten-2-one-4-yl)methyl ester).

The compound of formula (II) wherein $R^1$ and $R^2$ are H; J is D-Val; K is NMeArg; L is Gly; and M is Asp-(1-(2-(2-methoxypropyl)carbonyloxy)ethyl ester).

The compound of formula (II) wherein $R^1$ and $R^2$ are H; J is D-2-aminobutyric acid; K is NMeArg; L is Gly; and M is Asp-(methylcarbonyloxymethyl ester).

The compound of formula (II) wherein $R^1$ and $R^2$ are H; J is D-2-aminobutyric acid; K is NMeArg; L is Gly; and M is Asp-(ethylcarbonyloxymethyl ester).

The compound of formula (II) wherein $R^1$ and $R^2$ are H; J is D-2-aminobutyric acid; K is NMeArg; L is Gly; and M is Asp-(t-butylcarbonyloxymethyl ester).

The compound of formula (II) wherein $R^1$ and $R^2$ are H; J is D-2-aminobutyric acid; K is NMeArg; L is Gly; and M is Asp-(cyclohexylcarbonyloxymethyl ester).

The compound of formula (II) wherein $R^1$ and $R^2$ are H; J is D-2-aminobutyric acid; K is NMeArg; L is Gly; and M is Asp-(1-(methylcarbonyloxy)ethyl ester).

The compound of formula (II) wherein $R^1$ and $R^2$ are H; J is D-2-aminobutyric acid; K is NMeArg; L is Gly; and M is Asp-(1-(ethylcarbonyloxy)ethyl ester).

The compound of formula (II) wherein $R^1$ and $R^2$ are H; J is D-2-aminobutyric acid; K is NMeArg; L is Gly; and M is Asp-(1-(t-butylcarbonyloxy)ethyl ester).

The compound of formula (II) wherein $R^1$ and $R^2$ are H; J is D-2-aminobutyric acid; K is NMeArg; L is Gly; and M is Asp-(1-(cyclohexylcarbonyloxy)ethyl ester).

The compound of formula (II) wherein $R^1$ and $R^2$ are H; J is D-2-aminobutyric acid; K is NMeArg; L is Gly; and M is Asp-(i-propyloxycarbonyloxymethyl ester).

The compound of formula (II) wherein $R^1$ and $R^2$ are H; J is D-2-aminobutyric acid; K is NMeArg; L is Gly; and M is Asp-(cyclohexylcarbonyloxymethyl ester).

The compound of formula (II) wherein $R^1$ and $R^2$ are H; J is D-2-aminobutyric acid; K is NMeArg; L is Gly; and M is Asp-(t-butyloxycarbonyloxymethyl ester).

The compound of formula (II) wherein $R^1$ and $R^2$ are H; J is D-2-aminobutyric acid; K is NMeArg; L is Gly; and M is Asp-(1-(i-propyloxycarbonyloxy)ethyl ester).

The compound of formula (II) wherein $R^1$ and $R^2$ are H; J is D-2-aminobutyric acid; K is NMeArg; L is Gly; and M is Asp-(1-(cyclohexyloxycarbonyloxy)ethyl ester).

The compound of formula (II) wherein $R^1$ and $R^2$ are H; J is D-2-aminobutyric acid; K is NMeArg; L is Gly; and M is Asp-(1-(t-butyloxycarbonyloxy)ethyl ester).

The compound of formula (II) wherein $R^1$ and $R^2$ are H; J is D-2-aminobutyric acid; K is NMeArg; L is Gly; and M is Asp-(dimethylaminoethyl ester).

The compound of formula (II) wherein $R^1$ and $R^2$ are H; J is D-2-aminobutyric acid; K is NMeArg; L is Gly; and M is Asp-(diethylaminoethyl ester).

The compound of formula (II) wherein $R^1$ and $R^2$ are H; J is D-2-aminobutyric acid; K is NMeArg; L is Gty; and M is Asp-((1,3-dioxa-5-methyl-cyclopenten-2-one-4-yl)methyl ester).

The compound of formula (II) wherein $R^1$ and $R^2$ are H; J is D-2-aminobutyric acid; K is NMeArg; L is Gly; and M is Asp-((5-(t-butyl)-1,3-dioxa-cyclopenten-2-one-4-yl)methyl ester).

The compound of formula (II) wherein $R^1$ and $R^2$ are H; J is D-2-aminobutyric acid; K is NMeArg; L is Gly; and M is Asp-((1,3-dioxa-5-phenyl-cyclopenten-2-one-4-yl)methyl ester).

The compound of formula (II) wherein $R^1$ and $R^2$ are H; J is D-2-aminobutyric acid; K is NMeArg; L is Gly; and M is Asp-(1-(2-(2-methoxypropyl)carbonyloxy)ethyl ester).

Specifically preferred are the following compounds having $IC_{50}$ values of less than or equal to 100 uM for inhibiting the aggregation of platelets (as described below):

The compound of formula (II) wherein $R^1$ and $R^2$ are H; J is D-Val; K is NMeArg; L is Gly; and M is Asp.

The compound of formula (II) wherein $R^1$ and $R^2$ are H; J is D-2-aminobutyric acid; K is NMeArg; L is Gly; and M is Asp.

The compound of formula (II) wherein $R^1$ and $R^2$ are H; J is D-Leu; K is NMeArg; L is Gly; and M is Asp.

The compound of formula (II) wherein $R^1$ and $R^2$ are H; J is D-Ala; K is NMeArg; L is Gly; and M is Asp.

The compound of formula (II) wherein $R^1$ and $R^2$ are H; J is Gly; K is NMeArg; L is Gly; and M is Asp SEQ ID NO: 1.

The compound of formula (II) wherein $R^1$ and $R^2$ are H; J is D-PrO; K is NMeArg; L is Gty; and M is Asp.

The compound of formula (II) wherein $R^1$ and $R^2$ are H; J is D-Ser; K is Arg; L is Gly; and M is Asp.

The compound of formula (II) wherein $R^1$ and $R^2$ are H; J is D-LyS; K is NMeArg; L is Gly; and M is Asp.

The compound of formula (II) wherein $R^1$ and $R^2$ are H; J is D-2-aminobutyric acid; K is Arg; L is Gly; and M is Asp.

The compound of formula (II) wherein $R^1$ and $R^2$ are H; J is D-Ala; K is Arg; L is Gly; and M is Asp.

The compound of formula (II) wherein $R^1$ and $R^2$ are H; J is D-Val; K is Arg; L is Gly; and M is Asp.

The compound of formula (II) wherein R¹ and R² are H; J is β-Ala; K is NMeArg; L is Gly; and M is Asp SEQ ID NO: 2.

The compound of formula (II) wherein R¹ and R² are H; J is D-Val; K is NMeArg; L is β-Ala; and M is Asp.

The compound of formula (II) wherein R¹ and R² are H; J is Pro; K is NMeArg; L is Gly; and M is Asp SEQ ID NO: 32.

The compound of formula (II) wherein R¹ and R² are H; J is Phe; K is Arg; L is Gly; and M is Asp SEQ ID NO: 42.

The compound of formula (II) wherein R¹ and R² are H; J is Gly; K is Arg; L is Gly; and M is Asp SEQ ID NO: 36.

The compound of formula (II) wherein R¹ and R² are H; J is NMeGly; K is NMeArg; L is Gly; and M is Asp SEQ ID NO: 27.

The compound of formula (II) wherein R¹ and R² are H; J is D-Leu; K is Arg; L is Gly; and M is Asp.

The compound of formula (II) wherein R¹ is methyl (isomer 1); R² are H; J is D-Val; K is NMeArg; L is Gly; and M is Asp.

The compound of formula (II) wherein R¹ is methyl (isomer 2); R² are H; J is D-Val; K is NMeArg; L is Gly; and M is Asp.

The compound of formula (II) wherein R¹ is phenyl (isomer 1); R² are H; J is D-Val; K is NMeArg; L is Gly; and M is Asp.

The compound of formula (II) wherein R¹ is phenyl (isomer 2); R² are H; J is D-Val; K is NMeArg; L is Gly; and M is Asp.

The compound of formula (II) wherein J=Abu, K=NMeArg, L=Gly, M=Asp, R¹=H, R²=H.

The compound of formula (II) wherein J=D-Met, K=NMeArg, L=Gly, M=Asp, R¹=H, R²=H.

The compound of formula (II) wherein J=D-Abu, K=NMeArg, L=Gly, M=D-Asp, R¹=H, R²=H.

The compound of formula (II) wherein J=D-Abu, K=D-NMeArg, L=Gly, M=Asp, R¹=H, R²=H.

The compound of formula (II) wherein J=D-Ala, K=p-guanidinyl-Phe, L=Gly, M=Asp, R¹=H, R²=H.

The compound of formula (II) wherein J=D-Abu, K=diNMe-guanidinyl-Orn, L=Gly, M=Asp, R¹=H, R²=H.

The compound of formula (II) wherein J=D-Abu, K=diNMe-Lys, L=Gly, M=Asp, R¹=H, R²=H.

The compound of formula (II) wherein J=D-Abu, K=NMeLys, L=Gly, M=Asp, R¹=H, R²=H.

The compound of formula (III) wherein R¹ and R² are H; J is D-Val; K is NMeArg; L is Gly; and M is Asp.

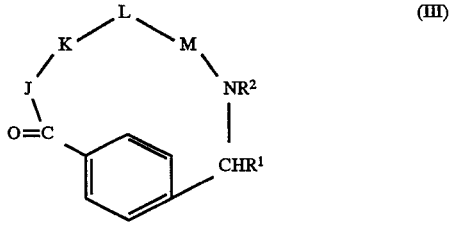

(III)

The compound of formula (II) wherein R¹ and R² are H; J is D-Val; K is D-NMeArg; L is Gly; and M is Asp.

The compound of formula (II) wherein R¹ and R² are H; J is D-Nle; K is NMeArg; L is Gly; and M is Asp.

The compound of formula (II) wherein R¹ and R² are H; J is D-Phg; K is NMeArg; L is Gly; and M is Asp.

The compound of formula (II) wherein R¹ and R² are H; J is D-Ile; K is NMeArg; L is Gly; and M is Asp.

The compound of formula (II) wherein R¹ and R² are H; J is D-Phe; K is NMeArg; L is Gly; and M is Asp.

The compound of formula (II) wherein R¹ and R² are H; J is NMeGly; K is NMeArg; L is Gly; and M is Asp SEQ ID NO: 27.

The compound of formula (II) wherein R¹ and R² are H; J is D-Nle; K is NMeArg; L is Gly; and M is Asp.

The compound of formula (II) wherein R¹ and R² are H; J is D-Tyr; K is NMeArg; L is Gly; and M is Asp.

The compound of formula (II) wherein R¹ and R² are H; J is Ala; K is Arg; L is Gly; and M is Asp SEQ ID NO: 37.

The compound of formula (II) wherein R¹ and R² are H; J is D-Phe; K is Arg; L is Gly; and M is Asp.

The compound of formula (II) wherein R¹ and R² are H; J is D-Val; K is NMeAmf; L is Gly; and M is Asp.

The compound of formula (II) wherein R¹ and R² are H; J is D-Val; K is NMeArg; L is Ala; and M is Asp.

The compound of formula (II) wherein R¹ and R² are H; J is D-Val; K is NMeArg; L is Gly; and M is αMeAsp.

The compound of formula (II) wherein R¹ and R² are H; J is D-Val; K is NMeArg; L is Gly; and M is βMeAsp.

The compound of formula (II) wherein R¹ and R² are H; J is D-Val; K is NMeArg; L is Gly; and M is NMeAsp.

The compound of formula (II) wherein R¹ and R² are H; J is D-Val; K is NMeArg; L is Gly; and M is D-Asp.

The compound of formula (II) wherein R¹ is H; R² is CH₃; J is D-Val; K is NMeArg; L is Gly; and M is Asp.

The compound of formula (II) wherein R¹ and R² are H; J is D-Abu; K is di-NMeOrn; L is Gly; and M is Asp.

The compound of formula (II) wherein R¹ and R² are H; J is N$^ε$-p-azidobenzoyl-D-Lysine; K is NMeArg; L is Gly; and M is Asp.

The compound of formula (II) wherein R¹ and R² are H; J is N$^ε$-p-benzoylbenzoyl-D-Lysine; K is NMeArg; L is Gly; and M is Asp.

The compound of formula (II) wherein R¹ and R² are H; J is N$^ε$-tryptophanyl-D-Lysine; K is NMeArg; L is Gly; and M is Asp.

The compound of formula (II) wherein R¹ and R² are H; J is N$^ε$-o-benzylbenzoyl-D-Lysine; K is NMeArg; L is Gly; and M is Asp.

The compound of formula (II) wherein R¹ and R² are H; J is N$^ε$-p-acetylbenzoyl-D-Lysine; K is NMeArg; L is Gly; and M is Asp.

The compound of formula (II) wherein R¹ and R² are H; J is N$^ε$-dansyl-D-Lysine; K is NMeArg; L is Gly; and M is Asp.

The compound of formula (II) wherein R¹ and R² are H; J is N$^ε$-glycyl-D-Lysine; K is NMeArg; L is Gly; and M is ASp.

The compound of formula (II) wherein R¹ and R² are H; J is N$^ε$-glycyl-p-benzoylbenzyl-D-Lysine; K is NMeArg; L is Gly; and M is Asp.

The compound of formula (II) wherein R¹ and R² are H; J is N$^ε$-p-phenylbenzoyl-D-Lysine; K is NMeArg; L is Gly; and M is Asp.

The compound of formula (II) wherein R¹ and R² are H; J is N$^ε$-m-benzoylbenzoyl-D-Lysine; K is NMeArg; L is Gly; and M is Asp.

The compound of formula (II) wherein R¹ and R² are H; J is N$^ε$-o-benzoylbenzoyl-D-Lysine; K is NMeArg; L is Gly; and M is Asp.

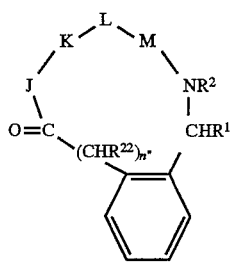

(V)

The compound of formula (V) wherein n"=1; $R^1$, $R^2$, and $R^{22}$ are H; J is D-Val; K is NMeArg; L is Gly; and M is Asp.

The compound of formula (V) wherein n"=0; $R^1$ and $R^2$ are H; J is D-Val; K is NMeArg; L is Gly; and M is Asp.

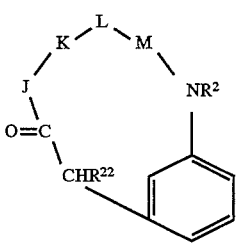

(VI)

The compound of formula (VI) wherein $R^2$ and $R^{22}$ are H; J is D-Val; K is NMeArg; L is Gly; and M is Asp.

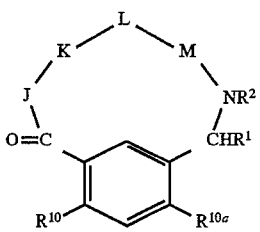

(VII)

The compound of formula (VII) wherein $R^1$, $R^2$, and $R^{10}$ are H; $R^{10a}$ is Cl; J is D-Val; K is NMeArg; L is Gly; and M is Asp.

The compound of formula (VII) wherein $R^1$, $R^2$, and $R^{10}$ are H; $R^{10a}$ is I; J is D-Val; K is NMeArg; L is Gly; and M is Asp.

The compound of formula (VII) wherein $R^1$, $R^2$, and $R^{10}$ are H; $R^{10a}$ is I; J is D-Abu; K is NMeArg; L is Gly; and M is Asp.

The compound of formula (VII) wherein $R^1$, $R^2$, and $R^{10}$ are H; $R^{10a}$ is OMe; J is D-Val; K is NMeArg; L is Gly; and M is Asp.

The compound of formula (VII) wherein $R^1$, $R^2$, and $R^{10}$ are H; $R^{10a}$ is Me; J is D-Val; K is NMeArg; L is Gly; and M is Asp.

The compound of formula (VII) wherein $R^1$, $R^2$, and $R^{10a}$ are H; $R^{10}$ is Cl; J is D-Val; K is NMeArg; L is Gly; and M is Asp.

The compound of formula (VII) wherein $R^1$, $R^2$, and $R^{10a}$ are H; $R^{10}$ is MeO; J is D-Val; K is NMeArg; L is Gly; and M is Asp.

The compound of formula (VII) wherein $R^1$, $R^2$, and $R^{10a}$ are H; $R^{10}$ is Me; J is D-Val; K is NMeArg; L is Gly; and M is Asp.

The compound of formula (VII) wherein $R^1$, $R^2$, and $R^{10}$ are H; $R^{10a}$ is Cl, J is D-Abu; K is NMeArg; L is Gly; and M is Asp.

The compound of formula (VII) wherein $R^1$, $R^2$, and $R^{10}$ are H; $R^{10a}$ is I; J is D-Abu; K is NMeArg; L is Gly; and M is Asp.

The compound of formula (VII) wherein $R^1$, $R^2$, and $R^{10}$ are H; $R^{10a}$ is Me; J is D-Abu; K is NMeArg; L is Gly; and M is Asp.

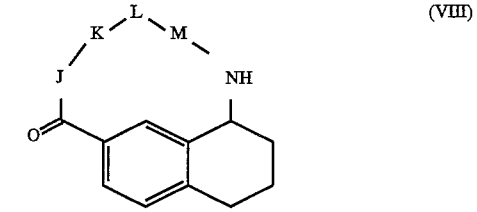

(VIII)

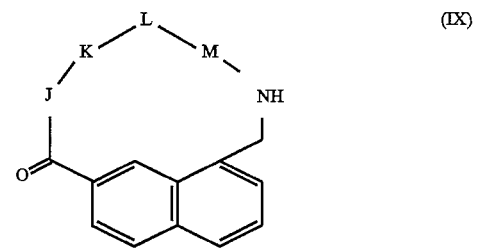

(IX)

The compound of formula (VIII) wherein J is D-Val; K is NMeArg; L is Gly; and M is Asp.

The compound of formula (IX) wherein J is D-Val; K is NMeArg; L is Gly; and M is Asp.

More specifically preferred are the following compounds of formula (I), all of which have $IC_{50}$ values of less than 1.0 uM for inhibiting the aggregation of platelets (as described below).

The compound of formula (II) wherein $R^1$ and $R^2$ are H; J is D-Val; K is NMeArg; L is Gly; and M is Asp.

The compound of formula (II) wherein $R^1$ and $R^2$ are H; J is D-2-aminobutyric acid; K is NMeArg; L is Gly; and M is Asp.

The compound of formula (II) wherein $R^1$ and $R^2$ are H; J is D-Leu; K is NMeArg; L is Gly; and M is Asp.

The compound of formula (II) wherein $R^1$ and $R^2$ are H; J is D-Ala; K is NMeArg; L is Gly; and M is Asp.

The compound of formula (II) wherein $R^1$ and $R^2$ are H; J is Gly; K is NMeArg; L is Gly; and M is Asp SEQ ID NO: 1.

The compound of formula (II) wherein $R^1$ and $R^2$ are H; J is D-Pro; K is NMeArg; L is Gly; and M is Asp.

The compound of formula (II) wherein $R^1$ and $R^2$ are H; J is D-Lys; K is NMeArg; L is Gly; and M is Asp.

The compound of formula (II) wherein $R^1$ and $R^2$ are H; J is β-Ala; K is NMeArg; L is Gly; and M is Asp SEQ ID NO: 2.

The compound of formula (II) wherein $R^1$ and $R^2$ are H; J is NMeGly; K is NMeArg; L is Gly; and M is Asp SEQ ID NO: 27.

The compound of formula (II) wherein $R^1$ is methyl (isomer 1); $R^2$ are H; J is D-Val; K is NMeArg; L is Gly; and M is Asp.

The compound of formula (II) wherein $R^1$ is methyl (isomer 2); $R^2$ are H; J is D-Val; K is NMeArg; L is Gly; and M is Asp.

The compound of formula (II) wherein $R^1$ is phenyl (isomer 1); $R^2$ are H; J is D-Val; K is NMeArg; L is Gly; and M is Asp.

The compound of formula (II) wherein J=D-Met, K=NMeArg, L=Gly, M=Asp, $R^1$=H, $R^2$=H.

The compound of formula (II) wherein J=D-Abu, K=diNMe-guanidinyl-Orn, L=Gly, M=Asp, $R^1$=H, $R^2$=H.

The compound of formula (II) wherein J=D-Abu, K=diNMe-Lys, L=Gly, M=Asp, $R^1$=H, $R^2$=H.

The compound of formula (II) wherein $R^1$ and $R^2$ are H; J is $N^\epsilon$-p-azidobenzoyl-D-Lysine; K is NMeArg; L is Gly; and M is Asp.

The compound of formula (II) wherein $R^1$ and $R^2$ are H; J is $N^\epsilon$-p-benzoylbenzoyl-D-Lysine; K is NMeArg; L is Gly; and M is Asp.

The compound of formula (II) wherein $R^1$ and $R^2$ are H; J is $N^\epsilon$-tryptophanyl-D-Lysine; K is NMeArg; L is Gly; and M is Asp.

The compound of formula (II) wherein $R^1$ and $R^2$ are H; J is $N^\epsilon$-o-benzylbenzoyl-D-Lysine; K is NMeArg; L is Gly; and M is Asp.

The compound of formula (II) wherein $R^1$ and $R^2$ are H; J is $N^\epsilon$-p-acetylbenzoyl-D-Lysine; K is NMeArg; L is Gly; and M is Asp.

The compound of formula (II) wherein $R^1$ and $R^2$ are H; J is $N^\epsilon$-dansyl-D-Lysine; K is NMeArg; L is Gly; and M is Asp.

The compound of formula (II) wherein $R^1$ and $R^2$ are H; J is $N^\epsilon$-glycyl-D-Lysine; K is NMeArg; L is Gly; and M is Asp.

The compound of formula (II) wherein $R^1$ and $R^2$ are H; J is $N^\epsilon$-glycyl-p-benzoyl-D-Lysine; K is NMeArg; L is Gly; and M is Asp.

The compound of formula (II) wherein $R^1$ and $R^2$ are H; J is $N^\epsilon$-p-phenylbenzoyl-D-Lysine; K is NMeArg; L is Gly; and M is Asp.

The compound of formula (II) wherein $R^1$ and $R^2$ are H; J is $N^\epsilon$-m-benzoylbenzoyl-D-Lysine; K is NMeArg; L is Gly; and M is Asp.

The compound of formula (II) wherein $R^1$ and $R^2$ are H; J is $N^\epsilon$-o-benzoylbenzoyl-D-Lysine; K is NMeArg; L is Gly; and M is Asp.

The compound of formula (III) wherein $R^1$ and $R^2$ are H; J is D-Val; K is NMeArg; L is Gly; and M is Asp.

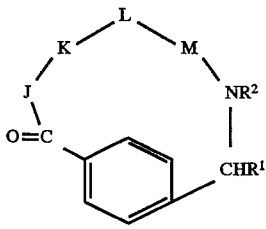

(III)

The compound of formula (II) wherein $R^1$ and $R^2$ are H; J is D-Val; K is D-NMeArg; L is Gly; and M is Asp.

The compound of formula (II) wherein $R^1$ and $R^2$ are H; J is D-Nle; K is NMeArg; L is Gly; and M is Asp.

The compound of formula (II) wherein $R^1$ and $R^2$ are H; J is D-Phg; K is NMeArg; L is Gly; and M is Asp.

The compound of formula (II) wherein $R^1$ and $R^2$ are H; J is D-Phe; K is NMeArg; L is Gly; and M is Asp.

The compound of formula (II) wherein $R^1$ and $R^2$ are H; J is D-Ile; K is NMeArg; L is Gly; and M is Asp.

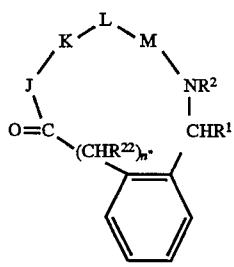

(V)

The compound of formula (V) wherein n"=1; $R^1$, $R^2$, and $R^{22}$ are H; J is D-Val; K is NMeArg; L is Gly; and M is Asp.

The compound of formula (V) wherein n"=0; $R^1$ and $R^2$ are H; J is D-Val; K is NMeArg; L is Gly; and M is Asp.

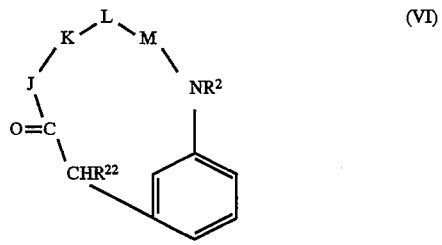

(VI)

The compound of formula (VI) wherein $R^2$ and $R^{22}$ are H; J is D-Val; K is NMeArg; L is Gly; and M is Asp.

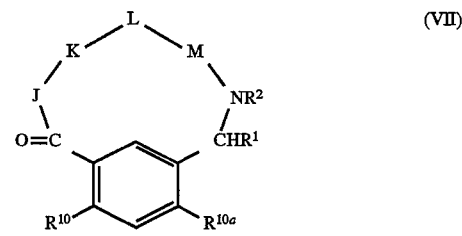

(VII)

The compound of formula (VII) wherein $R^1$, $R^2$, and $R^{10}$ are H; $R^{10a}$ is Cl; J is D-Val; K is NMeArg; L is Gly; and M is Asp.

The compound of formula (VII) wherein $R^1$, $R^2$, and $R^{10}$ are H; $R^{10a}$ is I; J is D-Val; K is NMeArg; L is Gly; and M is Asp.

The compound of formula (VII) wherein $R^1$, $R^2$, and $R^{10}$ are H; $R^{10a}$ is I; J is D-Abu; K is NMeArg; L is Gly; and M is Asp.

The compound of formula (VII) wherein $R^1$, $R^2$, and $R^{10}$ are H; $R^{10a}$ is Me; J is D-Val; K is NMeArg; L is Gly; and M is Asp.

The compound of formula (VII) wherein $R^1$, $R^2$, and $R^{10a}$ are H; $R^{10}$ is Cl; J is D-Val; K is NMeArg; L is Gly; and M is Asp.

The compound of formula (VII) wherein $R^1$, $R^2$, and $R^{10a}$ are H; $R^{10}$ is MeO; J is D-Val; K is NMeArg; L is Gly; and M is Asp.

The compound of formula (VII) wherein $R^1$, $R^2$, and $R^{10a}$ are H; $R^{10}$ is Me; J is D-Val; K is NMeArg; L is Gly; and M is Asp.

The compound of formula (VII) wherein $R^1$, $R^2$, and $R^{10}$ are H; $R^{10a}$ is Cl; J is D-Abu; K is NMeArg; L is Gly; and M is Asp.

The compound of formula (VII) wherein $R^1$, $R^2$, and $R^{10}$ are H; $R^{10a}$ is I; J is D-Abu; K is NMeArg; L is Gly; and M is Asp.

The compound of formula (VII) wherein $R^1$, $R^2$, and $R^{10}$ are H; $R^{10a}$ is Me; J is D-Abu; K is NMeArg; L is Gly; and M is Asp.

The compound of formula (II) wherein $R^1$ and $R^2$ are H; J is D-Tyr; K is NMeArg; L is Gly; and M is Asp.

The compound of formula (II) wherein $R^1$ and $R^2$ are H; J is D-Val; K is NMeAmf; L is Gly; and M is Asp.

The compound of formula (II) wherein $R^1$ and $R^2$ are H; J is D-Val;; K is NMeArg; L is Gly; and M is βMeAsp.

The compound of formula (II) wherein $R^1$ is H; $R^2$ is $CH_3$; J is D-Val; K is NMeArg; L is Gly; and M is Asp.

The compound of formula (III) wherein $R^1$ and $R^2$ are H; J is D-Val; K is NMeArg; L is Gly; and M is Asp.

The compound of formula (VIII) wherein J is D-Val; K is NMeArg; L is Gly; and M is Asp.

In the present invention it has been discovered that the compounds above are useful as inhibitors of glycoprotein IIb/IIIa (GPIIb/IIIa). As discussed above, GPIIb/IIIa mediates the process of platelet activation and aggregation. The compounds of the present invention inhibit the activation and aggregation of platelets induced by all known endogenous platelet agonists.

The present invention also provides methods for the treatment (including prevention) of conditions involving platelet activation and aggregation, such as arterial or venous cardiovascular or cerebrovascular thromboembolic disorders, including, for example, thromboembolic disorders associated with unstable angina, first or recurrent myocardial infarction, ischemic sudden death, transient ischemic attack, stroke, atherosclerosis, deep vein thrombosis, pulmonary embolism, or diabetes, by administering to a host in need of such treatment a pharmaceutically effective amount of the compounds described above. The compounds of the present invention are useful for inhibiting the binding of fibrinogen to blood platelets, inhibiting aggregation of blood platelets, treating thrombus formation or embolus formation, or preventing thrombus or embolus formation in a mammal. The compounds of the invention may be used as a medicament for blocking fibrinogen from acting at its receptor site in a mammal.

The compounds of the present invention can also be combined or co-administered with suitable anti-coagulant or coagulation inhibitory agents, such as heparin or warfarin, or anti-platelet or platelet inhibitory agents, such as aspirin, piroxicam or ticlopidine. Further, the compounds of this invention may be combined or co-administered with thrombin inhibitors such as boropeptides, hirudin or argatroban. The compounds of the present invention may also be combined or co-administered with thrombolytic or fibrinolytic agents, such as plasminogen activators, anistreplase, urokinase, or streptokinase. The compounds of the present invention may also be combined or co-administered with combinations of the foregoing agents and/or with other therapeutic agents. Such combination products may be employed to achieve synergistic effects or effects additive to those provided by the compounds of the present invention, such as, for example, in such uses as described above, particularly in the treatment, including prevention, of thromboembolic disorders.

The GPIIb/IIIa antagonists of the present invention inhibit platelet aggregation at the final common pathway required for platelet aggregation induced by any of the known platelet activators or even their combinations. On the other hand, platelet granular secretions, of various important biomolecules from the α-granule (PAI-1) or the dense granule (serotonin) are not affected by the GPIIb/IIIa antagonist. These molecules secreted from platelets might play an important role in arterial vasospasm (serotonin) and in reducing the efficiency of the natural lytics (PAI-1). Hence, the combination of the compounds of the present invention with other drugs which may affect these mechanisms and may thereby provide a particularly effective therapy for many different heterogenous thromboembolic disorders.

The GPIIb/IIIa antagonists of the present invention with high affinity for the platelet GPIIb/IIIa receptor (Kd<0.01 μM) are expected to be very effective not only in preventing thrombosis formation, but also in accelerating lysis of platelet rich thrombi, thereby providing a greater utility of such antiplatelet agents in the acute and chronic thromboembolic disorders. Such a strategy may be an effective adjunct therapy with thrombolytic therapy. Indeed, platelet activation after thrombolytic therapy may have a significant role in the delay of reperfusion and abrupt closure (reocclusion).

The term anti-coagulant agents (or coagulation inhibitory agents), as used herein, denotes agents that inhibit blood coagulation. Such agents include warfarin, heparin, or low molecular weight heparin (LMWH), including pharmaceutically acceptable salts or prodrugs thereof. For reasons of efficacy, the preferable anti-coagulant agents are warfarin or heparin or LMWH. The warfarin employed herein, may be, for example, crystalline warfarin or amorphous sodium warfarin. The heparin employed herein may be, for example, the sodium or sulfate salts thereof.

The term anti-platelet agents (or platelet inhibitory agents), as used herein, denotes agents that inhibit platelet function such as by inhibiting the aggregation, adhesion or granular secretion of platelets. Such agents include the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), which has been well researched and widely used with good results, and piroxicam, which exerts its anti-platelet effect when dosed once daily, are preferred compounds, especially aspirin. Piroxicam is commercially available from Pfizer Inc. (New York, NY), as FELDANE™. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include thromboxane-A2-receptor antagonists and thromboxane-A2-synthetase inhibitors, as well as pharmaceutically acceptable salts or prodrugs thereof.

The phrase thrombin inhibitors (or anti-thrombin agents), as used herein, denotes inhibitors of the serine protease thrombin. By inhibiting thrombin, various thrombinmediated processes, such as thrombin-mediated platelet activation (that is, for example, the aggregation of platelets, and/or the granular secretion of plasminogen activator inhibitor-1 and/or serotonin) and/or fibrin formation are disrupted. Such inhibitors include boropeptides, hirudin and argatroban, including pharmaceutically acceptable salts and prodrugs thereof. Preferably the thrombin inhibitors are boropeptides. By boropeptides, it is meant, N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

Preferable boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boropeptide thrombin inhibitors include those disclosed in PCT Application Publication Number 92/07869 and European Patent Application Publication Number 471 651 A2, the disclosures of which are hereby incorporated herein by reference, in their entirety.

The phrase thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. Tissue plasminogen activator (tPA) is commercially available from Genentech Inc., South San Francisco, Calif. The term anistreplase, as used herein, refers to anisoylated plasminogen streptokinase activator complex, as described, for example, in European Patent Application No. 0 28 489, the disclosures of which are hereby incorporated herein by reference herein, in their entirety. Anistreplase is commercially available from the Beecham Group, Middlesex, England, under the trademark EMINASE™. The term urokinase, as used herein, is intended to denote both dual and single chain urokinase, the latter also being referred to herein as prourokinase.

Combination products, where the cyclic compounds of the invention are combined or co-administered with suitable anti-coagulant agents, antiplatelet agents, thrombin inhibitors, and/or thrombolytic agents, may afford an efficacy advantage over the compounds and agents alone, and may do so while permitting the use of lower doses of each. A lower dosage minimizes the potential of side effects, thereby providing an increased margin of safety.

Clinical studies using anti-coagulant agents alone, including crystalline sodium warfarin, have provided evidence of their efficacy in the treatment or secondary prevention of coronary artery disease. Of three published, randomized, controlled trials of the treatment of acute myocardial infarction, oral anti-coagulants significantly reduced overall mortality and the frequency of reinfarction in one study. Of the four published large, randomized, controlled trials of oral anti-coagulants in the secondary prevention of myocardial infarction, three suggested a reduction in the incidence of reinfarction and early mortality. One additional study, the Warfarin Reinfarction Study, has also recently demonstrated a significant reduction in mortality, reinfarction, and stroke in people with a previous myocardial infarction who were treated with warfarin as compared to those treated with placebo.

The results of studies utilizing anti-platelet agents such as acetylsalicylic acid (ASA) alone in the prevention and treatment of coronary artery disease have also been promising. In patients with unstable angina, ASA has been demonstrated to reduce the incidence of subsequent myocardial infarction and mortality in two large, randomized, double-blind, placebo-controlled clinical studies. In addition, ASA has been approved for use in the secondary prevention of myocardial infarction, based on data from several trials which, when pooled, suggested a reduction in reinfarction and mortality. Furthermore, two recent studies evaluating ASA in the primary prevention of coronary artery disease have reported either a dramatic or inconsequential benefit. In addition to their utility in coronary artery disease, agents that inhibit platelet function such as ASA and ticlopidine have been shown to be effective in the prevention of stroke in people with cerebrovascular disease. Pooled data from nine randomized trials have provided overwhelming evidence of the efficacy of ASA alone in reducing the risk of completed stroke in people with transient ischemic attacks (TIAs). Recently, ticlopidine alone has also been demonstrated to have efficacy in treating TIAs.

With regard to thrombin inhibitors, such as boropeptides, studies have demonstrated that such compounds provide excellent candidates for the control of thrombinmediated processes. Studies with hirudin, another thrombin inhibitor, have shown this agent to be an effective compound in the treatment of venous and arterial thrombosis.

Current therapy in the treatment of patients with acute myocardial infarction includes thrombolytics such as plasminogen activators such as tPA, streptokinase, or urokinase. These standard thrombolytics, when employed alone, promote the generation of plasmin, which degrades platelet-rich fibrin clots.

Thromboembolic disorders are known, however, to have a diverse pathophysiological makeup. There is a need for a therapeutic approach to the treatment of these disorders which takes into account the diverse pathophysiological makeup of such diseases, and which includes components ameliorating each of the various pathophysiological aspects. A combination product containing an anti-coagulant agent such as warfarin or heparin, or an antiplatelet agent such as aspirin, piroxicam or ticlopidine, or a thrombin inhibitor such as a boropeptide, hirudin or argatroban, or a thrombolytic agent such as tissue plasminogen activator, anistreplase, urokinase or streptokinase, or combinations thereof, in combination with a novel cyclic compound of the invention, can provide such an approach. In addition, by administering lower doses of each, which is feasible where an additive or synergistic effect is involved, the incidence of any side effects associated with each alone at higher doses may be significantly reduced. Also, where a convenient single dosage form is offered, as in a preferred embodiment of the invention, it is generally accepted that such increased convenience to the patient results in an increase in compliance. Also, a single dosage form would reduce the likelihood of patient confusion often associated with concurrent dosing of medication not available in a single dosage form. The present combinations of an anticoagulant agent and a compound of this invention, or an anti-platelet agent and a compound of this invention, or a thrombin inhibitor and a compound of this invention, or a thrombolytic agent and a compound of this invention, or combinations thereof, are directed to meeting these, as well as other, needs.

GPIIb/IIIa is known to be overexpressed in metastatic tumor cells. The compounds or combination products of the present invention may also be useful for the treatment, including prevention, of metastatic cancer.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention contain asymmetrically substituted carbon atoms, and may be isolated in optically active or racemic forms. It is well known in the art how to prepare optically active forms, such as by resolution of racemic forms or by synthesis, from optically active starting materials. Two distinct isomers (cis and trans) of the peptide bond are known to occur; both can also be present in the compounds described herein, and all such stable isomers are contemplated in the present invention. Unless otherwise specifically noted, the L-isomer of the amino acid is used at positions J, K, L, and M of the compounds of the present invention. Except as provided in the preceding sentence, all chiral, diastereomeric, racemic forms and all geometric isomeric forms of a structure are intended, unless the specific stereochemistry or isomer form is specifically indicated. The D and L-isomers of a particular amino acid are designated herein using the conventional 3-letter abbreviation of the amino acid, as indicated by the following examples: D-Leu, D-Leu, L-Leu, or L-Leu.

When any variable (for example, $R^1$ through $R^8$, m, n, p, X, Y, etc.) occurs more than one time in any constituent or in any formula, its definition on each occurrence is independent of its definition at every other occurrence. Thus, for example, if a group is shown to be substituted with 0–2 $R^{11}$, then said group may optionally be substituted with up to two $R^{11}$ and $R^{11}$ at each occurrence is selected independently from the defined list of possible $R^{11}$. Also, by way of example, for the group —N($R^{13}$)$_2$, each of the two $R^{13}$ substituents on N is independently selected from the defined list of possible $R^{13}$.

When a bond to a substituent is shown to cross the bond connecting two atoms in a ring, then such substituent may be bonded to any atom on the ring.

Combinations of substituents and/or variables are permissible only if such combinations result in stable compounds.

By "stable compound" or "stable structure" is meant herein a compound that is sufficiently robust to survive isolation to a useful degree of purity from a reaction mixture, and formulation into an efficacious therapeutic agent.

The term "substituted", as used herein, means that an one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, "alkyl" is intended to include both branched and straight-chain saturated aliphatic hydrocarbon groups having the specified number of carbon atoms; "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-,bi- or poly-cyclic ring systems, such as cyclopropyl, cyclobutyl, cyclopentyl, cyclohexyl, cycloheptyl, cyclooctyl and adamantyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

The phrase "boronic acid" as used herein means a group of the formula —$B(R^{34})(R^{35})$, wherein $R^{34}$ and $R^{35}$ are independently selected from: —OH; —F; —$NR^{13}R^{14}$; or $C_1$-$C_8$-alkoxy; or $R^{34}$ and $R^{35}$ can alternatively be taken together to form: a cyclic boron ester where said chain or ring contains from 2 to 20 carbon atoms and, optionally, 1–4 heteroatoms independently selected from N, S, or O, a divalent cyclic boron amide where said chain or ring contains from 2 to 20 carbon atoms and, optionally, 1–4 heteroatoms independently selected from N, S, or O, a cyclic boron amide-ester where said chain or ring contains from 2 to 20 carbon atoms and, optionally, 1–4 heteroatoms independently selected from N, S, or O. Such cyclic boron esters, boron amides, or boron amide-esters may also be optionally substituted with 1–5 groups independently selected from $R^{11}$.

Boron esters include boronic acid protecting groups, including moieties derived from diols, for example pinanediol and pinacol to form pinanediol boronic acid ester and the pinacol boronic acid, respectively. Other illustrations of diols useful for deriving boronic acid esters are perfluoropinacol, ethylene glycol, diethylene glycol, 1,2-ethanediol, 1,3-propanediol, 1,2-propanediol, 1,2-butanediol, 1,4-butanediol, 2,3-butanediol, 2,3-hexanediol, 1,2-hexanediol, catechol, 1,2-diisopropylethanediol, 5,6-decanediol, 1,2-dicyclohexylethanediol.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl. As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic ring system" is intended to mean a stable 5- to 7- membered monocyclic or bicyclic or 7- to 10-membered bicyclic heterocyclic ring which may be saturated, partially unsaturated, or aromatic, and which consists of carbon atoms and from 1 to 4 heteroatoms selected independently from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, benzopyranyl, thiadiazine, tetrazolyl, benzofuranyl, benzothiophenyl, indolene, quinoline, isoquinolinyl or benzimidazolyl, piperidinyl, 4-piperidone, 2-pyrrolidone, tetrahydrofuran, tetrahydroquinoline, tetrahydroisoquinoline, decahydroquinoline, octahydroisoquinoline, azocine, triazine (including 1,2,3-, 1,2,4-, and 1,3,5-triazine), 6H-1,2,5-thiadiazine, 2H, 6H-1, 5,2-dithiazine, thiophene, tetrahydrothiophene, thianthrene, furan, pyran, isobenzofuran, chromene, xanthene, phenoxathiin, 2H-pyrrole, pyrrole, imidazole, pyrazole, thiazole, isothiazole, oxazole (including 1,2,4- and 1,3,4-oxazole), isoxazole, triazole, pyridine, pyrazine, pyrimidine, pyridazine, indolizine, isoindole, 3H-indole, indole, 1H-indazole, purine, 4H-quinolizine, isoquinoline, quinoline, phthalazine, naphthyridine, quinoxaline, quinazoline, cinnoline, pteridine, 4aH-carbazole, carbazole, β-carboline, phenanthridine, acridine, perimidine, phenanthroline, phenazine, phenarsazine, phenothiazine, furazan, phenoxazine, isochroman, chroman, pyrrolidine, pyrroline, imidazolidine, imidazoline, pyrazolidine, pyrazoline, piperazine, indoline, isoindoline, quinuclidine, or morpholine. Also included are fused ring and spiro compounds containing, for example, the above heterocycles.

As used herein, the term "any group that, when administered to a mammalian subject, cleaves to form a free hydroxyl, amino or sulfhydryl" means any group bonded to an O, N, or S atom, respectively, which is cleaved from the O, N, or S atom when the compound is administered to a mammalian subject to provide a compound having a remaining free hydroxyl, amino, or sulfhydryl group, respectively. Examples of groups that, when administered to a mammalian subject, are cleaved to form a free hydroxyl, amino or sulfhydryl, include but are not limited to, $C_1$–$C_6$ alkyl substituted with 0–3 $R^{11}$, $C_3$–$C_6$ alkoxyalkyl substituted with 0–3 $R^{11}$, $C_1$–$C_6$ alkylcarbonyl substituted with 0–3 $R^{11}$, $C_1$–$C_6$alkoxycarbonyl substituted with 0–3 $R^{11}$, $C_1$–$C_6$alkylaminocarbonyl substituted with 0–3 $R^{11}$, benzoyl substituted with 0–3 $R^{12}$, phenoxycarbonyl substituted with 0–3 $R^{12}$, phenylaminocarbonyl substituted with 0–3 $R^{12}$. Examples of groups that, when administered to a mammalian subject, are cleaved to form a free hydroxyl, amino or sulfhydryl, include hydroxy, amine or sulfhydryl protecting groups, respectively.

As used herein, the term "amine protecting group" means any group known in the art of organic synthesis for the protection of amine groups. Such amine protecting groups include those listed in Greene, "Protective Groups in Organic Synthesis" John Wiley & Sons, New York (1981) and "The Peptides: Analysis, Synthesis, Biology, Vol. 3, Academic Press, New York (1981), the disclosure of which is hereby incorporated by reference. Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. Also included in the term "amine protecting group" are acyl groups such as azidobenzoyl, p-benzoylbenzoyl, o-benzylbenzoyl, p-acetylbenzoyl, dansyl, glycyl-p-benzoylbenzoyl, phenylbenzoyl, m-benzoylbenzoyl, benzoylbenzoyl.

As used herein, "pharmaceutically acceptable salts" refer to derivatives of the disclosed compounds wherein the parent compound of formula (1) is modified by making acid or base salts of the compound of formula (I). Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to formula (I) in vivo when such prodrug is administered to a mammalian subject. Prodrugs of the compounds of formula (I) are prepared by modifying functional groups present in the compounds in such a way that the modifications are cleaved, either in routine manipulation or in vivo, to the parent compounds. Prodrugs include compounds of formula (I) wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of formula (I); and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The term "amino acid" as used herein means an organic compound containing both a basic amino group and an acidic carboxyl group. Included within this term are modified and unusual amino acids, such as those disclosed in, for example, Roberts and Vellaccio (1983) *The Peptides*, 5: 342–429, the teaching of which is hereby incorporated by reference. Modified or unusual amino acids which can be used to practice the invention include, but are not limited to, D-amino acids, hydroxylysine, 4-hydroxyproline, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, 4-aminopiperidine-4-carboxylic acid, 6-aminocaproic acid, trans-4-(aminomethyl) cyclohexanecarboxylic acid, 2-, 3-, and 4-(aminomethyl) benzoic acid, 1-aminocyclopentanecarboxylic acid, 1-aminocyclopropanecarboxylic acid, and 2-benzyl-5-aminopentanoic acid.

The term "amino acid residue" as used herein means that portion of an amino acid (as defined herein) that is present in a peptide.

The term "peptide" as used herein means a linear compound that consists of two or more amino acids (as defined herein) that are linked by means of a peptide bond. The term "peptide"also includes compounds containing both peptide and non-peptide components, such as pseudopeptide or peptide mimetic residues or Other non-amino acid components. Such a compound containing both peptide and non-peptide components may also be referred to as a "peptide analog".

A "pseudopeptide" or "peptide mimetic" is a compound which mimics the structure of an amino acid residue or a peptide, for example, by using linking groups other than amide linkages between the peptide mimetic and an amino acid residue (pseudopeptide bonds) and/or by using non-amino acid substituents and/or a modified amino acid residue.

A "pseudopeptide residue" means that portion of an pseudopeptide or peptide mimetic (as defined herein) that is present in a peptide.

The term "peptide bond" means a covalent amide linkage formed by loss of a molecule of water between the carboxyl group of one amino acid and the amino group of a second amino acid.

The term "pseudopeptide bonds" includes peptide bond isosteres which may be used in place of or as substitutes for the normal amide linkage. These substitute or amide "equivalent" linkages are formed from combinations of atoms not normally found in peptides or proteins which mimic the spatial requirements of the amide bond and which should stabilize the molecule to enzymatic degradation.

The compounds of the present invention can be prepared in a number of ways well known to one skilled in the art of organic synthesis. Preferred methods include but are not limited to those methods described below.

The following abbreviations are used herein:

| | |
|---|---|
| D-Abu | D-2-aminobutyric acid |
| β-Ala, b-Ala or βAla | 3-aminopropionic acid |
| Boc | t-butyloxycarbonyl |
| Boc-iodo-Mamb | t-butyloxycarbonyl-3-aminomethyl-4-iodo-benzoic acid |
| Boc-Mamb | t-butyloxycarbonyl-3-aminomethylbenzoic acid |

| | |
|---|---|
| Boc-ON | [2-(tert-butyloxycarbonyloxylimino)-2-phenylacetonitrile |
| Cl₂Bzl | dichlorobenzyl |
| CBZ or Cbz | Carbobenzyloxy |
| DCC | dicyclohexylcarbodiimide |
| DIEA | diisopropylethylamine |
| di-NMeOrn | N-αMe-N-γMe-ornithine |
| DMAP | 4-dimethylaminopyridine |
| HBTU | 2-(1H-Benzotriazol-1-yl)-1,1,3,3-tetramethyluronium hexafluorophosphate |
| NMeArg or MeArg | α-N-methyl arginine |
| NMeAmf | N-Methylaminomethylphenylalanine |
| NMeAsp | α-N-methyl aspartic acid |
| MeGly or MeGly | N-methyl glycine |
| NMe-Mamb | N-methyl-3-aminomethylbenzoic acid |
| NMM | N-methylmorpholine |
| OcHex | O-cyclohexyl |
| OBzl | O-benzyl |
| TBTU | 2-(1H-Benzotriazol-1-yl)-1,1,3,3-tetramethyluronium tetrafluoroborate |
| Tos | tosyl |

The following conventional three-letter amino acid abbreviations are used herein; the conventional one-letter amino acid abbreviations are not used herein:

Ala=alanine
Arg=arginine
Asn=asparagine
Asp=aspattic acid
Cys=cysteine
Gln=glutamine
Glu=glutamic acid
Gly=glycine
His=histidine
Ile=isoleucine
Leu=leucine
Lys=lysine
Met=methionine
Nle=norleucine
Phe=phenylalanine
Phg=phenylglycine
Pro=proline
Ser=serine
Thr=threonine
Trp=tryptophan
Tyr=tyrosine
Val=valine Peptide Synthesis The compounds of the present invention can be synthesized using standard synthetic methods known to those skilled in the art. Preferred methods include but are not limited to those methods described below.

Generally, peptides are elongated by deprotecting the α-amine of the C-terminal residue and coupling the next suitably protected amino acid through a peptide linkage using the methods described. This deprotection and coupling procedure is repeated until the desired sequence is obtained. This coupling can be performed with the constituent amino acids in a stepwise fashion, or condensation of fragments (two to several amino acids), or combination of both processes, or by solid phase peptide synthesis according to the method originally described by Merrifield, J. Am. Chem. Soc., 85, 2149–2154 (1963), the disclosure of which is hereby incorporated by reference.

The compounds of the invention may also be synthesized using automated peptide synthesizing equipment. In addition to the foregoing, procedures for peptide synthesis are described in Stewart and Young, "Solid Phase Peptide Synthesis", 2nd ed, Pierce Chemical Co., Rockford, Ill. (1984); Gross, Meienhofer, Udenfriend, Eds., "The Peptides: Analysis, Synthesis, Biology, Vol. 1, 2, 3, 5, and 9, Academic Press, New York, (1980–1987); Bodanszky, "Peptide Chemistry: A Practical Textbook", Springer-Verlag, New York (1988); and Bodanszky et al. "The Practice of Peptide Sythesis" Springer-Verlag, New York (1984), the disclosures of which are hereby incorporated by reference.

The coupling between two amino acid derivatives, an amino acid and a peptide, two peptide fragments, or the cyclization of a peptide can be carried out using standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, Woodward reagent K method, carbonyldiimidazole method, phosphorus reagents such as BOP-Cl, or oxidation-reduction method. Some of these methods (especially the carbodiimide) can be enhanced by the addition of 1-hydroxybenzotriazole. These coupling reactions may be performed in either solution (liquid phase) or solid phase.

The functional groups of the constituent amino acids must be protected during the coupling reactions to avoid undesired bonds being formed. The protecting groups that can be used are listed in Greene, "Protective Groups in Organic Synthesis" John Wiley & Sons, New York (1981) and "The Peptides: Analysis, Sythesis, Biology, Vol. 3, Academic Press, New York (1981), the disclosure of which is hereby incorporated by reference.

The α-carboxyl group of the C-terminal residue is usually protected by an ester that can be cleaved to give the carboxylic acid. These protecting groups include: 1) alkyl esters such as methyl and t-butyl, 2) aryl esters such as benzyl and substituted benzyl, or 3) esters which can be cleaved by mild base treatment or mild reductive means such as trichloroethyl and phenacyl esters. In the solid phase case, the C-terminal amino acid is attached to an insoluble carrier (usually polystyrene). These insoluble carriers contain a group which will react with the carboxyl group to form a bond which is stable to the elongation conditions but readily cleaved later. Examples of which are: oxime resin (DeGrado and Kaiser (1980) J. Org. Chem. 45, 1295–1300) chloro or bromomethyl resin, hydroxymethyl resin, and aminomethyl resin. Many of these resins are commercially available with the desired C-terminal amino acid already incorporated.

The α-amino group of each amino acid must be protected. Any protecting group known in the art can be used. Examples of these are: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. The preferred α-amino protecting group is either Boc or Fmoc. Many amino acid derivatives suitably protected for peptide synthesis are commercially available.

The α-amino protecting group is cleaved prior to the coupling of the next amino acid. When the Boc group is used, the methods of choice are trifluoroacetic acid, neat or in dichloromethane, or HCl in dioxane. The resulting ammonium salt is then neutralized either prior to the coupling or in situ with basic solutions such as aqueous buffers, or tertiary amines in dichloromethane or dimethylformamide. When the Fmoc group is used, the reagents of choice are piperidine or substituted piperidines in dimethylformamide, but any secondary amine or aqueous basic solutions can be used. The deprotection is carried out at a temperature between 0° C. and room temperature.

Any of the amino acids bearing side chain functionalities must be protected during the preparation of the peptide using any of the above-identified groups. Those skilled in the art will appreciate that the selection and use of appropriate protecting groups for these side chain functionalities will depend upon the amino acid and presence of other protecting groups in the peptide. The selection of such a protecting group is important in that it must not be removed during the deprotection and coupling of the α-amino group.

For example, when Boc is chosen for the α-amine protection the following protecting groups are acceptable: p-toluenesulfonyl (tosyl) moieties and nitro for arginine; benzyloxycarbonyl, substituted benzyloxycarbonyls, or tosyl for lysine; benzyl or alkyl esters such as cyclopentyl for glutamic and aspartic acids; benzyl ethers for serine and threonine; benzyl ethers, substituted benzyl ethers or 2-bromobenzyloxycarbonyl for tyrosine; p-methylbenzyl, p-methoxybenzyl, acetamidomethyl, benzyl, or t-butylsulfonyl for cysteine; and the indole of tryptophan can either be left unprotected or protected with a formyl group.

When Fmoc is chosen for the α-amine protection usually tert-butyl based protecting groups are acceptable. For instance, Boc can be used for lysine, tert-butyl ether for serine, threonine and tyrosine, and tert-butyl ester for glutamic and aspartic acids.

Once the elongation and cyclization of the peptide is completed all of the protecting groups are removed. For the liquid phase synthesis the protecting groups are removed in whatever manner as dictated by the choice of protecting groups. These procedures are well known to those skilled in the art.

When a solid phase synthesis is used, the peptide should be removed from the resin without simultaneously removing protecting groups from functional groups that might interfere with the cyclization process. Thus, if the peptide is to be cyclized in solution, the cleavage conditions need to be chosen such that a free α-carboxylate and a free α-amino group are generated without simultaneously removing other protecting groups. Alternatively, the peptide may be removed from the resin by hydrazinolysis, and then coupled by the azide method. Another very convenient method involves the synthesis of peptides on an oxime resin, followed by intramolecular nucleophilic displacement from the resin, which generates a cyclic peptide (Osapay, Profit, and Taylor (1990) *Tetrahedron Letters* 43, 6121–6124). When the oxime resin is employed, the Boc protection scheme is generally chosen. Then, the preferred method for removing side chain protecting groups generally involves treatment with anhydrous HF containing additives such as dimethyl sulfide, anisole, thioanisole, or p-cresol at 0° C. The cleavage of the peptide can also be accomplished by other acid reagents such as trifluoromethanesulfonic acid/trifluoroacetic acid mixtures.

Unusual amino acids used in this invention can be synthesized by standard methods familiar to those skilled in the art ("The Peptides: Analysis, Sythesis, Biology, Vol. 5, pp. 342–449, Academic Press, New York (1981)). N-Alkyl amino acids can be prepared using procedures described in previously (Cheung et al., (1977) *Can. J. Chem.* 55, 906; Freidinger et al., (1982) *J. Org. Chem.* 48, 77 (1982)), which are incorporated here by reference.

The compounds of the present invention may be prepared using the procedures further detailed below.

Representative materials and methods that may be used in preparing the compounds of the invention are described further below.

Manual solid phase peptide synthesis was performed in 25 mL polypropylene filtration tubes purchased from BioRad Inc. Oxime resin (substitution level=0.96 mmol/g) was prepared according to published procedures (DeGrado and Kaiser (1980) *J. Org. Chem.* 45, 1295). All chemicals and solvents (reagent grade) were used as supplied from the vendors cited without further purification. t-Butyloxycarbonyl (Boc) amino acids and other starting amino acids may be obtained commercially from Bachem Inc., Bachem Biosciences Inc. (Philadelphia, Pa.), Advanced ChemTech (Louisville, Ky.), Peninsula Laboratories (Belmont, Calif.), or Sigma (St. Louis, Mo.). 2-(1H-Benzotriazol-1-yl)-1,1,3,3-tetramethyluronium hexafluorophosphate (HBTU) and TBTU were purchased from Advanced ChemTech. N-methylmorpholine (NMM), m-cresol, D-2-aminobutyric acid (Abu), trimethylacetylchloride, diisopropylethylamine (DIEA), 3-cyanobenzoic acid and [2-(tert-butyloxycarbonyloxylimino)-phenylacetonitrile] (Boc-ON) were purchased from Aldrich Chemical Company. Dimethylformamide (DMF), ethyl acetate, chloroform ($CHCl_3$), methanol (MeOH), pyridine and hydrochloric acid (HCl) were obtained from Baker. Acetonitrile, dichloromethane (DCM), acetic acid (HOAc), trifluoroacetic acid (TFA), ethyl ether, triethylamine, acetone, and magnesium sulfate were purchased from EM Science. Palladium on carbon catalyst (10% Pd) was purchased from Fluka Chemical Company. Absolute ethanol was obtained from Quantum Chemical Corporation. Thin layer chromatography (TLC) was performed on Silica Gel 60 $F_{254}$ TLC plates (layer thickness 0.2 mm) which were purchased from EM Separations. TLC visualization was accomplished using UV light, iodine, and/or ninhydrin spray. Melting points were determined using a Thomas Hoover or Electrothermal 9200 melting point apparatus and are uncorrected. HPLC analyses were performed on either a Hewlett Packard 1090, Waters Delta Prep 3000, Rainin, or DuPont 8800 system. NMR spectra were recorded on a 300 MHz General Electric QE-300, Varian 300, or Varian 400 spectrometer. Fast atom bombardment mass spectrometry (FAB-MS) was performed on a VG Zab-E double-focusing mass spectrometer using a Xenon FAB gun as the ion source or a Finnigan MAT 8230.

Synthesis of 3 and 4-substituted Boc-aminomethylbenzoic Acid Derivatives 3 and 4-substituted Boc-aminomethylbenzoic acid derivatives useful as intermediates in the synthesis of the compounds of the invention are prepared using standard procedures, for example, as described in *Tett. Lett.*, 4393 (1975); *Modern Synthetic Reactions*, H.O. House (1972); or Harting et al. *J. Am. Chem. Soc.*, 50: 3370 (1928), and as shown schematically below.

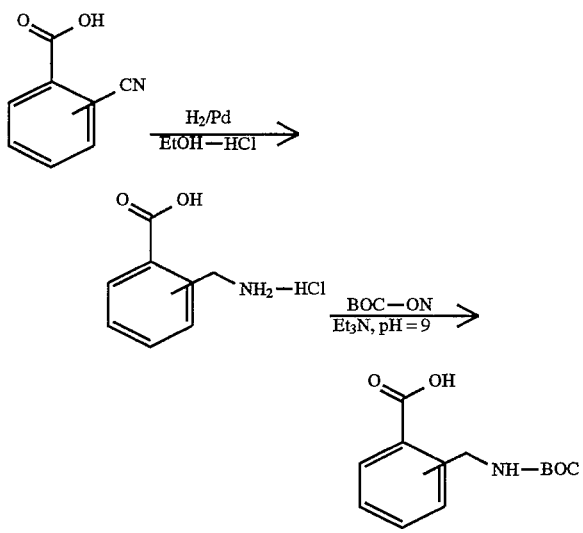

3-Aminomethylbenzoic acid.HCl

3-Cyanobenzoic acid (10.0 g, 68 mmol) was dissolved in 200 ml ethanol by heating in a 35°–50° C. water bath. Concentrated HCl (6.12 ml, 73 mmol) was added and the solution was transferred to a 500 ml nitrogen-flushed round bottom flask containing palladium on carbon catalyst (1.05 g, 10% Pd/C). The suspension was stirred under an atmosphere of hydrogen for 38 hours, filtered through a scintered glass funnel, and washed thoroughly with $H_2O$. The ethanol was removed under reduced pressure and the remaining aqueous layer, which contained a white solid, was diluted to 250 ml with additional $H_2O$. Ethyl ether (250 ml) was added and the suspension was transferred to a separatory funnel. Upon vigorous shaking, all solids dissolved and the aqueous layer was then washed two times with ether, evaporated under reduced pressure to a volume of 150 ml, and lyophilized to give the title compound (3-aminomethylbenzoic acid.HCl) (8.10 g, 64%) as a beige solid. $^1$H NMR ($D_2O$) 4.27 (s, 2H), 7.60 (t, 1H), 7.72 (d, 1H), 8.06 (d, 2H).

t-Butyloxycarbonyl-3-aminomethylbenzoic Acid (Boc-Mamb)

The title compound was prepared according to a modification of standard procedures previously reported in the literature (Itoh, Hagiwara, and Kamiya (1975) *Tett. Lett.*, 4393). 3-Aminomethylbenzoic acid (hydrochloride salt) (3.0 g, 16.0 mmol) was dissolved in 60 ml $H_2O$. To this was added a solution of Boc-ON (4.33 g, 17.6 mmol) in 60 ml acetone followed by triethylamine (5.56 ml, 39.9 mmol). The solution turned yellow and the pH was adjusted to 9 (wet pH paper) by adding an additional 1.0 ml (7.2 mmol) triethylamine. The solution was stirred overnight at room temperature at which time the acetone was removed under reduced pressure and the remaining aqueous layer was washed three times with ether. The aqueous layer was then acidified to pH 2 with 2N HCl and then extracted three times with ethyl acetate. The combined organic layers were washed three times with $H_2O$, dried over anhydrous magnesium sulfate, and evaporated to dryness under reduced pressure. The material was recrystallized from ethyl acetate/ hexane to give two crops of the title compound (2.58 g, 64%) as an off-white solid. mp 123°–125° C.; $^1$H NMR ($CDCl_3$) 1.47 (s, 9H), 4.38 (br s, 2H), 4.95 (br s, 1H), 7.45 (t, 1H), 7.55 (d, 1H), 8.02 (d, 2H).

t-Butyloxycarbonyl-N-methyl-3-aminomethylbenzoic Acid (Boc-NMeMamb)

The title compound can be prepared according to standard procedures, for examples, as disclosed in Olsen, *J. Org. Chem.* (1970) 35: 1912), and as shown schematically below.

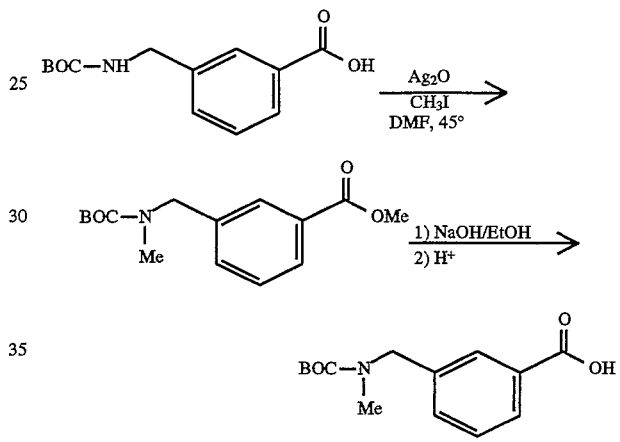

Synthesis of Aminomethylbenzoic Acid Analogs

Intermediates of the formula below may be prepared using standard synthetic procedures, for example, as shown in the indicated reaction schemes shown below.

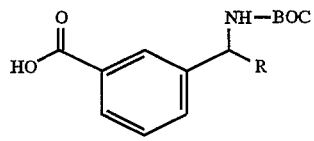

For R=$CH_3$, $CH_2CH_3$, $CH_2CH_2CH_3$, $CH_2CH_2CH_2CH_3$, $CH(CH_3)_2$, $C(CH_3)_3$, $CH(CH_3)CH_2CH_3$, benzyl, cyclopentyl, cyclohexyl; see Scheme 1.

For R=$CH_3$, $CH_2CH_2CH_2CH_3$, phenyl; see Scheme 2.

For R=$CH_3$, phenyl; see Scheme 3 and 4.

Scheme 1:
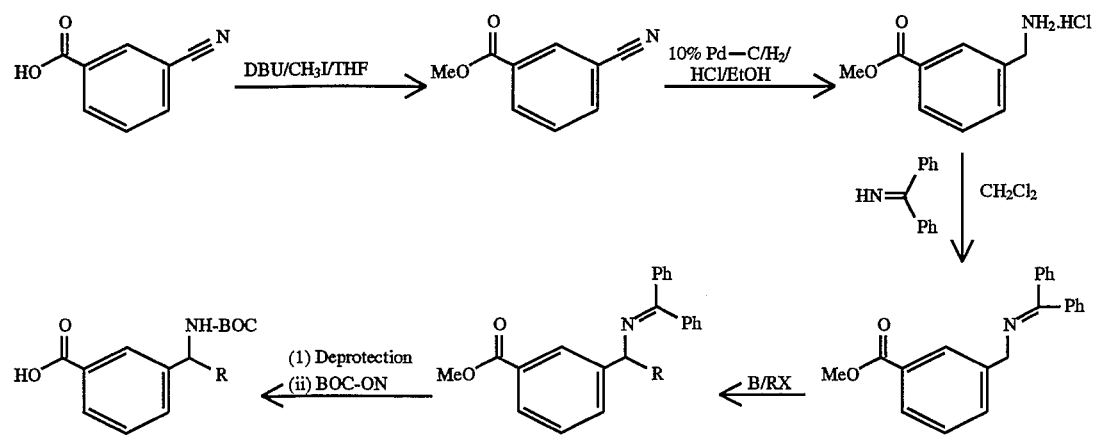
Scheme 2:
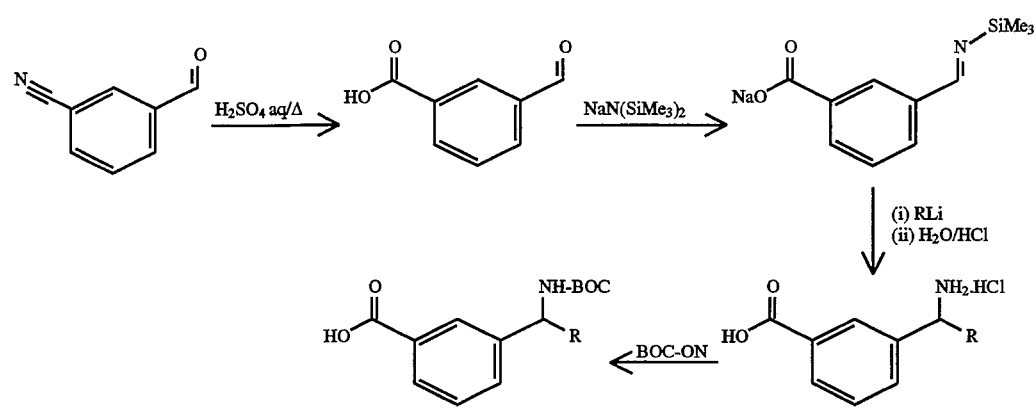
Scheme 3:
Scheme 4:
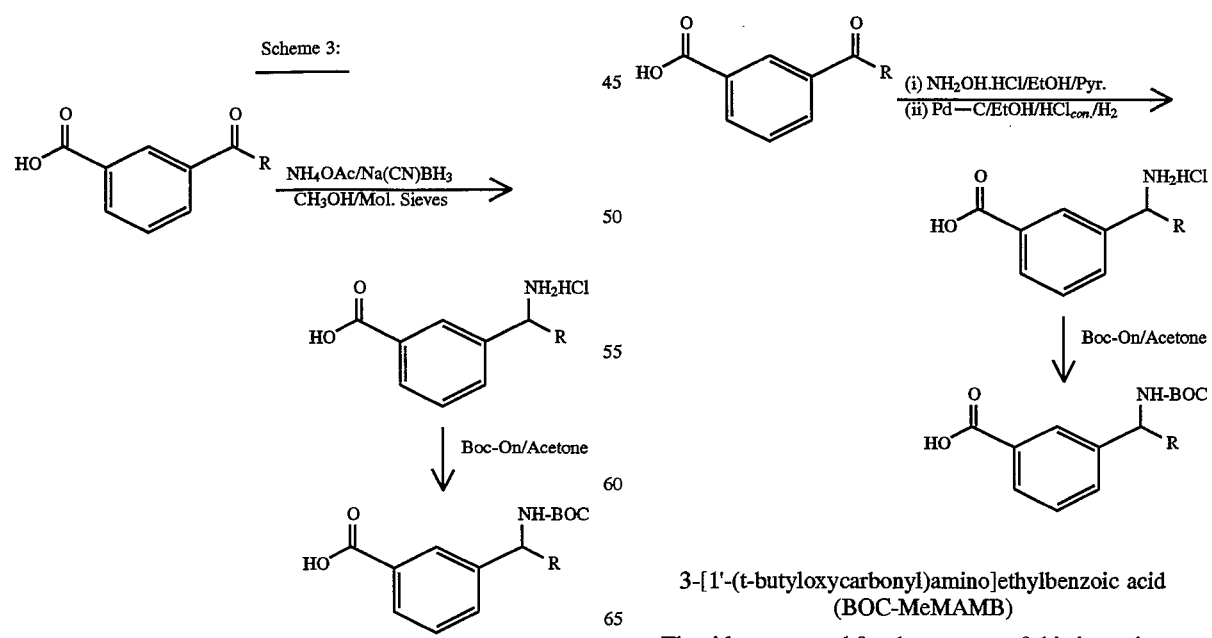
3-[1'-(t-butyloxycarbonyl)amino]ethylbenzoic acid (BOC-MeMAMB)
The title compound for the purpose of this invention was prepared according to the Scheme 4 (above).

3-Acetylbenzoic acid (0.50 g, 3 mmol), hydroxylamine hydrochloride (0.70 g, 10 mmol) and pyridine (0.70 ml, 9 mmol) were refluxed in 10 ml ethanol, for 2 h. Reaction mixture was concentrated, residue triturated with water, filtered and dried. Oxime was isolated as a white solid (0.51 g; 94.4% yield).

¹HNMR (CD₃OD) 7.45–8.30(m, 4H), 2.30(s, 3H). MS (CH₄—CI) [M+H—O]=164.

A solution of the oxime (0.51 g, 3 mmol) in ethanol, containing 10% Pd on carbon (1.5 g) and conc. HCl (0.25 ml, 3 mmol) was hydrogenated at 30 psi H₂ pressure in a Parr hydrogenator for 5 h. Catalyst was filtered and the filtrate concentrated. Residue was triturated with ether. Amine hydrochloride was isolated as a white solid (0.48 g; 85.7% yield). ¹HNMR (CD₃OD) 7.6–8.15(m, 4H), 4.55(q, 1H), 1.70(s, 3H). MS [M+H]=166.

Amine hydrochloride (0.40 g, 2 mmol) was dissolved in 15 ml water. A solution of BOC—ON (0.52 g, 2.1 mmol) in 15 ml acetone was added, followed by the addition of triethylamine (0.8 ml, 6 mmol). Reaction was allowed to proceed for 20 h. Reaction mixture was concentrated, partitioned between ethyl acetate and water. Aqueous layer was acidified to pH 2 using 10% HCl solution. Product was extracted in ethyl acetate, which after the usual work up and recrystallization from ethyl acetate/hexane, gave the title compound as a white solid (0.30 g; 57% yield). m.p. 116°–118° C. ¹HNMR (CDCl₃) 7.35–8.2(m, 4H), 4.6(bs, 1.5H), 1.50(d, 3H), 1.40(s, 9H). MS (NH₃—CI) [M+NH₄]=283.

3-[1'-(t-butyloxycarbonyl)amino]benzylbenzoic acid (BOC-PhMAMB)

The title compound for the purpose of this invention was prepared according to the Scheme 4 (above), by the procedure similar to that for the methyl derivative.

A solution of 3-benzoylbenzoic acid (2.00 g, 9 mmol), hydroxylamine hydrochloride (2.00 g, 29 mmol) and pyridine (2.00 ml, 25 mmol) in ethanol was refluxed for 12 h. After the usual extractive work up, white solid was obtained (2.41 g). The product still contained traces of pyridine, but was used in the next step without further purification.

The crude product (2.00 g, ~8 mmol) was dissolved in 200 ml ethanol. 10% Pd—C (2.00 g) and con. HCl (1.3 ml, 16 mmol) were added. Reaction mixture was hydrogenated at 30 psi for 1 h. The catalyst was filtered and the reaction mixture concentrated. Upon trituration of the residue with ether and drying under vacuum, amine hydrochloride was obtained as a white solid (2.12 g; 97% yield). ¹HNMR (CD₃OD) 7.4–8.15(m, 10H), 5.75(s, 1H). MS (CH₄—CI) [M+H—OH]=211.

Amine hydrochloride (1.00 g, 4 mmol) was converted to its BOC-derivative by a procedure similar to the methyl case. 0.60 g (48% yield) of the recrystallized (from ethanol/hexane) title compound was obtained as a white solid. m.p. 190°–192° C. ¹HNMR (CD₃OD) 7.2–8.0(m, 10H), 5.90 (2s, 1H, 2 isomers), 1.40(s, 9H). MS (NH₃—CI) [M+NH₄—C₄H₈]=289 t-Butyloxycarbonyl-D-2-aminobutyric Acid

The title compound was prepared by a modification of procedures previously reported in the literature (Itoh, Hagiwara, and Kamiya (1975) *Tett. Lett.*, 4393), as shown in the scheme below.

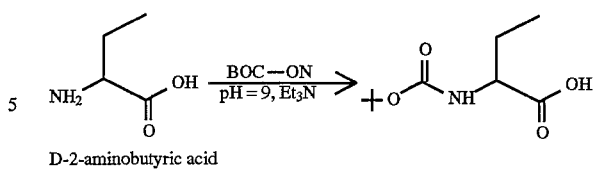

D-2-aminobutyric acid

D-2-aminobutyric acid (1.0 g, 9.70 mmol) was dissolved in 20 ml H₂O and a solution of Boc-ON (2.62 g, 10.6 mmol) in 20 ml acetone was added. A white precipitate formed which dissolved upon addition of triethylamine (3.37 ml, 24.2 mmol) to give a pale yellow solution (pH=9, wet pH paper). The solution was stirred at room temperature overnight at which time the acetone was removed under reduced pressure. The remaining aqueous layer was extracted with ether three times, acidified to pH 2 with concentrated HCl, and then extracted with ethyl acetate three times. The combined organic layers were dried over anhydrous magnesium sulfate and evaporated under reduced pressure to give t-butyloxycarbonyl-D-2-aminobutyric acid as an oil (2.05 g, greater than quantitative yield, contains solvent), which was used without further purification. ¹H NMR (CDCl₃) 0.98 (t, 3H), 1.45 (s, 9H), 1.73 (m, 1H), 1.90 (m, 1H), 4.29 (m, 1H), 5.05 (m, 1H).

Synthesis of t-Butyloxycarbonyl-3-aminophenylacetic Acid t-Butyloxycarbonyl-3-aminophenylacetic acids useful as intermediates in the synthesis of the compounds of the invention are prepared using standard procedures, for example, as described in Collman and Groh (1982) *J. Am. Chem. Soc.*, 104: 1391, and as shown schematically below.

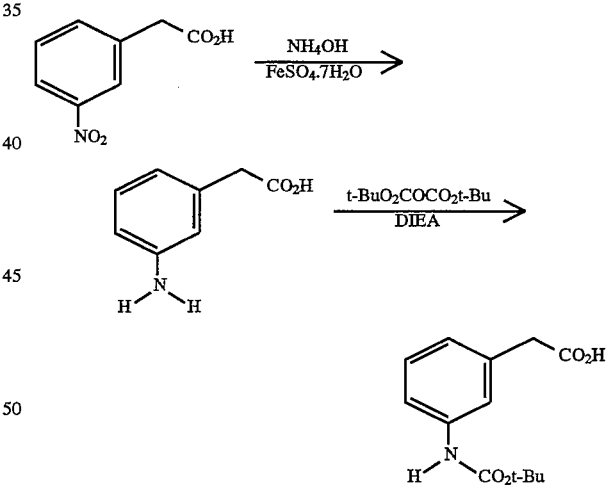

t-Butyloxycarbonyl-3-aminophenylacetic Acid

A solution of 3-aminophenylacetic acid (Aldrich, 10 g, 66 mmol), di-tert-butyl dicarbonate (15.8 g, 72 mmol), and DIEA (8.6 g, 66 mmol) in 50 ml of dichloromethane was stirred overnight at room temperature. The reaction mixture was concentrated, partitioned between dichloromethane-H₂O, the water layer was separated, acidified to pH 3 with 1N HCl, and extracted with dichloromethane. The extracts were washed with H₂O, brine, dried over anhydrous sodium sulfate, and evaporated to dryness under reduced pressure. This material was purified by recrystallization from heptane to provide the title compound (3.7 g, 22%) as a white solid.

mp 105° C.; $^1$H NMR (CDCl$_3$) 7.35 (s, 1H), 7.25 (m, 3H), 6.95 (m, 1H), 6.60 (br s, 1H), 3.65 (s, 2H), 1.50 (s, 9H).

Synthesis of 4, 5, and 6-Substituted 3-Aminomethylbenzoic Acid.HCl, and 4, 5, and 6-Substituted t-Butyloxycarbonyl-3-aminomethylbenzonic Acid Derivatives 4, 5, and 6-Substituted 3-aminomethylbenzoic acid.HCl, and 4, 5, and 6-substituted t-butyloxycarbonyl-3-aminomethylbenzoic acid derivatives useful as intermediates in the synthesis of the compounds of the invention are prepared using standard procedures, for example, as described in Felder et al *Helv. Chim. Acta*, 48: 259 (1965); de Diesbach *Helv. Chim. Acta*, 23: 1232 (1949); Truitt and Creagn *J. Org. Chem.*, 27: 1066 (1962); or Sekiya et al *Chem. Pharm. Bull.*, 11: 551 (1963), and as shown schematically below.

t-Butyloxycarbonyl-4-chloro-3-aminomethylbenzoic Acid

A suspension of 4-chloro-3-aminomethylbenzoic acid.HCl (6.7 g, 30 mmol) and triethylamine (9.3 g, 92 mmol) in 50 ml of H$_2$O, was added to a solution of Boc-ON (9.2 g, 38 mmol) in 50 ml of tetrahydrofuran cooled to 0° C. The reaction mixture was stirred at room temperature overnight, and the volatile compounds were removed by concentration under reduced pressure. The residue was diluted with H$_2$O, washed with ether, acidified to pH 3 with 1N HCl, and extracted with ethyl acetate. The extracts were washed with H$_2$O, brine, dried over anhydrous magnesium sulfate, and evaporated to dryness under reduced pressure. This material was triturated with ether-hexane to provide the title compound (7.4 g, 87%) as a white powder. mp 159° C. (dec);

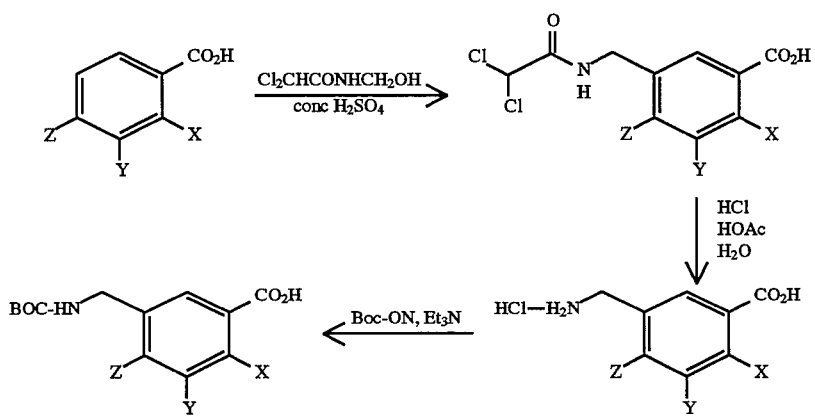

Synthesis of 4-Chloro-3-aminomethylbenzoic Acid. HCl

The title compound was prepared by modification of procedures previously reported in the literature (Felder et al (1965) *Helv. Chim. Acta*, 48: 259). To a solution of 4-chlorobenzoic acid (15.7 g, 100 mmol) in 150 ml of concentrated sulfuric acid was added N-hydroxymethyl dichloroacetamide (23.7 g, 150 mmol) in portions. The reaction mixture was stirred at room temperature for 2 days, poured onto 375 g of ice, stirred for 1 hour, the solid was collected by filtration, and washed with H$_2$O. The moist solid was dissolved in 5% sodium bicarbonate solution, filtered, and acidified to pH 1 with concentrated HCl. The solid was collected by filtration, washed with H$_2$O, and air-dryed overnight to give 4-chloro-3-dichloroacetylaminomethylbenzoic acid (26.2 g, 89%) as a white powder.

A suspension of 4-chloro-3-dichloroacetylaminomethylbenzoic acid (26.2 g, 88 mmol) in 45 ml of acetic acid, 150 ml of concentrated HCl, and 150 ml of H$_2$O was heated to reflux for 3 hours, filtered while hot, and allowed to cool to room temperature. The solid was collected by filtration, washed with ether, washed with acetone-ether, and air-dryed overnight to give the title compound (7.6 g, 39%) as off-white crystals. mp 278°-9° C.; $^1$H NMR (D$_6$-DMSO) 13.40 (br s, 1H), 8.75 (br s, 3H), 8.20 (s, 1H), 7.95 (dd, 1H), 7.70 (d, 1H), 4.20 (br s, 2H).

$^1$H NMR (D$_6$-DMSO) 13.20 (br s, 1H), 7.90 (s, 1H), 7.80 (dd, 1H), 7.60 (br s, 1H), 7.55 (d, 1H), 4.20 (br d, 2H), 1.40 (s, 9H).

4 and 6-Substituted t-Butyloxycarbonyl-3-aminomethylbenzoic Acid Derivatives The compounds listed below were prepared using the general procedure described above for t-butyloxycarbonyl-4-chloro-3-aminomethylbenzoic acid.

| R$^{10a}$ | R$^{10}$ | mp °C. |
|---|---|---|
| H | Cl | 159 |
| H | I | 168 |
| H | Me | 155 |
| H | MeO | 171 |
| Cl | H | 150 |
| I | H | 182 |
| Me | H | 166 |
| MeO | H | 79 |

Synthesis of 2-Aminomethylbenzoic Acid.HCl and 2-Aminomethylphenylacetic Acid.HCl 2-Aminomethylbenzoic acid.HCl and 2-aminomethylphenylacetic acid.HCl useful as intermediates in the synthesis of the compounds of the invention are prepared using standard procedures, for example, as described in Naito et al *J. Antibiotics*, 30:698 (1977); or Young and Sweet *J. Am. Chem. Soc.*, 80: 800 (1958), and as shown schematically below.

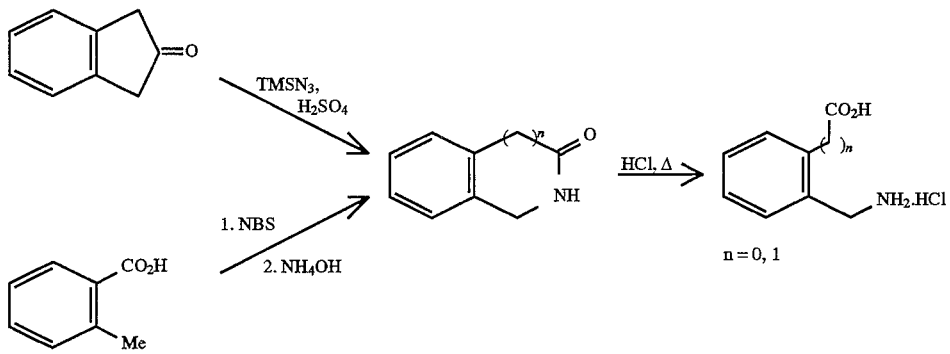

2-Aminomethylphenylacetic Acid d-Lactam

The title compound was prepared by modification of procedures previously reported in the literature (Naito et al. (1977) *J. Antibiotics*, 30: 698). To an ice-cooled suspension of 2-indanone (10.8 g, 82 mmol) and azidotrimethylsilane (9.4 g, 82 mmol) in 115 ml of chloroform was added 25 ml of concentrated sulfuric acid at a rate to maintain the temperature between 30°–40° C. After an additional 3 hours, the reaction mixture was poured onto ice, and the water layer was made basic with concentrated ammonium hydroxide. The chloroform layer was separated, washed with $H_2O$, brine, dried over anhydrous magnesium sulfate, and evaporated to dryness under reduced pressure. This material was purified by sublimation (145° C., <1 mm), followed by recrystallization from benzene to give the title compound (5.4 g, 45%) as pale yellow crystals. mp 149°–150° C.; $^1H$ NMR ($CDCl_3$) 7.20 (m, 5H), 4.50 (s, 2H), 3.60 (s, 2H).

2-Aminomethylphenylacetic Acid.HCl

The title compound was prepared by modification of procedures previously reported in the literature (Naito et al. (1977) *J. Antibiotics*, 30: 698). A mixture of 2-aminomethylphenylacetic acid d-lactam (6.4 g, 44 mmol) and 21 ml of 6N HCl was heated to reflux for 4 hours. The reaction mixture was treated with activated carbon (Norit A), filtered, evaporated to dryness, and the residual oil triturated with acetone. Filtration provided the title compound (5.5 g, 62%) as colorless crystals. mp 168° C. (dec); 1H NMR ($D_6$-DMSO) 12.65 (br s, 1H), 8.35 (br s, 3H), 7.50 (m, 1H), 7.35 (m, 3H), 4.05 (ABq, 2H), 3.80 (s, 2H).

2-Aminomethylbenzoic Acid g-Lactam

The title compound was prepared by modification of procedures previously reported in the literature (Danishefsky et al. (1975) *J. Org. Chem.*, 40: 796). A mixture of methyl o-toluate (45 g, 33 mol), N-bromosuccinimide (57 g, 32 mol), and dibenzoyl peroxide (0.64 g) in 175 ml of carbon tetrachloride was heated to reflux for 4 hours. The cooled reaction mixture was filtered, evaporated to dryness under reduced pressure, dissolved in 250 ml of methanol, and concentrated ammonium hydroxide (75 ml, 1.11 mol) was added. The reaction mixture was heated to reflux for 5 hours, concentrated, filtered, and the solid washed with $H_2O$ followed by ether. This material was purified by recrystallization from $H_2O$ to give the title compound (11.0 g, 26%) as a white solid. mp 150° C.; $^1H$ NMR ($CDCl_3$) 7.90 (d, 1H), 7.60 (t, 1H), 7.50 (t, 2H), 7.00 (br s, 1H), 4.50 (s, 2H).

2-Aminomethylbenzoic Acid.HCl

The title compound was prepared using the general procedure described above for 2-aminomethylphenylacetic acid.HCl. The lactam (3.5 g, 26 mmol) was converted to the title compound (2.4 g, 50%) as colorless crystals. mp 233° C. (dec); $^1H$ NMR ($D_6$-DMSO) 13.40 (br s, 1H), 8.35 (br s, 3H), 8.05 (d, 1H), 7.60 (m, 3H), 4.35 (br s, 2H).

Alternatives to Mamb: Other Cyclic Peptide Intermediates

Alternatives to Mamb useful as carbocylic residues $R^{31}$ in the cyclic peptides of the invention include aminoalkyl-naphthoic acid and aminoalkyl-tetrahydronaphthoic acid residues. Representative aminoalkyl-naphthoic acid and aminoalkyl-tetrahydronaphthoic acid intermediates useful in the synthesis of cyclic peptides of the present invention are described below. The synthesis of these intermediates is outlined below in Scheme 4a.

Scheme 4a

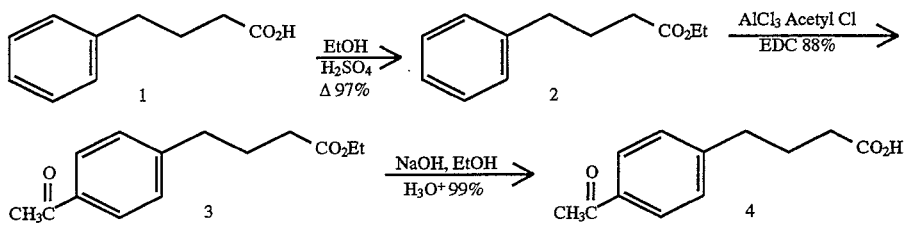

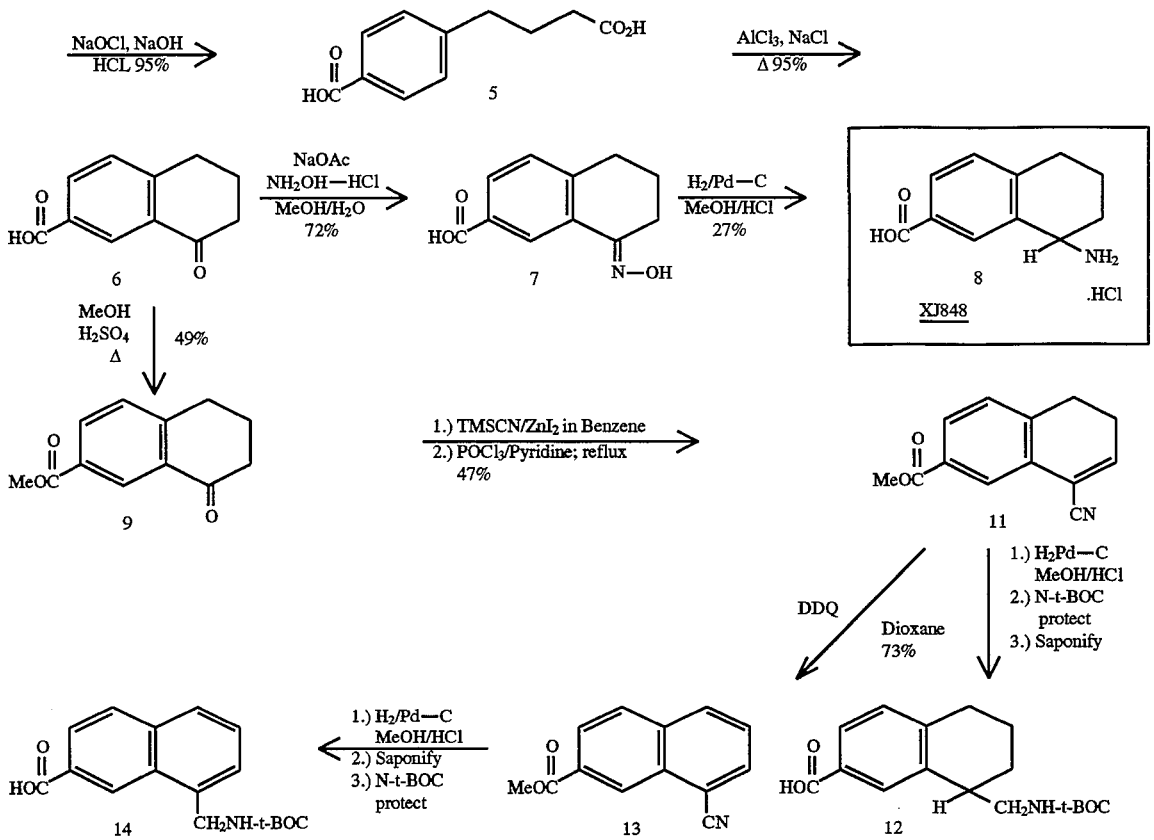

The title compound was prepared according to a modification of standard procedures previously reported in the literature (Earnest, I., Kalvoda, J., Ribs, G., and Mutter, M., Tett. Lett., Vol. 31, No. 28, pp 4011–4014, 1990).

8-Amino-5,6,7,8-tetrahydro-2-naphthoic Acid Hydrochloride (8)

As shown below in Scheme 4a, 4-phenylbutyric acid (1) was converted to the ethyl ester (2) which was acylated via aluminum chloride and acetylchloride to give 4-acetylphenylbutyric acid ethyl ester (3). This ester was subjected to saponification to give 4-acetylphenylbutyric acid (4). Subsequently, the acetyl group was oxidized to give 4-carboxyphenylbutyric acid (5) which was converted to the 1-tetralin-7-carboxylic acid (6) using aluminum chloride in a Friedel-Crafts cyclization with reasonably high yield. At that point, the tetralone was split into two portions and some was converted to the oxime (7) using sodium acetate and hydroxylamine hydrochloride. The oxime was subjected to hydrogenolysis to give the racemic mixture of 8-amino-5,6,7,8-tetrahydro-2-naphthoic acid as the hydrochloride (8) for use as an intermediate for incorporation into the cyclic peptide.

Part A—A solution of 4-phenylbutyric acid (50.0 g, 0.3 mol) in ethanol (140 mL) with concentrated sulfuric acid (0.53 mL) was stirred at reflux over 5 hours. The cooled solution was poured into ice water and extracted with ethyl acetate. The combined organic layers were backwashed with brine, dried over anhydrous magnesium sulfate and evaporated to dryness under reduced pressure to give 4-phenylbutyric acid ethyl ester (56.07 g, 0.29 mol, 97%) as a yellow liquid. $^1$H NMR (CDCl$_3$) d 7.3–7.1 (m, 5H), 4.1 (q, 2H, J=7.1Hz), 2.7 (t, 2H, J=7.7Hz), 2.3 (t, 2H, J=7.5Hz), 1.95 (quintet, 2H, J=7.5Hz), 1.25 (t, 3H, J=7.1Hz).

Part B—To a solution of aluminum chloride (153 g, 1.15 mol), and acetyl chloride (38.5 mL, 42.5 g, 0.54 mol) in dichloromethane (1500 mL) was added, dropwise, a solution of 4-phenylbutyric acid ethyl ester (50.0 g, 0.26 mol) in dichloromethane (500 mL). All was stirred at ambient temperature for 15 minutes. The solution was poured into cold concentrated hydrochloric acid (2000 mL) and then extracted with dichloromethane. The combined organic layers were backwashed with brine, dried over anhydrous magnesium sulfate and evaporated to dryness under reduced pressure to give 4-acetylphenylbutyric acid ethyl ester (53.23 g, 0.23 mol, 88%) as a dark yellow liquid. $^1$H NMR (CDCl$_3$) d 7.9 (d, 2H, J=8.1Hz), 7.25 (d, 2H, J=8.4 Hz), 4.1 (q, 2H, J=7.1 Hz), 2.75 (t, 2H, J=7.6 Hz), 2.6 (s, 3H), 2.35 (t, 2H, J=7.6 Hz), 2.0 (quintet, 2H, J=7.5 Hz), 1.25 (t, 3H, J=7.1 Hz).

Part C—To a solution of 4-acetylphenylbutyric acid ethyl ester (50.0 g, 0.21 mol) in ethanol (1250 mL) was added, dropwise, a solution of sodium hydroxide (50.0 g) in water (1250 mL). All was stirred at reflux over 4 hours. The solution was concentrated to half volume and then acidified to a pH equal to 1.0 using hydrochloric acid (1N). The resulting precipitate was collected and washed with water to give 4-acetylphenylbutyric acid (53.76 g, 0.26 mol, 99%) as a white solid. mp=50°–52° C.;

$^1$H NMR (CDCl$_3$) d 7.9 (d, 2H, J=8.1 Hz), 7.25 (d, 2H, J=9.1 Hz), 2.75 (t, 2H, J=7.7 Hz), 2.6 (s, 3H), 2.4 (t, 2H, J=7.3 Hz), 2.0 (quintet, 2H, J=7.4 Hz).

Part D—To a solution of sodium hypochlorite (330 mL, 17.32 g, 0.234 mol) in a solution of sodium hydroxide (50%, 172 mL), warmed to 55° C., was added, portionwise as a solid, 4-acetylphenylbutyric acid (16.0 g, 0.078 mol) while keeping the temperature between 60°–70° C. All was stirred at 55° C. over 20 hours. The cooled solution was quenched by the dropwise addition of a solution of sodium bisulfite (25%, 330 mL). The mixture was then transferred to a beaker and acidified by the careful addition of concentrated hydrochloric acid. The resulting solid was collected, washed with water and dried, then triturated sequentially with chlorobutane and hexane to give 4-carboxyphenylbutyric acid (15.31 g, 0.074 mol, 95%) as a white solid. mp=190°–195° C.; $^1$H NMR (DMSO) d 12.55 (bs, 1H), 8.1 (s, 1H), 7.85 (d, 2H, J=8.1 Hz), 7.3 (d, 2H, J=8.1 Hz), 2.7 (t, 2H, J=7.5 Hz), 2.2 (t, 2H, J=7.4 Hz), 1.8 (quintet, 2H, J=7.5 Hz).

Part E—A mixture of 4-carboxyphenylbutyric acid (10.40 g, 0.05 mol), aluminum chloride (33.34 g, 0.25 mol) and sodium chloride (2.90 g, 0.05 mol) was heated with continual stirring to 190° C. over 30 minutes. As the mixture cooled to 60° C., cold hydrochloric acid (1N, 250 mL) was carefully added. The mixture was extracted with dichloromethane. The combined organic layers were backwashed with dilute hydrochloric acid and water, dried over anhydrous magnesium sulfate and evaporated to dryness under reduced pressure. The resulting solid was triturated with chlorobutane to give 1-tetralon-7-carboxylic acid (9.59 g, 0.05 mol, 100%) as a brown solid. mp=210°–215° C.; $^1$H NMR (DMSO) d 8.4 (s, 1H), 8.1 (d, 2H, J=8.0 Hz), 7.5 (d, 1H, J=7.9 Hz), 3.0 (t, 2H, J=6.0 Hz), 2.65 (t, 2H, J=6.6 Hz), 2.1 (quintet, 2H, J=6.3 Hz).

Part F—A solution of 1-tetralon-7-carboxylic acid (1.0 g, 0.0053 mol) and sodium acetate (1.93 g, 0.024 mol) and hydroxylamine hydrochloride (1.11 g, 0.016 mol) in a mixture of methanol and water (1:1, 15 mL) was stirred at reflux over 4 hours. The mixture was cooled and then added was more water (50 mL). The solid was collected, washed with water and dried, then triturated with hexane to give 1-tetralonoxime-7-carboxylic acid (0.78 g, 0.0038 mol, 72%) as a white solid. mp=205°–215° C.; $^1$H NMR (DMSO) d 11.3 (s, 2H), 8.4 (s, 1H), 7.8 (d, 1H, J=7.7 Hz), 7.3 (d, 1H, J=7.7 Hz), 2.8 (t, 2H, J=5.9 Hz), 2.7 (d, 2H, J=6.6 Hz), 1.9–1.7 (m, 2H).

Part G—A mixture of 1-tetralonoxime-7-carboxylic acid (0.75 g, 0.0037 tool) in methanol (25 mL) with concentrated hydrochloric acid (0.54 mL, 0.20 g, 0.0056 mol) and palladium on carbon catalyst (0.10 g, 5% Pd/C) was shaken for 20 hours at ambient temperature under an atmosphere of hydrogen (60 psi). The reaction mixture was filtered over Celite@ and washed with methanol. The filtrate was evaporated to dryness under reduced pressure and the residue was purified by flash chromatography using hexane :ethyl acetate:: 1:1 to give the racemic mixture of 8-amino-5,6,7,8-tetrahydro-2-naphthoic acid hydrochloride (0.225 g, 0.001 mol. 27%) as a white solid. mp=289°–291° C.; $^1$H NMR (DMSO) d 8.55 (bs, 3H), 8.2–8.1 (m, 1H), 7.85–7.8 (m, 1H), 7.35–7.25 (m, 1H), 4.5 (m, 1H), 2.9–2.8 (m, 2H), 2.1–1.9 (m, 3H), 1.85–1.7 (m, 1H).

N-(BOC)-8-Aminomethyl-5,6,7,8-tetrahydro-2-naphthoic Acid (12)

As shown below in Scheme 4a, the remaining tetralone was then converted to the methyl ester (9). Using a procedure from Gregory, G. B. and Johnson, A. L, JOC, 1990, 55, 1479, the tetralone methyl ester (9) was converted, first, to the cyanohydrin by treatment with trimethylsilylcyanide and zinc iodide and then, via the in situ dehydration with phosphorous oxychloride in pyridine, to the methyl 8-cyano-5,6-dihydro-2-naphthoate (11). This naphthoate was divided into two portions and some was subjected to hydrogenolysis, N-BOC-protection and saponification to give N-(BOC)-8-aminomethyl-5,6,7,8-tetrahydro-2-naphthoic acid (12) as an intermediate for incorporation into the cyclic peptide.

Part A—A mixture of 1-tetralon-7-carboxylic acid (7.0 g, 0.037 mol) in methanol (13.6 mL, 10.8 g, 0.30 mol) with a catalytic amount of hydrochloric acid (0.07 mL, 0.12 g, 0.0012 mol) was stirred at reflux over 5 hours. The cooled reaction mixture was poured into ice water and extracted with ethyl acetate. The combined organic layers were backwashed with water and brine, dried over anhydrous magnesium sulfate and evaporated to dryness under reduced pressure. The resulting solid was purified by flash chromatography using hexane:ethyl acetate::75:25. The resulting solid was triturated with hexane to give 1-tetralon-7-carboxylic acid methyl ester (3.61 g, 0.018 mol, 49%) as a yellow solid. mp=170°–172° C.; $^1$H NMR (CDCl$_3$) d 8.7 (s, 1H), 8.15 (d, 1H, J=8.1 Hz), 7.35 (d, 1H, J=8.1 Hz), 3.95 (s, 3H), 3.05 (d, 2H, J=6.1 Hz), 2.7 (t, 2H, J=6.4 Hz), 2.15 (quintet, 2H, J=6.2 Hz).

Part B—A solution of 1-tetralon-7-carboxylic acid methyl ester (3.50 g, 0.017 mol), trimethylsilylcyanide (1.98 g, 0.02 mol) and zinc iodide (0.10 g) in benzene 5 (20 mL) was stirred at ambient temperature over 15 hours. Then added, sequentially and dropwise, was pyridine (20 mL) and phosphorous oxychloride (4.0 mL, 6.55 g, 0.0425 mol). The reaction mixture was stirred at reflux over 1 hour then evaporated to dryness under reduced pressure. The residue was taken up in chloroform, backwashed with water, dried over anhydrous magnesium sulfate and evaporated to dryness under reduced pressure to give methyl 8-cyano-5,6-dihydro-2-naphthoate (1.70 g, 0.008 mol, 47%) as a yellow solid. mp=73°–75° C.; $^1$H NMR (CDCl$_3$) d 8.0–7,9 (m, 1H), 7.3–7.2 (m, 1H), 6.95 (t, 1H, J=4.8 Hz), 3.95 (s, 3H), 2.9 (t, 2H, J=8.3 Hz), 2.6–2.4 (m, 3H)

Part C—A mixture of methyl 8-cyano-5,6-dihydro-2-naphthoate (0.80 g, 0.0038 mol) in methanol (25 mL) with concentrated hydrochloric acid (0.56 mL) and palladium on carbon catalyst (0.40 g, 5% Pd/C) was shaken for 20 hours at ambient temperature under an atmosphere of hydrogen (50 psi). The reaction mixture was filtered over Celite and washed with methanol. The filtrate was evaporated to dryness under reduced pressure and the residue was triturated with hexane to give the racemic mixture of methyl 8-aminomethyl-5,6,7,8-tetrahydro-2-naphthoate (0.80 g, 0.0037 mol, 97%) as a white solid. mp=172°–179° C.; $^1$H NMR (DMSO) d 8.2–8.0 (m, 4H), 7.9–7.7 (m, 6H), 7.5–7.2 (m, 4H), 3.9–3.8 (m, 7H), 3.3–2.7 (m, 10H), 2.0–1.6 (m, 8H).

Part D—A solution of methyl 8-aminomethyl-5,6,7,8-tetrahydro-2-naphthoate (0.78 g, 0.0036 mol) and triethylamine (0.55 mL, 0.40 g, 0.004 mol) in aqueous tetrahydrofuran (50%, 75 mL) was added, portionwise as a solid, 2-(tert-butoxycarbonyloxyimino)-2-phenylacetonitrile (0.99 g, 0.004 mol). All was stirred at ambient temperature over 3 hours. The solution was concentrated to half volume and extracted with diethylether. The aqueous layer was then acidified to a pH of 1.0 using hydrochloric acid (1N) and then extracted with ethyl acetate. The combined organic layers were dried over anhydrous magnesium sulfate and evaporated to dryness under reduced pressure. The residue was purified by flash chromatography using hexane:ethyl acetate::8:2 to give methyl N-(BOC)-8-aminomethyl-5,6,7,8-tetrahydro-2-naphthoate (0.54 g, 0.0017 mol, 47%) as a white solid. mp=72°–80° C.; 1H NMR (DMSO) d 13.8 (s, 1H), 7.8–7.65 (m, 3H), 7.6–7.5 (m, 3H), 7.25–7.20 (m, 1H), 7.15–7.05 (m, 1H), 3.9–3.8 (m, 1H), 3.2–2.8 (m, 4H), 1.8–1.6 (m, 3H), 1.4 (s, 6H).

Part E—To a solution of methyl N-(BOC)-8-aminomethyl-5,6,7,8-tetrahydro-2-naphthoate (0.50 g, 0.0016 mol) in ethanol (12.5 mL) was added, dropwise, a solution of sodium hydroxide (0.50 g) in water (12.5 mL). All was stirred a reflux over 4 hours. The reaction mixture was concentrated to half volume and then acidified to a pH equal to 1.0 using hydrochloric acid (1N). The residue was purified by flash chromatography using a gradient of hexane:ethyl acetate::1:1 to ethyl acetate to ethyl acetate:methanol::9:1 to give the racemic mixture of the title compound, N-(BOC)-2-aminomethyl-5,6,7,8-tetrahydro-2-naphthoic acid (0.19 g, 0.00062 mol, 39%) as a white solid. mp=172°–176° C.; $^1$H NMR (DMSO) d 7.8 (s, 1H), 7.65 (d, 1H, J=8.1 Hz), 7.15 (d, 1H, J=8.1 Hz), 7.1–7.0 (m, 1H), 3.2–3.1 (m, 2H), 3.0–2.7 (m, 4H), 1.8–1.6 (m, 4H), 1.4 (s, 9H).

N-(BOC)-8-aminomethyl-2-naphthoic acid (14)

The remaining naphthoate (11) was treated with 2,3-dichloro-5,6-dicyano-1,4-benzoquinone (DDQ) in dioxane to aromatize the adjacent ring to give the methyl 8-cyano-2-naphthoate (13). Then, the nitrile was reduced via hydrogentation and the methyl ester saponified to the carboxylic acid. This acid was then N-BOC-protected to give N-(BOC)-8-aminomethyl-2-naphthoic acid (14) as an intermediate for incorporation into the cyclic peptide.

Part A—A solution of methyl 8-cyano-5,6-dihydro-2-naphthoate (1.0 g, 0.0047 mol) and 2,3-dichloro-5,6-dicyano-1,4-benzoquinone (1.07 g, 0.0047 mol) in dioxane (50 mL) was stirred at 120° C. over 16 hours. The reaction mixture was poured into ice water and extracted with ethyl acetate. The combined organic layers were dried over anhydrous magnesium sulfate and evaporated to dryness under reduced pressure. The residue was purified by flash chromatography using ethyl acetate to give methyl 8-cyano-2-naphthoate (0.72 g, 0.0034 mol, 73%) as a tan solid. mp=178°–182° C.; $^1$H NMR (CDCl$_3$) d 8.95 (s, 1H), 8.3–8.2 (m, 1H), 8.15–8.10 (m, 1H), 8.0–7.95 (m, 2H), 7.7–7.6 (m, 1H), 4.05 (s, 1H).

Part B—A mixture of methyl 8-cyano-2-naphthoate (1.0 g, 0.0047 mol) in methanol (35 mL) with concentrated hydrochloric acid (0.69 mL) and palladium on carbon catalyst (0.20 g, 5% Pd/C) was shaken for 6 hours at ambient temperature under an atmosphere of hydrogen (50 psi). The reaction mixture was filtered over Celite@ and washed with methanol. The filtrate was evaporated to dryness under reduced pressure and the residue was triturated with hexane to give methyl 8-aminomethyl-2-naphthoate (0.76 g, 0.0035 mol, 75%) as an oil. $^1$H NMR (DMSO) d 8.75 (s, 1H), 8.5 (bs, 2H), 8.2–8.05 (m, 3H), 7.75–7.70 (m, 2H), 4.6 (s, 2H), 3.95 (m, 3H).

Part C—To a solution of methyl 8-aminomethyl-2-naphthoate (0.75 g, 0.0035 mol) in dry tetrahydrofuran (50 mL), cooled to 0° C., was added a solution of lithium hydroxide (0.5M, 5.83 mL). All was stirred at ambient temperature over 20 hours. Another aliquot of lithium hydroxide was added and all was stirred for an additional 20 hours. The solid was collected and the filtrate was evaporated to dryness under reduced pressure. The solids were triturated with diethyl ether to give 8-aminomethyl-2-naphthoic acid (0.67 g, 0.0033 mol, 95%) as a white solid. mp=223°–225° C.; $^1$H NMR (DMSO) d 8.6 (s, 1H), 8.1–7.9 (m, 1H), 7.8–7.7 (m, 4H), 7.55–7.5 (m, 1H), 7,45–7.35 (m, 2H), 4.2 (s, 2H).

Part D—A solution of 8-aminomethyl-2-naphthoic acid (0.50 g, 0.00025 mol) and triethylamine (0.038 mL, 0.028 g, 0.000275 mol) in aqueous tetrahydrofuran (50%, 5 mL) was added, portionwise as a solid, 2-(tert-butoxycarbonyloxyimino)-2-phenylacetonitrile (0.068 g, 0.000275 mol). All was stirred at ambient temperature over 5 hours. The solution was concentrated to half volume and extracted with diethylether. The aqueous layer was then acidified to a pH of 1.0 using hydrochloric acid (1N) and then extracted with ethyl acetate. The combined organic layers were dried over anhydrous magnesium sulfate and evaporated to dryness under reduced pressure to give the title compound, N-(BOC)-8-aminomethyl-2-naphthoic acid (0.050 g, 0.00017 mol) as a white solid. mp=190°–191° C.; $^1$H NMR (DMSO) d 13.1 (bs, 1H), 8.8 (s, 1H), 8.0 (q, 2H, J=7.9 Hz), 7.9 (d, 1H, J=8.1 Hz), 7.6 (t, 1H, J=7.5 Hz), 7.65–7.55 (m, 2H), 4.6 (d, 2H, J=5.5 Hz), 1.4 (s, 9H).

Synthesis of Cyclic Peptides t-Butyloxycarbonyl-3-aminomethylbenzoic acid (Boc-Mamb) is coupled to oxime resin by a modification of the method described by DeGrado and Kaiser (1980) *J. Org. Chem.* 45, 1295 using 1 equivalent of the 3-aminomethylbenzoic acid (with respect to the substitution level of the resin), 1 equivalent of HBTU, and 3 equivalent of NMM. Alternatively, Boc-Mamb (1 equivalent) may be coupled to the oxime resin using 1 equivalent each of DCC and DMAP in methylene chloride. Coupling times range from 15 to 96 hours. The substitution level is then determined using either the picric acid test (Satin, Kent, Tam, and Merrifield, (1981) *Anal. Biochem.* 117, 145–157) or the quantitative ninhydrin assay (Gisin (1972) *Anal. Chim. Acta* 58, 248–249). Unreacted oxime groups are blocked using 0.5M trimethylacetylchloride/0.5M diisopropylethylamine in DMF for 2 hours. Deprotection of the Boc protecting group is accomplished using 25% TFA in DCM for 30 minutes. The remaining amino acids or amino acid derivatives are coupled using between a two and ten fold excess (based on the loading of the first amino acid or amino acid derivative) of the appropriate amino acid or amino acid derivatives and HBTU in approximately 8 ml of DMF. The resin is then neutralized in situ using 3 eq. of NMM (based on the amount of amino acid used) and the coupling times range from 1 hour to several days. The completeness of coupling is monitored by qualitative ninhydrin assay, or picric acid assay in cases where the amino acid was coupled to a secondary amine. Amino acids are recoupled if necessary based on these results.

After the linear peptide had been assembled, the N-terminal Boc group is removed by treatment with 25% TFA in DCM for 30 minutes. The resin is then neutralized by treatment with 10% DIEA in DCM. Cyclization with concomitant cleavage of the peptide is accomplished using the method of Osapay and Taylor ((1990) *J. Am. Chem. Soc.*, 112, 6046) by suspending the resin in approximately 10 ml/g of DMF, adding one equivalent of HOAc (based on the loading of the first amino acid), and stirring at 50°–60° C. for 60 to 72 hours. Following filtration through a scintered glass funnel, the DMF filtrate is evaporated, redissolved in HOAc or 1:1 acetonitrile: H$_2$O, and lyophilized to obtain protected, cyclized material. Alternatively, the material may be dissolved in methanol and precipitated with ether to obtain the protected, cyclized material. This is then treated using standard procedures with anhydrous hydrogen fluoride (Stewart and Young (1984) "Solid Phase Peptide Synthesis", 2nd. edition, Pierce Chemical Co., 85) containing 1 ml/g m-cresol or anisole as scavenger at 0° C. for 20 to 60 minutes to remove side chain protecting groups. The crude product may be purified by reversed-phase HPLC using a 2.5 cm preparative Vydac C18 column with a linear acetonitrile gradient containing 0.1% TFA to produce pure cyclized material. The following N-α-Boc-protected amino acids may be used for the syntheses: Boc-Arg(Tos), Boc-N-a-MeArg(Tos), Boc-Gly, Boc-Asp(OcHex), Boc-3-aminomethyl-4-iodo-benzoic acid, Boc-D-Ile, Boc-NMeAsp(OcHex), Boc-NMe-Mamb, Boc-D-Phg, Boc-D-Asp(OBzl), Boc-L-Asp(OcHex), Boc-aMe-Asp(OcHex), Boc-bMe-Asp(OcHex), Boc-L-Ala, Boc-L-Pro, Boc-D-Nle, Boc-D-Leu, Boc-D-Val, Boc-D-2-aminobutyric acid (Boc-D-Abu), Boc-Phe, Boc-D-Ser(Bzl), Boc-D-Ala, Boc-3-aminomethylbenzoic acid (Boc-Mamb), Boc-D-Lys(2-ClZ), Boc-β-Ala, Boc-D-Pro, Boc-D-Phe, Boc-D-Tyr(Cl$_2$Bzl), Boc-NMe-Amf(CBZ), Boc-aminotetralincarboxylic acid, Boc-aminomethylnaphthoic acid, Boc-4-aminomethylbenzoic acid, or Boc-NMeGly.

The synthesis of the compounds of the invention is further exemplified below. The Tables below set forth representative compounds of the present invention.

EXAMPLE 1 cyclo-(Gly-NMeArg-Gly-Asp-Mamb); the compound of formula (II) wherein J=Gly, K= NMeArg, L=Gly, M=Asp, R$^1$=R$^2$=H (SEQ ID NO:1)

The title compound was prepared using the general procedure described below for cyclo-(D-Val-NMeArg-Gly-Asp-Mamb). The peptide was prepared on a 0.336 mmol scale to give the protected cyclic peptide (218 mg, 84%). The peptide (200 mg) and 200 mL of m-cresol were treated with anhydrous hydrogen fluoride at 0° C. for 1 hour. The crude material was precipitated with ether, redissolved in aqueous HOAc, and lyophilized to generate the title compound as a pale yellow solid (158 mg, greater than quantitative yield; calculated as the acetate salt). Purification was accomplished by reversed-phase HPLC on a preparative Vydac C18 column (2.5 cm) using a 0.23% /min. gradient of 2 to 11% acetonitrile containing 0.1% TFA and then lyophilized to give the TFA salt of the title compound as a fluffy white solid (21% recovery, overall yield 16.3%). Mass spectrum: M+H=533.26.

EXAMPLE 2 cyclo-(D-Ala-NMeArg-Gly-Asp-Mamb); the compound of formula (II) wherein J=D-Ala, K= NMeArg, L=Gly, M=Asp, R$^1$=R$^2$=H The title compound was prepared using the general procedure described below for cyclo-(D-Val-NMeArg-Gly-Asp-Mamb). Recoupling of the Boc-N-MeArg(Tos) residue was found to be necessary. The peptide was prepared on a 0.244 mmol scale to give the protected cyclic peptide (117 mg, 61%). The peptide (110 mg) and 110 mL of m-cresol were treated with anhydrous hydrogen fluoride at 0° C. for 1 hour. The crude material was precipitated with ether, redissolved in aqueous HOAc, and lyophilized to generate the title compound as a pale yellow solid. Purification was accomplished by reversed-phase HPLC on a preparative Vydac C18 column (2.5 cm) using a 0.25% /min. gradient of 2 to 11% acetonitrile containing 0.1% TFA and then lyophilized to give the TFA salt of the title compound as a fluffy white solid. Mass spectrum: M+H=547.23.

EXAMPLE 3 cyclo-(D-Abu-NMeArg-Gly-Asp-Mamb); the compound of formula (II) wherein J=D-Abu, K= NMeArg, L=Gly, M=Asp, R$^1$=R$^2$=H The title compound was prepared using the general procedure described below for Example 4. The peptide was prepared on a 0.101 mmol scale to give the protected cyclic peptide (51 mg, 63%). The peptide (43 mg) and 50 μL of m-cresol were treated with anhydrous hydrogen fluoride at 0° C for 30 minutes The crude material was precipitated with ether, redissolved in aqueous HOAc, and lyophilized to generate the title compound as a pale yellow solid (23 mg, 68.7%; calculated as the acetate salt). Purification was accomplished by reversed-phase HPLC on a preparative Vydac C18 column (2.5 cm) using a 0.23% /min. gradient of 7 to 14% acetonitrile containing 0.1% trifluoroacetic acid and then lyophilized to give the TFA salt of the title compound as a fluffy white solid (31% recovery; overall yield 12.4%). Mass spectrum: M+H=561.46.

EXAMPLE 3a cyclo-(Abu-NMeArg-Gly-Asp-Mamb); the compound of formula (II) wherein J=Abu, K= NMeArg, L=Gly, M=Asp, R$^1$=H, R$^2$=H (SEW ID NO:3)

The title compound was prepared using the general procedure described for cyclo-(D-Val-NMeArg-Gly-Asp-Mamb) (Example 4). The DCC/DMAP method was used for attachment of Boc-Mamb to the oxime resin. TBTU was used as the coupling reagent. The peptide was prepared on a 0.596 mmol scale to give the protected cyclic peptide (182 mg,38.4%). The peptide (176 mg) and 0.176 mL of anisole were treated with anhydrous hydrogen fluoride at 0° C. for 20 minutes. The crude material was 0 precipitated with ether, redissolved in aqueous acetonitrile, and lyophilized to generate the title compound (116 mg; 90.4%; calculated as the fluoride salt). Purification was accomplished by reversed-phase HPLC on a preparative Vydac C18 column (2.5 cm) using a 0.45% /min. gradient of 9 to 27% acetonitrile containing 0.1% TFA and then lyophilized to give the TFA salt of the title compound as a fluffy white solid (1.92% recovery, overall yield 0.574%); FAB-MS: [M+H]=561.39.

EXAMPLE 4 cyclo-(D-Val-NMeArg-Gly-Asp-Mamb); the compound of formula (II) wherein J=D-Val, K= NMeArg, L=Gly, M=Asp, R$^1$=R$^2$=H To a 25 ml polypropylene tube fitted with a frit was added Boc-Mamb (0.126 g, 0.5 mmol) and 6 ml of DMF. To this was added HBTU (0.194 g, 0.5 mmol), oxime resin (0.52 g, substitution level=0.96 mmol/g), and N-methylmorpholine (0.165 ml, 1.50 mmol). The suspension was mixed at room temperature for 24 hours. The resin was then washed thoroughly (10–12 ml volumes) with DMF (3×), MeOH (1×), DCM (3×), MeOH (2×) and DCM (3×). The substitution level was determined to be 0.389 mmol/g by quantitative ninhydrin assay. Unreacted oxime groups were blocked by treatment with 0.5M trimethylacetylchloride/0.5M DIEA in DMF for 2 hours.

The following steps were then performed: (Step 1) The resin was washed with DMF(3×), MeOH (1×), DCM (3×), MeOH (2×), and DCM (3×). (Step 2) The t-Boc group was deprotected using 25% TFA in DCM for 30 minutes. (Step 3) The resin was washed with DCM (3×), MeOH (1×), DCM (2×), MeOH (3×) and DMF(3×) (Step 4) Boc-Asp(OcHex) (0.613 g, 1.94 mmol), HBTU (0.753 g, 1.99 mmol), 8 ml of DMF, and N-methylmorpholine (0.642 ml, 5.84 mmol) were added to the resin and the reaction allowed to proceed for 2.5 hours. (Step 5) The coupling reaction was found to be complete as assessed by the qualitative ninhydrin assay. Steps 1–5 were repeated until the desired sequence had been attained. The coupling of Boc-D-Val to NMeArg was monitored by the picric acid test.

After the linear peptide was assembled, the N-terminal t-Boc group was removed by treatment with 25% TFA in DCM (30 min.) The resin was washed thoroughly with DCM (3×), MeOH (2×) and DCM (3×), and then neutralized with 10% DIEA in DCM (2×1 min.) The resin was washed thoroughly with DCM (3×) and MeOH (3×) and then dried. Half of the resin (0.101 mmol) was cyclized by treating with 6 ml of DMF containing HOAc (5.8 mL, 0.101 mmol) and heating at 50 C for 72 hours. The resin was then filtered through a scintered glass funnel and washed thoroughly with DMF. The DMF filtrate was evaporated to an oil, redissolved in 1:1 acetonitrile: $H_2O$, and lyophilized to give the protected cyclic peptide (49 mg, 60%). The peptide (42 mg) was treated with anhydrous hydrogen fluoride at 0° C., in the presence of 50 mL of m-cresol as scavenger, for 30 minutes to remove side chain protecting groups The crude material was precipitated with ether, redissolved in aqueous HOAc, and lyophilized to generate the title compound as a pale yellow solid (23 mg, 70%; calculated as the acetate salt). Purification was accomplished using reversed-phase HPLC with a preparative Vydac C18 column (2.5 cm) and a 0.23%/minute gradient of 7 to 18% acetonitrile containing 0.1% trifluoroacetic acid to give the TFA salt of the title compound as a fluffy white solid (24% recovery; overall yield 9.4%); FAB-MS: [M+H]=575.45.

Solution Phase Synthesis of Example 4

The following abbreviations are used below for TLC solvent systems: chloroform/methanol 95:5=CM; chloroform/acetic acid 95:5=CA; chloroform/methanol/acetic acid 95:5=CMA BocNMeArg(Tos)-Gly-O Bzl—25 mmol BocNMeArg (Tos) (11.07 g, Bachem), 30 mmol Gly-O Bzl tosylate (10.10 g, Bachem), 25 mmol HBTU (0-Benzotriazole-N,N, N',N',-tetramethyl-uronium-hexafluorophosphate; 9.48 g; Advanced Chemtech), and 75 mmol DIEA (diisopropylethylamine; Aldrich) were dissolved in 25 ml $CH_2Cl_2$. The reaction was allowed to proceed 1 hr, the solvent was evaporated under reduced pressure at 50° to a syrup, which was dissolved in 400 ml ethyl acetate. This solution was extracted with (150 ml each) 2×5% citric acid, 1×water, 2×sat. $NaHCO_3$, 1×sat. NaCl. The organic layer was dried over $MgSO_4$, and the solvent evaporated under reduced pressure. The resulting oil was triturated with petroleum ether and dried under high vacuum for a minimum of 1 hr. yield 14.7 g (99.5%); TLC $R_{f(CM)}$=0.18 $R_{f(CA)}$=0.10; NMR is consistent with structure; FABMS M+H$^+$=590.43 (expected 590.26).

NMeArg(Tos)-Gly-O Bzl—14.5 g (BocNMeArg(Tos)-Gly-O Bzl (24.5 mmol) was dissolved in 30 ml TFA, allowed to react for 5 min., and the solvent evaporated at 1 mm mecury pressure at r.t. The resulting syrup was dissolved in 400 ml ice cold ethyl acetate, and extracted with 100 ml ice cold sat. NaHCO 3, the aqueous phase was extracted twice with 200 ml ethyl acetate, and the combined organic phases were extracted once with 25 ml sat. NaCl. The solvent was evaporated under reduced pressure giving a viscous oil that was triturated with 300 ml ether. The resulting solid was filtered and washed with ether, giving a hydroscopic compound that was dried in a vacuum desiccator: yield 10.33 g (86.2%); TLC $R_{f(CM)}$=0.03; $R_{f(CMA)}$=0.20; NMR is consistent with structure; FABMS M+H$^+$=490.21 (expected 490.20).

Boc-D-Val-NMeArg(Tos)-Gly-O Bzl—9.80 mmol NMeArg(Tos)-Gly-OBzl (4.80 g), 9.82 mmol Boc-D-Val (2.13 g, Bachem), and 10.0 mmol HBTU (3.79 g) were dissolved in 10 ml methylene chloride. The flask was placed on an ice bath, and 20 mmol DIEA (3.48 ml) was added. The reaction was allowed to proceed at 0° for 15 min and 2 days at r.t. The reaction mixture was diluted with 400 ml ethyl acetate, extracted (200 ml each) 2×5% citric acid, 1×sat. NaCl , dried over $MgSO_4$ and evaporated under reduced pressure. The resulting oil was triturated with 50, then 30 ml ether for 30 min with efficient mixing: yield 4.58 g (69%); TLC $R_{f(CM)}$=0.27 (also contains a spot near the origin, which is an aromatic impurity that is removed during trituration of the product in the next step); NMR is consistent with structure; FABMS M+H$^+$=689.59 (expected 689.43).

Boc-D-Val-NMeArg(Tos)-Gly—4.50 g Boc-D-Val-NMeArg(Tos)-Gly-OBzl (4.44 mmol) dissolved in 80 ml methanol was purged with $N_2$ for 10 min. 1.30 g Pd/C catalyst (10% Fluka lot #273890) was then added, and then $H_2$ was passed directly over the surface of the reaction. TLC showed the reaction to be complete within approximately 0.5 hr. After 1 hr. the catalyst was removed by filtering through a bed of Celite, and the solvent removed at 40° under reduced pressure. The resulting solid was triturated well with 50 ml refluxing ether, filtered, and washed with petroleum ether: yield 3.05 g (78%); TLC $R_{f(CM)}$=0.03; $R_{f(CMA)}$=0.37; NMR is consistent with structure; FABMS M+H$^+$=599.45 (expected 599.29).

4-Nitrobenzophenone Oxime (Ox)—50 g 4-nitrobenzophenone (220 mmol, Aldrich) and 30.6 g hydroxylamine hydrochloride (Aldrich, 440 mmol) were heated at reflux in 0.5 L methanol/pyridine (9:1) for 1 hr. The reaction mixture was evaporated under reduced pressure, dissolved in 500 ml ether, and extracted with 200 ml each of 5% citric acid (2 times) and sat. NaCl (1 time), dried over $MgSO_4$, evaporated under reduced pressure and triturated with ether giving 44.35 g (83%) of the oxime as a mixture of the cis and trans isomers: TLC $R_{f(CM)}$=0.50; $R_{f(CMA)}$=0.82; NMR is consistent with structure; FABMS M+H$^+$=242.07 (expected 242.07). BocMamb-Ox—22 mmol Boc-Mamb (5.522 g), 20 mmol nitrobenzophenone oxime (4.84 g), and 20 mmol DMAP (4-dimethylaminopyridine; Aldrich) were dissolved in 40 ml $CH_2Cl_2$ The flask was placed on an ice bath, and 21 mmol DCC (Dicyclohexylcarbodiimide; 4.33 g) was added. The reaction was allowed to proceed on ice for 30 min and at r.t. over night. The dicyclohexylurea formed was filtered, and washed with 40 ml methylene chloride. The filtrate was evaporated under reduced pressure at r.t. to a syrup, and dissolved in 400 ml ethyl acetate. This solution was extracted with (150 ml each) 2×5% citric acid, 1×water, 2×sat. $NaHCO_3$, 1×sat. NaCl. The organic layer was dried over $MgSO_4$, and the solvent evaporated under reduced pressure. The resulting oil was triturated with petroleum ether and dried under high vacuum for a minimum of 1 hr.: yield 7.51 g (79%); TLC $R_{f(CM)}$=0.41; $R_{f(CMA)}$=0.66; NMR is consistent with structure; FABMS M+H$^+$=476.30 (expected 476.18).

TFA.MAMB-Ox—BocMamb-Ox, 7.4 g (15.5 mmol) was dissolved in 30 ml methylene chloride plus 10 ml TFA (25%

TFA). The reaction was allowed to proceed at r.t. for 1 hr, and the solvent evaporated under reduced pressure at r.t. for 10 min, then at 40° for 15 min. The resulting syrup was triturated with ether (200 ml) at −5°, giving. The resulting crystals were filtered after 1 hr and washed well with ether: yield 7.22 g (95%); $R_{f(CMA)}$=0.25; NMR is consistent with structure; FABMS M+H$^+$=376.22 (expected 376.12).

Boc-Asp(OcHex)-Mamb-Ox—20 mmol Boc-Asp (OcHex) (6.308 g, Bachem) and 44 mmol DIEA (7.66 ml) were dissolved in 20 ml DMF. 20 mmol HBTU (7.58 g, Advanced Chemtech) was added, and the reaction allowed to proceed for 2 minutes with vigorous stirring. TFA-Mamb-Ox (7.13 g, 15 mmol) was added, and the reaction allowed to proceed o.n. at r.t. The solvent was removed under reduced pressure giving an oil, which was dissolved in 500 ml ethyl acetate, and this solution was extracted with (150 ml each) 2×5% citric acid, 1×water, 2×sat. NaHCO$_3$, 1 ×sat. NaCl. The organic layer was dried over MgSO$_4$, and the solvent evaporated under reduced pressure. The resulting oil was triturated with petroleum ether and dried under high vacuum: yield 9.76 g (97%); TLC $R_{f(CM)}$=0.55; NMR is consistent with structure; FABMS M+H$^+$=673.45 (expected 673.23).

TFA Asp(OcHex)-MAMB-Ox—15 mmol Boc-Asp (OcHex)-MAMB-Ox was dissolved in 50 ml 35% TFA in CH$_2$Cl$_2$, and allowed to react 90 min. The solvent was evaporated under reduced pressure at r.t. for 10 min, then at 40° for 15 min. To remove traces of TFA, 25 ml DMF was added and the solvent evaporated at 50°. The resulting syrup was triturated with ether (200 ml), then dried under high vacuum: yield 9.61 g (93%); $R_{f(CMA)}$=0.45; NMR is consistent with structure; FABMS M+H$^+$=573.56 (expected 573.23).

Boc-D-Val-NMeArg(Tos)-Gly-Asp(OcHex)-MAMB-Ox 10.0 mmol each TFA Asp(OcHex)-MAMB-Ox, Boc-D-Val-NMeArg(Tos)-Gly, and HBTU, plus 30 mmol DIEA were dissolved in 20 ml DMF. After 4 hr., the solvent was removed under reduced pressure, and the residue taken up in 600 ml ethyl acetate, which was extracted with 300 ml each of 5% citric acid, water and sat. NaCl. The organic layer was dried over MgSO$_4$, evaporated under reduced pressure, triturated with ether and dried in vacuo: yield 9.90 g (86%); $R_{f(CM)}$=0.10; NMR is consistent with structure; FABMS M+H$^+$=1153.22 (expected 1153.47).

TFA.D-Val-NMeArg(Tos)-Gly-Asp(OcHex)-MAMB-Ox This compound was prepared from Boc-D-Val-NMeArg (Tos)-Gly-Asp(OcHex)-MAMB-Ox (9.8 g, 8.5 mmol) by treatment with TFA/CH$_2$Cl$_2$ (1:1) for 45 min. The solvent was evaporated and the product triturated with ether: yield 9.73 g (98%); $R_{f(CM)}$=0.10; NMR is consistent with structure; FABMS M+H$^+$=1053.22 (expected 1053.4).

cyclo (.D-Val-NMeArg(Tos)-Gly-Asp(OcHex)-MAMB) TFA.D-Val-NMeArg(Tos)-Gly-Asp(OcHex)-MAMB-Ox (1.80 g, 1.54 mmol), and 2 mmol each of DIEA and acetic acid were dissolved in 200 ml DMF. The mixture was heated to 50° for 2 days, then evaporated under reduced pressure. The syrup was dissolved in 400 ml ethyl acetate/n-butanol (1:1), and extracted with 200 ml each of 5% citric acid (3×) and sat. NaCl (1×). The organic layer was dried over MgSO$_4$ and triturated twice with 200 ml ether: yield 1.07 g (86%); $R_{f(CM)}$=0.10; NMR is consistent with structure; FABMS M+H$^+$=811.25 (expected 811.38).

cyclo(.D-Val-NMeArg-Gly-Asp-MAMB) 0.50 g cyclo (D-Val-NMeArg(Tos)-Gly-Asp(OcHex)-MAMB) was treated with 5 ml HF at 0° C., in the presence of 0.5 ml of anisole for 30 min. The HF was removed under reduced pressure and the crude peptide triturated with ether, ethyl acetate and ether. The resulting solid was dissolved in 10% acetic acid and lyophilized: yield 0.321 g (82% calculated as the acetate salt). The product was purified with a recovery of approximately 40% using the same method as described for the material synthesized by the solid phase procedure.

CRYSTALLIZATION OF THE COMPOUND OF EXAMPLE 4 AND THE PREPARATION OF SALT FORMS OF THE COMPOUND OF EXAMPLE 4

It has been discovered that the compounds of the present invention may be isolated by crystallization of the compound from organic and aqueous solvents.

The zwitterion of Example 4 was converted to the mesyl (methanesulfonate) salt of Example 4 (Example 4 (methanesulfonate)) by refluxing the zwitterion with stirring in isopropanol at 25 mg/ml and slowly adding a solution of 1.0 molar equivalent methanesulfonic acid (correcting for the water content of the zwitterion) dissolved in isopropanol. The heat was turned off and the solution cooled to 5° C. in an ice bath. After stirring 1 hour, the solution was filtered and the solid rinsed three times with cold isopropanol and dried under vacuum to constant weight.

The following salts of the compound of Example 4 were prepared using the same procedure, by adding 1.0 equivalent of the appropriate acid:

Example 4 (biphenylsulfonate):
zwitterion+1.0 equivalent biphenylsulfonic acid.

Example 4 (α-naphthalenesulfonate):
zwitterion+1.0 equiv. α-naphthalenesulfonic acid.

Example 4 (β-naphthalenesulfonate):
zwitterion +1.0 equiv. β-naphthalenesulfonic acid.

Example 4 (benzenesulfonate):
zwitterion+1.0 equiv. benzene-sulfonic acid.

Example 4 (p-toluenesulfonate):
zwitterion+1.0 equiv. p-toluene-sulfonic acid.

The following salts of the compound of Example 4 were prepared by crystallization of the compound from aqueous systems.

Example 4 (sulfate)

10 mg amorphous Example 4 (made by lyophilizing the zwitterion from a solution of 2 molar equivalents of acetic acid in water) dissolved per ml 1N H$_2$SO$_4$, pH adjusted to 2.5. On standing at room temperature, a precipitate formed. This was filtered through a sintered glass funnel and dried under vacuum to constant weight.

Example 4 (methanesulfonate (mesyl))

100 mg amorphous DMP728 dissolved per ml water+1.2 molar equiv. methanesulfonic acid (this was obtained as a 4M aqueous solution). On standing at room temperature, a large flat crystal was formed.

Example 4 (benzenesulfonate)

100 mg zwitterion dissolved per ml water+1.2 equiv. benzenesulfonic acid added. On standing at room temperature, a precipitate formed. This was filtered through a sintered glass funnel, rinsed with a small volume of isopropanol, and dried under vacuum to constant weight.

Example 4 (p-toluenesulfonate)

100 mg zwitterion dissolved per ml water+1.2 molar equiv. toluenesulfonic acid added. On standing at room temperature, a precipitate formed. This was filtered through a sintered glass funnel and dried under vacuum to constant weight.

EXAMPLE 4b cyclo-(D-Val-D-NMeArg-Gly-Asp-Mamb); J=D-Val, K=D-NMeArg, L=Gly, M=Asp, $R^1$=H, $R^2$=H The title compound was prepared using the general procedure described for cyclo-(D-Val-NMeArg-Gly-Asp-Mamb) (Example 4). The DCC/DMAP method was used for attachment of Boc-Mamb to the oxime resin. The peptide was prepared on a 0.596 mmol scale to give the protected cyclic peptide (186 mg, 38.6%). The peptide (183 mg) and 0.183 mL of anisole were treated with anhydrous hydrogen fluoride at 0° C. for 30 minutes. The crude material was precipitated with ether, redissolved in aqueous acetonitrile, and lyophilized to generate the title compound (145 mg, greater than quantitative yield; calculated as the fluoride salt). Purification was accomplished by reversed-phase HPLC on a preparative Vydac C18 column (2.5 cm) using a 0.23% /min. gradient of 9 to 22.5% acetonitrile containing 0.1% TFA and then lyophilized to give the TFA salt of the title compound as a fluffy white solid (14.8% recovery, overall yield 5.3%); FAB-MS: [M+H]=575.31.

EXAMPLE 5 cyclo-(D-Leu-NMeArg-Gly-Asp-Mamb); the compound of formula (II) wherein J=D-Leu, K=NMeArg, L=Gly, M=Asp, $R^1$=$R^2$=H The title compound was prepared using the general procedure described above for cyclo-(D-Val-NMeArg-Gly-Asp-Mamb). The peptide was prepared on a 0.115 mmol scale to give the protected cyclic peptide (92.4 mg, 98%). The peptide (92.4 mg) and 93 mL of m-cresol were treated with anhydrous hydrogen fluoride at 0° C. for 20 minutes. The crude material was precipitated with ether, redissolved in aqueous HOAc, and lyophilized to generate the title compound as a pale yellow solid (45.7 mg, 63%; calculated as the acetate salt). Purification was accomplished by reversed-phase HPLC on a preparative C18 reversed-phase column (2.5 cm) (Vydac) using a 0.23% /min. gradient of 7 to 21% acetonitrile containing 0.1% TFA and then lyophilized to give the TFA salt of the title compound as a fluffy white solid (29% recovery, overall yield 16.5%);FAB-MS: [M+H]=589.48.

EXAMPLE 7 cyclo-(D-Nle-NMeArg-Gly-Asp-Mamb); the compound of formula (II) wherein J=D-Nle, K=NMeArg, L=Gly, M=Asp, $R^1$=H, $R^2$=H The title compound was prepared using the general procedure described for cyclo-(D-Val-NMeArg-Gly-Asp-Mamb) (Example 4). The DCC/DMAP method was used for attachment of Boc-Mamb to the oxime resin. The peptide was prepared on a 0.586 mmol scale to give the protected cyclic peptide (305 mg, 63.3%). The peptide (295 mg) and 0.295 mL of anisole were treated with anhydrous hydrogen fluoride at 0° C. for 30 minutes. The crude material was precipitated with ether, redissolved in aqueous acetonitrile, and lyophilized to generate the title compound (207 mg, 95.4%; calculated as the fluoride salt). Purification was accomplished by reversed- phase HPLC on a preparative C18 reversed-phase column (2.5 cm (Vydac) using a 0.23% /min. gradient of 5.4 to 18% acetonitrile containing 0.1% TFA and then lyophilized to give the TFA salt of the title compound as a fluffy white solid (44% recovery, overall yield 22.9%); FAB-MS: [M+H]=589.26.

EXAMPLE 11 cyclo-(D-Phg-NMeArg-Gly-Asp-Mamb); the compound of formula (II) wherein J=D-Phg, K=NMeArg, L=Gly, M=Asp, $R^1$=H, $R^2$=H The title compound was prepared using the general procedure described for cyclo-(D-Val-NMeArg-Gly-Asp-Mamb) (Example 4). The DCC/DMAP method was used for attachment of Boc-Mamb to the oxime resin. The peptide was prepared on a 0.611 mmol scale to give the protected cyclic peptide (296 mg, 57.4%). The peptide (286 mg) and 0.286 mL of anisole were treated with anhydrous hydrogen fluoride at 0° C. for 30 minutes. The crude material was precipitated with ether, redissolved in aqueous acetonitrile, and lyophilized to generate the title compound (210 mg, 98.9%; calculated as the fluoride salt). Purification was accomplished by reversed-phase HPLC on a preparative C18 reversed-phase column (2.5 cm) (Vydac) using a 0.23% /min. gradient of 5.4 to 18% acetonitrile containing 0.1% TFA and then lyophilized to give the TFA salt of the title compound as a fluffy white solid (24.2% recovery, overall yield 11.9%); FAB-MS: [M+H]=609.27.

EXAMPLE 12 cyclo-(D-Phe-NMeArg-Gly-Asp-Mamb); the compound of formula (II) wherein J=D-Phe, K=NMeArg, L=Gly, M=Asp, $R^1$=H, $R^2$=H The title compound was prepared using the general procedure described for cyclo-(D-Val-NMeArg-Gly-Asp-Mamb) (Example 4). The DCC/DMAP method was used for attachment of Boc-Mamb to the oxime resin. The peptide was prepared on a 0.611 mmol scale to give the protected cyclic peptide (140 mg, 26.7%). The peptide (135 mg) and 0.135 mL of anisole were treated with anhydrous hydrogen fluoride at 0° C. for 30 minutes. The crude material was precipitated with ether, redissolved in aqueous acetonitrile, and lyophilized to generate the title compound (108 mg, greater than quantitative yield; calculated as the fluoride salt). Purification was accomplished by reversed-phase HPLC on a preparative C18 reversed-phase column (2.5 cm) (Vydac) using a 0.23% /min. gradient of 7.2 to 22.5% acetonitrile containing 0.1% TFA and then lyophilized to give the TFA salt of the title compound as a fluffy white solid (35% recovery, overall yield 8.7%); FAB-MS: [M+H]=623.28.

EXAMPLE 13f cyclo-(D-Lys-NMeArg-Gly-Asp-Mamb); the compound of formula (II) wherein J=D-Lys, K=NMeArg, L=Gly, M=Asp, $R^1$=$R^2$=H The title compound was prepared using the general procedure described above for cyclo-(D-Val-NMeArg-Gly-Asp-Mamb). The DCC/DMAP method was used for attachment of Boc-Mamb to the oxime resin. The peptide was prepared on a 0.586 mmol scale to give the protected cyclic peptide (349 mg, 58.9%). The peptide (334 mg) and 334 mL of anisole were treated with anhydrous hydrogen fluoride at 0° C. for 30 minutes. The crude material was precipitated with ether, redissolved in aqueous acetonitrile, and lyophilized to generate the title compound as a pale yellow solid (168 mg, 79.1%; calculated as the difluoride salt). Purification was accomplished by reversed-phase HPLC on a preparative C18 reversed-phase column (2.5 cm) (Vydac) using a 0.23% /min. gradient of 5.4 to 14.4% acetonitrile containing 0.1% TFA and then lyophilized to give the TFA salt of the title compound as a fluffy white solid (33.6% recovery, overall yield 12.1%); FAB-MS: [M+H]=604.32

EXAMPLE 13r cyclo-(D-Ile-NMeArg-Gly-Asp-Mamb); the compound of formula (II) wherein J=D-Ile, K=NMeArg, L=Gly, M=Asp, $R^1$=H, $R^2$=H The title compound was prepared using the general procedure described for cyclo-(D-Val-NMeArg-Gly-Asp-Mamb) (example 4). The DCC/DMAP method was used for attachment of Boc-Mamb to the oxime resin. The peptide was prepared on a 0.611 mmol scale to give the protected cyclic peptide (349 mg, 69.2%). The peptide (342 mg) and 0.342 mL of anisole were treated with anhydrous hydrogen fluoride at 0° C. for 30 minutes. The crude material was precipitated with ether, redissolved in aqueous acetonitrile, and lyophilized to generate the title compound (227 mg, 90%; calculated as the fluoride salt). Purification was accomplished by reversed-phase HPLC on a preparative C18 reversed-phase column (2.5 ) (Vydac) using a 0.23% /min. gradient of 10.8 to 19.8% acetonitrile containing 0.1% TFA and then lyophilized to give the TFA salt of the title compound as a fluffy white solid (22.5% recovery, overall yield 12.1%); FAB-MS: [M+H]=589.34.

EXAMPLE 17 cyclo-(D-Met-NMeArg-Gly-Asp-Mamb); the compound of formula (II) wherein J=D-Met, K=NMeArg, L=Gly, M=Asp, $R^1$=H, $R^2$=H The title compound was prepared using the general procedure described for cyclo-(D-Val-NMeArg-Gly-Asp-Mamb) (Example 4). The DCC/DMAP method was used for the attachment of Boc-Mamb to the resin. The peptide was prepared on a 0.179 mmol scale to give the protected cyclic peptide (105 mg, 69.7%). The peptide (105 mg) and 0.105 mL of anisole were treated with anhydrous hydrogen fluoride at 0° C. for 20 minutes. The crude material was precipitated with ether, redissolved in aqueous acetonitrile, and lyophilized to generate the title compound (72 mg; 92.3% yield; calculated as the fluoride salt). Purification was accomplished by reversed-phase HPLC on a preparative C18 reversed-phase column (2.5 cm) (Vydac) using a 0.23% /min. gradient of 14.4 to 23.4% acetonitrile containing 0.1% TFA and then lyophilized to give the TFA salt of the title compound as a fluffy white solid (13.2% recovery, overall yield 7.4%); FAB-MS: [M+H]=607.3.

EXAMPLE 18 cyclo-(NMeGly-NMeArg-Gly-Asp-Mamb); the compound of formula (II) wherein J=NMeGly, K=NMeArg, L=Gly, M=Asp, $R^1$=$R^2$=H (SEQ ID NO:27)

The title compound was prepared using the general procedure described above for cyclo-(D-Val-NMeArg-Gly-Asp-Mamb). The DCC/DMAP method was used for attachment of Boc-Mamb to the oxime resin. The peptide was prepared on a 0.43 mmol scale to give the protected cyclic peptide (205 mg, 60%). The peptide (200 mg) and 200 mL of m-cresol were treated with anhydrous hydrogen fluoride at 0° C. for 30 minutes. The crude material was precipitated with ether, redissolved in aqueous HOAc, and lyophilized to generate (18) as a pale yellow solid (148 mg, 97%; calculated as the acetate salt). Purification was accomplished by reversed-phase HPLC on a preparative C18 reversed-phase column (2.5 cm) (Vydac) using a 0.23% /min. gradient of 7 to 22% acetonitrile containing 0.1% TFA and then lyophilized to give the TFA salt of (18) as a fluffy white solid (14.7% recovery, overall yield 7.9%); FAB-MS: [M+H]=547.34.

EXAMPLE 24 cyclo-(Pro-NMeArg-Gly-Asp-Mamb); the compound of formula (II) wherein J=Pro, K=NMeArg, L=Gly, M=Asp, $R^1$=$R^2$=H The title compound was prepared using the general procedure described above for cyclo-(D-Val-NMeArg-Gly-Asp-Mamb). The DCC/DMAP method was used for attachment of Boc-Mamb to the oxime resin. The peptide was prepared on a 0.43 mmol scale to give the protected cyclic peptide (170 mg, 48.8%). The peptide (164 mg) and 164 mL of m-cresol were treated with anhydrous hydrogen fluoride at 0° C. for 30 minutes. The crude material was precipitated with ether, redissolved in aqueous HOAc, and lyophilized to generate (24) as a pale yellow solid (101 mg, 79%; calculated as the acetate salt). Purification was accomplished by reversed-phase HPLC on a preparative C18 reversed--phase column (2.5 cm) (Vydac) using a 0.23% /min. gradient of 7 to 22% acetonitrile containing 0.1% TFA and then lyophilized to give the TFA salt of (24) as a fluffy white solid (5.8% recovery, overall yield 2.1%);FAB-MS: [M+H]=573.46.

EXAMPLE 25 cyclo-(D-Pro-NMeArg-Gly-Asp-Mamb); the compound of formula (II) wherein J=D-Pro, K=NMeArg, L=Gly, M=Asp, $R^1$=$R^2$=H The title compound was prepared using the general procedure described above for cyclo-(D-Val-NMeArg-Gly-Asp-Mamb). The DCC/DMAP method was used for attachment of Boc-Mamb to the oxime resin. The peptide was prepared on a 0.43 mmol scale to give the protected cyclic peptide (211mg, 60.8%). The peptide (200 mg) and 200 mL of m-cresol were treated with anhydrous hydrogen fluoride at 0° C. for 30 minutes. The crude material was precipitated with ether, redissolved in aqueous HOAc, and lyophilized to generate (25) as a pale yellow solid (145 mg, 93.3%; calculated as the acetate salt). Purification was accomplished by reversed-phase HPLC on a preparative C18 reversed--phase column (2.5 cm) (Vydac) using a 0.23% /min. gradient of 7 to 22% acetonitrile containing 0.1% TFA and then lyophilized to give the TFA salt of (25) as a fluffy white solid (6.4% recovery, overall yield 3.3%); FAB-MS: [M+H]==573.35.

EXAMPLE 28c cyclo-(b-Ala-NMeArg-Gly-Asp-Mamb); the compound of formula (II) wherein J=b-Ala, K=NMeArg, L=Gly, M=Asp, $R^1$=$R^2$=H (SEQ ID NO:34)

The title compound was prepared using the general procedure described above for cyclo-(D-Val-NMeArg-Gly- Asp-Mamb). The DCC/DMAP method was used for attachment of Boc-Mamb to the oxime resin. The peptide was prepared on a 0.586 mmol scale to give the protected cyclic peptide (264 mg, 57.5%). The peptide (258 mg) and 258 mL of anisole were treated with anhydrous hydrogen fluoride at 0° C. for 30 minutes. The crude material was precipitated with ether, redissolved in aqueous acetonitrile, and lyophilized to generate the title compound as a pale yellow solid (231 mg, greater than quantitative yield; calculated as the fluoride salt). Purification was accomplished by reversed-phase HPLC on a preparative C18 reversed-phase column (2.5 cm) (Vydac) using a 0.23% /min. gradient of 5.4 to 14.4% acetonitrile containing 0.1% TFA and then lyophilized to give the TFA salt of the title compound as a fluffy white solid (53.2% recovery, overall yield 32.5%); FAB-MS: [M+H]=547.28.

EXAMPLE 28f cyclo-(D-Tyr-NMeArg-Gly-Asp-Mamb); the compound of formula (II) wherein J=D-Tyr, K=NMeArg, L=Gly, M=Asp, $R^1$=H, $R^2$=H The title compound was prepared using the general procedure described for cyclo-(D-Val-NMeArg-Gly-Asp-Mamb) (Example 4). The DCC/DMAP method was used for attachment of Boc-Mamb to the oxime resin. The peptide was prepared on a 0.313 mmol scale to give the protected cyclic peptide (342 mg, greater than quantitative yield). The peptide (331 mg) and 0.330 mL of anisole were treated with anhydrous hydrogen fluoride at 0° C. for 30 minutes. The crude material was precipitated with ether, redissolved in aqueous acetonitrile, and lyophilized to generate the title compound (218 mg, greater than quantitative yield; calculated as the fluoride salt). Purification was accomplished by reversed-phase HPLC on a preparative Vydac C18 column (2.5 cm) using a 0.23% /min. gradient of 9 to 18% acetonitrile containing 0.1% TFA and then lyophilized to give the TFA salt of the title compound as a fluffy white solid (11.3% recovery, overall yield 10.8%); FAB-MS: [M+H]=639.54.

EXAMPLE 29 cyclo-(Gly-Arg-Gly-Asp-Mamb); the compound of formula (II) wherein j=Gly, K=Arg, L=Gly, M=Asp, $R^1$=$R^2$=H (SEQ ID NO:36)

The title compound was prepared using the general procedure described above for cyclo-(D-Val-NMeArg-Asp-Mamb). The peptide was prepared on a 0.283 mmol scale and half was cyclized to give the protected cyclic peptide (62 mg, 58%). The peptide (60 mg) and 60 mL of m-cresol were treated with anhydrous hydrogen fluoride at 0° C. for 1 hour. The crude material was precipitated with ether, redissolved in aqueous HOAc, and lyophilized to generate the title compound as a pale yellow solid (48 mg, >quantitative yield; calculated as the acetate salt). Purification was accomplished by reversed-phase HPLC on a preparative Vydac C18 column (2.5 cm) using a 0.30% /min. gradient of 0 to 9% acetonitrile containing 0.1% TFA and then lyophilized to give the TFA salt of the title compound as a fluffy white solid (36% recovery, overall yield 19.9%); FAB-MS: [M+H]=519.26.

EXAMPLE 30 cyclo-(D-Ala-Arg-Gly-Asp-Mamb); the compound of formula (II) wherein J=D-Ala, K=Arg, L=Gly, M=Asp, $R^1$=$R^2$=H The title compound was prepared using the general procedure described above for cyclo-(D-Val-NMeArg-Gly-Asp-Mamb). The peptide was prepared on a 0.189 mmol scale to give the protected cyclic peptide (211 mg, >quantitative yield). The peptide (195 mg) and 195 mL of m-cresol were treated with anhydrous hydrogen fluoride at 0° C. for 1 hour. The crude material was precipitated with ether, redissolved in aqueous HOAc, and lyophilized to generate the title compound as a pale yellow solid (125 mg, 83%; calculated as the acetate salt). Purification was accomplished by reversed-phase HPLC on a preparative Vydac C18 column (2.5 cm) using a 0.23% /min. gradient of 2 to 11% acetonitrile containing 0.1% TFA and then lyophilized to give the TFA salt of the title compound as a fluffy white solid (12.5% recovery, overall yield 13.8%); FAB-MS: [M+H]=533.26.

EXAMPLE 31 cyclo-(Ala-Arg-Gly-Asp-Mamb); the compound of formula (II) wherein J=Ala, K=Arg, L=Gly, M=Asp, $R^1$=$R^2$=H The title compound was prepared using the general procedure described above for cyclo-(D-Val-NMeArg-Gly-Asp-Mamb). The peptide was prepared on a 0.324 mmol scale to give the protected cyclic peptide (191 mg, 76.4%). The peptide (100 mg) and 100 mL of m-cresol were treated with anhydrous hydrogen fluoride at 0° C. for 1 hour. The crude material was precipitated with ether, redissolved in aqueous HOAc, and lyophilized to generate the title compound as a pale yellow solid (75 mg, 97.4%; calculated as the acetate salt). Purification was accomplished by reversed-phase HPLC on a preparative Vydac C18 column (2.5 cm) using a 0.23% /min. gradient of 2 to 11% acetonitrile containing 0.1% TFA and then lyophilized to give the TFA salt of the title compound as a fluffy white solid (15.5% recovery, overall yield 10.5%); FAB-MS: [M+H]=533.25.

EXAMPLE 32 cyclo-(D-Val-Arg-Gly-Asp-Mamb); the compound of formula (II) wherein J=D-Val, K=Arg, L=Gly, M=Asp, $R^1$=$R^2$=H The title compound was prepared using the general procedure described above for cyclo-(D-Val-NMeArg-Gly-Asp-Mamb). The peptide was prepared on a 0.193 mmol scale to give the protected cyclic peptide (199 mg, >quantitative yield). The peptide (193 mg) and 193 mL of m-cresol were treated with anhydrous hydrogen fluoride at 0° C. for 1 hour. The crude material was precipitated with ether, redissolved in aqueous HOAc, and lyophilized to generate the title compound as a pale yellow solid (130 mg, 86%; calculated as the acetate salt). Purification was accomplished by reversed-phase HPLC on a preparative Vydac C18 column (2.5 cm) using a 0.23% /min. gradient of 2 to 13% acetonitrile containing 0.1% TFA and then lyophilized to give the TFA salt of the title compound as a fluffy white solid (57% recovery, overall yield 58.1%); FAB-MS: [M+H]=561.22.

EXAMPLE 33 cyclo-(D-Leu-Arg-Gly-Asp-Mamb); the compound of formula (II) wherein J=D-Leu, K=Arg, L=Gly, M=Asp, $R^1$=$R^2$=H The title compound was prepared using the general procedure described above for cyclo-(D-Val-NMeArg-Gly-Asp-Mamb). The peptide was prepared on a 0.202 mmol scale to give the protected cyclic peptide (152 mg, 93%). The peptide (150 mg) and 150 mL of m-cresol were treated with anhydrous hydrogen fluoride at 0° C. for 1 hour. The crude material was precipitated with ether, redissolved in aqueous HOAc, and lyophilized to generate the title compound as a pale yellow solid (78 mg, 66%; calculated as the acetate salt). Purification was accomplished by reversed-phase HPLC on a preparative Vydac C18 column (2.5 cm) using a 0.23% /min. gradient of 5 to 18% acetonitrile containing 0.1% trifluoroacetic acid and then lyophilized to give the TFA salt of the title compound as a fluffy white solid (26% recovery, overall yield 14.8%); FAB-MS: [M+H]= 575.45.

EXAMPLE 34 cyclo-(D-Abu-Arg-Gly-Asp-Mamb); the compound of formula (II) wherein J=D-Abu, K=Arg, L=Gly, M=Asp, $R^1=R^2=H$ The title compound was prepared using the general procedure described above for cyclo-(D-Val-NMeArg-Gly-Asp-Mamb). The peptide was prepared on a 0.193 mmol scale to give the protected cyclic peptide (210 mg, >quantitative yield). The peptide (206 mg) and 206 mL of m-cresol were treated with anhydrous hydrogen fluoride at 0° C. for 1 hour. The crude material was precipitated with ether, redissolved in aqueous HOAc, and lyophilized to generate the title compound as a pale yellow solid (158 mg, 99%; calculated as the acetate salt). Purification was accomplished by reversed-phase HPLC on a preparative Vydac C18 column (2.5 cm) using a 0.23% /min. gradient of 2 to 11% acetonitrile containing 0.1% TFA and then lyophilized to give the TFA salt of the title compound as a fluffy white solid (57% recovery, overall yield 72.2%); FAB-MS: [M+H]= 547.21.

EXAMPLE 35 cyclo-(D-Ser-Arg-Gly-Asp-Mamb); the compound of formula (II) wherein J=D-Ser, K=Arg, L=Gly, M=Asp, $R^1=R^2=H$ The title compound was prepared using the general procedure described above for cyclo-(D-Val-NMeArg-Gly-Asp-Mamb). The peptide was prepared on a 0.193 mmol scale to give the protected cyclic peptide (224 mg, >quantitative yield). The peptide (210 mg) and 210 ml of m-cresol were treated with anhydrous hydrogen fluoride at 0° C. for 1 hour. The crude material was precipitated with ether, redissolved in aqueous HOAc, and lyophilized to generate the title compound as a pale yellow solid (145 mg, 89%; calculated as the acetate salt). Purification was accomplished by reversed-phase HPLC on a preparative Vydac C18 column (2.5 cm) using a 0.23% /min. gradient of 2 to 13% acetonitrile containing 0.1% TFA and then lyophilized to give the TFA salt of the title compound as a fluffy white solid (22% recovery, overall yield 27%); FAB-MS: [M+H]= 549.31.

EXAMPLE 36 cyclo-(D-Phe-Arg-Gly-Asp-Mamb); the compound of formula (II) wherein J=D-Phe, K=Arg, L=Gly, M=Asp, $R^1=R^2=H$ The title compound was prepared using the general procedure described above for cyclo-(D-Val-NMeArg-Gly-Asp-Mamb). The peptide was prepared on a 0.266 mmol scale to give the protected cyclic peptide (202 mg, 90%). The peptide (157 mg) and 157 mL of m-cresol were treated with anhydrous hydrogen fluoride at 0° C. for 1 hour. The crude material was precipitated with ether, redissolved in aqueous HOAc, and lyophilized to generate the title compound as a pale yellow solid (125 mg, >quantitative yield; calculated as the acetate salt). Purification was accomplished by reversed-phase HPLC on a preparative Vydac C18 column (2.5 cm) using a 0.23% /min. gradient of 7 to 23% acetonitrile containing 0.1% TFA and then lyophilized to give the TFA salt of the title compound as a fluffy white solid (35% recovery, overall yield 29.3%); FAB-MS: [M+H]= 609.25

EXAMPLE 37 cyclo-(Phe-Arg-Gly-Asp-Mamb); the compound of formula (II) wherein J=Phe, K=Arg, L=Gly, M= Asp, $R^1=R^2=H$ The title compound was prepared using the general procedure described above for cyclo-(D-Val-NMeArg-Gly-Asp-Mamb). The peptide was prepared on a 0.335 mmol scale to give the protected cyclic peptide (306 mg, >quantitative yield). The peptide (275 mg) and 275 mL of m-cresol were treated with anhydrous hydrogen fluoride at 0° C. for 1 hour. The crude material was precipitated with ether, redissolved in aqueous HOAc, and lyophilized to generate the title compound as a pale yellow solid (214 mg, 98%; calculated as the acetate salt). Purification was accomplished by reversed-phase HPLC on a preparative Vydac C18 column (2.5 cm) using a 0.23% /min. gradient of 9 to 23% acetonitrile containing 0.1% TFA and then lyophilized to give the TFA salt of the title compound as a fluffy white solid (32% recovery, overall yield 31.5%); FAB-MS: [M+H]= 609.26

EXAMPLE 40 cyclo-(D-Val-NMeAmf-Gly-Asp-Mamb); the compound of formula (II) wherein J=D-Val, K= NMeAmf, L=Gly, M=Asp, $R^1=R^2=H$ (SEQ ID NO:42)

The title compound was prepared using the general procedure described for cyclo-(D-Val-NMeArg-Gly-Asp-Mamb) (Example 4). The DCC/DMAP method was used for attachment of Boc-Mamb to the oxime resin. The peptide was prepared on a 0.586 mmol scale to give the protected cyclic peptide (189 mg, 39.9%). The peptide (189 mg) and 0.189 mL of anisole were treated with anhydrous hydrogen fluoride at 0° C. for 30 minutes. The crude material was precipitated with ether, redissolved in aqueous acetonitrile, and lyophilized to generate the title compound (212 mg, greater than quantitative yield; calculated as the fluoride salt). Purification was accomplished by reversed-phase HPLC on a preparative Vydac C18 column (2.5 cm) using a 0.23% /min. gradient of 10.8 to 22.5% acetonitrile containing 0.1% TFA and then lyophilized to give the TFA salt of the title compound as a fluffy white solid (8.1% recovery, overall yield 4.1%}; FAB-MS: [M+H]=595.23.

EXAMPLE 48a

The title compound may be synthesized using procedures described in Mosher et al. Tett. Lett. 29: 3183–3186, and as shown schematically below. This same procedure is a generally useful method for converting a primary amine into a guanidine functionality.

81
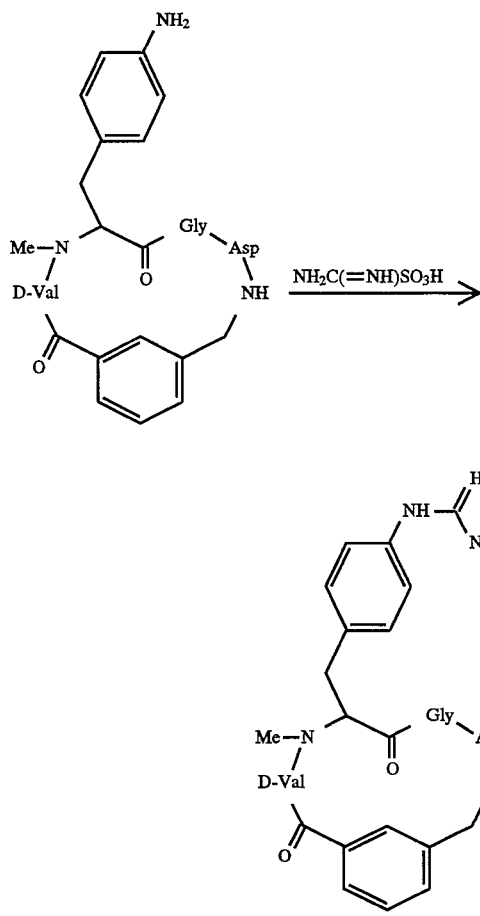
EXAMPLES 42–45
The synthesis of Examples 42–45 is shown schematically below.
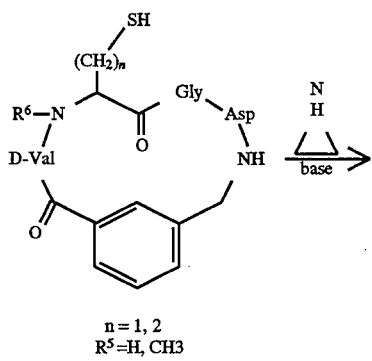
82
-continued
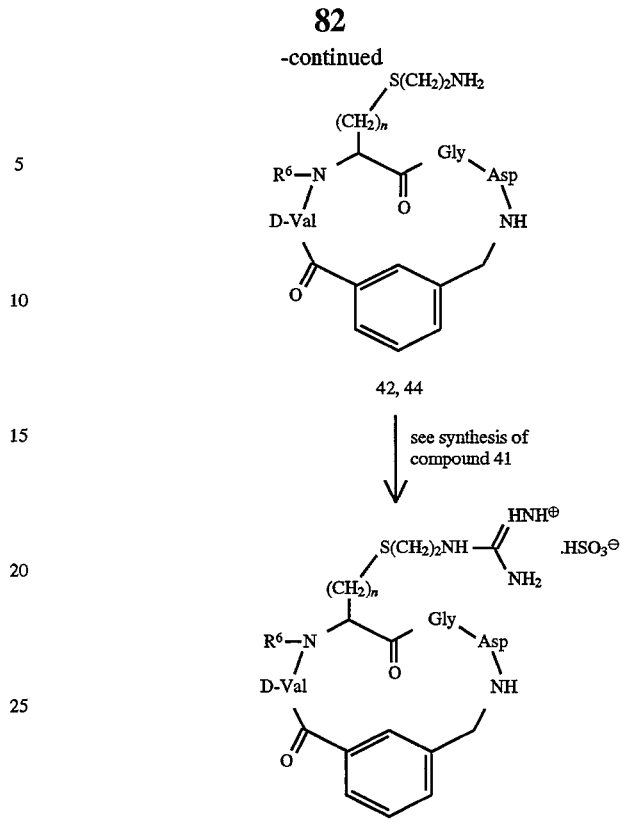
EXAMPLES 46 and 47
Examples 46 and 47 are prepared according to standard procedures, for example, as described in Garigipati, *Tett. Lett.* (1990) 31: 1969–1972 and in Canadian Patent 2008311, as is shown schematically below. The aspartic acid group may be protected (e.g., with a phenacyl protection group) to avoid side reactions.
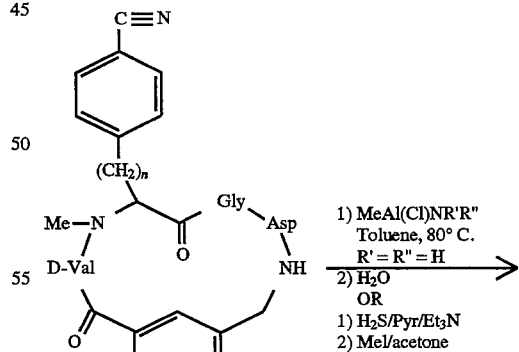

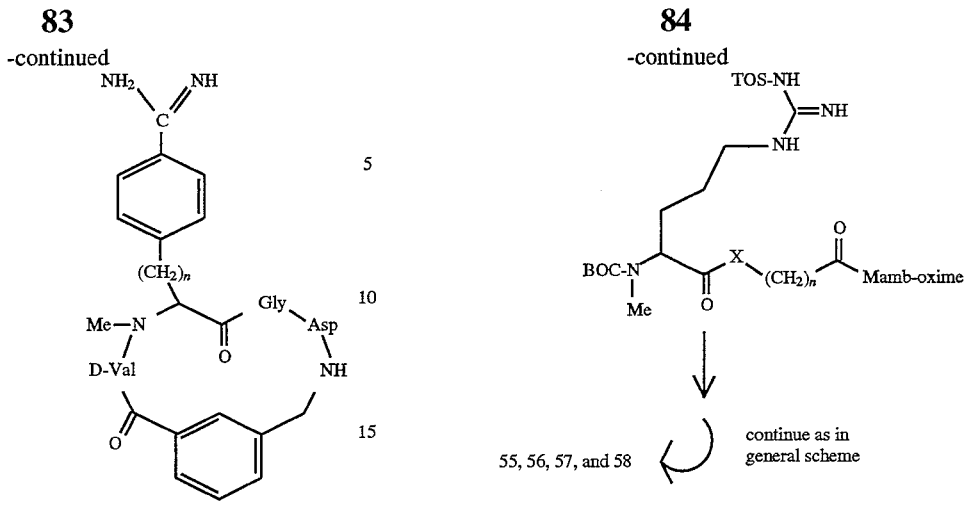

EXAMPLE 54 cyclo-(D-Val-NMeArg-b-Ala-Asp-Mamb); J=D-Val, K=NMeArg, L=b-Ala, M=Asp, R$^1$=R$^2$=H The title compound was prepared using the general procedure described above for cyclo-(D-Val-NMeArg-Gly-Asp-Mamb). The DCC/DMAP method was used for attachment of Boc-Mamb to the oxime resin. The peptide was prepared on a 0.586 mmol scale to give the protected cyclic peptide (227 mg, 46.9%). The peptide (219 mg) and 219 mL of anisole were treated with anhydrous hydrogen fluoride at 0° C. for 30 minutes. The crude material was precipitated with ether, redissolved in aqueous acetonitrile, and lyophilized to generate (54) as a pale yellow solid (150 mg, 93.2%; calculated as the fluoride salt). Purification was accomplished by reversed-phase HPLC on a preparative Vydac C18 column (2.5 cm) using a 0.23% /min. gradient of 7.2 to 16.2% acetonitrile containing 0.1% TFA and then lyophilized to give the TFA salt of (54) as a fluffy white solid (43.6% recovery, overall yield 16.5%); FAB-MS: [M+H]= 589.32.

EXAMPLES 55–58

The synthesis of Examples 55–58 is shown schematically below.

EXAMPLE 58c cyclo-(D-Val-NMeArg-L-Ala-Asp-Mamb); the compound of formula (II) wherein J=D-Val, K= NMeArg, L=L-Ala, M=Asp, R$^1$=H, R$^2$=H The title compound was prepared using the general procedure described for cyclo-(D-Val-NMeArg-Gly-Asp-Mamb) (Example 4). The DCC/DMAP method was used for attachment of Boc-Mamb to the oxime resin. The peptide was prepared on a 0.611 mmol scale to give the protected cyclic peptide (375 mg, 74.6%). The peptide (360 mg) and 0.360 mL of anisole were treated with anhydrous hydrogen fluoride at 0° C. for 30 minutes. The crude material was precipitated with ether, redissolved in aqueous acetonitrile, and lyophilized to generate the title compound (220 mg, 83%; calculated as the fluoride salt). Purification was accomplished by reversed-phase HPLC on a preparative Vydac C18 column (2.5 cm) using a 0.23% /min. gradient of 9 to 18% acetonitrile containing 0.1% TFA and then lyophilized to give the TFA salt of the title compound as a fluffy white solid (19.9% recovery, overall yield 10.6%); FAB-MS: [M+H]=589.31.

EXAMPLE 63 and 63a cyclo-(D-Val-NMeArg-Gly-α-MeAsp-Mamb); the compounds of formula (II) wherein J is D-Val; K is NMeArg; L is Gly; M is α-MeAsp; R$^1$=R$^2$=H The title compound was prepared using the general procedure described for cyclo-(D-Val-NMeArg-Gly-Asp-Mamb). The DCC/DMAP method was used for attachment of Boc-Mamb to the oxime resin. The peptide was prepared on a 0.794 mmol scale to give the protected cyclic peptide (237 mg, 36.1%). The peptide (237 mg) and 0.237 mL of anisole were treated with anhydrous hydrogen fluoride at 0° C. for 30 minutes. The crude material was precipitated with ether, redissolved in aqueous acetonitrile, and lyophilized to generate the title compound (165 mg, 94.3%; calculated as the fluoride salt). Purification was accomplished by reversed-phase HPLC on a preparative Vydac C18 column (2.5 cm) using a 0.23% /min. gradient of 9 to 18% acetonitrile containing 0.1% TFA and then lyophilized to give the TFA salt of the title compound as a fluffy white solid; isomer #1 (8.36% recovery, overall yield 2.5%); FAB-MS: [M+H]=589.29; isomer #2 (9.16% recovery, overall yield 2.7%); FAB-MS: [M+H]=589.27.

EXAMPLE 64 and 64a cyclo-(D-Val-NMeArg-Gly-B-MeAsp-Mamb); the compounds of formula (II) wherein J=D-Val, K= NMeArg, L=Gly, M=B-MeAsp, R$^1$=H, R$^2$=H The title compound was prepared using the general procedure described for cyclo-(D-Val-NMeArg-Gly-Asp- Mamb) (Example 4). The DCC/DMAP method was used for attachment of Boc-Mamb to the oxime resin. The peptide was prepared on a 0.611 mmol scale to give the protected cyclic peptide (201 mg, 40.0%). The peptide (200 mg) and 0.200 mL of anisole were treated with anhydrous hydrogen fluoride at 0° C. for 30 minutes. The crude material was precipitated with ether, redissolved in aqueous acetonitrile, and lyophilized to generate the title compound (162 mg, greater than quantitative yield; calculated as the fluoride salt). Purification was accomplished by reversed-phase HPLC on a preparative Vydac C18 column (2.5 cm) using a 0.23% /min. gradient of 9 to 18% acetonitrile containing 0.1% TFA and then lyophilized to give the TFA salt of the title compound as a fluffy white solid; isomer #1 (12.7% recovery, overall yield 4.8%); FAB-MS: [M+H]=589.43; isomer #2 (13.9% recovery, overall yield 5.3%); FAB-MS: [M+H]=589.45.

EXAMPLE 64b cyclo-(D-Val-NMeArg-Gly-NMeAsp-Mamb); the compound of formula (II) wherein J=D-Val, K= NMeArg, L=Gly, M=NMeAsp, $R^1$=H, $R^2$=H The title compound was prepared using the general procedure described for cyclo-(D-Val-NMeArg-Gly-Asp-Mamb) (Example 4). The DCC/DMAP method was used for attachment of Boc-Mamb to the oxime resin. The peptide was prepared on a 0.611 mmol scale to give the protected cyclic peptide (232 mg, 46.1%). The peptide (225 mg) and 0.225 mL of anisole were treated with anhydrous hydrogen fluoride at 0° C. for 30 minutes. The crude material was precipitated with ether, redissolved in aqueous acetonitrile, and lyophilized to generate the title compound (160 mg, 96.4%; calculated as the fluoride salt). Purification was accomplished by reversed-phase HPLC on a preparative Vydac C18 column (2.5 cm) using a 0.23% /min. gradient of 9 to 18% acetonitrile containing 0.1% TFA and then lyophilized to give the TFA salt of the title compound as a fluffy white solid (28.2% recovery, overall yield 10.9%); FAB-MS: [M+H]=589.42.

EXAMPLE 64c cyclo-(D-Val-NMeArg-Gly-D-Asp-Mamb); the compound of formula (II) wherein J=D-Val, K= NMeArg, L=Gly, M=D-Asp, $R^1$=H, $R^2$=H The title compound was prepared using the general procedure described above for cyclo-(D-Val-NMeArg-Gly-Asp-Mamb). The DCC/DMAP method was used for attachment of Boc-Mamb to the oxime resin. The peptide was prepared on a 0.611 mmol scale to give the protected cyclic peptide (257 mg, 51.9%). The peptide (250 mg) and 0.250 mL of anisole were treated with anhydrous hydrogen fluoride at 0° C. for 30 minutes. The crude material was precipitated with ether, redissolved in aqueous acetonitrile, and lyophilized to generate the title compound (192 mg, greater than quantitative yield; calculated as the fluoride salt). Purification was accomplished by reversed-phase HPLC on a preparative Vydac column (2.5 cm) using a 0.23% /min. gradient of 9 to 18% acetonitrile containing 0.1% TFA and then lyophilized to give the TFA salt of the title compound as a fluffy white solid (44.4% recovery, overall yield 20.7%); FAB-MS: [M+H]=575.42.

EXAMPLES 65 and 68a cyclo-(D-Val-NMeArg-Gly-Asp-MeMamb); the compound of formula (II) wherein J=D-Val, K= NMeArg, L=Gly, M=Asp, $R^1$=$CH_3$, $R^2$=H MeMAMB linker was prepared via Scheme 4 (described earlier). The title compound was made by following the solution phase synthetic route to attach MeMAMB to the tripeptide. Cyclization gave the protected cyclic peptide. Deprotection was achieved by treatment of the peptide (390 mg) and anisol (0.390 ml) with anhydrous HF at 0° C. for 30 minutes. The crude material was precipitated with ether, redissolved in 10% aqueous acetic acid, and lyophilized to give a mixture of the two isomers (330 mg; greater than quantitative yield; calculated as the acetate salt). Purification and the separation of the isomers was accomplished by Reverse-Phase HPLC on a preparative Vydac C18 column (2.5 cm) using a 0.48% /min gradient of 7 to 23% acetonitrile containing 0.1% TFA. Fractions collected at Rf 24.1 min and 26.8 min were lyophilized to give the TFA salts of the isomers 1 and 2 respectively. FAB-MS (Isomer 1): [M+H]=589.31; FAB-MS (isomer 2): [M+H]=589.31.

EXAMPLES 76 and 76a cyclo-(D-Val-NMeArg-Gly-Asp-PhMamb); the compound of formula (II) wherein J=D-Val, K= NMeArg, L=Gly, M=Asp, $R^1$=Ph, $R^2$=H PhMAMB linker was prepared via Scheme 4 (described earlier). The title compound was made by following the solution phase synthetic route to attach PhMAMB to the tripeptide. Cyclization gave the protected cyclic peptide. Deprotection was achieved by treatment of the peptide (470 mg) and anisol (0.470 ml) with anhydrous HF at 0° C. for 30 minutes. The crude material was precipitated with ether, redissolved in 10% aqueous acetic acid, and lyophilized to give a mixture of the two isomers (310 mg; 82.4% overall recovery). Purification and the separation of the isomers was accomplished by Reverse-Phase HPLC on a preparative Vydac C18 column (2.5 cm) using a 0.55% /min gradient of 18 to 36% acetonitrile containing 0.1% TFA. Fractions collected at Rf 22 min and 24.6 min were lyophilized to give the TFA salts of the isomers 1 and 2 respectively. FAB-MS (Isomer 1): [M+H]=651.33; FAB-MS (isomer 2): [M+H]= 651.33.

EXAMPLE 79 cyclo-(D-Val-NMeArg-Gly-Asp-NMeMamb); the compound of formula (II) wherein J=D-Val, K= NMeArg, L=Gly, M=Asp, $R^1$=H, $R^2$=$CH_3$ The title compound was prepared using the general procedure described for cyclo-(D-Val-NMeArg-Gly-Asp-Mamb) (Example 4). The DCC/DMAP method was used for attachment of Boc-NMeMamb to the oxime resin. The peptide was prepared on a 0.456 mmol scale to give the protected cyclic peptide (406 mg, greater than quantitative yield). The peptide (364 mg) and 0.364 mL of anisole were treated with anhydrous hydrogen fluoride at 0° C. for 30 minutes. The crude material was precipitated with ether, redissolved in aqueous acetonitrile, and lyophilized to generate the title compound (251 mg, 93.5%; calculated as the fluoride salt). Purification was accomplished by reversed-phase HPLC on a preparative Vydac C18 column (2.5 cm) using a 0.23% /min. gradient of 9 to 18% acetonitrile containing 0.1% TFA and then lyophilized to give the TFA salt of the title compound as a fluffy white solid (34.2% recovery, overall yield 29.9%); FAB-MS: [M+H]=589.33.

EXAMPLE 87, 88 cyclo-(D-Val-NMeArg-Gly-Asp-4-aminomethylbenzoic acid); the compound of formula (III) wherein J=D-Val, K=NMeArg, L=Gly, M=Asp, $R^1$=H, $R^2$=H The title compound was prepared using the general procedure described above for cyclo-(D-Val-NMeArg-Gly-Asp-Mamb). The DCC/DMAP method was used for attachment of Boc-4-aminomethylbenzoic acid to the oxime resin. The peptide was prepared on a 0.43 mmol scale to give the protected cyclic peptide (212 mg, 60.8%). The peptide (200 mg) and 200 mL of m-cresol were treated with anhydrous hydrogen fluoride at 0° C. for 30 minutes. The crude material was precipitated with ether, redissolved in aqueous HOAc, and lyophilized to generate the crude peptide as a pale yellow solid (152 mg, 97%; calculated as the acetate salt). Purification was accomplished by reversed-phase HPLC on a preparative Vydac C18 column (2.5 cm) using a 0.23% /min. gradient of 7 to 22% acetonitrile containing 0.1% TFA. Two peaks were isolated to give isomer #1 (87) (17.1% recovery, overall yield 9.3%) and isomer #2 (88) (13.4% recovery, overall yield 7.3%); FAB-MS: [M+H]= 575.41 (isomer #1; 87); 575.44 (isomer #2; 88).

EXAMPLE 89a and 89b cyclo-(D-Val-NMeArg-Gly-Asp-aminotetralincarboxylic acid); the compound of formula (VIII) wherein J=D-Val, K=NMeArg, L=Gly, M=Asp, $R^1$=$R^2$=H The title compound was prepared using the general procedure described for cyclo-(D-Val-NMeArg-Gly-Asp-Mamb) (Example 4). The DCC/DMAP method was used for attachment of Boc-aminotetralin-carboxylic acid to the oxime resin. The peptide was prepared on a 0.164 mmol scale to give the protected cyclic peptide (69 mg, 49.3%). The peptide (69 mg) and 0.069 mL of anisole were treated with anhydrous hydrogen fluoride at 0° C. for 30 minutes. The crude material was precipitated with ether, redissolved in aqueous acetonitrile, and lyophilized to generate the title compound (59.7 mg, greater than quantitative yield; calculated as the fluoride salt). Purification was accomplished by reversed-phase HPLC on a preparative Vydac C18 column (2.5 cm) using a 0.23% /min. gradient of 16.2 to 27% acetonitrile containing 0.1% TFA and then lyophilized to give the TFA salt of the title compound as a fluffy white solid. Two isomers were obtained; isomer #1 (12.5% recovery, overall yield 6.2%, FAB-MS: [M+H]=615.34; isomer #2 (18.6% recovery, overall yield 9.3%, FAB-MS: [M+H]=615.35.

EXAMPLE 89c cyclo-(D-Val-NMeArg-Gly-Asp-aminomethylnaphthoic acid); the compound of formula (IX) wherein J=D-Val, K=NMeArg, L=Gly, M=Asp, $R^1$=H, $R^2$=H The title compound was prepared using the general procedure described for cyclo-(D-Val-NMeArg-Gly-Asp-Mamb) (Example 4). The DCC/DMAP method was used for attachment of Boc-aminomethyl-naphthoic acid to the oxime resin. The peptide was prepared on a 0.737 mmol scale to give the protected cyclic peptide (463 mg, 73.1%). The peptide (463 mg) and 0.463 mL of anisole were treated with anhydrous hydrogen fluoride at 0° C. for 20 minutes. The crude material was precipitated with ether, redissolved in aqueous acetonitrile, and lyophilized to generate the title compound (349 mg, greater than quantitative yield; calculated as the fluoride salt). Purification was accomplished by reversed-phase HPLC on a preparative Vydac C18 column (2.5 cm) using a 0.45% /min. gradient of 4.5 to 22.5% acetonitrile containing 0.1% TFA and then lyophilized to give the TFA salt of the title compound as a fluffy white solid (12.1% recovery, overall yield 7.8%); FAB-MS: [M+H]= 625.32.

EXAMPLE 89d cyclo-(D-Abu-NMeArg-Gly-Asp-iodo-Mamb); the compound of formula (VII) wherein J=D-Abu, K= NMeArg, L=Gly, M=Asp, $R^1$ =$R^2$=H, $R^{10}$=H, $R^{10a}$=I The title compound was prepared using the general procedure described above for cyclo-(D-Val-NMeArg-Gly-Asp-Mamb) (Example 4). The DCC/DMAP method was used for attachment of Boc-iodo-Mamb to the oxime resin. The peptide was prepared on a 3.53 mmol scale to give the protected cyclic peptide (4.07 g, greater than quantitative yield). The peptide (4.07 g) and 4.0 mL of anisole were treated with anhydrous hydrogen fluoride at 0° C. for 30 minutes. The crude material was precipitated with ether, redissolved in aqueous acetic acid, and lyophilized to generate the title compound (2.97 g, greater than quantitative yield; calculated as the acetate salt). Purification was accomplished by reversed-phase HPLC on a preparative Vydac C18 column (2.5 cm) using a 0.16% /min. gradient of 16.2 to 22.5% acetonitrile containing 0.1% TFA and then lyophilized to give the TFA salt of the title compound as a fluffy white solid (28.7% recovery, overall yield 30.2%); FAB-MS: [M+H]=687.33.

EXAMPLE 89e cyclo-(D-Abu-di-NMeOrn-Gly-Asp-Mamb); the compound of formula (II) wherein J=D-Abu, K=di-NMeOrn, L=Gly, M=Asp, $R^1$=$R^2$=H The title compound was prepared using the general procedure described for cyclo-(D-Val-NMeArg-Gly-Asp-Mamb) (Example 4). The DCC/DMAP method was used for attachment of Boc-Mamb to the oxime resin. The peptide was prepared on a 0.498 mmol scale to give the protected cyclic peptide (150 mg, 39.3%). The peptide (150 mg) and 0.150 mL of anisole were treated with anhydrous hydrogen fluoride at 0° C. for 30 minutes. The crude material was precipitated with ether, redissolved in aqueous acetonitrile, and lyophilized to generate the title compound (93 mg, 86%; calculated as the fluoride salt). Purification was accomplished by reversed-phase HPLC on a preparative Vydac C18 column (2.5 cm) using a 0.45% /min. gradient of 3.6 to 18% acetonitrile containing 0.1% TFA and then lyophilized to give the TFA salt of the title compound as a fluffy white solid (49.3% recovery, overall yield 14.2%); FAB-MS: [M+H]=533.34.

EXAMPLE 401 cyclo-(D-Abu-NMeArg-Gly-D-Asp-Mamb); compound of formula (II) wherein J=D-Abu, K=NMeArg, L=Gly, M=D-Asp, $R^1$=H, $R^2$=H The title compound was prepared using the general procedure described for cyclo-(D-Val-NMeArg-Gly-Asp-Mamb) (example 4). The DCC/DMAP method was used for attachment of Boc-Mamb to the oxime resin. TBTU was used as the coupling reagent. The peptide was prepared on a 0.596 mmol scale to give the protected cyclic peptide (273 mg, 57.6%). The peptide (263 mg) and 0.263 mL of anisole were treated with anhydrous hydrogen fluoride at 0° C. for 20 minutes. The crude material was precipitated with ether, redissolved in aqueous acetonitrile, and lyophilized to generate the title compound (218 mg; greater than quantitative yield; calculated as the fluoride salt). Purification was accomplished by reversed-phase HPLC on a preparative Vydac C18 column (2.5 cm) using a 0.23% /min. gradient of 10.8 to 19.8% acetonitrile containing 0.1% TFA and then lyophilized to give the TFA salt of the title compound as a fluffy white solid (40.4% recovery, overall yield 21.9%); FAB-MS: [M+H]=561.37.

EXAMPLE 402 cyclo-(D-Abu-D-NMeArg-Gly-Asp-Mamb); the compound of formula (II) J=D-Abu, K=D-NMeArg, L=Gly, M=Asp, $R^1$=H, $R^2$=H The title compound was prepared using the general procedure described for cyclo-(D-Val-NMeArg-Gly-Asp-Mamb) (example 4). The DCC/DMAP method was used for attachment of Boc-Mamb to the oxime resin. TBTU was used as the coupling reagent. The peptide was prepared on a 0.596 mmol scale to give the protected cyclic peptide (241 mg, 50.8%). The peptide (235 mg) and 0.235 mL of anisole were treated with anhydrous hydrogen fluoride at 0° C. for 20 minutes. The crude material was precipitated with ether, redissolved in aqueous acetonitrile, and lyophilized to generate the title compound (168 mg; 98.3%; calculated as the fluoride salt). Purification was accomplished by reversed-phase HPLC on a preparative Vydac C18 column (2.5 cm) using a 0.23% /min. gradient of 12.6 to 21.6% acetonitrile containing 0.1% TFA and then lyophilized to give the TFA salt of the title compound as a fluffy white solid (2.3% recovery, overall yield 0.99%); FAB-MS: [M+H]=561.36.

EXAMPLE 403

Cyclo-(D-Ala-p-guanidinyl-Phe-Gly-Asp-Mamb); the compound of formula (II) wherein J=D-Ala, K=p-guanidinyl-Phe, L=Gly, M=Asp $R^1$=H, $R^2$=H

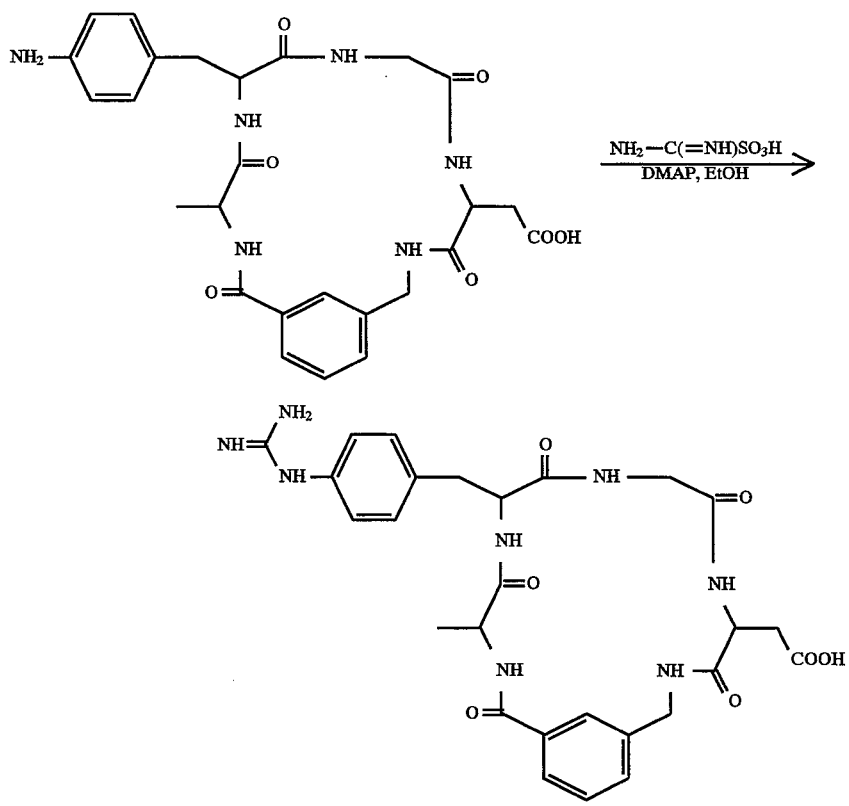

Dissolved 25 mg (38.3 μmoles) of cyclo-(D-Ala-p-amino-Phe-Gly-Asp-Mamb) (TFA salt), 14.3 mg (114.9 umoles) formamidine sulfonic acid, and 18.7 mg (153.2 umoles) of 4-dimethyl-aminopyridine in 5 ml of ethanol in a 10 ml round bottom flask. Refluxed the mixture for 3 hours, then added an additional 14.3 mg of formamidine sulfonic acid and 18.7 mg of 4-dimethyl-aminopyridine. After refluxing for an additional 3 hours, the reaction was found to be ~75% complete by reversed-phase HPLC. The ethanol was evaporated under reduced pressure, and the residue was purified on a preparative Vydac C18 column (2.5 cm) using a 0.45% /min. gradient of 0 to 18% acetonitrile containing 0.1% TFA. Lyophilization afforded the TFA salt of the title compound as a white solid (28% recovery), overall yield 26.4%); FAB-MS: [M+H]=581.30.

EXAMPLE 404 cyclo-(D-Abu-(DiNMe,guanidinyl-Orn)-Gly-Asp-Mamb); the compound of formula (II) wherein J= D-Abu, K=diNMe,guanidinyl-Orn, L=Gly, D=Asp, $R^1$=H, $R^2$=H pound as a white solid (57.2% recovery), overall yield 53.5%); FAB-MS: [M+H]=575.34.

EXAMPLES 405 cyclo-(D-Abu-Di-NMeLys-Gly-Asp-Mamb); the compound of formula (II) wherein J=D-Abu, K= Di-NMeLys, L=Gly, M=Asp, $R^1$=H, $R^2$=H cyclo-(D-Abu-NMeLys-Gly-Asp-Mamb); the compound of formula (II) wherein J=D-Abu, K= NMeLys, L=Gly, M=Asp, $R^1$=H, $R^2$=H Di-N-methyl amino acid derivatives may be prepared using methods which have been described previously (Olsen, J. Org. Chem. (1970) 35: 1912) or, alternatively, through the use of $NaH/CH_3I$. The mono-NMe-Lysine

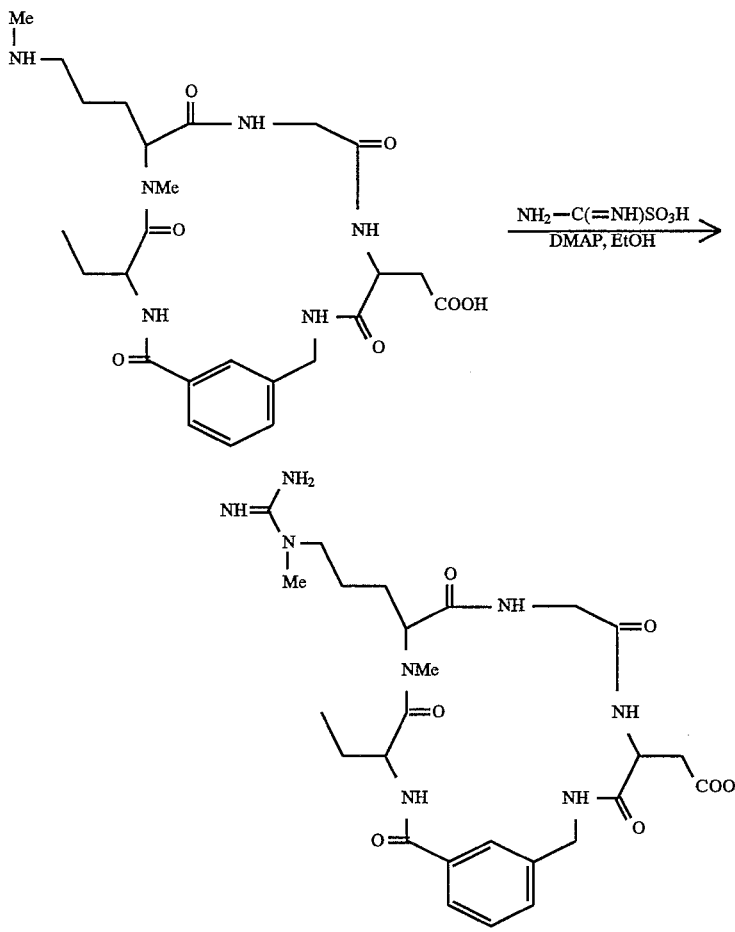

Dissolved 10.53 mg (16.3 μmoles) of cyclo-(D-Abu-diNMeOrn-Gly-Asp-Mamb) (TFA salt), 6.08 mg (48.99 umoles) formamidine sulfonic acid, and 8.00 mg (65.57 umoles) of 4-dimethyl-aminopyridine in 2.5 ml of ethanol in a 10 ml round bottom flask. Refluxed the mixture for 2 hours and then stirred at room temperature overnight. Refluxed for one hour, added an additional 6.08 mg of formamidine sulfonic acid and 8.00 mg of 4-dimethylaminopyridine and then refluxed for an additional 2 hours. Evaporated the ethanol under reduced pressure and purified the residue on a preparative Vydac C18 column (2.5 cm) using a 0.45% /min. gradient of 3.6 to 18% acetonitrile containing 0.1% TFA. Lyophilization afforded the TFA salt of the title comamino acid was obtained as a side product during the synthesis of the corresponding di-NMe-lysine derivative. The title compounds were prepared using conventional solution phase peptide chemistry techniques described previously. Cyclo-(D-Abu-diNMeLys-Gly-Asp-Mamb) was obtained in 0.31% overall yield, FAB-MS: [M+H]=547.3. Cyclo-(D-Abu-NMeLys-Gly-Asp-Mamb) was obtained in 0.25% overall yield, FAB-MS: [M+H]=533.3.

EXAMPLE 90 cyclo-(D-Val-NMeArg-Gly-Asp-2-aminomethylphenylacetic acid)

The title compound was prepare by a modification of the general solution-phase chemistry route. This approach employed an amino acid succinimide ester coupling to the aromatic linker, and the dinitrobenzophenone oxime as shown schematically below in the Scheme below (n=1).

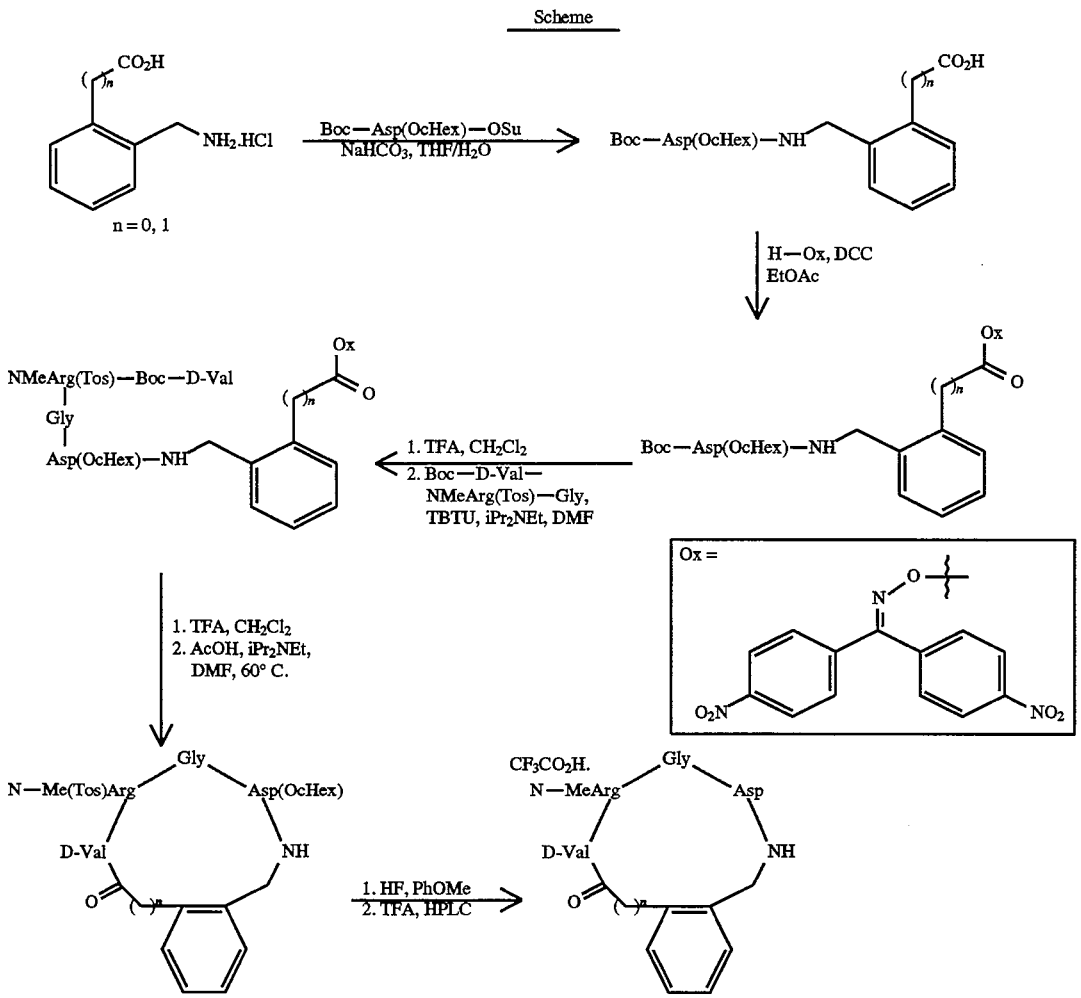

Scheme

Boc-Asp(OcHex)-2-aminomethylphenylacetic Acid

To a suspension of 2-aminomethylphenylacetic acid.HCl (4.0 g, 20 mmol) in H$_2$O (20 ml) was added NaHCO$_3$ (5.0 g, 60 mmol), followed by a solution of Boc-Asp(OcHex)-OSu (7.5 g, 18 mmol) in THF (20 ml). The reaction mixture was stirred at room temperature for 3 hours, filtered, diluted with H$_2$O, acidified with 1N HCl, and extracted with ethyl acetate. The extracts were washed with H$_2$O, brine, dried over anhydrous magnesium sulfate, and evaporated to dryness under reduced pressure. This material was triturated with ether to provide the title compound (7.0 g, 83%) as a white powder. $^1$H NMR (D$_6$-DMSO) 12.40 (br s, 1H), 8.30 (br t, 1H), 7.20 (m, 5H), 4.65 (m, 1H), 4.35 (q, 1H), 4.25 (m, 2H), 3.65 (s, 2H), 2.70 (dd, 1H), 2.55 (dd, 1H), 1.70 (m, 4H), 1.40 (s, 9H), 1.35 (m, 6H).

4,4'-Dinitrobenzophenone Oxime

The title compound was prepared by modification of procedures previously reported in the literature (Chapman and Fidler (1936) *J. Chem. Soc*, 448; Kulin and Leffek (1973) *Can. J. Chem.*, 51: 687). A solution of chromic anhydride (20 g, 200 mmol) in 125 ml of H$_2$O was added dropwise over 4 hours, to a suspension of bis(4-nitrophenyl) methane (25 g, 97 mmol) in 300 ml of acetic acid heated to reflux. The reaction mixture was heated at reflux for 1 hour, cooled to room temperature, and poured into water. The solid was collected by filtration, washed with H$_2$O, 5% sodium bicarbonate, H$_2$O , and air-dryed to provide a 1:1 mixture of bis(4-nitrophenyl)methane/4,4'-dinitrobenzophenone via $^1$H NMR. This material was oxidized with a second portion of chromic anhydride (20 g, 200 mmol), followed by an identical work-up procedure to provide the crude product. Trituration with 200 ml of benzene heated to reflux for 16 hours provided 4,4'-dinitrobenzophenone (20.8 g, 79%) as a yellow powder.

A solution of hydroxylamine hydrochloride (10.2 g, 147 mmol) was added to a suspension of 4,4'-dinitrobenzophenone (19 g, 70 mmol) in 100 ml of ethanol. The reaction mixture was heated to reflux for 2 hours, cooled to room temperature, and the solid collected by filtration. Recrystallization from ethanol provided the title compound (14.0 g, 70%) as pale yellow crystals. mp 194° C.; $^1$H NMR (D$_6$-DMSO) 12.25 (s, 1H), 8.35 (d, 2H), 8.20 (d, 2H), 7.60 (d, 4H). 4,4'-Dinitrobenzophenone Oxime Boc-Asp(OcHex) -2-aminomethylphenylacetate To an ice-cooled solution of Boc-Asp(OcHex)-2-aminomethylphenylacetic acid (3.5 g, 7.6 mmol) and 4,4'-dinitrobenzophenone oxime (2.2 g, 7.5 mmol) in 50 ml of ethyl acetate and 5 ml of DMF was added DCC (1.6 g, 7.8 mmol). The reaction mixture was stirred at room temperature for 8 hours, filtered, diluted with ethyl acetate, washed with saturated sodium bicarbonate solution, H$_2$O, brine, dried over anhydrous magnesium sulfate, and evaporated to dryness under reduced pressure. This material was purified by column chromatography on silica gel (EM Science, 230–400 mesh) using 10:1 dichloromethane/ethyl acetate to give the title compound (4.3 g, 78%) as pale yellow crystals. $^1$H NMR (D$_6$-DMSO) 8.30 (dd, 5H), 7.80 (d, 2H), 7.65 (d, 2H), 7.15 (m, 5H), 4.65 (m, 1H), 4.35 (q, 1H), 4.15 (m, 2H), 3.90 (s, 2H), 2.70 (dd, 1H), 2.50 (dd, 1H), 1.70 (m, 4H), 1.40 (s, 9H), 1.35 (m, 6H).

4,4'-Dinitrobenzophenone Oxime Boc-D-Val-NMeArg(Tos)-Gly-ASp(OcHex)-2-aminomethylphenylacetate To a solution of 4,4'-dinitrobenzophenone oxime Boc-Asp(OcHex)-2-aminomethylphenylacetate (1.5 g, 2 mmol) in 4 ml of dichloromethane was added 2 ml of trifluoroacetic acid. The reaction mixture was stirred at room temperature for 1 hour, diluted with dichloromethane, and evaporated to dryness under reduced pressure. The oily residue was concentrated under high vacuum to remove traces of excess trifluoroacetic acid.

To a solution of the crude TFA salt and Boc-D-Val-NMeArg(Tos)-Gly (1.2 g, 2 mmol) in 5 ml of DMF was added TBTU (640 mg, 2 mmol) and DIEA (780 mg, 6 mmol). The reaction mixture was stirred at room temperature for 16 hours, concentrated under high vacuum, diluted with ethyl acetate, washed with 5% citric acid, H$_2$O, brine, dried over anhydrous magnesium sulfate, and evaporated to dryness under reduced pressure. This material was triturated with ether to provide the title compound (2.3 g, 95%) as a yellow powder. This material was used without further purification.

cyclo-(D-Val-NMeArg(Tos)-Gly-Asp(OcHex)-2-aminomethylphenylacetic acid)

To a solution of 4,4'-dinitrobenzophenone oxime Boc-D-Val-NMeArg(Tos)-Gly-Asp(OcHex)-2-aminomethylphenylacetate (1.2 g, 1 mmol) in 4 ml of dichloromethane was added 2 ml of trifluoroacetic acid. The reaction mixture was stirred at room temperature for 3 hours, diluted with dichloromethane, and evaporated to dryness under reduced pressure. The oily residue was concentrated under high vacuum to remove traces of excess trifluoroacetic acid.

To a solution of the crude TFA salt in 100 ml of DMF was added acetic acid (0.50 ml, 8.7 mmol) and DIEA (1.52 ml, 8.7 mmol). The reaction mixture was stirred at 60° C. for 3 days, concentrated under high vacuum, diluted with ethyl acetate, and the solution allowed to crystallize overnight. Filtration provided the title compound (563 mg, 68%) as a yellow powder. $^1$H NMR (D$_6$-DMSO) 8.70 (d, 1H), 8.40 (br s, 1H), 8.30 (br s, 1H), 8.05 (t, 1H), 7.65 (d, 2H), 7.25 (d, 2H), 7.20 (m, 4H), 7.10 (br d, 1H), 6.80 (br s, 1H), 6.60 (br s, 1H), 5.10 (dd, 1H), 4.65 (m, 1H), 4.55 (m, 1H), 4.40 (m, 2H), 3.85 (m, 2H), 3.65 (d, 1H), 3.45 (m, 2H), 3.05 (m, 2H), 2.80 (s, 3H), 2.80 (m, 1H), 2.60 (dd, 1H), 2.30 (s, 3H), 1.70 (m, 6H), 1.30 (m, 9H), 0.95 (d, 3H), 0.80 (d, 3H); DCI (NH$_3$)-MS: [M+H]=825.

cyclo-(D-Val-NMeArg-Gly-Asp-2-aminomethylphenylacetic acid)

A mixture of 352 mg (0.43 mmol) of cyclo-(D-Val-NMeArg(Tos)-Gly-Asp(OcHex)-2-aminomethylphenylacetic acid) and 352 µl of anisole was treated at 0° C. with 5 ml of HF for 20 minutes. The excess HF was removed under reduced pressure, the residue triturated with ether, dissolved in 50% acetonitrile/H$_2$O, and lyophilized to provide the crude cyclic peptide.HF salt as an off-white powder. Purification was accomplished by reversed-phase HPLC on a preparative Vydac C18 column (2.5 cm) using a 0.8% / minute gradient of 10 to 38% acetonitrile containing 0.1% trifluoroacetic acid to give the TFA salt of the title compound (225 mg, 75%) as a fluffy white solid; 1H NMR (D$_6$-DMSO) 8.70 (d, 1H), 8.35 (d, 1H), 8.20 (t, 1H), 8.00 (t, 1H), 7.45 (t, 1H), 7.20 (m, 3H), 7.10 (m, 1H), 7.00 (br s, 4H), 5.10 (dd, 1H), 4.50 (dt, 1H), 4.40 (m, 2H), 3.85 (dt, 2H), 3.65 (d, 1H), 3.50 (dd, 1H), 3.45 (d, 1H), 3.10 (m, 2H), 2.90 (s, 3H), 2.75 (dd, 1H), 2.55 (dd, 1H), 2.00 (m, 1H), 1.85 (m, 1H), 1.65 (m, 1H), 1.30 (m, 2H), 0.95 (d, 3H), 0.85 (d, 3H); FAB-MS: [M+H]=589.

EXAMPLE 91 cyclo-(D-Val-NMeArg-Gly-Asp-2-aminomethylbenzoic acid)

The title compound was prepare by the general solution-phase procedure described above for cyclo-(D-Val-NMeArg-Gly-Asp-2-aminomethylphenylacetic acid), and as shown schematically above in the Example 90 Scheme (n =0). The cyclic peptide (192 mg, 0.24 mmol) was deprotected with excess HF in the presence of anisole as scavenger. Purification was accomplished by reversed-phase HPLC on a preparative Vydac C18 column (2.5 cm) using a 0.8% /minute gradient of 10 to 38% acetonitrile containing 0.1% trifluoroacetic acid to give the TFA salt of the title compound (20 mg, 12%) as a fluffy white solid; 1H NMR (D$_6$-DMSO) 8.75 (d, 1H), 8.50 (d, 1H), 7.65 (t, 1H), 7.60 (t, 1H), 7.50 (m, 2H), 7.40 (m, 3H), 7.00 (br s, 4H), 5.05 (dd, 1H), 4.50 (t, 1H), 4.30 (m, 2H), 4.10 (dd, 1H), 3.70 (m, 2H), 3.15 (q, 2H), 3.05 (s, 3H), 2.80 (dd, 1H), 2.55 (dd, 1H), 2.10 (m, 1H), 1.95 (m, 1H), 1.60 (m, 1H), 1.40 (m, 2H), 1.05 (d, 3H), 0.95 (d, 3H); FAB-MS: [M+H]=575.

EXAMPLE 92 cyclo-(D-Val-NMeArg-Gly-Asp-3-aminophenylacetic acid)

The title compound was prepare by the general solution-phase procedure described above for cyclo-(D-Val-NMeArg-Gly-Asp-Mamb), and as shown schematically in the Scheme below. The cyclic peptide (360 mg, 0.44 mmol) was deprotected with excess HF in the presence of anisole as scavenger. Purification was accomplished by reversed-phase HPLC on a preparative LiChrospher RP-18 column (5 cm) using a 2.3% /minute gradient of 22 to 90% acetonitrile containing 0.1% trifluoroacetic acid to give the TFA salt of the title compound (150 mg, 50%) as a fluffy white solid; 1H NMR (D$_6$-DMSO) 12.40 (br s, 1H), 8.95 (s, 1H), 8.55 (m, 2H), 8.45 (t, 1H), 7.90 (d, 1H), 7.50 (m, 1H), 7.20 (t, 1H), 7.00 (br s, 4H), 6.90 (m, H), 5.15 (dd, 1H), 4.65 (q, 1H), 4.55 (t, 1H), 3.65 (m, H), 3.60 (dd, 1H), 3.10 (m, 2H), 2.85 (s, 3H), 2.85 (d, 1H), 2.70 (dd, 2H), 2.00 (m, 2H), 1.75 (m, 1H), 1.35 (m, H), 0.90 (d, 3H), 0.85 (d, 3H); FAB-MS: [M+H] =575.

Scheme:

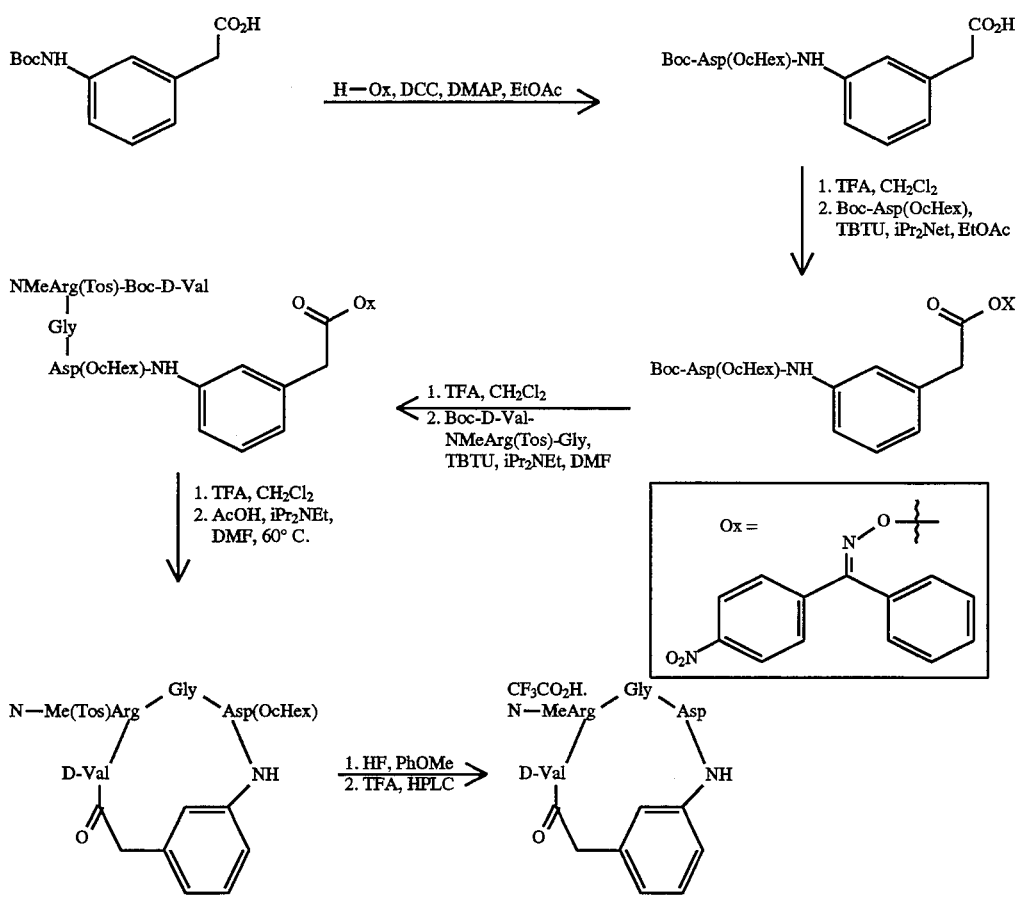

EXAMPLE 93 cyclo-(D-Val-NMeArg-Gly-Asp-3-aminomethyl-4-chlorobenzoic acid)

The title compound was prepare by the general solution-phase procedure described above for cyclo-(D-Val-NMeArg-Gly-Asp-Mamb). The cyclic peptide (240 mg, 0.28 mmol) was deprotected with excess HF in the presence of anisole as scavenger. Purification was accomplished by reversed-phase HPLC on a preparative LiChrospher RP-18 column (5 cm) using a 1.4% /minute gradient of 22 to 90% acetonitrile containing 0.1% trifluoroacetic acid to give the TFA salt of the title compound (80 mg, 39%) as a fluffy white solid; 1H NMR ($D_6$-DMSO) 9.00 (d, 1H), 8.50 (d, 1H), 8.45 (t, 1H), 7.60 (d, 2H), 7.45 (s, 1H), 7.45 (d, 2H), 7.00 (br s, 4H), 5.15 (dd, 1H), 4.45 (m, 2H), 4.20 (m, 2H), 4.10 (d, 1H), 3.55 (d, 1H), 3.10 (m, 2H), 2.90 (s, 3H), 2.65 (dd, 1H), 2.50 (m, 1H), 2.05 (m, 2H), 1.50 (m, 1H), 1.30 (m, 2H), 1.05 (d, 3H), 0.85 (d, 3H); FAB-MS: [M+H]=609.

EXAMPLE 94 cyclo-(D-Val-NMeArg-Gly-Asp-iodo-Mamb); the compound of formula (VII) wherein J=D-Val, K =NMeArg, L=Gly, M=Asp, $R^1=R^2=H$, $R^{10}=H$, $R^{10a}=I$ The title compound was prepared using the general procedure described for cyclo-(D-Val-NMeArg-Gly-Asp-Mamb) (Example 4). The DCC/DMAP method was used for attachment of Boc-iodo-Mamb to the oxime resin. The peptide was prepared on a 1.05 mmol scale to give the protected cyclic peptide (460 mg, 46.8%). The peptide (438 mg) and 0.5 mL of anisole were treated with anhydrous hydrogen fluoride at 0° C. for 30 minutes. The crude material was precipitated with ether, redissolved in aqueous acetic acid, and lyophilized to generate the title compound (340 mg, 95.6%; calculated as the acetate salt). Purification was accomplished by reversed-phase HPLC on a preparative Vydac C18 column (2.5 cm) using a 0.23% /min. gradient of 12.6 to 22.5% acetonitrile containing 0.1% TFA and then lyophilized to give the TFA salt of the title compound as a fluffy white solid (39.7% recovery, overall yield 16.6%); FAB-MS: [M+H]=701.37.

EXAMPLE 95 cyclo-(D-Val-NMeArg-Gly-Asp-3-aminomethyl-4-methoxybenzoic acid)

The title compound was prepare by the general solution-phase procedure described above for cyclo-(D-Val-NMeArg-Gly-Asp-Mamb). The cyclic peptide (600 mg, 0.71 mmol) was deprotected with excess HF in the presence of anisole as scavenger. Purification was accomplished by reversed-phase HPLC on a preparative Vydac C18 column (2.5 cm) using a 0.33% /minute gradient of 7 to 18% acetonitrile containing 0.1% trifluoroacetic acid to give the TFA salt of the title compound (104 mg, 32%) as a fluffy white solid; $^1$H NMR ($D_6$-DMSO) 12.40 (br s, 1H), 8.25 (d, 1H), 8.20 (br s, 1H), 8.00 (br s, 2H), 7.85 (d, 1H), 7.75 (s, 1H), 7.65 (br s, 1H), 7.05 (d, 1H), 7.05 (br s, 4H), 5.00 (dd, 1H), 4.60 (q, 1H), 4.30 (d, 1H), 4.25 (d, 2H), 3.85 (s, 3H), 3.85 (dd, 1H), 3.70 (dd, 1H), 3.10 (q, 2H), 3.00 (s, 3H), 2.70 (m, 1H), 2.50 (m, 1H), 2.10 (m, 1H), 1.90 (m, 1H), 1.65 (m, 1H), 1.35 (m, 2H), 1.00 (d, 3H), 0.90 (d, 3H); FAB-MS: [M+H$_2$O +H]=623.

EXAMPLE 96 cyclo-(D-Val-NMeArg-Gly-Asp-3-aminomethyl-4-methylbenzoic acid)

The title compound was prepare by the general solution-phase procedure described above for cyclo-(D-Val-NMeArg-Gly-Asp-Mamb). The cyclic peptide (210 mg, 0.25 mmol) was deprotected with excess HF in the presence of anisole as scavenger. Purification was accomplished by reversed-phase HPLC on a preparative LiChrospher RP-18 column (5 cm) using a 2.3% /minute gradient of 22 to 90% acetonitrile containing 0.1% trifluoroacetic acid to give the TFA salt of the title compound (75 mg, 42%) as a fluffy white solid; $^1$H NMR (D$_6$-DMSO) 12.30 (br s, 1H), 8.85 (d, 1H), 8.55 (d, 1H), 8.30 (t, 1H), 7.75 (d, 1H), 7.55 (m, 2H), 7.40 (s, 1H), 7.20 (s, 1H), 7.00 (br s, 4H), 5.20 (dd, 1H), 4.55 (q, 1H), 4.45 (dd, 1H), 4.30 (m, 2H), 4.05 (dd, 1H), 3.60 (d, 1H), 3.10 (q, 2H), 3.00 (s, 3H), 2.70 (dd, 1H), 2.50 (m, 1H), 2.25 (s, 3H), 2.10 (m, 2H), 1.60 (m, 1H), 1.35 (m, 2H), 1.10 (d, 3H), 0.90 (d, 3H); FAB-MS: [M+H]=589.

EXAMPLE 97 cyclo-(D-Val-NMeArg-Gly-Asp-3-aminomethyl-6-chlorobenzoic acid)

The title compound was prepare by the general solution-phase procedure described above for cyclo-(D-Val-NMeArg-Gly-Asp-Mamb), except that 4,4'-dinitrobenzophenone oxime was employed. The cyclic peptide (550 mg, 0.65 mmol) was deprotected with excess HF in the presence of anisole as scavenger. Purification was accomplished by reversed-phase HPLC on a preparative Vydac C18 column (2.5 cm) using a 0.8% /minute gradient of 10 to 38% acetonitrile containing 0.1% trifluoroacetic acid to give the TFA salt of the title compound (254 mg, 54%) as a fluffy white solid; $^1$H NMR (D$_6$-DMSO) 12.30 (br s, 1H), 9.05 (d, 1H), 8.45 (m, 2H), 7.50 (t, 1H), 7.35 (d, 1H), 7.30 (m, 2H), 7.10 (s, 1H), 7.05 (br s, 4H), 5.15 (dd, 1H), 4.45 (dd, 1H), 4.40 (q, 2H), 4.05 (dt, 2H), 3.55 (dd, 1H), 3.15 (q, 2H), 3.10 (s, 3H), 2.70 (dd, 1H), 2.50 (m, 1H), 2.05 (m, 2H), 1.65 (m, 1H), 1.35 (m, 2H), 1.10 (d, 3H), 0.90 (d, 3H); FAB-MS: [M+H]=609.

EXAMPLE 98 cyclo-(D-Val-NMeArg-Gly-Asp-3-aminomethyl-6-iodobenzoic acid)

The title compound was prepare by the general solution-phase procedure described above for cyclo-(D-Val-NMeArg-Gly-Asp-Mamb), except that 4,4'-dinitrobenzophenone oxime was employed. The cyclic peptide (490 mg, 0.52 mmol) was deprotected with excess HF in the presence of anisole as scavenger. Purification was accomplished by reversed-phase HPLC on a preparative Vydac C18 column (2.5 cm) using a 0.8% /minute gradient of 10 to 38% acetonitrile containing 0.1% trifluoroacetic acid to give the TFA salt of the title compound (194 mg, 46%) as a fluffy white solid; $^1$H NMR (D$_6$-DMSO) 12.30 (br s, 1H), 9.00 (d, 1H), 8.40 (m, 2H), 7.70 (d, 1H), 7.50 (m, 1H), 7.30 (m, 1H), 7.05 (d, 1H), 7.00 (s, 1H), 7.00 (br s, 4H), 5.15 (dd, 1H), 4.40 (d, 1H), 4.40 (q, 2H), 4.0 (m, 2H), 3.55 (dd, 1H), 3.15 (q, 2H), 3.10 (s, 3H), 2.70 (dd, 1H), 2.50 (m, 1H), 2.05 (m, 2H), 1.65 (m, 1H), 1.35 (m, 2H), 1.15 (d, 3H), 0.90 (d, 3H); FAB-MS: [M+H]=701.

EXAMPLE 99 cyclo-(D-Val-NMeArg-Gly-Asp-3-aminomethyl-6-methoxybenzoic acid)

The title compound was prepare by the general solution-phase procedure described above for cyclo-(D-Val-NMeArg-Gly-Asp-Mamb), except that 4,4'-dinitrobenzophenone oxime was employed. The cyclic peptide (256 mg, 0.30 mmol) was deprotected with excess HF in the presence of anisole as scavenger. Purification was accomplished by reversed-phase HPLC on a preparative Vydac C18 column (2.5 cm) using a 0.8% /minute gradient of 10 to 38% acetonitrile containing 0.1% trifluoroacetic acid to give the TFA salt of the title compound (137 mg, 63%) as a fluffy white solid; $^1$H NMR (D$_6$-DMSO) 8.45 (d, 1H), 8.40 (d, 1H), 8.30 (t, 1H), 7.65 (d, 1H), 7.50 (t, 1H), 7.40 (s, 1H), 7.35 (d, 1H), 7.05 (d, 1H), 7.00 (br s, 4H), 5.20 (dd, 1H), 4.55 (dd, 1H), 4.50 (q, 1H), 4.35 (dd, 1H), 4.25 (dd, 1H), 3.95 (dd, 1H), 3.90 (s, 3H), 3.55 (d, 1H), 3.10 (q, 2H), 3.00 (s, 3H), 2.70 (dd, 1H), 2.50 (m, 1H), 2.05 (m, 2H), 1.60 (m, 1H), 1.35 (m, 2H), 1.10 (d, 3H), 0.95 (d, 3H); FAB-MS: [M+H]=605.

EXAMPLE 100 cyclo-(D-Val-NMeArg-Gly-Asp-3-aminomethyl-6-methylbenzoic acid)

The title compound was prepare by the general solution-phase procedure described above for cyclo-(D-Val-NMeArg-Gly-Asp-Mamb), except that 4,4'-dinitrobenzophenone oxime was employed. The cyclic peptide (230 mg, 0.28 mmol) was deprotected with excess HF in the presence of anisole as scavenger. Purification was accomplished by reversed-phase HPLC on a preparative Vydac C18 column (2.5 cm) using a 0.8% /minute gradient of 10 to 38% acetonitrile containing 0.1% trifluoroacetic acid to give the TFA salt of the title compound (54 mg, 27%) as a fluffy white solid; $^1$H NMR (D$_6$-DMSO) 12.30 (br s, 1H), 8.80 (d, 1H), 8.40 (d, 1H), 8.30 (t, 1H), 7.45 (m, 2H), 7.15 (q, 2H), 7.00 (s, 1H), 7.00 (br s, 4H), 5.15 (dd, 1H), 4.45 (m, 3H), 4.05 (m, 2H), 3.55 (dd, 1H), 3.10 (q, 2H), 3.05 (s, 3H), 2.70 (dd, 1H), 2.50 (m, 1H), 2.30 (s, 3H), 2.05 (m, 2H), 1.60 (m, 1H), 1.35 (m, 2H), 1.05 (d, 3H), 0.90 (d, 3H); FAB-MS: [M+H]=589.

EXAMPLE 100a cyclo-(D-Abu-NMeArg-Gly-Asp-3-aminomethyl-6-chlorobenzoic acid)

The title compound was prepare by the general solution-phase procedure described above for cyclo-(D-Val-NMeArg-Gly-Asp-Mamb), except that 4,4'-dinitrobenzophenone oxime was employed. The cyclic peptide (330 mg, 0.40 mmol) was deprotected with excess HF in the presence of anisole as scavenger. Purification was accomplished by reversed-phase HPLC on a preparative Vydac C18 column (2.5 cm) using a 1.0% /minute gradient of 10 to 38% acetonitrile containing 0.1% trifluoroacetic acid to give the TFA salt of the title compound (114 mg, 41%) as a fluffy white solid; $^1$H NMR (D$_6$-DMSO) 9.00 (d, 1H), 8.40 (m, 2H), 7.50 (m, 1H), 7.40 (d, 1H), 7.30 (m, 2H), 7.15 (s, 1H), 7.00 (br s, 4H), 5.15 (dd, 1H), 4.65 (q, 1H), 4.50 (dd, 1H), 4.40 (q, 1H), 4.05 (dd, 1H), 3.95 (dd, 1H), 3.65 (dd, 1H), 3.10 (q, 2H), 3.05 (s, 3H), 2.75 (dd, 1H), 2.50 (m, 1H), 1.95 (m, 1H), 1.75 (m, 2H), 1.60 (m, 1H), 1.35 (m, 2H), 0.95 (t, 3H); FAB-MS: [M+H]=595.4.

EXAMPLE 100b cyclo-(D-Abu-NMeArg-Gly-Asp-3-aminomethyl-6-iodobenzoic acid)

The title compound was prepare by the general solution-phase procedure described above for cyclo-(D-Val-NMeArg-Gly-Asp-Mamb), except that 4,4'-dinitrobenzophenone oxime was employed. The cyclic peptide (350 mg, 0.38 mmol) was deprotected with excess HF in the presence of anisole as scavenger. Purification was accomplished by reversed-phase HPLC on a preparative Vydac C18 column (2.5 cm) using a 1.0% /minute gradient of 10 to 38% acetonitrile containing 0.1% trifluoroacetic acid to give the TFA salt of the title compound (150 mg, 49%) as a fluffy white solid; $^1$H NMR (D$_6$-DMSO) 8.90 (d, 1H), 8.40 (m, 2H), 7.70 (d, 1H), 7.50 (m, 1H), 7.30 (m, 1H), 7.05 (s, 1H), 7.00 (d, 1H), 7.00 (br s, 4H), 5.15 (dd, 1H), 4.65 (q, 1H), 4.45 (dd, 1H), 4.40 (q, 1H), 4.00 (q, 1H), 3.90 (q, 1H), 3.65 (dd, 1H), 3.10 (q, 2H), 3.05 (s, 3H), 2.70 (dd, 1H), 2.50 (m, 1H), 1.95 (m, 1H), 1.75 (m, 2H), 1.60 (m, 1H), 1.40 (m, 2H), 0.95 (t, 3H); FAB-MS: [M+H]=687.3.

EXAMPLE 100c cyclo-(D-Abu-NMeArg-Gly-Asp-3-aminomethyl-6-methylbenzoic acid) (the compound of formula (VII) wherein J=D-Abu, K=NMeArg, L=Gly, M=Asp, $R^{10}$=Me)

The title compound was prepare by the general solution-phase procedure described above for cyclo-(D-Val-NMeArg-Gly-Asp-Mamb), except that 4,4'-dinitrobenzophenone oxime was employed. The cyclic peptide (130 mg, 0.16 mmol) was deprotected with excess HF in the presence of anisole as scavenger. Purification was accomplished by reversed-phase HPLC on a preparative Vydac C18 column (2.5 cm) using a 1.0% /minute gradient of 10 to 38% acetonitrile containing 0.1% trifluoroacetic acid to give the TFA salt of the title compound (31 mg, 28%) as a fluffy white solid; $^1$H NMR (D$_6$-DMSO) 8.70 (d, 1H), 8.40 (d, 1H), 8.30 (t, 1H), 7.50 (m, 1H), 7.45 (m, 1H), 7.15 (q, 2H), 7.05 (s, 1H), 7.00 (br s, 4H), 5.15 (dd, 1H), 4.65 (q, 1H), 4.45 (m, 2H), 4.00 (m, 2H), 3.65 (dd, 1H), 3.10 (q, 2H), 3.05 (s, 3H), 2.75 (dd, 1H), 2.50 (m, 1H), 2.30 (s, 3H), 2.00 (m, 1H), 1.75 (m, 2H), 1.60 (m, 1H), 1.35 (m, 2H), 0.95 (t, 3H); FAB-MS: [M+H]=575.4.

Representative Prodrugs

Step 1: $N^\alpha$-benzyloxycarbonyl-$N^\alpha$-methyl-4-cyano-L-2-aminobutyric acid Z-Gln (28.03 g, 100 mmol) was dissolved in 300 mL THF in a flask bottle protected from moisture and to it was added 100 mL 1.93M phosgene in toluene (193 mmol). The solution was stirred at room temperature for 2 h and concentrated at 30° C. to 200 mL. Water (200 mL) was added slowly with stirring. After stirring at room temperature for 2 h, the organic phase was separated, and the water phase was extracted with ethyl acetate twice. The combined organic solution was washed with brine four times, dried (MgSO$_4$), and concentrated. The oily product was dried over KOH overnight.

The dried oily product was taken up in 300 mL dry THF and 49.8 mL (800 mmol) methyl iodide in a flask bottle protected from moisture and the solution was cooled in an ice bath. To it was slowly added 10 g sodium hydride (250 mmol, 60% dispersion in oil). The mixture was stirred in the ice bath for 1 h and then at room temperature for 22 h. Ethyl acetate (50 mL) was added, and after stirring for 10 min, 100 mL water was added slowly. The solution was acidified with a few drops of 4N HCl to pH$_8$-9 and then concentrated at 30° C. to remove the organic solvents. Water (100 mL) was added followed by 10 mL 0.1N sodium thiosulfate, and the solution was extracted with ether twice. The water layer was cooled in an ice bath and to it was slowly added 4N HCl to pH 3 with stirring. The product, which crystallized during the acidification, was filtered, washed with water several times, and dried. Yield 26.0 g (94%). mp 81°-83° C. $^1$H-NMR (CDCl$_3$): δ=2.15 (m, 1H); 2.38 (m, 1H); 2.42 (m, 2H); 2.96 & 2.98 (2 s, cis & trans N-CH$_3$); 4.62 (m, 1H); 4.90 (b, 1H); 5.19 (s, 2H); 7.35 (m, 5H).

Step 2: $N^\alpha$-methyl-4-cyano-L-2-aminobutyric acid-N-carboxyanhydride

To a solution of example 1 (11.05 g, 40 mmol) in 50 mL dry THF cooled in an ice bath was added phosphorus pentachloride (15 g, 72 mmol) and the mixture was stirred for 2 h and concentrated to dryness. The residue was triturated with petroleum ether to give a solid which was filtered, washed with petroleum ether and dissolved in dry acetonitrile. Insoluble material was filtered off and the solution was concentrated. The solid was washed with cold ether and dried. Yield 5.86 g (87%). mp 90°-92° C. $^1$H-NMR (CDCl$_3$): δ=2.18 (m, 1H); 2.39 (m, 1H); 2.60 (m, 2H); 3.02 (s, 3H); 4.28 (m, 1H).

Step 3: N-Boc-D-2-aminobutyryl-$N^\alpha$-methyl-4-cyano-L-2-aminobutyryl-glycine t-butyl ester To a solution of glycine t-butyl ester hydrochloride (3.68 g, 22 mmol) in 40 mL chloroform and 4.84 mL N-methylmorpholine cooled to –40° C. was added a solution of example 2 (3.36 g, 20 mmol) in 20 mL dry acetonitrile, the solution was stirred at –20° C. for 1 h, and the solvent was reduced to about 10 mL.

To a solution of N-Boc-D-2-aminobutyric acid dicyclohexylamine salt (8.08 g, 21 mmol) in 30 mL chloroform cooled to –10° C. was added diphenylphosphinic chloride (3.91 mL, 20.5 mmol) and the mixture was stirred at –5° to –10° C. for 1 h. To it was added the above prepared solution (10 mL) followed by 2.42 mL N-methylmorpholine. The mixture was stirred at 0° to –50° C. for 24 h, and then concentrated. Ethyl acetate was added and insoluble material was filtered off. The filtrate was washed with NaHCO$_3$ four times and with brine three times, dried over MgSO$_4$, and concentrated to a small amount at which time the product crystallized. Petroleum ether was added, and after cooling, the solid was filtered, washed with petroleum ether, and dried. Yield 6.2 g (70%). mp 90°-92° C. FAB-MS (MH+): Calculated 441.3; Found 441.3.

Step 4: N-Boc-D-2-aminobutyryl-$N^\alpha$-methyl-$N^\omega$, $N^{\omega'}$-(bisbenzyloxycarbonyl)-L-arginyl-glycine t-butyl ester The compound of Step 3 (4.63 g, 10.5 mmol) was dissolved in 70 mL methanol in a Parr bottle and to it was added a cold solution of 1.2 mL concentrated hydrochloric acid (38%) in 10 mL methanol followed by 200 mg platinum (IV) oxide. The mixture was hydrogenated at 55 psi for 1 h, the catalyst was filtered off, and 2.09 mL (15 mmol) triethylamine was added. The solvent was removed under reduced pressure and the residue was taken up in 20 mL THF. To it was added N,N'-bisbenzyloxycarbonyl-S-methylisothiourea (3.58 g, 10 mmol) followed by 2.09 mL (15 mmol) triethylamine. The mixture was stirred overnight during which time the bottle was evacuated several times to remove the byproduct methanethiol. Ethyl acetate was added, and the solution was washed with 1% citric acid, brine, 5% NaHCO$_3$ and brine, dried (MgSO$_4$), and concentrated. Crystallization from ethyl ether-petroleum ether gave 7.2 g (95%) product. FAB-MS (MH+): Calculated 755.4; Found 755.4.

Step 5: D-2-aminobutyryl-N$^\alpha$-methyl-N$^\omega$, N$^{\omega\prime}$-(bisbenzyloxycarbonyl)-L-arginyl-glycine TFA salt A solution of the compound of Step 4 (9 g, 11.9 mmol) in 90 mL 50% TFA in methylene chloride was stirred at room temperature for 2 h and the solution was concentrated at 30° C. Cold ether was added, and after standing, the solid was filtered, washed with ether, and dried. Yield 8.4 g (99%). FAB-MS (MH+): Calculated 599.3; Found 599.3.

Step 6: 3-(aminomethyl)benzoic acid hydrochloride 3-cyanobenzoic acid (5.88 g, 40 mmol) was suspended in 50 mL THF and the mixture was warmed up with stirring. After all solid went into solution, 50 mL isopropanol was added and the solution was allowed to cool to room temperature. To it was added 4.2 mL precooled concentrated HCl followed by 300 mg platinum(IV) oxide. The mixture was hydrogenated at 55 psi overnight. Ether (50 mL) was added, and the precipitate was filtered, washed with ether and dissolved in methanol. The catalyst was filtered off and the solvent was removed under reduced pressure to give 6.2 g (82%) product. $^1$H-NMR (DMSO-d$_6$): δ=4.08 (d, 2H); 7.53 (t, 1H); 7.80 (d, 1H); 7.94 (d, 1H); 8.10 (s, 1H); 8.65 (s, 3H).

Step 7: Fmoc-L-aspartyl (t-butyl)-3-(aminomethyl)-benzoic acid

To a solution of FmocAsp (Bu$^t$) OPfp (17.33 g, 30 mmol) and the compound of Step 6 (6.19 g, 33 mmol) in 50 mL DMF cooled in an ice bath was added 11.5 mL (66 mmol) diisopropylethylamine, and after stirring at room temperature for 5 h, 200 mL 5% citric acid was added and the solution was extracted with ethyl acetate twice. The combined extracts were washed with brine, dried (MgSO$_4$), and concentrated to give a solid which was washed with ether-petroleum ether and dried. Yield 16.3 g (100%).

$^1$H-NMR (DMSO-d$_6$): δ=1.35 (s, 8H); 2.48 (dd, 1H); 2.70 (dd, 1H); 4.2–4.4 (m, 6H); 7.30 (t, 2H); 7.4–7.5 (m, 4H); 7.7–7.9 (m, 7H); 8.55 (t, 1H); 12.92 (s, 1H).

Step 8: Fmoc-L-aspartyl(t-butyl)-3-(aminomethyl)benzoyl-D-2-aminobutyryl-N$^\alpha$-methyl-N$^\omega$, N$^{\omega\prime}$-(bisbenzyloxycarbonyl)-L-arginyl-glycine A mixture containing the compound of Step 7 (10.89 g, 20 mmol), pentafluorophenol (4.05 g, 22 mmol) and DCC (4.13 g, 20 mmol) in 50 mL THF was stirred at room temperature overnight. Dicyclohexylurea was filtered off, rinsed with THF, and the filtrate was concentrated. To it was added a solution of the compound of Step 5 (14.25 g, 20 mmol) in 40 mL DMF followed by 7.32 mL (42 mmol) diisopropylethylamine. The mixture was stirred at room temperature for 4 h, insoluble material was filtered off, and the filtrate was added to 200 mL 3% citric acid with stirring. The solution was extracted with ethyl acetate twice and the combined extracts were washed with brine, dried (MgSO$_4$), and concentrated. The residue was triturated with ether-petroleum ether to give 22 g (98%) product. FAB-MS (MH+): Calculated 1125.5; Found 1125.7.

Step 9: Cyclo[L-aspartyl(t-butyl)-3-(aminomethyl)benzoyl-D-2-aminobutyryl-N$^\omega$, N$^{\omega\prime}$-(bisbenzyloxycarbonyl)-L-arginyl-glycyl]

A solution of the compound of Step 8 (22.5 g, 20 mmol) and 4-dimethylaminopyridine (14.66 g, 120 mmol) in 100 mL DMF was stirred overnight at room temperature and added slowly to a solution of TBTU (6.42 g, 20 mmol) in 200 mL DMF over 3 h and stirring was continued for 1 h. Ethyl acetate (1000 mL) was added and the solution was washed with 1% citric acid 2 times, brine 3 times and concentrated to dryness. The residue was taken up in THF and after filtration, the solvent was removed under reduced pressure to give a solid which was washed with ether and dried. Yield 16 g (90% FAB-MS (MH+): Calculated 885.4; Found 885.2.

Step 10: Cyclo[L-aspartyl-3-(aminomethyl)benzoyl-D-2-aminobutyryl-N$^\omega$, N$^{\omega\prime}$-(bisbenzyloxycarbonyl)-L-arginyl-glycyl]

A solution of the compound of Step 9 (16 g, 18 mmol) in 200 mL 50% TFA in methylene chloride was stirred at room temperature for 1.5 h and then concentrated. The residue was triturated with ether to give 14.5 g (97%) product. FAB-MS (MH+): Calculated 829.4; Found 829.1.

EXAMPLE 301

Cyclo[L-aspartyl(acetoxymethyl)-3-(aminomethyl) benzoyl-D-2-aminobutyryl-L-arginyl-glycyl]

A mixture containing the compound of Step 10 (above) (1.42 g, 1.7 mmol), bromomethyl acetate (980 mL, 10 mmol) and triethylamine (976 mL, 7 mmol) in 10 mL DMF was stirred at room temperature overnight. Ethyl acetate was added and the solution was washed with brine 3 times, dried (MgSO$_4$), concentrated, and dried. The residue was taken up in 8 mL DMF and to it was added 130 mL (2 mmol) methanesulfonic acid followed by 150 mg 10% palladium on carbon. The mixture was hydrogenated at atmospheric pressure for 2 h, the catalyst was filtered off, and the solution was diluted with water. Purification using semipreparative HPLC gave 650 mg (51) pure product. FAB-MS (MH+): Calculated 633.3; Found 633.2.

EXAMPLE 308

Cyclo[L-aspartyl(pivaloyloxymethyl)-3-(aminomethyl)benzoyl-D-2-aminobutyryl-L-arginyl-glycyl]

A mixture containing the compound of Step 10 (above) (4.14 g, 5 mmol), chloromethyl pivalate (4.3 mL, 30 mmol), triethylamine (2.8 mL, 20 mmol), NaI (4.5 g, 30 mmol) in 10 mL DMF was stirred at room temperature for 18 h. Ethyl acetate (100 mL) was added and the solution was washed with brine 3 times, dried (MgSO$_4$), and concentrated. The residue was taken up in 15 mL ethyl acetate and passed through a silica gel column using ethyl acetate-THF (1:1) as eluent to give 1.5 g pure product. The product was dissolved in 10 mL DMF and hydrogenated at atmospheric pressure using 10% palladium on carbon (130 mg) in the presence of methanesulfonic acid (100 mL) for 2 h. The catalyst was filtered off, rinsed with DMF, and the solution was diluted with water. Purification using semipreparative HPLC gave 1 g (26%) pure product. FAB-MS (MH+): Calculated 675.3; Found 675.3.

EXAMPLE 351

Cyclo[L-aspartyl-(isopropyloxycarbonyl-oxymethyl) -3-aminomethyl)benzoyl-D-2-aminobutyryl-L-arginyl-glycyl]

A mixture containing the compound of Step 10 (4.14 g, 5 mmol), chloromethyl isopropyl carbonate (4.58 g, 30 mmol), triethylamine (2.8 mL, 20 mmol), NaI (4.5 g, 30 mmol) in 10 mL DMF at stirred at room temperature for 18 h. Ethyl acetate (100 mL) was added and the solution was washed with brine 3 times, dried (MgSO$_4$), and concentrated. The residue was taken up in 10 mL ethyl acetate-THF (1:1) and passed through a silica column using ethyl acetate-THF (1:1) as eluent to give 1.6 g product. The product was dissolved in 10 mL DMF and hydrogenated at atmospheric pressure using 10% palladium on carbon (150 mg) in the presence of 130 mL for 2 h. The catalyst was filtered off, rinsed with DMF, and the solution was diluted with water. Purification using semipreparative HPLC gave 1 g (25%) pure product. FAB-MS (MH+): Calculated 667.3; Found 667.3.

Incorporated herein by reference in their entirety are the following copending, commonly assigned U.S. Patent Applications: U.S. Ser. No. 08/038,443, named inventor Maduskuie; U.S. Ser. No. 08/038,434, named inventor Zhang, Ma, and DeGrado; and U.S. Ser. No. 08/038,961, named inventors De Grado, Dorow, Ward, and Xue.

Utility

The compounds of this invention possess antiplatelet efficacy, as evidenced by their activity in standard platelet aggregation assays or platelet fibrinogen binding assays, as described below. A compound is considered to be active in these assays if it has an IC$_{50}$ value of less than about 1 mM. Platelet aggregation and fibrinogen binding assays which may used to demonstrate the antiplatelet activity of the compounds of the invention are described below.

Platelet Aggregation Assay: Venous blood was obtained from the arm of a healthy human donor who was drug-free and aspirin-free for at least two weeks prior to blood collection. Blood was collected into 10 ml citrated Vacutainer tubes. The blood was centrifuged for 15 minutes at 150×g at room temperature, and platelet-rich plasma (PRP) was removed. The remaining blood was centrifuged for 15 minutes at 1500×g at room temperature, and platelet-poor plasma (PPP) was removed. Samples were assayed on a aggregometer (PAP-4 Platelet Aggregation Profiler), using PPP as the blank (100% transmittance). 200 µl of PRP was added to each micro test tube, and transmittance was set to 0%. 20 µl of various agonists (ADP, collagen, arachidonate, epinephrine, thrombin) were added to each tube, and the aggregation profiles were plotted (% transmittance versus time). The results were expressed as % inhibition of agonist-induced platelet aggregation. For the IC$_{50}$ evaluation, the test compounds were added at various concentrations prior to the activation of the platelets.

Platelet-Fibrinogen Binding Assay: Binding of $^{125}$I-fibrinogen to platelets was performed as described by Bennett et al. (1983) Proc. Natl. Acad. Sci. USA 80: 2417–2422, with some modifications as described below. Human PRP (h-PRP) was applied to a Sepharose column for the purification of platelet fractions. Aliquots of platelets (5×10$^8$ cells) along with 1 mM calcium chloride were added to removable 96 well plates prior to the activation of the human gel purified platelets (h-GPP). Activation of the human gel purified platelets was achieved using ADP, collagen, arachidonate, epinephrine, and/or thrombin in the presence of the ligand, $^{125}$I-fibrinogen. The $^{125}$I-fibrinogen bound to the activated, platelets was separated from the free form by centrifugation and then counted on a gamma counter. For an IC$_{50}$ evaluation, the test compounds were added at various concentrations prior to the activation of the platelets.

The novel cyclic glycoprotein IIb/IIIa compounds of the invention also possess thrombolytic efficacy, that is, they are capable of lysing (breaking up) already formed platelet-rich fibrin blood clots, and thus are useful in treating a thrombus formation, as evidenced by their activity in the tests described below. Preferred cyclic compounds of the present invention for use in thrombolysis include those compounds having an IC$_{50}$ value (that is, the molar concentration of the cyclic compound capable of achieving 50% clot lysis) of less than about 1 mM, more preferably an IC$_{50}$ value of less than about 0.1 mM, even more preferably an IC$_{50}$ value of less than about 0.01 mM, still more preferably an IC$_{50}$ value of less than about 0.001 mM, and most preferably an IC$_{50}$ value of about 0.0005 mM.

IC$_{50}$ determinations may be made using a standard thrombolysis assay, as described below. Another class of preferred thrombolytic compounds of the invention include those compounds which have a Kd of <100 nM, preferably <10 nM, most preferably 0.1 to 1.0 nM.

Thrombolytic Assay: Venous blood was obtained from the arm of a healthy human donor who was drug-free and aspirin free for at least two weeks prior to blood collection, and placed into 10 ml citrated Vacutainer tubes. The blood was centrifuged for 15 minutes at 1500 ×g at room temperature, and platelet rich plasma (PRP) was removed. To the PRP was then added 1×10$^-$3M of the agonist ADP, epinephrine, collagen, arachidonate, serotonin or thrombin, or a mixture thereof, and the PRP incubated for 30 minutes. The PRP was centrifuged for 12 minutes at 2500×g at room temperature. The supernatant was then poured off, and the platelets remaining in the test tube were resuspended in platelet poor plasma (PPP), which served as a plasminogen source. The suspension was then assayed on a Coulter Counter (Coulter Electronics, Inc., Hialeah, Fla.), to determine the platelet count at the zero time point. After obtaining the zero time point, test compounds were added at various concentrations. Test samples were taken at various time points and the platelets were counted using the Coulter Counter. To determine the percent of lysis, the platelet count at a time point subsequent to the addition of the test compound was subtracted from the platelet count at the zero time point, and the resulting number divided by the platelet count at the zero time point. Multiplying this result by 100 yielded the percentage of clot lysis achieved by the test compound. For the IC$_{50}$ evaluation, the test compounds were added at various concentrations, and the percentage of lysis caused by the test compounds was calculated.

Platelet Granular Secretion Studies. The role of the claimed platelet GPIIb/IIIa receptor antagonists on the modulation of platelet granular secretion from the α-granules, dense granules or intracellular Ca$^{+2}$ binding proteins was examined. This class of compounds did not have any significant effect on platelet granular secretion of plasminogen activator inhibitor type-1 (PAI-1) from α-granules, the mobilization of intracellular calcium stores or the secretion of the vasoconstrictor serotonin from the dense granules. However, other antiplatelet agents such as aspirin or the antithrombin hirudin has been shown to inhibit platelet granular secretion of the antifibrinolytic (PAI-1) or the vasoconstrictor (serotonin) Hence the combination between a universal antiaggregatory as well as an inhibitor of platelet secretion might provide optimal clinical benefits.

The novel cyclic compounds of the invention are also useful in combination products, that is, in pharmaceutical compositions containing the novel cyclic compounds of the invention in combination with anti-coagulant agents such as warfarin or heparin, or antiplatelet agents such as aspirin, piroxicam or ticlopidine, or thrombin inhibitors such as boropeptides, hirudin or argatroban, or thrombolytic agents such as tissue plasminogen activator, anistreplase, urokinase or streptokinase, or combinations thereof. Such combination products possess anti-platelet and thrombolytic efficacy, as evidenced by their activity in the tests described below.

These and other uses for the novel cyclic compounds of this invention, and combination products containing the same, will be readily apparent from the disclosures herein.

Platelet GPIIb/IIIa Binding Affinity

In the human gel-purified platelet (h-GPP) $^{125}$I-fibrinogen binding assay, representative compounds of the present invention demonstrated high affinity in inhibiting the $^{125}$I-fibrinogen binding to h-GPP ($IC_{50}$=5–100 nM) regardless of the agonist used. In an enzyme-linked immunosorbent assay (ELISA) using purified GPIIb/IIIa receptors obtained from human platelets, the representative compounds of the invention demonstrated direct inhibition of fibrinogen binding to RGD recognition site(s), with an $IC_{50}$ of 0.5–10 nM. The inhibitory efficacy of the presently claimed compounds on fibrinogen binding to the platelet GPIIb/IIIa receptor was shown to be related to the number of binding sites, as is evident from the decrease in $IC_{50}$ when platelet number was decreased.

Compound A (Example 3) was shown to displace $^{125}$I-fibrinogen bound to activated platelets In this study, fibrinogen bound to activated platelets was incubated for 20 minutes prior to the addition of Compound A. This suggests a high affinity for Compound A in displacing fibrinogen from an already formed platelet-rich clot. This effect may explain the lytic efficacy of the compounds of the present invention. A high affinity binding (Kd=0.1 nM) of $^3$H-labeled Compound A to activated human platelets was determined based on Scatchard analysis. Additionally, in the purified GPIIb/IIIa-biotinylated fibrinogen ELISA, Compound A demonstrated competitive inhibitory efficacy with a $K_i$ of 0.4 nM based on Michaelis-Menten analysis.

As shown below, in the human PRP aggregation assay, Compound A was shown not only to inhibit platelet aggregation induced by agonists, but also to deaggregate platelets after the initiation of aggregation. The deaggregation efficacy of Compound A was dependent on its concentration and the time of addition post-initiation of platelet activation. The earlier the addition of Compound A after the induction of aggregation, the greater its deaggregatory efficacy (FIG. Ia).

The effect of Compound A on the lysis of a pre-formed platelet-rich clot was also examined. In this regard, the thrombolytic efficacy of Compound A was also evaluated (FIG. Ib and II). Compounds A and B (Example 4) both demonstrated a significant lytic efficacy of pre-formed platelet rich-clot (FIG. Ib). Furthermore, Compound A demonstrated in vitro and in vivo synergistic efficacy with standard thrombolytics in lysing a platelet-rich thrombus (FIG. IIIb). A concentration-dependent lytic effect with an $IC_{50}$ of 0.5–1.0 uM for compounds A and B was shown (FIG. Ib). In contrast the tetrapeptide, RGDS, was shown to be ineffective under similar conditions (FIG. Ib).

Additionally, in vitro studies revealed synergy between Compound A (0.1–1.0 uM) and streptokinase, urokinase or t-PA in lysing a pre-formed platelet-rich clot (FIG. III). These results suggest an in vivo lytic potential for disclosed compounds of the present invention. Additionally, administration of these novel antagonists is expected to significantly reduce the dosage of a thrombolytic agent being used for clot lysis and the prevention of reocclusion and/or restenosis. In this regard, increasing evidence suggests that platelet activation after thrombolytic therapy might have a significant role in delaying reperfusion and abrupt closure. Hence, the disclosed analogs might be an effective adjunct to thrombolytic therapy or angioplasty.

The cyclic glycoprotein IIb/III antagonist compounds of this invention have also been shown to displace $^{125}$I-fibrinogen bound to activated platelets in a platelet-fibrinogen binding assay similar to the platelet-fibrinogen binding assay previously described. The results indicated that the compounds have a high affinity in displacing fibrinogen from an already formed platelet-rich clot. Although not intending to be bound by any theory of operation, this result may help explain the surprising thrombolytic efficacy possessed by compounds of the invention, as illustrated in the preceding examples.

FIG. 1

Figure 1B:
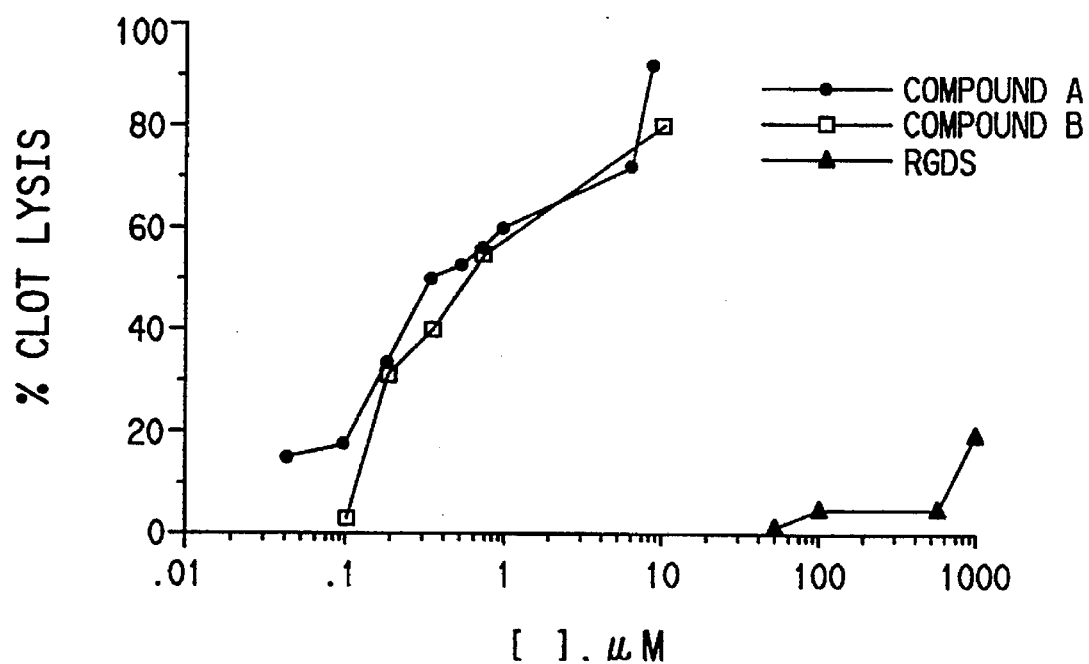
Figure 6:
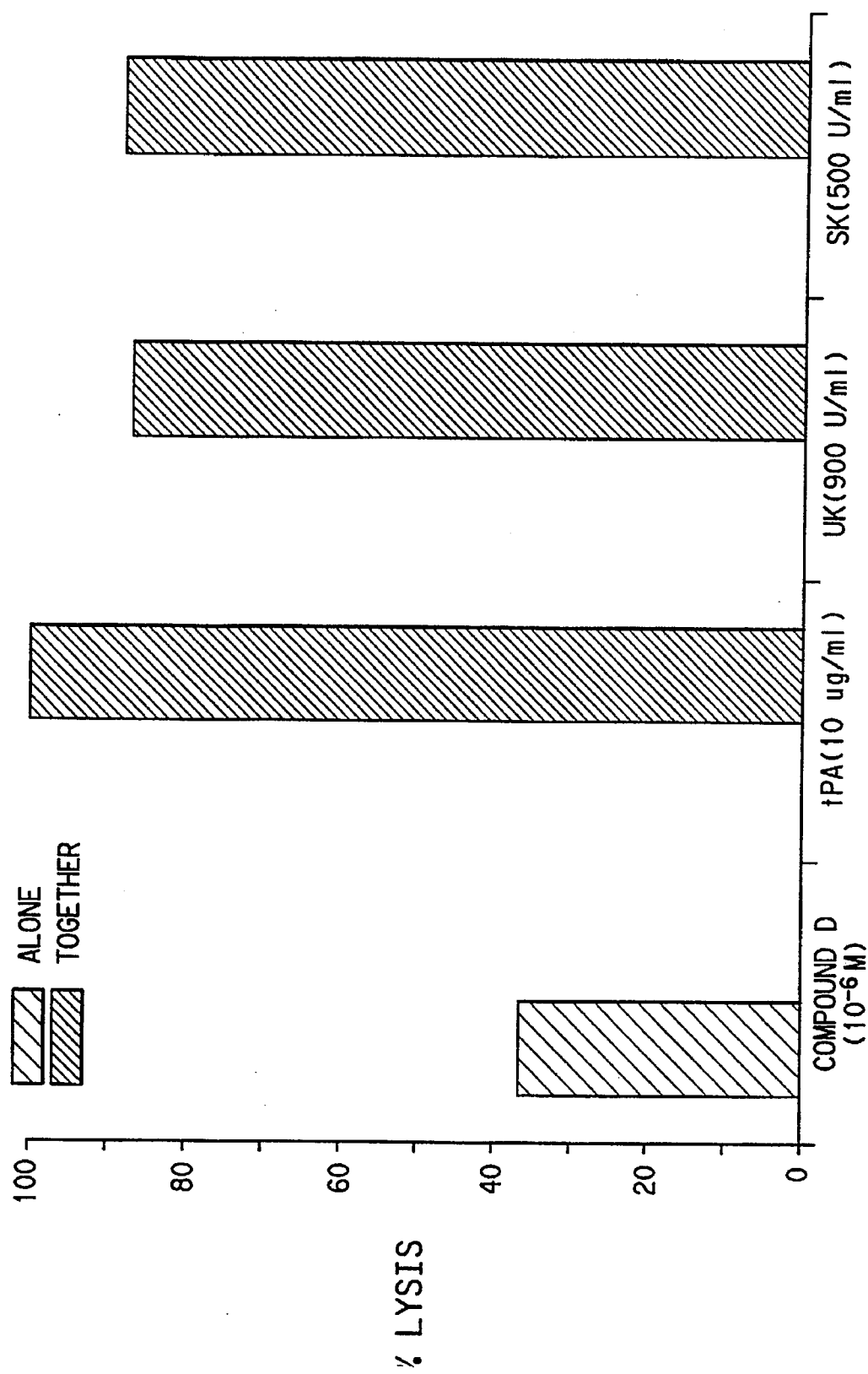
Figure 7:
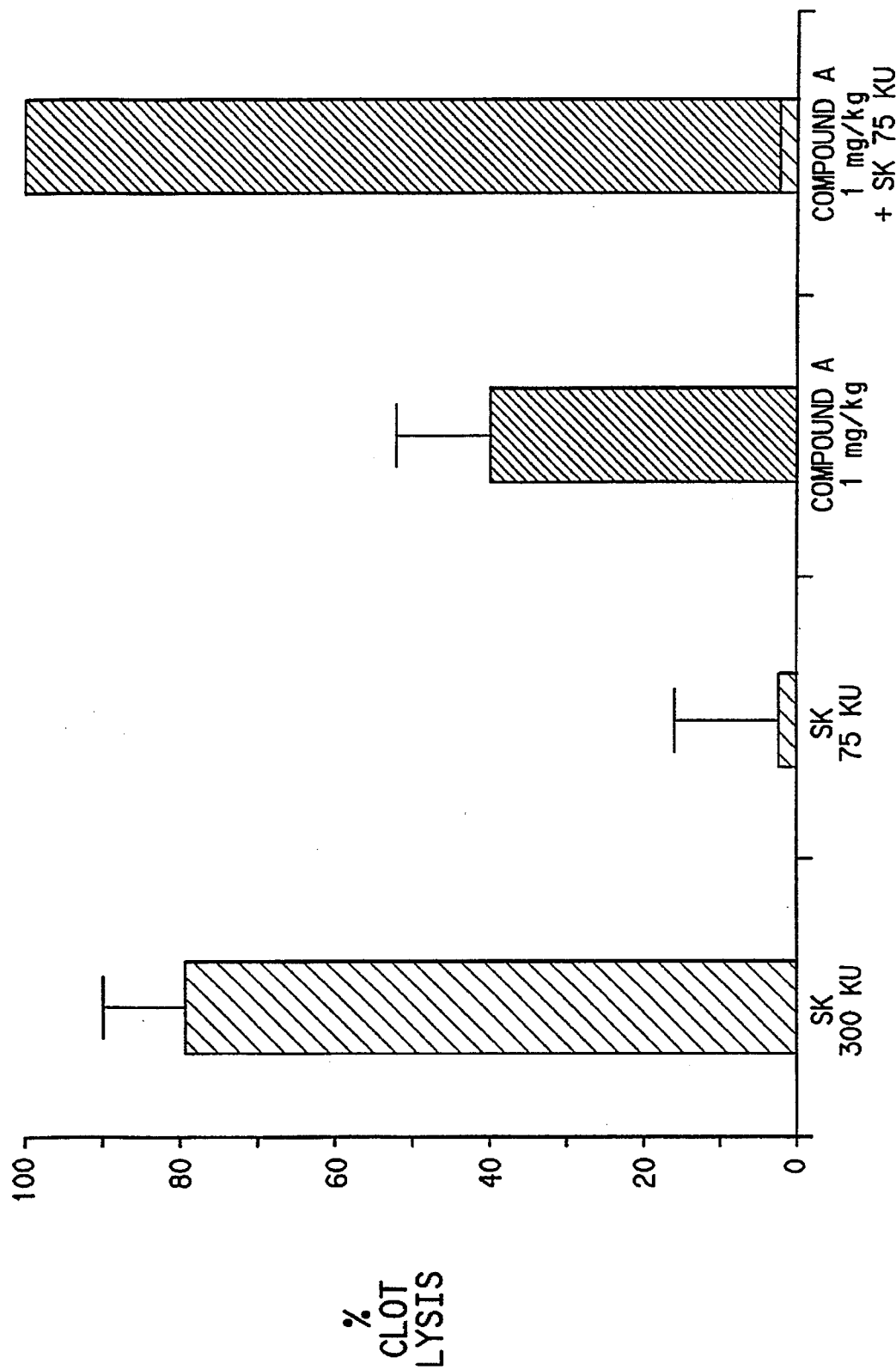
Figure 8B:
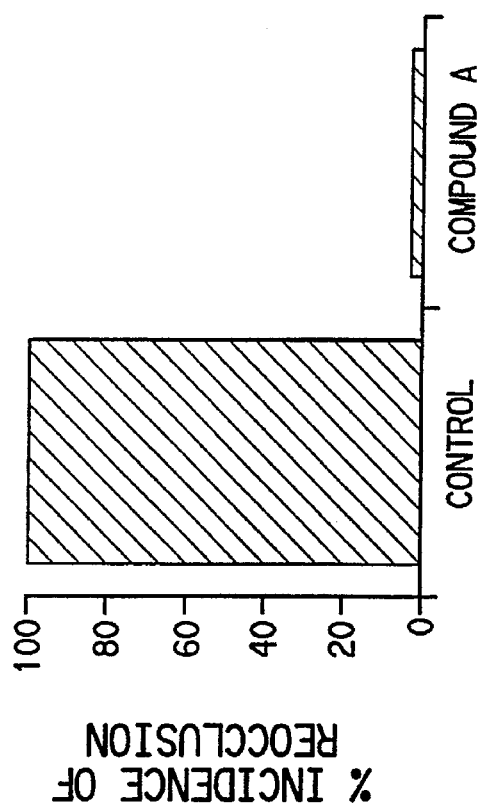
Figure 8A:
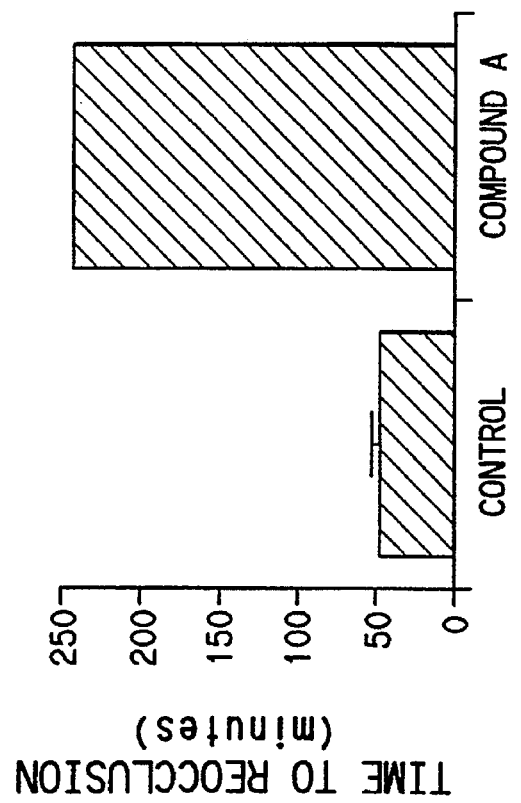

Representative cyclic compounds of the present invention, namely the compound of Example 3 (cyclo-(D-Abu-NMeArg-Gly-Asp-Mamb; the compound of formula (II) wherein $R^1$ and $R^2$ are H, J is D-2-aminobutyric acid, K is α-N-methylarginine, L is glycine, and M is aspartic acid) (designated here as Compound A) and the compound of Example 4 (cyclo-(D-Val-NMeArg-Gly-Asp-Mamb; the compound of formula (II) wherein $R^1$ and $R^2$ are H, J is D-valine, K is α-N-methyl-arginine, L is glycine, and M is aspartic acid) (designated here as Compound B) were then tested in the human PRP aggregation assay (FIG. Ia). FIG. 1 shows the effect of 0.1 uM Compound on the reversal of the aggregatory response (deaggregation) to 10 uM ADP when added at 1.5 min post-initiation of aggregation.

In the human PRP aggregation assay, representative compounds of the present invention are shown not only to inhibit platelet aggregation induced by agonists, but also to deaggregate platelets after the initiation of aggregation (FIG. Ia). The deaggregation efficacy of compound A was dependent on its concentration and the time of addition post-initiation of platelet activation. The earlier the addition of Compound A after the induction of aggregation, the greater its deaggregatory efficacy.

Compounds A and B were also tested at varying concentrations using the thrombolytic assay described above (FIG. Ib). FIG. Ib shows the lytic effect of Compound A and B on an already formed platelet rich clot. The clot was formed by incubating platelets with a mixture of agonists (TEAC mixture), which consists of thrombin (0.01 U/ml), epinephrine (250 uM), ADP (250 uM), and collagen (10 ug.ml), for 30 minutes. As a comparison, a linear peptide of sequence arginine-glycine-aspartic acid-serine (RGDS) was also tested in the thrombolytic assay. The results are shown in FIG. I. The compounds of the invention (Compounds A and B) demonstrated a significant effect on the lysis of an already formed platelet-rich clot. As the results indicated, Compounds A and B had $IC_{50}$ values of about 0.5–1.0 uM. By comparison, the RGDS linear peptide was much less effective, even at substantially higher concentrations ($IC_{50}$>1 mM).

FIG. II

Compounds A and B was tested at a concentration of 0.001 mM using the thrombolytic assay described above, with platelet stimulation being carried out using 1×10⁻3M concentration of ADP. As a comparison, the standard thrombolytics tissue plasminogen activator (tPA; 10 µg/ml), urokinase (UK; 900 units/ml) and streptokinase (SK; 500 units/ml) were also tested in the thrombolytic assay. The results are shown in FIG. II. The compounds of the invention (Compounds A and B) demonstrated a significant effect on the lysis of an already formed platelet-rich clot, with Compound A providing significantly better clot lysis than tissue plasminogen activator, urokinase, and streptokinase, and Compound B providing significantly better clot lysis than streptokinase. As the results indicated, Compound A had an excellent lysis percentage of 70% or greater.

FIG. III

FIG. III shows the effect of 1 uM of Compound A on the lysis of an already formed platelet-rich clot. The clot was formed by the addition of TEAC mixture (which consists of thrombin (0.01 U/ml), epinephrine (250 uM), ADP (250 uM), and collagen (10 ug.ml)) for 30 minutes. Compound A resulted in significant clot lysis by itself as compared to tissue plasminogen activator (tPA; 10 µg/ml), urokinase (UK; 900 units/ml) and streptokinase (SK; 500 units/ml). A synergy (greater than additive effect between the standard thrombolytics and the IIb/IIIa antagonist Compound A was demonstrated. Data represent mean±SEM, n=3 in each group.

FIG. V

Compound C was tested at a concentration of 1 uM using the thrombolytic assay described above, both alone and in combination with the standard thrombolytics tissue plasminogen activator (tPA; 10 µg/ml), urokinase (UK; 900 units/ml) and streptokinase (SK; 500 units/ml). As the results indicate, the combination of Compound C with tissue plasminogen activator, urokinase or streptokinase gave a greater than additive effect than either agent alone.

FIG. VI

Compound D was tested at a concentration of 1 uM using the thrombolytic assay described above, both alone and in combination with the standard thrombolytics tissue plasminogen activator (tPA; 10 µg/ml), urokinase (UK; 900 units/ml) and streptokinase (SK; 500 units/ml). As the results indicate, the combination of Compound D with tissue plasminogen activator, urokinase or streptokinase gave a greater than additive effect than either agent alone.

FIG. VII

VII a.

Effect of 1 uM Compound A on the lysis of an already formed platelet-rich clot. The clot was formed by the addition of TEAC mixture (which consists of thrombin [0.001 U/ml], epinephrine [250 uM], adenosine diphosphate [250 uM] and collagen [10 ug/ml] for 30 min. Compound A resulted in a significant clot lysis by itself as compared to SK (500 U/ml), UK (900 U/ml) or t-PA (10 ug/ml). A synergistic effect between the standard thrombolytics and the IIb/IIIa antagonist Compound A was demonstrated. Data represent mean±SEM, N=3 in each group.

VII b.

In vivo thrombolytic efficacy of Compound A and its interaction with standard thrombolytics: Compound A at 1 mg/kg I.V. in the modified Lucchesi model resulted in significant lysis of an already formed thrombus in the femoral artery. Additionally, Compound A in combination with sub-optimum doses of the standard thrombolytic, streptokinase (75 KU) resulted in a significant synergistic effect in fully lysing the thrombus with subsequent restoration of flow, and the prevention of reocclusion. Data represent mean±SEM. n=3–6 in each group.

FIG. VIII

Effects of Compound A vs saline, when given to anesthetized canine (male or female mongrel dogs) at 1.0 mg/kg I.V., on the incidence of femoral artery reocclusion post-thrombolysis with streptokinase (250–300×1000 IU/kg) or t-PA. Compound A resulted in 100% prevention of reocclusion for a period >240 minutes, in comparison to saline-treated animals which were shown to reocclude at 42±10 min. Compound A (1.0 mg/kg, I.V.) resulted in % prevention of the incidence of reocclusion post-thrombolysis with SK or t-PA. Data represents mean ±SEM. n=6 in each group. Antiplatelet combination of the cyclic GPIIb/IIIa receptor antagonist of the present invention and aspirin and/or heparin.

Methods: Twelve purpose bred mongrel dogs (8–15 months of age) of either sex weighing between 8–12 kg were anesthetized with thiamylal sodium (15 mg/kg, i.v.) and alpha-chloralose (100 ng/kg, i.v.) Dogs were placed on positive pressure ventilation (15 mg/kg (a) 20 breaths/min). The femoral artery and vein were dissected and cannulated for arterial blood pressure and heart rate monitoring, blood sampling, and intravenous injections.

Treatment Groups:

Group I (Saline): I.V. bolus of saline.

Group II (Aspirin): 10 mg/kg, po—30 min prior to blood sampling.

Group III (Compound A): 0.08 mg/kg, I.V. bolus.

Group IV (Aspirin/Compound A) : Aspirin at 10 mg/kg, po—30 min prior to the administration of Compound A at 0.08 mg/kg, i.v.

(a) Serial blood samples were withdrawn for ex vivo platelet aggregation and platelet counts.

(b) Bleeding time (min) was monitored over time as well.

(c) Plasma levels of Compound A were determined by an ELISA in all groups.

Results: The Compound A/aspirin, Compound A/heparin, and Compound A/warfarin combinations demonstrated an improved antiplatelet efficacy as compared to Compound A alone. This was achieved without any significant effects on bleeding time or platelet counts.

Dosage and Formulation

The compounds of this invention can be administered by any means that produces contact of the active agent with the agent's site of action, glycoprotein IIb/IIIa (GPIIb/IIIa), in the body of a mammal. They can be administered by any conventional means available for use in conjunction with pharmaceuticals, either as individual therapeutic agents or in a combination of therapeutic agents, such as a second antiplatelet agent such as aspirin, piroxicam, or ticlopidine which are agonist-specific, or an anti-coagulant such as warfarin or heparin, or a thrombin inhibitor such as a boropeptide, hirudin or argatroban, or a thrombolytic agent such as tissue plasminogen activator, anistreplase, urokinase or streptokinase, or combinations thereof. The compounds of the invention, or compounds of the invention in combination with other therapeutic agents, can be administered alone, but generally administered with a pharmaceutical carrier selected on the basis of the chosen route of administration and standard pharmaceutical practice.

The dosage of the novel cyclic compounds of this invention administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.01 to 10 milligrams per kilogram of body weight.

Dosage forms (compositions suitable for administration) contain from about 1 milligram to about 100 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

The combination products of this invention, such as the novel cyclic IIb/IIIa antagonist compounds of this invention in combination with an anti-coagulant agent such as warfarin or heparin, or an anti-platelet agent such as aspirin, piroxicam or ticlopidine, or a thrombin inhibitor such as a boropeptide, hirudin or argatroban, or a thrombolytic agent such as tissue plasminogen activator, anistreplase, urokinase or streptokinase, or combinations thereof, can be in any dosage form, such as those described above, and can also be administered in various ways, as described above.

In a preferred embodiment, the combination products of the invention are formulated together, in a single dosage form (that is, combined together in one capsule, tablet, powder, or liquid, etc.). When the combination products are not formulated together in a single dosage form, the cyclic glycoprotein IIb/IIIa compounds of this invention and the anti-coagulant agent, anti-platelet agent, thrombin inhibitor, and/or thrombolytic agent may be administered at the same time (that is, together), or in any order, for example the compounds of this invention are administered first, followed by administration of the anti-coagulant agent, anti-platelet agent, thrombin inhibitor, and/or thrombolytic agent. When not administered at the same time, preferably the administration of the compound of this invention and any anti-coagulant agent, anti-platelet agent, thrombin inhibitor, and/or thrombolytic agent occurs less than about one hour apart, more preferably less than about 30 minutes apart, even more preferably less than about 15 minutes apart, and most preferably less than about 5 minutes apart. Preferably, administration of the combination products of the invention is oral. The terms oral agent, oral inhibitor, oral compound, or the like, as used herein, denote compounds which may be orally administered. Although it is preferable that the cyclic IIb/IIIa antagonist compounds of this invention and the anti-coagulant agent, anti-platelet agent, thrombin inhibitor, and/or thrombolytic agent are both administered in the same fashion (that is, for example, both orally), if desired, they may each be administered in different fashions (that is, for example, one component of the combination product may be administered orally, and another component may be administered intravenously). The dosage of the combination products of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Although the proper dosage of the combination products of this invention will be readily ascertainable by one skilled in the art, once armed with the present disclosure, by way of general guidance, where the cyclic compounds of this invention are combined with anti-coagulant agents, for example, typically a daily dosage may be about 0.01 to 10 milligrams of the cyclic compound of this invention and about 1 to 7.5 milligrams of the anticoagulants, preferably about 0.1 to 1 milligrams of the cyclic compounds of this invention and about 1 to 5 milligrams of the anti-coagulants, per kilogram of patient body weight. With regard to a typical dosage form of this type of combination product, such as a tablet, the novel compounds of this invention generally may be present in an amount of about 5 to 10 milligrams, and the anti-coagulants in an amount of about 1 to 5 milligrams.

Where the novel compounds of this invention are combined with another anti-platelet agent, by way of general guidance, typically a daily dosage may be about 0.01 to 25 milligrams of the cyclic compounds of this invention and about 50 to 150 milligrams of the additional anti-platelet agents, preferably about 0.1 to 1 milligrams of the novel compounds of this invention and about 1 to 3 milligrams of antiplatelet agents, per kilogram of patient body weight. With regard to a typical dosage form of this type of combination product, such as a tablet, the novel compounds of this invention may be present, for example, in an amount of about 5 milligrams, and the additional anti-platelet agent in an amount of about 150 milligrams, or, for example, in an amount of about 25 milligrams of the cyclic compound of this invention and about 50 milligrams of the additional antiplatelet agent.

Further, in terms of general guidance, where the novel compounds of this invention are combined with thrombolytic agents, typically a daily dosage may be about 0.1 to 1 milligrams of the cyclic compound of this invention, per kilogram of patient body weight and, in the case of the thrombolytic agents, the usual dosage of the thrombolytic agent when administered alone may be reduced by about 70–80% when administered with a compound of the present invention. With regard to a typical dosage form of this type of combination product, such as a tablet, the novel compounds of this invention may be present, for example, in an amount of about 10 milligrams.

As discussed above, where two or more of the foregoing therapeutic agents are combined or co-administered with the compounds of this invention, generally the amount of each component in a typical daily dosage and typical dosage form may be reduced relative to the usual dosage of the agent when administered alone, in view of the additive or synergistic effect which would be obtained as a result of addition of further agents in accordance with the present invention.

Particularly when provided as a single dosage form, the potential exists for a chemical interaction between the combined active ingredients (for example, a novel compound of this invention and an anti-coagulant such as warfarin or heparin, or a novel compound of this invention and an anti-platelet agent such as aspirin, piroxicam or ticlopidine, or a novel compound of this invention and a thrombin inhibitor such as a boropeptide, hirudin or argatroban, or a novel compound of this invention and a thrombolytic agent such as tissue plasminogen activator, anistreplase, urokinase or streptokinase, or combinations thereof). For this reason, the preferred dosage forms of the combination products of this invention are formulated such that although the active ingredients are combined in a single dosage form, the physical contact between the active ingredients is minimized (that is, reduced).

In order to minimize contact, one embodiment of this invention where the product is orally administered provides for a combination product wherein one active ingredient is enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time by the same manner, will be readily apparent to those skilled in the art, once armed with the present disclosure.

Pharmaceutical kits useful in, for example, the inhibition of platelet aggregation, the treatment of blood clots, and/or the treatment of thromboembolic disorders, which comprise a therapeutically effective amount of a novel cyclic platelet glycoprotein IIb/IIIa compound of this invention along with a therapeutically effective amount of an anti-coagulant agent such as warfarin or heparin, or an antiplatelet agent such as aspirin, piroxicam or ticlopidine, or a thrombin inhibitor such as a boropeptide, hirudin or argatroban, or a thrombolytic agent such as tissue plasminogen activator, anistreplase, urokinase or streptokinase, or combinations thereof, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ twopart container (available from Abbott Labs, Chicago, Ill.), as desired. The novel compounds of the invention and the anti-coagulant agent, anti-platelet agent, thrombin inhibitor, thrombolytic agent, and/or combinations thereof, may be separate, or combined into a single dosage form as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

The Tables below set forth representative compounds of the present invention. In the Tables below the biological activity of the compounds is indicated as the $IC_{50}$ value in the platelet aggregation assay described above. The $IC_{50}$ values are expressed as: +++=$IC_{50}$ value of less than 1 uM; ++=$IC_{50}$ value of 1 uM to 10 uM; and; +=$IC_{50}$ value of greater than 10 uM to about 100 uM. As used herein "μM" means micromolar. Where a mixture of isomers of a compound were tested, for example isomers designated as isomer 1 and isomer 2, the biological activity of the mixture is indicated in parentheses for each isomer.

TABLE 1

The optical isomer of J is indicated. $R^{10}$ = H unless otherwise indicated.
Example Numbers 1, 2a, 3a, 4a, 5a, 6a, 7a,
8a, 9a, 10a, 11a, 12a, 13a, 13c, 13e, 13g, 13i, 13k, 13m, 13o, 13q,
13s, 14a, 15a, 16a, 17a, 18, 21a, 22a, 23c, 23b, 24, 28b, 28c, 28g
correspond to SEQ ID NO: 1, 2, 3, 4, 5, 6, 7, 8, 9, 10, 11, 12, 13, 14,
15, 16, 17, 18, 19, 20, 21, 22, 23, 24, 25, 26, 27, 28, 29, 30, 31,
32, 33, 34, 35, respectively.

| Ex. No. | $R^3$ | $R^4$ | $R^5$ | FAB-MS (M+H) | Optical Isomer | $IC_{50}$ |
|---|---|---|---|---|---|---|
| 1 | H | H | H | 533.26 | | +++ |
| 2 | H | H | $CH_3$ | 547.23 | (D) | +++ |
| 2a | H | H | $CH_3$ | | (L) | |
| 3 | H | H | $CH_2CH_3$ | 561.46 | (D) | +++ |
| 3a | H | H | $CH_2CH_3$ | | (L) | |
| 3c | H | H | $CH_2CH_3$ $R^{10}$ = I | 687.33 | (D) | +++ |
| 4 | H | H | $CH(CH_3)_2$ | 575.45 | (D) | +++ |
| 4a | H | H | $CH(CH_3)_2$ | | (L) | |
| 5 | H | H | $CH_2CH(CH_3)_2$ | 589.48 | (D) | +++ |
| 5a | H | H | $CH_2CH(CH_3)_2$ | | (L) | |
| 6 | H | H | $CH_2CH_2CH_3$ | | (D) | |
| 6a | H | H | $CH_2CH_2CH_3$ | | (L) | |
| 7 | H | H | $CH_2CH_2CH_2CH_3$ | 589.26 | (D) | +++ |
| 7a | H | H | $CH_2CH_2CH_2CH_3$ | | (L) | |
| 8 | H | H | $(CH_2)_5CH_3$ | | (D) | |
| 8a | H | H | $(CH_2)_5CH_3$ | | (L) | |
| 9 | H | H | $(CH_2)_7CH_3$ | | (D) | |
| 9a | H | H | $(CH_2)_7CH_3$ | | (L) | |
| 10 | H | H | $C(CH_3)_3$ | | (D) | |
| 10a | H | H | $C(CH_3)_3$ | | (L) | |
| 11 | H | H | phenyl | 609.27 | (D) | +++ |
| 11a | H | H | phenyl | | (L) | |
| 12 | H | H | phenylmethyl | 623.28 | (D) | +++ |
| 12a | H | H | phenylmethyl | | (L) | |
| 13 | H | H | $CH_2OH$ | | (D) | |
| 13a | H | H | $CH_2OH$ | | (L) | |
| 13b | H | H | $(CH_2)_3NH_2$ | | (D) | |
| 13c | H | H | $(CH_2)_3NH_2$ | | (L) | |
| 13d | H | H | $(CH_2)_3NHC(=NH)NH_2$ | | (D) | |
| 13e | H | H | $(CH_2)_3NHC(=NH)NH_2$ | | (L) | |
| 13f | H | H | $(CH_2)_4NH_2$ | 604.32 | (D) | +++ |
| 13g | H | H | $(CH_2)_4NH_2$ | | (L) | |
| 13h | H | H | $(CH_2)_4NHC(=NH)NH_2$ | | (D) | |
| 13i | H | H | $(CH_2)_4NHC(=NH)NH_2$ | | (L) | |
| 13j | H | H | $(CH_2)_5NH_2$ | | (D) | |
| 13k | H | H | $(CH_2)_5NH_2$ | | (L) | |
| 13l | H | H | $(CH_2)_5NHC(=NH)NH_2$ | | (D) | |
| 13m | H | H | $(CH_2)_5NHC(=NH)NH_2$ | | (L) | |
| 13n | H | H | $(CH_2)_4CH_3$ | | (D) | |
| 13o | H | H | $(CH_2)_4CH_3$ | | (L) | |
| 13p | H | H | $(CH_2)_6CH_3$ | | (D) | |
| 13q | H | H | $(CH_2)_6CH_3$ | | (L) | |
| 13r | H | H | $CH(CH_3)CH_2CH_3$ | 589.34 | (D) | +++ |
| 13s | H | H | $CH(CH_3)CH_2CH_3$ | | (L) | |
| 14 | H | H | $CH_2SH$ | | (D) | |
| 14a | H | H | $CH_2SH$ | | (L) | |
| 15 | H | H | $CH_2OCH_3$ | | (D) | |
| 15a | H | H | $CH_2OCH_3$ | | (L) | |
| 16 | H | H | $CH_2SCH_3$ | | (D) | |
| 16a | H | H | $CH_2SCH_3$ | | (L) | +++ |

TABLE 1-continued

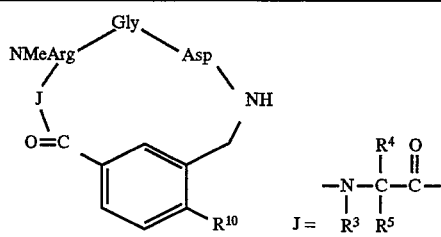

The optical isomer of J is indicated. $R^{10} = H$ unless otherwise indicated.
Example Numbers 1, 2a, 3a, 4a, 5a, 6a, 7a,
8a, 9a, 10a, 11a, 12a, 13a, 13c, 13e, 13g, 13i, 13k, 13m, 13o, 13q,
13s, 14a, 15a, 16a, 17a, 18, 21a, 22a, 23c, 23b, 24, 28b, 28c, 28g
correspond to SEQ ID NO: 1, 2, 3, 4, 5, 6, 7, 8, 9, 10, 11, 12, 13, 14,
15, 16, 17, 18, 19, 20, 21, 22, 23, 24, 25, 26, 27, 28, 29, 30, 31,
32, 33, 34, 35, respectively.

| | | | | | | |
|---|---|---|---|---|---|---|
| 17 | H | H | $CH_2CH_2SCH_3$ | | (D) | |
| 17a | H | H | $CH_2CH_2SCH_3$ | | (L) | |
| 18 | $CH_3$ | H | H | 547.34 | | +++ |
| 19 | H | $CH_3$ | $CH_3$ | | | |
| 20 | H | $CH_2CH_3$ | $CH_2CH_3$ | | | |
| 21 | H | H | cyclopentyl | | (D) | |
| 21a | H | H | cyclopentyl | | (L) | |
| 22 | H | H | cyclohexyl | | (D) | |
| 22a | H | H | cyclohexyl | | (L) | +++ |
| 23 | H | H | cyclohexylmethyl | | (D) | |
| 23c | H | H | cyclohexylmethyl | | (L) | |
| 23a | H | H | $CH(CH_3)_2$  $R^{10} = I$ | 701.37 | (D) | |
| 23b | H | H | $CH(CH_3)_2$  $R^{10} = I$ | | (L) | |
| 23d | H | H | ![structure] —$(CH_2)_4$—N(H)—C(=O)—C₆H₄—N=N≡N | | | +++ |
| 23e | H | H | —$(CH_2)_4$—N(H)—C(=O)—C₆H₄—C(=O)—C₆H₅ | | | +++ |
| 23f | H | H | —$(CH_2)_4$—N(H)—C(=O)—CH($NH_2$)—CH(H)—(indol-3-yl) | | | +++ |
| 23g | H | H | —$(CH_2)_4$—N(H)—C(=O)—(2-benzyl-phenyl) | | | +++ |
| 23h | H | H | —$(CH_2)_4$—N(H)—C(=O)—C₆H₄—C(=O)—$CH_3$ | | | +++ |

TABLE 1-continued
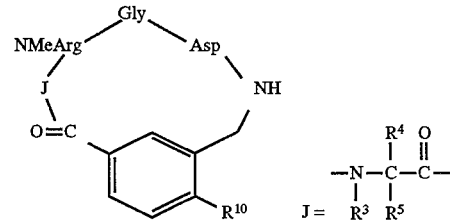
The optical isomer of J is indicated. $R^{10} = H$ unless otherwise indicated.
Example Numbers 1, 2a, 3a, 4a, 5a, 6a, 7a, 8a, 9a, 10a, 11a, 12a, 13a, 13c, 13e, 13g, 13i, 13k, 13m, 13o, 13q, 13s, 14a, 15a, 16a, 17a, 18, 21a, 22a, 23c, 23b, 24, 28b, 28c, 28g correspond to SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, respectively.
| | | | | |
|---|---|---|---|---|
| 23j | H | H | 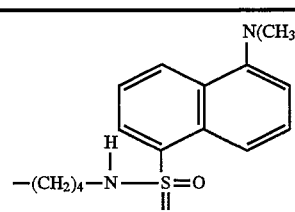 | +++ |
| 23k | H | H | 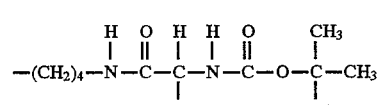 | ++ |
| 23l | H | H | 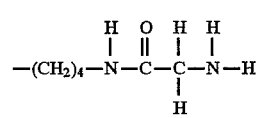 | +++ |
| 23m | H | H | 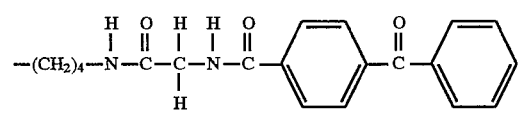 | +++ |
| 23n | H | H | 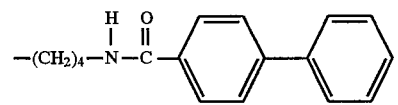 | +++ |
| 23o | H | H | 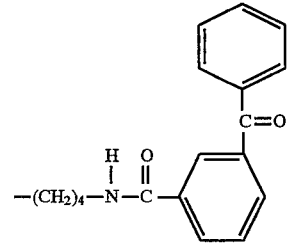 | +++ |
| 23p | H | H | 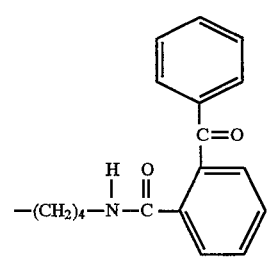 | ++ |

TABLE 1-continued
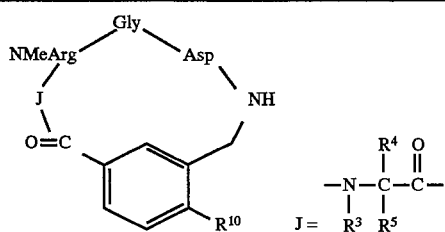
The optical isomer of J is indicated. $R^{10}$ = H unless otherwise indicated.
Example Numbers 1, 2a, 3a, 4a, 5a, 6a, 7a, 8a, 9a, 10a, 11a, 12a, 13a, 13c, 13e, 13g, 13i, 13k, 13m, 13o, 13q, 13s, 14a, 15a, 16a, 17a, 18, 21a, 22a, 23c, 23b, 24, 28b, 28c, 28g correspond to SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, respectively.
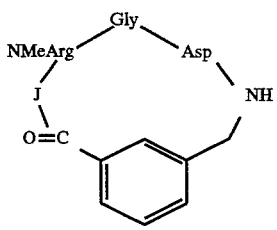
| Ex. No. | J | FAB-MS (M+S) | Optical Isomer | $IC_{50}$ |
|---|---|---|---|---|
| 24 | | 573.46 | (L) | |
| 25 | | 573.35 | (D) | +++ |
| 26 | | | | |
| 27 | | | | |
| 28 | | | | |
| 28a | | | (D) | |

TABLE 1-continued

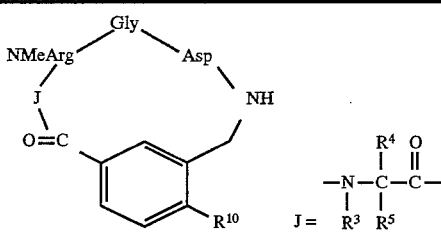

The optical isomer of J is indicated. $R^{10}$ = H unless otherwise indicated.
Example Numbers 1, 2a, 3a, 4a, 5a, 6a, 7a,
8a, 9a, 10a, 11a, 12a, 13a, 13c, 13e, 13g, 13i, 13k, 13m, 13o, 13q,
13s, 14a, 15a, 16a, 17a, 18, 21a, 22a, 23c, 23b, 24, 28b, 28c, 28g
correspond to SEQ ID NO: 1, 2, 3, 4, 5, 6, 7, 8, 9, 10, 11, 12, 13, 14,
15, 16, 17, 18, 19, 20, 21, 22, 23, 24, 25, 26, 27, 28, 29, 30, 31,
32, 33, 34, 35, respectively.

| Ex. No. | Structure | | Optical Isomer |
|---|---|---|---|
| 28b | 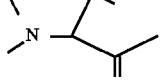 | | (L) |
| 28c | —NHCH₂CH₂C(=O)— | 547.28 | +++ |
| 28d | 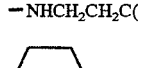 | | (D) |
| 28e | 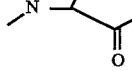 | | (L) |

| Ex. No. | $R^3$ | $R^4$ | $R^5$ | FAB-MS (M+S) | Optical Isomer | $IC_{50}$ |
|---|---|---|---|---|---|---|
| 28f | H | H |  | 639.54 | (D) | +++ |
| 28g | H | H | 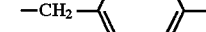 | | (L) | |

Specifically provided by the present invention are those compounds of Table 1 wherein Asp is replaced by a residue selected from: αMeAsp; βMeAsp; NMeAsp; D-Asp;

Asp-(methylcarbonyloxymethyl ester);
Asp-(ethylcarbonyloxymethyl ester);
Asp-(t-butylcarbonyloxymethyl ester);
Asp-(cyclohexylcarbonyloxymethyl ester);
Asp-(1-(methylcarbonyloxy)ethyl ester);
Asp-(1-(ethylcarbonyloxy)ethyl ester);
Asp-(1-(t-butylcarbonyloxy)ethyl ester);
Asp-(1-(cyclohexylcarbonyloxy)ethyl ester);
Asp-(i-propyloxycarbonyloxymethyl ester);
Asp-(cyclohexylcarbonyloxymethyl ester);
Asp-(t-butyloxycarbonyloxymethyl ester);
Asp-(1-(i-propyloxycarbonyloxy)ethyl ester);
Asp -(1-(cyclohexyloxycarbonyloxy)ethyl ester);
Asp-(1-(t-butyloxycarbonyloxy)ethyl ester);
Asp-(dimethylaminoethyl ester);
Asp-(diethylaminoethyl ester);
Asp-((1,3-dioxa-5-methyl-cyclopenten-2-one-4-yl) methyl ester);
Asp-((5-(t-butyl)-1,3-dioxa-cyclopenten-2-one-4-yl) methyl ester);
Asp-((1,3-dioxa-5-phenyl-cyclopenten-2-one-4-yl) methyl ester);

Asp-(1-(2-(2-methoxypropyl)carbonyloxy)ethyl ester).

TABLE 2

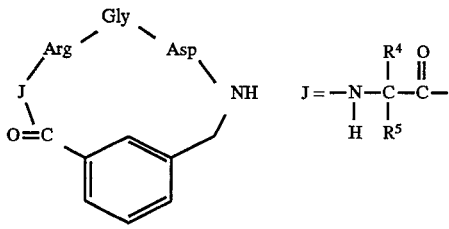

J = —N(H)—C(R⁵)(R⁴)—C(=O)—

The optical isomer of J is indicated.
Example Numbers 29, 31, 32a, 33a, 34a, 35a, 37 correspond to SEQ ID NO: 36, 37, 38, 39, 40, 41, 42, respectively.

| Ex. No. | $R^4$ | $R^5$ | FAB-MS (M+H) | Optical Isomer | $IC_{50}$ |
|---|---|---|---|---|---|
| 29 | H | H | 519.26 | | ++ |
| 30 | H | $CH_3$ | 533.26 | (D) | ++ |
| 31 | H | $CH_3$ | 533.25 | (L) | |
| 32 | H | $CH(CH_3)_2$ | 561.22 | (D) | ++ |
| 32a | H | $CH(CH_3)_2$ | | (L) | |
| 33 | H | $CH_2CH(CH_3)_2$ | 575.45 | (D) | ++ |
| 33a | H | $CH_2CH(CH_3)_2$ | | (L) | |
| 34 | H | $CH_2CH_3$ | 547.21 | (D) | ++ |
| 34a | H | $CH_2CH_3$ | | (L) | |
| 35 | H | $CH_2OH$ | 549.31 | (D) | ++ |
| 35a | H | $CH_2OH$ | | (L) | |
| 36 | H | phenylmethyl | 609.25 | (D) | + |
| 37 | H | phenylmethyl | 609.26 | (L) | + |

TABLE 3

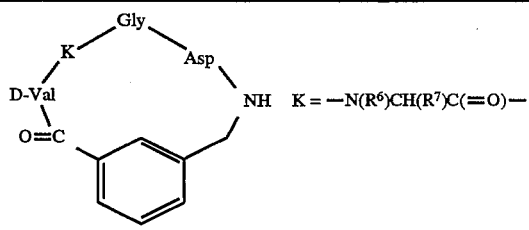

$K = -N(R^6)CH(R^7)C(=O)-$

The optical isomer of K is indicated.

| Ex. No. | $R^6$ | $R^7$ | FAB-MS (M+H) | Optical Isomer | $IC_{50}$ |
|---|---|---|---|---|---|
| 32 | H | $-(CH_2)_3NHC(=NH)(NH_2)$ | 561.22 | (L) | ++ |
| 38 | H | $-(CH_2)_3NHC(=NH)(NH_2)$ | | (D) | |
| 4 | $CH_3$ | $-(CH_2)_3NHC(=NH)(NH_2)$ | 575.45 | (L) | +++ |
| 4b | $CH_3$ | $-(CH_2)_3NHC(=NH)(NH_2)$ | 575.31 | (D) | ++ |
| 38 | $CH_3$ | $-(CH_2)_4NHC(=NH)(NH_2)$ | | (L) | |
| 38a | $CH_3$ | $-(CH_2)_4NHC(=NH)(NH_2)$ | | (D) | |
| 39 | H | $-CH_2-C_6H_4-CH_2NH_2$ | | (L) | |
| 39a | H | $-CH_2-C_6H_4-CH_2NH_2$ | | (D) | |

TABLE 3-continued

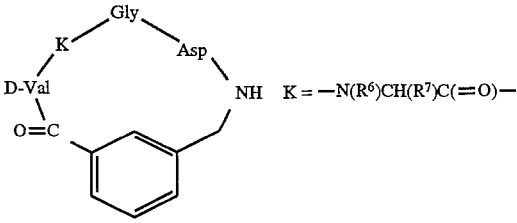

The optical isomer of K is indicated.

| | | | | | |
|---|---|---|---|---|---|
| 40 | CH₃ |  —CH₂—⟨C₆H₄⟩—CH₂NH₂ | 595.23 | (L) | +++ |
| 40a | CH₃ | —CH₂—⟨C₆H₄⟩—CH₂NH₂ | | (D) | |
| 41 | CH₃ |  —CH₂—⟨C₆H₄⟩—CH₂NH—C(=NH)NH₂ | | (L) | |
| 41a | CH₃ | —CH₂—⟨C₆H₄⟩—CH₂NH—C(=NH)NH₂ | | (D) | |
| 42 | CH₃ | —CH₂SCH₂CH₂NH₂ | | (L) | |
| 42a | CH₃ | —CH₂SCH₂CH₂NH₂ | | (D) | |
| 43 | CH₃ | —CH₂SCH₂CH₂NHC(=NH)(NH₂) | | (L) | |
| 43a | CH₃ | —CH₂SCH₂CH₂NHC(=NH)(NH₂) | | (D) | |
| 44 | CH₃ | —CH₂CH₂SCH₂CH₂NH₂ | | (L) | |
| 44a | CH₃ | —CH₂CH₂SCH₂CH₂NH₂ | | (D) | |
| 45 | CH₃ | —CH₂CH₂SCH₂CH₂NHC(=NH)(NH₂) | | (L) | |
| 45a | CH₃ | —CH₂CH₂SCH₂CH₂NHC(=NH)(NH₂) | | (D) | |
| 46 | CH₃ | 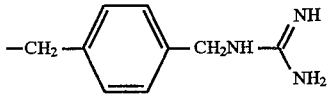 —⟨C₆H₄⟩—C(=NH)NH₂ | | (L) | |
| 46a | CH₃ | —⟨C₆H₄⟩—C(=NH)NH₂ | | (D) | |
| 47 | CH₃ | 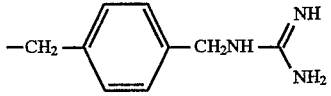 —CH₂—⟨C₆H₄⟩—C(=NH)NH₂ | | (L) | |
| 47a | CH₃ | —CH₂—⟨C₆H₄⟩—C(=NH)NH₂ | | (D) | |
| 48 | CH₃ | 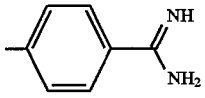 —CH₂—⟨C₆H₁₀⟩—CH₂NH₂ | | (L) | |
| 48b | CH₃ | —CH₂—⟨C₆H₁₀⟩—CH₂NH₂ | | (D) | |

TABLE 3-continued

[Structure: cyclic peptide with D-Val, Gly, Asp, K, connected via NH-CH₂-phenyl-C(=O)]

K = —N(R⁶)CH(R⁷)C(=O)—

The optical isomer of K is indicated.

| 48a | CH₃ | —CH₂—[phenyl]—NH—C(=NH)NH₂ | (L) |
| 48d | CH₃ | —CH₂—[phenyl]—NH—C(=NH)NH₂ | (D) |
| 49 | CH₃ | —CH₂—[cyclohexyl]—CH₂NH—C(=NH)NH₂ | (L) |
| 49a | CH₃ | —CH₂—[cyclohexyl]—CH₂NH—C(=NH)NH₂ | (D) |

| Ex. No. | K | FAB-MS (M+H) |
|---|---|---|
| 52 | [pyrrolidine with N-methyl, C(=O)- and guanidino-substituted ring] | |
| 53 | [pyrrolidine with N-methyl, C(=O)- and CH₂-NH-C(=NH)NH₂ substituent] | |

TABLE 4

Structure: NMeArg-L-Asp cycle with D-Val, O=C attached to benzene ring with NH-CH2 linker.

| Ex. No. | L | FAB-MS (M+H) | Optical Isomer | IC$_{50}$ |
|---|---|---|---|---|
| 4 | —NHCH$_2$C(=O)— | 575.45 | | +++ |
| 54 | —NHCH$_2$CH$_2$C(=O)— | 589.32 | | ++ |
| 55 | —OCH$_2$C(=O)— | | | |
| 56 | —OCH$_2$CH$_2$C(=O)— | | | |
| 57 | —SCH$_2$C(=O)— | | | |
| 58 | —SCH$_2$CH$_2$C(=O)— | | | |
| 58c | —NHCH(CH$_3$)C(=O)— | 589.31 | (L) | + |

TABLE 5

Structure: NMeArg-Gly, M-NH cycle with D-Val, O=C attached to benzene ring.

$M = -N(R^{10})C(R^8)(R^9)C(=O)-$

| Ex. No. | R$^8$ | R$^9$ | R$^{10}$ | FAB-MS (M+H) | Optical Isomer | IC$_{50}$ |
|---|---|---|---|---|---|---|
| 4 | —CH$_2$COOH | H | H | 575.45 | (L) | +++ |
| 63 | —CH$_2$COOH | CH$_3$ | H | 589.29 | isomer 1 | ++ |
| 63a | —CH$_2$COOH | CH$_3$ | H | 589.27 | isomer 2 | + |
| 64 | —CH(CH$_3$)COOH | H | H | 589.43 | isomer 1 | +++ |
| 64a | —CH(CH$_3$)COOH | H | H | 589.45 | isomer 2 | + |
| 64b | —CH$_2$COOH | H | CH$_3$ | 589.42 | | ++ |
| 64c | —CH$_2$COOH | H | H | 575.42 | (D) | ++ |
| 66 | —CH$_2$SO$_3$H | H | H | | | |

TABLE 6

Structure: NMeArg-Gly-Asp cycle with D-Val, O=C attached to benzene ring with N—R$^2$ and CH-R$^1$.

The optical isomer of —CH(R$^1$)N(R$^2$)— is indicated.

| Ex. No. | R$^1$ | R$^2$ | FAB-MS (M+H) | Optical Isomer | IC$_{50}$ |
|---|---|---|---|---|---|
| 4 | H | H | 575.45 | | +++ |
| 68 | CH$_3$ | H | 589.31 | isomer 1 | +++ |
| 68a | CH$_3$ | H | 589.31 | isomer 2 | +++ |
| 69 | CH$_2$CH$_3$ | H | | R | |

TABLE 6-continued

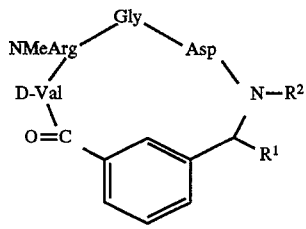

The optical isomer of —CH(R¹)N(R²)— is indicated.

| Ex. No. | R¹ | R² | FAB-MS (M+H) | Optical Isomer | IC$_{50}$ |
|---|---|---|---|---|---|
| 69a | CH$_2$CH$_3$ | H | | S | |
| 70 | CH(CH$_3$)$_2$ | H | | R | |
| 70a | CH(CH$_3$)$_2$ | H | | S | |
| 71 | CH$_2$CH$_2$CH$_3$ | H | | R | |
| 71a | CH$_2$CH$_2$CH$_3$ | H | | S | |
| 72 | CH$_2$CH$_2$CH$_2$CH$_3$ | H | R | | |
| 72a | CH$_2$CH$_2$CH$_2$CH$_3$ | H | | S | |
| 73 | C(CH$_3$)$_3$ | H | | R | |
| 73a | C(CH$_3$)$_3$ | H | | S | |
| 74 | CH(CH$_3$)CH$_2$CH$_3$ | H | | R | |
| 74a | CH(CH$_3$)CH$_2$CH$_3$ | H | | S | |
| 75 | benzyl | H | | R | |
| 75a | benzyl | H | | S | |
| 76 | phenyl | H | 651.33 | isomer 1 | ++ |
| 76a | phenyl | H | 651.33 | isomer 2 | ++ |
| 77 | cyclopentyl | H | | R | |
| 77a | cyclopentyl | H | | S | |
| 78 | cyclohexyl | H | | R | |
| 78a | cyclohexyl | H | | S | |
| 79 | H | CH$_3$ | 589.33 | | |
| 80 | H | CH$_2$CH$_3$ | | | |
| 81 | H | CH$_2$CH$_2$CH$_3$ | | | |
| 82 | H | CH(CH$_3$)$_2$ | | | |
| 83 | H | CH$_2$CH$_2$CH$_2$CH$_3$ | | | |
| 84 | H | C(CH$_3$)$_3$ | | | |
| 85 | H | CH(CH$_3$)CH$_2$CH$_3$ | | | |
| 86 | H | benzyl | | | |

TABLE 7

| Ex. No. | Structure | FAB-MS (M+H) | IC$_{50}$ |
|---|---|---|---|
| 87 | NMeArg, D-Val, Gly, Asp, NH (isomer 1) | 575.41 | +++ |
| 88 | NMeArg, D-Val, Gly, Asp, NH (isomer 2) | 575.44 | +++ |

TABLE 7-continued
| Ex. No. | Structure | FAB-MS (M+H) | IC$_{50}$ |
|---|---|---|---|
| 89a | 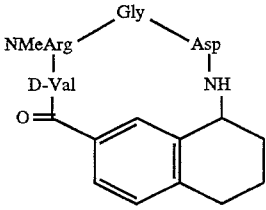 isomer 1 | 615.34 | +++ |
| 89b | 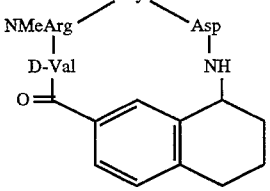 isomer 2 | 615.35 | +++ |
| 89c | 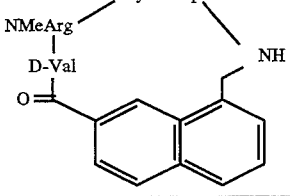 | 625.32 | ++ |
TABLE 8
| Ex. No. | Structure | FAB-MS [M+H] | IC$_{50}$ |
|---|---|---|---|
| 89d | 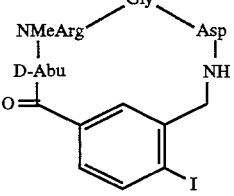 | 687.33 | +++ |
| 89e | 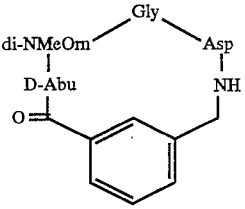 | 533.34 | ++ |
| 90 | 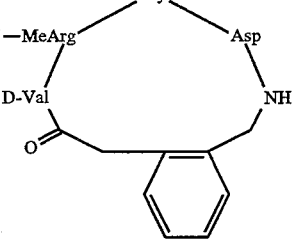 | 589 | +++ |
| 91 | 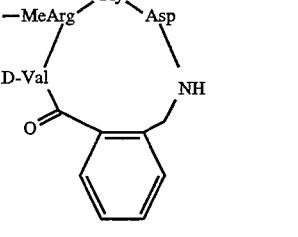 | 575 | +++ |

TABLE 8-continued

| Ex. No. | Structure | FAB-MS [M+H] | IC$_{50}$ |
|---|---|---|---|
| 92 | 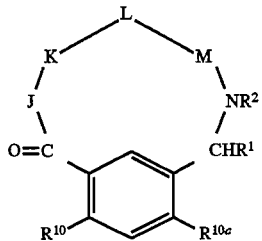 | 575 | +++ |

TABLE 9

(VII)

[Structure showing cyclic compound with J, K, L, M, NR², CHR¹, O=C, R¹⁰, R¹⁰ᵃ and benzene ring]

| Example Number | R¹⁰ᵃ | R¹⁰ | FAB-MS (M+H) | IC$_{50}$ |
|---|---|---|---|---|
| wherein J = D-Val, K = NMeArg, L = Gly, M = Asp | | | | |
| 93 | Cl | H | 609 | +++ |
| 94 | I | H | 701.37 | +++ |

TABLE 9-continued (VII)

| Example Number | R¹⁰ᵃ | R¹⁰ | FAB-MS (M+H) | IC$_{50}$ |
|---|---|---|---|---|
| 95 | MeO | H | 623 (+H$_2$O) | |
| 96 | Me | H | 589 | +++ |
| 97 | H | Cl | 609 | +++ |
| 98 | H | I | 701 | |
| 99 | H | MeO | 605 | +++ |
| 100 | H | Me | 589 | +++ |
| wherein J = D-Abu, K = NMeArg, L = Gly, M = Asp | | | | |
| 100a | H | Cl | 595.4 | +++ |
| 100b | H | I | 687.3 | +++ |
| 100c | H | Me | 575.4 | +++ |

Specifically disclosed by the present invention are those compounds of Tables 3–9 wherein D-Val is replaced by a residue selected from: D-2-aminobutyric acid, D-Leu, D-Ala, Gly, D-Pro, D-Ser, D-Lys, β-Ala, Pro, Phe, NMeGly, D-Nle, D-Phg, D-Ile, D-Phe, D-Tyr, Ala.

TABLE 10

[Structure showing cyclic compound with J, K, L, M, NR², CHR¹, O=C and benzene ring]

wherein L = Gly, M = Asp, R² and R¹ = H,
K = —N(R⁶)CH(R⁷)C(=O)—
J = D-Val

| Ex. No. | R⁶ | R⁷ | Optical Isomer | IC$_{50}$ |
|---|---|---|---|---|
| 101 | CH$_3$ | —(CH$_2$)$_2$—[cyclohexyl-NH] | L | |
| 102 | CH$_3$ | —(CH$_2$)$_2$—[cyclohexyl-NH] | D | |
| 103 | CH$_3$ | —(CH$_2$)$_3$—[cyclohexyl-NH] | L | |

TABLE 10-continued

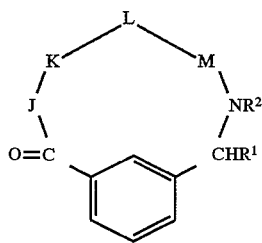

wherein L = Gly, M = Asp, R² and R¹ = H,
K = —N(R⁶)CH(R⁷)C(=O)—
J = D-Val

| Ex. No. | R⁶ | R⁷ | | Optical Isomer | IC₅₀ |
|---|---|---|---|---|---|
| 104 | CH₃ | —(CH₂)₃— | <piperidine>NH | D | |
| 105 | CH₃ | —(CH₂)₄— | <piperidine>NH | L | |
| 106 | CH₃ | —(CH₂)₄— | <piperidine>NH | D | |
| 107 | CH₃ | —CH₂O— | <piperidine>NH | L | |
| 108 | CH₃ | —CH₂O— | <piperidine>NH | D | |
| 109 | CH₃ | —CH₂OCH₂— | <piperidine>NH | L | |
| 110 | CH₃ | —CH₂OCH₂— | <piperidine>NH | D | |
| 111 | CH₃ | —CH₂O(CH₂)₂— | <piperidine>NH | L | |
| 112 | CH₃ | —CH₂O(CH₂)₂— | <piperidine>NH | D | |
| 113 | CH₃ | —(CH₂)₂O— | <piperidine>NH | L | |
| 114 | CH₃ | —(CH₂)₂O— | <piperidine>NH | D | |

TABLE 10-continued
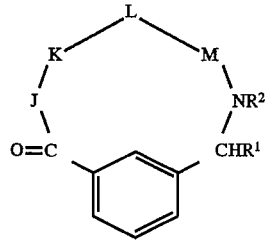
wherein L = Gly, M = Asp, R² and R¹ = H,
K = —N(R⁶)CH(R⁷)C(=O)—
J = D-Val
| Ex. No. | R⁶ | R⁷ | Optical Isomer | IC$_{50}$ |
|---|---|---|---|---|
| 115 | CH$_3$ | —(CH$_2$)$_2$OCH$_2$—⟨NH⟩ | L | |
| 116 | CH$_3$ | —(CH$_2$)$_2$OCH$_2$—⟨NH⟩ | D | |
| 117 | CH$_3$ | —CH$_2$S—⟨NH⟩ | L | |
| 118 | CH$_3$ | —CH$_2$S—⟨NH⟩ | D | |
| 119 | CH$_3$ | —CH$_2$SCH$_2$—⟨NH⟩ | L | |
| 120 | CH$_3$ | —CH$_2$SCH$_2$—⟨NH⟩ | D | |
| 121 | CH$_3$ | —CH$_2$S(CH$_2$)$_2$—⟨NH⟩ | L | |
| 122 | CH$_3$ | —CH$_2$S(CH$_2$)$_2$—⟨NH⟩ | D | |
| 123 | CH$_3$ | —(CH$_2$)$_2$S—⟨NH⟩ | L | |
| 124 | CH$_3$ | —(CH$_2$)$_2$S—⟨NH⟩ | D | |
| 125 | CH$_3$ | —(CH$_2$)$_2$SCH$_2$—⟨NH⟩ | L | |

TABLE 10-continued

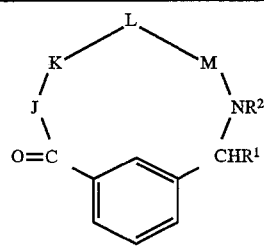

wherein L = Gly, M = Asp, $R^2$ and $R^1$ = H,
K = —N($R^6$)CH($R^7$)C(=O)—
J = D-Val

| Ex. No. | $R^6$ | $R^7$ | Optical Isomer | $IC_{50}$ |
|---|---|---|---|---|
| 126 | $CH_3$ | —$(CH_2)_2SCH_2$—⟨cyclohexyl⟩—NH | D | |
| 127 | $CH_3$ | —$CH_2$—S—$(CH_2)_3$—NH—$CH_3$ | L | |
| 128 | $CH_3$ | —$CH_2$—S—$(CH_2)_3$—NH—$CH_3$ | D | |
| 129 | $CH_3$ | —$CH_2$—S—$(CH_2)_3$—NH—$CH_2CH_3$ | L | |
| 130 | $CH_3$ | —$CH_2$—S—$(CH_2)_3$—NH—$CH_2CH_3$ | D | |
| 131 | $CH_3$ | —$CH_2$—S—$(CH_2)_3$—NH—$CH(CH_3)_2$ | L | |
| 132 | $CH_3$ | —$CH_2$—S—$(CH_2)_3$—NH—$CH(CH_3)_2$ | D | |
| 133 | $CH_3$ | —$CH_2$—S—$(CH_2)_3$—NH—$CH_2CH_2$—$CH_3$ | L | |
| 134 | $CH_3$ | —$CH_2$—S—$(CH_2)_3$—NH—$CH_2CH_2$—$CH_3$ | D | |
| 135 | $CH_3$ | —$CH_2$—S—$(CH_2)_3$—NH—$C(CH_3)_3$ | L | |
| 136 | $CH_3$ | —$CH_2$—S—$(CH_2)_3$—NH—$C(CH_3)_3$ | D | |
| 137 | $CH_3$ | $CH_2$—O—$(CH_2)_3$—NH—$CH_3$ | L | |
| 138 | $CH_3$ | $CH_2$—O—$(CH_2)_3$—NH—$CH_3$ | D | |
| 139 | $CH_3$ | $CH_2$—O—$(CH_2)_3$—NH—$CH_2CH_3$ | L | |
| 140 | $CH_3$ | $CH_2$—O—$(CH_2)_3$—NH—$CH_2CH_3$ | D | |
| 141 | $CH_3$ | $CH_2$—O—$(CH_2)_3$—NH—$CH(CH_3)_2$ | L | |
| 142 | $CH_3$ | $CH_2$—O—$(CH_2)_3$—NH—$CH(CH_3)_2$ | D | |
| 143 | $CH_3$ | $CH_2$—O—$(CH_2)_3$—NH—$CH_2CH_2CH_3$ | L | |
| 144 | $CH_3$ | $CH_2$—O—$(CH_2)_3$—NH—$CH_2CH_2CH_3$ | D | |
| 145 | $CH_3$ | $CH_2$—O—$(CH_2)_3$—NH—$C(CH_3)_3$ | L | |
| 146 | $CH_3$ | $CH_2$—O—$(CH_2)_3$—NH—$C(CH_3)_3$ | D | |
| 147 | $CH_3$ | —$CH_2$—S—$(CH_2)_2$—NH—$CH_3$ | L | |
| 148 | $CH_3$ | —$CH_2$—S—$(CH_2)_2$—NH—$CH_3$ | D | |
| 149 | $CH_3$ | —$CH_2$—S—$(CH_2)_2$—NH—$CH_2CH_3$ | L | |
| 150 | $CH_3$ | —$CH_2$—S—$(CH_2)_2$—NH—$CH_2CH_3$ | D | |
| 151 | $CH_3$ | —$CH_2$—S—$(CH_2)_2$—NH—$CH(CH_3)_2$ | L | |
| 152 | $CH_3$ | —$CH_2$—S—$(CH_2)_2$—NH—$CH(CH_3)_2$ | D | |
| 153 | $CH_3$ | —$CH_2$—S—$(CH_2)_2$—NH—$CH_2CH_2$—$CH_3$ | L | |
| 154 | $CH_3$ | —$CH_2$—S—$(CH_2)_2$—NH—$CH_2CH_2$—$CH_3$ | D | |
| 155 | $CH_3$ | —$CH_2$—S—$(CH_2)_2$—NH—$C(CH_3)_3$ | L | |
| 156 | $CH_3$ | —$CH_2$—S—$(CH_2)_2$—NH—$C(CH_3)_3$ | D | |
| 157 | $CH_3$ | $CH_2$—O—$(CH_2)_2$—NH—$CH_3$ | L | |
| 158 | $CH_3$ | $CH_2$—O—$(CH_2)_2$—NH—$CH_3$ | D | |
| 159 | $CH_3$ | $CH_2$—O—$(CH_2)_2$—NH—$CH_2CH_3$ | L | |
| 160 | $CH_3$ | $CH_2$—O—$(CH_2)_2$—NH—$CH_2CH_3$ | D | |
| 161 | $CH_3$ | $CH_2$—O—$(CH_2)_2$—NH—$CH(CH_3)_2$ | L | |
| 162 | $CH_3$ | $CH_2$—O—$(CH_2)_2$—NH—$CH(CH_3)_2$ | D | |
| 163 | $CH_3$ | $CH_2$—O—$(CH_2)_2$—NH—$CH_2CH_2CH_3$ | L | |
| 164 | $CH_3$ | $CH_2$—O—$(CH_2)_2$—NH—$CH_2CH_2CH_3$ | D | |
| 165 | $CH_3$ | $CH_2$—O—$(CH_2)_2$—NH—$C(CH_3)_3$ | L | |
| 166 | $CH_3$ | $CH_2$—O—$(CH_2)_2$—NH—$C(CH_3)_3$ | D | |
| 167 | $CH_3$ | —$CH_2$—S—$(CH_2)_4$—NH—$CH_3$ | L | |
| 168 | $CH_3$ | —$CH_2$—S—$(CH_2)_4$—NH—$CH_3$ | D | |
| 169 | $CH_3$ | —$CH_2$—S—$(CH_2)_4$—NH—$CH_2CH_3$ | L | |
| 170 | $CH_3$ | —$CH_2$—S—$(CH_2)_4$—NH—$CH_2CH_3$ | D | |
| 171 | $CH_3$ | —$CH_2$—S—$(CH_2)_4$—NH—$CH(CH_3)_2$ | L | |
| 172 | $CH_3$ | —$CH_2$—S—$(CH_2)_4$—NH—$CH(CH_3)_2$ | D | |
| 173 | $CH_3$ | —$CH_2$—S—$(CH_2)_4$—NH—$CH_2CH_2$—$CH_3$ | L | |
| 174 | $CH_3$ | —$CH_2$—S—$(CH_2)_4$—NH—$CH_2CH_2$—$CH_3$ | D | |
| 175 | $CH_3$ | —$CH_2$—S—$(CH_2)_4$—NH—$C(CH_3)_3$ | L | |
| 176 | $CH_3$ | —$CH_2$—S—$(CH_2)_4$—NH—$C(CH_3)_3$ | D | |
| 177 | $CH_3$ | $CH_2$—O—$(CH_2)_4$—NH—$CH_3$ | L | |
| 178 | $CH_3$ | $CH_2$—O—$(CH_2)_4$—NH—$CH_3$ | D | |
| 179 | $CH_3$ | $CH_2$—O—$(CH_2)_4$—NH—$CH_2CH_3$ | L | |
| 180 | $CH_3$ | $CH_2$—O—$(CH_2)_4$—NH—$CH_2CH_3$ | D | |
| 181 | $CH_3$ | $CH_2$—O—$(CH_2)_4$—NH—$CH(CH_3)_2$ | L | |

TABLE 10-continued

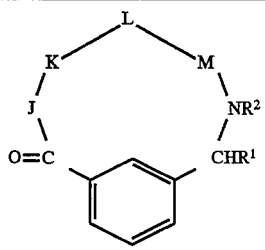

wherein L = Gly, M = Asp, R$^2$ and R$^1$ = H,
K = —N(R$^6$)CH(R$^7$)C(=O)—
J = D-Val

| Ex. No. | R$^6$ | R$^7$ | Optical Isomer | IC$_{50}$ |
|---|---|---|---|---|
| 182 | CH$_3$ | CH$_2$—O—(CH$_2$)$_4$—NH—CH(CH$_3$)$_2$ | D | |
| 183 | CH$_3$ | CH$_2$—O—(CH$_2$)$_4$—NH—CH$_2$CH$_2$CH$_3$ | L | |
| 184 | CH$_3$ | CH$_2$—O—(CH$_2$)$_4$—NH—CH$_2$CH$_2$CH$_3$ | D | |
| 185 | CH$_3$ | CH$_2$—O—(CH$_2$)$_4$—NH—C(CH$_3$)$_3$ | L | |
| 186 | CH$_3$ | CH$_2$—O—(CH$_2$)$_4$—NH—C(CH$_3$)$_3$ | D | |
| 187 | CH$_3$ | —CH$_2$—S—(CH$_2$)$_5$—NH—CH$_3$ | L | |
| 188 | CH$_3$ | —CH$_2$—S—(CH$_2$)$_5$—NH—CH$_3$ | D | |
| 189 | CH$_3$ | —CH$_2$—S—(CH$_2$)$_5$—NH—CH$_2$CH$_3$ | L | |
| 190 | CH$_3$ | —CH$_2$—S—(CH$_2$)$_5$—NH—CH$_2$CH$_3$ | D | |
| 191 | CH$_3$ | —CH$_2$—S—(CH$_2$)$_5$—NH—CH(CH$_3$)$_2$ | L | |
| 192 | CH$_3$ | —CH$_2$—S—(CH$_2$)$_5$—NH—CH(CH$_3$)$_2$ | D | |
| 193 | CH$_3$ | —CH$_2$—S—(CH$_2$)$_5$—NH—CH$_2$CH$_2$—CH$_3$ | L | |
| 194 | CH$_3$ | —CH$_2$—S—(CH$_2$)$_5$—NH—CH$_2$CH$_2$—CH$_3$ | D | |
| 195 | CH$_3$ | —CH$_2$—S—(CH$_2$)$_5$—NH—C(CH$_3$)$_3$ | L | |
| 196 | CH$_3$ | —CH$_2$—S—(CH$_2$)$_5$—NH—C(CH$_3$)$_3$ | D | |
| 197 | CH$_3$ | CH$_2$—O—(CH$_2$)$_5$—NH—CH$_3$ | L | |
| 198 | CH$_3$ | CH$_2$—O—(CH$_2$)$_5$—NH—CH$_3$ | D | |
| 199 | CH$_3$ | CH$_2$—O—(CH$_2$)$_5$—NH—CH$_2$CH$_3$ | L | |
| 200 | CH$_3$ | CH$_2$—O—(CH$_2$)$_5$—NH—CH$_2$CH$_3$ | D | |
| 201 | CH$_3$ | CH$_2$—O—(CH$_2$)$_5$—NH—CH(CH$_3$)$_2$ | L | |
| 202 | CH$_3$ | CH$_2$—O—(CH$_2$)$_5$—NH—CH(CH$_3$)$_2$ | D | |
| 203 | CH$_3$ | CH$_2$—O—(CH$_2$)$_5$—NH—CH$_2$CH$_2$CH$_3$ | L | |
| 204 | CH$_3$ | CH$_2$—O—(CH$_2$)$_5$—NH—CH$_2$CH$_2$CH$_3$ | D | |
| 205 | CH$_3$ | CH$_2$—O—(CH$_2$)$_5$—NH—C(CH$_3$)$_3$ | L | |
| 206 | CH$_3$ | CH$_2$—O—(CH$_2$)$_5$—NH—C(CH$_3$)$_3$ | D | |
| 207 | CH$_3$ | —(CH$_2$)$_2$—S—(CH$_2$)$_3$—NH—CH$_3$ | L | |
| 208 | CH$_3$ | —(CH$_2$)$_2$—S—(CH$_2$)$_3$—NH—CH$_3$ | D | |
| 209 | CH$_3$ | —(CH$_2$)$_2$—S—(CH$_2$)$_3$—NH—CH$_2$CH$_3$ | L | |
| 210 | CH$_3$ | —(CH$_2$)$_2$—S—(CH$_2$)$_3$—NH—CH$_2$CH$_3$ | D | |
| 211 | CH$_3$ | —(CH$_2$)$_2$—S—(CH$_2$)$_3$—NH—CH(CH$_3$)$_2$ | L | |
| 212 | CH$_3$ | —(CH$_2$)$_2$—S—(CH$_2$)$_3$—NH—CH(CH$_3$)$_2$ | D | |
| 213 | CH$_3$ | —(CH$_2$)$_2$—S—(CH$_2$)$_3$—NH—CH$_2$CH$_2$—CH$_3$ | L | |
| 214 | CH$_3$ | —(CH$_2$)$_2$—S—(CH$_2$)$_3$—NH—CH$_2$CH$_2$—CH$_3$ | D | |
| 215 | CH$_3$ | —(CH$_2$)$_2$—S—(CH$_2$)$_3$—NH—C(CH$_3$)$_3$ | L | |
| 216 | CH$_3$ | —(CH$_2$)$_2$—S—(CH$_2$)$_3$—NH—C(CH$_3$)$_3$ | D | |
| 217 | CH$_3$ | —(CH$_2$)$_2$—O—(CH$_2$)$_3$—NH—CH$_3$ | L | |
| 218 | CH$_3$ | —(CH$_2$)$_2$—O—(CH$_2$)$_3$—NH—CH$_3$ | D | |
| 219 | CH$_3$ | —(CH$_2$)$_2$—O—(CH$_2$)$_3$—NH—CH$_2$CH$_3$ | L | |
| 220 | CH$_3$ | —(CH$_2$)$_2$—O—(CH$_2$)$_3$—NH—CH$_2$CH$_3$ | D | |
| 221 | CH$_3$ | —(CH$_2$)$_2$—O—(CH$_2$)$_3$—NH—CH(CH$_3$)$_2$ | L | |
| 222 | CH$_3$ | —(CH$_2$)$_2$—O—(CH$_2$)$_3$—NH—CH(CH$_3$)$_2$ | D | |
| 223 | CH$_3$ | —(CH$_2$)$_2$—O—(CH$_2$)$_3$—NH—CH$_2$CH$_2$CH$_3$ | L | |
| 224 | CH$_3$ | —(CH$_2$)$_2$—O—(CH$_2$)$_3$—NH—CH$_2$CH$_2$CH$_3$ | D | |
| 225 | CH$_3$ | —(CH$_2$)$_2$—O—(CH$_2$)$_3$—NH—C(CH$_3$)$_3$ | L | |
| 226 | CH$_3$ | —(CH$_2$)$_2$—O—(CH$_2$)$_3$—NH—C(CH$_3$)$_3$ | D | |
| 227 | CH$_3$ | —(CH$_2$)$_2$—S—(CH$_2$)$_2$—NH—CH$_3$ | L | |
| 228 | CH$_3$ | —(CH$_2$)$_2$—S—(CH$_2$)$_2$—NH—CH$_3$ | D | |
| 229 | CH$_3$ | —(CH$_2$)$_2$—S—(CH$_2$)$_2$—NH—CH$_2$CH$_3$ | L | |
| 230 | CH$_3$ | —(CH$_2$)$_2$—S—(CH$_2$)$_2$—NH—CH$_2$CH$_3$ | D | |
| 231 | CH$_3$ | —(CH$_2$)$_2$—S—(CH$_2$)$_2$—NH—CH(CH$_3$)$_2$ | L | |
| 232 | CH$_3$ | —(CH$_2$)$_2$—S—(CH$_2$)$_2$—NH—CH(CH$_3$)$_2$ | D | |
| 233 | CH$_3$ | —(CH$_2$)$_2$—S—(CH$_2$)$_2$—NH—CH$_2$CH$_2$—CH$_3$ | L | |
| 234 | CH$_3$ | —(CH$_2$)$_2$—S—(CH$_2$)$_2$—NH—CH$_2$CH$_2$—CH$_3$ | D | |
| 235 | CH$_3$ | —(CH$_2$)$_2$—S—(CH$_2$)$_2$—NH—C(CH$_3$)$_3$ | L | |
| 236 | CH$_3$ | —(CH$_2$)$_2$—S—(CH$_2$)$_2$—NH—C(CH$_3$)$_3$ | D | |
| 237 | CH$_3$ | —(CH$_2$)$_2$—O—(CH$_2$)$_2$—NH—CH$_3$ | L | |
| 238 | CH$_3$ | —(CH$_2$)$_2$—O—(CH$_2$)$_2$—NH—CH$_3$ | D | |
| 239 | CH$_3$ | —(CH$_2$)$_2$—O—(CH$_2$)$_2$—NH—CH$_2$CH$_3$ | L | |
| 240 | CH$_3$ | —(CH$_2$)$_2$—O—(CH$_2$)$_2$—NH—CH$_2$CH$_3$ | D | |
| 241 | CH$_3$ | —(CH$_2$)$_2$—O—(CH$_2$)$_2$—NH—CH(CH$_3$)$_2$ | L | |
| 242 | CH$_3$ | —(CH$_2$)$_2$—O—(CH$_2$)$_2$—NH—CH(CH$_3$)$_2$ | D | |

TABLE 10-continued

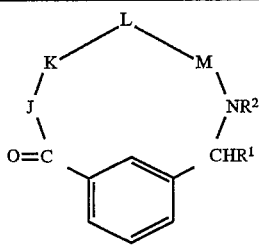

wherein L = Gly, M = Asp, $R^2$ and $R^1$ = H,
K = $-N(R^6)CH(R^7)C(=O)-$
J = D-Val

| Ex. No. | $R^6$ | $R^7$ | Optical Isomer | $IC_{50}$ |
|---|---|---|---|---|
| 243 | $CH_3$ | $-(CH_2)_2-O-(CH_2)_2-NH-CH_2CH_2CH_3$ | L | |
| 244 | $CH_3$ | $-(CH_2)_2-O-(CH_2)_2-NH-CH_2CH_2CH_3$ | D | |
| 245 | $CH_3$ | $-(CH_2)_2-O-(CH_2)_2-NH-C(CH_3)_3$ | L | |
| 246 | $CH_3$ | $-(CH_2)_2-O-(CH_2)_2-NH-C(CH_3)_3$ | D | |
| 247 | $CH_3$ | $-(CH_2)_2-S-(CH_2)_4-NH-CH_3$ | L | |
| 248 | $CH_3$ | $-(CH_2)_2-S-(CH_2)_4-NH-CH_3$ | D | |
| 249 | $CH_3$ | $-(CH_2)_2-S-(CH_2)_4-NH-CH_2CH_3$ | L | |
| 250 | $CH_3$ | $-(CH_2)_2-S-(CH_2)_4-NH-CH_2CH_3$ | D | |
| 251 | $CH_3$ | $-(CH_2)_2-S-(CH_2)_4-NH-CH(CH_3)_2$ | L | |
| 252 | $CH_3$ | $-(CH_2)_2-S-(CH_2)_4-NH-CH(CH_3)_2$ | D | |
| 251 | $CH_3$ | $-(CH_2)_2-S-(CH_2)_4-NH-CH_2CH_2-CH_3$ | L | |
| 254 | $CH_3$ | $-(CH_2)_2-S-(CH_2)_4-NH-CH_2CH_2-CH_3$ | D | |
| 255 | $CH_3$ | $-(CH_2)_2-S-(CH_2)_4-NH-C(CH_3)_3$ | L | |
| 256 | $CH_3$ | $-(CH_2)_2-S-(CH_2)_4-NH-C(CH_3)_3$ | D | |
| 257 | $CH_3$ | $-(CH_2)_3-NH-CH_3$ | L | |
| 258 | $CH_3$ | $-(CH_2)_3-NH-CH_3$ | D | |
| 259 | $CH_3$ | $-(CH_2)_3-NH-CH_2CH_3$ | L | |
| 260 | $CH_3$ | $-(CH_2)_3-NH-CH_2CH_3$ | D | |
| 261 | $CH_3$ | $-(CH_2)_3-NH-CH(CH_3)_2$ | L | |
| 262 | $CH_3$ | $-(CH_2)_3-NH-CH(CH_3)_2$ | D | |
| 263 | $CH_3$ | $-(CH_2)_3-NH-CH_2CH_2CH_3$ | L | |
| 264 | $CH_3$ | $-(CH_2)_3-NH-CH_2CH_2CH_3$ | D | |
| 265 | $CH_3$ | $-(CH_2)_3-NH-C(CH_3)_3$ | L | |
| 266 | $CH_3$ | $-(CH_2)_3-NH-C(CH_3)_3$ | D | |
| 267 | $CH_3$ | $-(CH_2)_4-NH-CH_3$ | L | |
| 268 | $CH_3$ | $-(CH_2)_4-NH-CH_3$ | D | |
| 269 | $CH_3$ | $-(CH_2)_4-NH-CH_2CH_3$ | L | |
| 270 | $CH_3$ | $-(CH_2)_4-NH-CH_2CH_3$ | D | |
| 271 | $CH_3$ | $-(CH_2)_4-NH-CH(CH_3)_2$ | L | |
| 272 | $CH_3$ | $-(CH_2)_4-NH-CH(CH_3)_2$ | D | |
| 273 | $CH_3$ | $-(CH_2)_4-NH-CH_2CH_2CH_3$ | L | |
| 274 | $CH_3$ | $-(CH_2)_4-NH-CH_2CH_2CH_3$ | D | |
| 275 | $CH_3$ | $-(CH_2)_4-NH-C(CH_3)_3$ | L | |
| 276 | $CH_3$ | $-(CH_2)_4-NH-C(CH_3)_3$ | D | |
| 277 | $CH_3$ | $-(CH_2)_5-NH-CH_3$ | L | |
| 278 | $CH_3$ | $-(CH_2)_5-NH-CH_3$ | D | |
| 279 | $CH_3$ | $-(CH_2)_5-NH-CH_2CH_3$ | L | |
| 280 | $CH_3$ | $-(CH_2)_5-NH-CH_2CH_3$ | D | |
| 281 | $CH_3$ | $-(CH_2)_5-NH-CH(CH_3)_2$ | L | |
| 282 | $CH_3$ | $-(CH_2)_5-NH-CH(CH_3)_2$ | D | |
| 283 | $CH_3$ | $-(CH_2)_5-NH-CH_2CH_2CH_3$ | L | |
| 284 | $CH_3$ | $-(CH_2)_5-NH-CH_2CH_2CH_3$ | D | |
| 285 | $CH_3$ | $-(CH_2)_5-NH-C(CH_3)_3$ | L | |
| 286 | $CH_3$ | $-(CH_2)_5-NH-C(CH_3)_3$ | D | |
| 287 | $CH_3$ | $-(CH_2)_6-NH-CH_3$ | L | |
| 288 | $CH_3$ | $-(CH_2)_6-NH-CH_3$ | D | |
| 289 | $CH_3$ | $-(CH_2)_6-NH-CH_2CH_3$ | L | |
| 290 | $CH_3$ | $-(CH_2)_6-NH-CH_2CH_3$ | D | |
| 291 | $CH_3$ | $-(CH_2)_6-NH-CH(CH_3)_2$ | L | |
| 292 | $CH_3$ | $-(CH_2)_6-NH-CH(CH_3)_2$ | D | |
| 293 | $CH_3$ | $-(CH_2)_6-NH-CH_2CH_2CH_3$ | L | |
| 294 | $CH_3$ | $-(CH_2)_6-NH-CH_2CH_2CH_3$ | D | |
| 295 | $CH_3$ | $-(CH_2)_6-NH-C(CH_3)_3$ | L | |
| 296 | $CH_3$ | $-(CH_2)_6-NH-C(CH_3)_3$ | D | |

Specifically disclosed by the present invention are those compounds of Table 10 wherein D-Val is replaced by a residue selected from: D-2-aminobutyric acid, D-Leu, D-Ala, Gly, D-Pro, D-Ser, D-Lys, β-Ala, Pro, Phe, NMeGly, D-Nle, D-Phg, D-Ile, D-Phe, D-Tyr, Ala.

149

Also specifically disclosed by the present invention are those compounds of Table 10 wherein Asp is replaced by a residue selected from: αMeAsp; βMeAsp;

NMeAsp; D-Asp; Asp-(methylcarbonyloxymethyl ester);
Asp-(ethylcarbonyloxymethyl ester);
Asp-(t-butylcarbonyloxymethyl ester);
Asp-(cyclohexylcarbonyloxymethyl ester);
Asp-(1-(methylcarbonyloxy)ethyl ester);
Asp-(1-(ethylcarbonyloxy)ethyl ester);
Asp-(1-(t-butylcarbonyloxy)ethyl ester);
Asp-(1-(cyclohexylcarbonyloxy)ethyl ester);
Asp-(i-propyloxycarbonyloxymethyl ester);
Asp-(cyclohexylcarbonyloxymethyl ester);

150

Asp-(t-butyloxycarbonyloxymethyl ester);
Asp-(1-(i-propyloxycarbonyloxy)ethyl ester);
Asp-(1-(cyclohexyloxycarbonyloxy)ethyl ester);
Asp-(1-(t-butyloxycarbonyloxy)ethyl ester);
Asp-(dimethylaminoethyl ester);
Asp-(diethylaminoethyl ester);
Asp-((1,3-dioxa-5-methyl-cyclopenten-2-one-4-yl) methyl ester);
Asp-((5-(t-butyl)-1,3-dioxa-cyclopenten-2-one-4-yl) methyl ester);
Asp-((1,3-dioxa-5-phenyl-cyclopenten-2-one-4-yl) methyl ester);
Asp-(1-(2-(2-methoxypropyl)carbonyloxy)ethyl ester).

TABLE 11

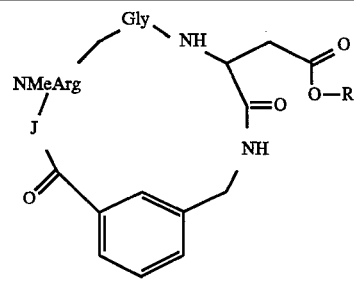

J = D-Abu

| Ex. No. | R | FABMS (M + H) |
|---|---|---|
| 301 | —CH$_2$—O—C(=O)—CH$_3$ | 633.2 |
| 302 | —CH$_2$—O—C(=O)—CH$_2$CH$_3$ | |
| 303 | —CH$_2$—O—C(=O)—CH(CH$_3$)$_2$ | |
| 304 | —CH$_2$—O—C(=O)—(CH$_2$)$_2$—CH$_3$ | |
| 305 | —CH$_2$—O—C(=O)—(CH$_2$)$_3$—CH$_3$ | |
| 306 | —CH$_2$—O—C(=O)—CH$_2$—CH(CH$_3$)$_2$ | |
| 307 | —CH$_2$—O—C(=O)—CH(CH$_3$)—CH$_2$—CH$_3$ | |
| 308 | —CH$_2$—O—C(=O)—C(CH$_3$)$_3$ | 675.3 |
| 309 | —CH$_2$—O—C(=O)-cyclopropyl | |
| 310 | —CH$_2$—O—C(=O)-cyclobutyl | |
| 311 | —CH$_2$—O—C(=O)-cyclopentyl | |
| 312 | —CH$_2$—O—C(=O)-cyclohexyl | |
| 313 | —CH$_2$—O—C(=O)-phenyl | |
| 314 | —CH$_2$—O—C(=O)-4-methylphenyl | |
| 315 | —CH$_2$—O—C(=O)-4-ethylphenyl | |
| 316 | —CH$_2$—O—C(=O)-4-isopropylphenyl | |
| 317 | —CH$_2$—O—C(=O)-4-propylphenyl | |
| 318 | —CH$_2$—O—C(=O)-4-t-butylphenyl | |
| 319 | —CH$_2$—O—C(=O)-4-methoxyphenyl | |
| 320 | —CH$_2$—O—C(=O)-4-ethoxyphenyl | |
| 321 | —CH$_2$—O—C(=O)-4-isopropyloxyphenyl | |
| 322 | —CH$_2$—O—C(=O)-4-propyloxyphenyl | |
| 323 | —CH$_2$—O—C(=O)-4-t-butoxyphenyl | |
| 324 | —CH$_2$—O—C(=O)-4-biphenyl | |
| 325 | —CH(CH$_3$)—O—C(=O)—CH$_3$ | |
| 326 | —CH(CH$_3$)—O—C(=O)—CH$_2$CH$_3$ | |
| 327 | —CH(CH$_3$)—O—C(=O)—CH(CH$_3$)$_2$ | |
| 328 | —CH(CH$_3$)—O—C(=O)—(CH$_2$)$_2$—CH$_3$ | |
| 329 | —CH(CH$_3$)—O—C(=O)—(CH$_2$)$_3$—CH$_3$ | |
| 330 | —CH(CH$_3$)—O—C(=O)—CH$_2$—CH(CH$_3$)$_2$ | |
| 331 | —CH(CH$_3$)—O—C(=O)—CH(CH$_3$)—CH$_2$—CH$_3$ | |
| 332 | —CH(CH$_3$)—O—C(=O)—C(CH$_3$)$_3$ | |
| 333 | —CH(CH$_3$)—O—C(=O)-cyclopropyl | |
| 334 | —CH(CH$_3$)—O—C(=O)-cyclobutyl | |
| 335 | —CH(CH$_3$)—O—C(=O)-cyclopentyl | |
| 336 | —CH(CH$_3$)—O—C(=O)-cyclohexyl | |
| 337 | —CH(CH$_3$)—O—C(=O)-phenyl | |
| 338 | —CH(CH$_3$)—O—C(=O)-4-methylphenyl | |
| 339 | —CH(CH$_3$)—O—C(=O)-4-ethylphenyl | |

TABLE 11-continued

J = D-Abu

| Ex. No. | R | FABMS (M + H) |
|---|---|---|
| 340 | —CH(CH$_3$)—O—C(=O)-4-isopropylphenyl | |
| 341 | —CH(CH$_3$)—O—C(=O)-4-propylphenyl | |
| 342 | —CH(CH$_3$)—O—C(=O)-4-t-butylphenyl | |
| 343 | —CH(CH$_3$)—O—C(=O)-4-methoxyphenyl | |
| 344 | —CH(CH$_3$)—O—C(=O)-4-ethoxyphenyl | |
| 345 | —CH(CH$_3$)—O—C(=O)-4-isopropyloxyphenyl | |
| 346 | —CH(CH$_3$)—O—C(=O)-4-propyloxyphenyl | |
| 347 | —CH(CH$_3$)—O—C(=O)-4-t-butoxyphenyl | |
| 348 | —CH(CH$_3$)—O—C(=O)-4-biphenyl | |
| 349 | —CH$_2$—O—C(=O)—O—CH$_3$ | |
| 350 | —CH$_2$—O—C(=O)—O—CH$_2$CH$_3$ | |
| 351 | —CH$_2$—O—C(=O)—O—CH(CH$_3$)$_2$ | 667.3 |
| 352 | —CH$_2$—O—C(=O)—O—(CH$_2$)$_2$—CH$_3$ | |
| 353 | —CH$_2$—O—C(=O)—O—(CH$_2$)$_3$—CH$_3$ | |
| 354 | —CH$_2$—O—C(=O)—O—CH$_2$—CH(CH$_3$)$_2$ | |
| 355 | —CH$_2$—O—C(=O)—O—CH(CH$_3$)—CH$_2$—CH$_3$ | |
| 356 | —CH$_2$—O—C(=O)—O—C(CH$_3$)$_3$ | |
| 357 | —CH$_2$—O—C(=O)—O-cyclopropyl | |
| 358 | —CH$_2$—O—C(=O)—O-cyclobutyl | |
| 359 | —CH$_2$—O—C(=O)—O-cyclopentyl | |
| 360 | —CH$_2$—O—C(=O)—O-cyclohexyl | |
| 361 | —CH$_2$—O—C(=O)—O-phenyl | |
| 362 | —CH$_2$—O—C(=O)—O-4-methylphenyl | |
| 363 | —CH$_2$—O—C(=O)—O-4-ethylphenyl | |
| 364 | —CH$_2$—O—C(=O)—O-4-isopropylphenyl | |
| 365 | —CH$_2$—O—C(=O)—O-4-propylphenyl | |
| 366 | —CH$_2$—O—C(=O)—O-4-t-butylphenyl | |
| 367 | —CH$_2$—O—C(=O)—O-4-methoxyphenyl | |
| 368 | —CH$_2$—O—C(=O)—O-4-ethoxyphenyl | |
| 369 | —CH$_2$—O—C(=O)—O-4-isopropyloxyphenyl | |
| 370 | —CH$_2$—O—C(=O)—O-4-propyloxyphenyl | |
| 371 | —CH$_2$—O—C(=O)—O-4-t-butoxyphenyl | |
| 372 | —CH$_2$—O—C(=O)—O-4-biphenyl | |
| 373 | —CH(CH$_3$)—O—C(=O)—O—CH$_3$ | |
| 374 | —CH(CH$_3$)—O—C(=O)—O—CH$_2$CH$_3$ | |
| 375 | —CH(CH$_3$)—O—C(=O)—O—CH(CH$_3$)$_2$ | |
| 376 | —CH(CH$_3$)—O—C(=O)—O—(CH$_2$)$_2$—CH$_3$ | |
| 377 | —CH(CH$_3$)—O—C(=O)—O—(CH$_2$)$_3$—CH$_3$ | |
| 378 | —CH(CH$_3$)—O—C(=O)—O—CH$_2$—CH(CH$_3$)$_2$ | |
| 379 | —CH(CH$_3$)—O—C(=O)—O—CH(CH$_3$)—CH$_2$—CH$_3$ | |
| 380 | —CH(CH$_3$)—O—C(=O)—O—C(CH$_3$)$_3$ | |
| 381 | —CH(CH$_3$)—O—C(=O)—O-cyclopentyl | |
| 382 | —CH(CH$_3$)—O—C(=O)—O-cyclobutyl | |
| 383 | —CH(CH$_3$)—O—C(=O)—O-cyclopentyl | |
| 384 | —CH(CH$_3$)—O—C(=O)—O-cyclohexyl | |
| 385 | —CH(CH$_3$)—O—C(=O)—O-phenyl | |
| 386 | —CH(CH$_3$)—O—C(=O)—O-4-methylphenyl | |
| 387 | —CH(CH$_3$)—O—C(=O)—O-4-ethylphenyl | |
| 388 | —CH(CH$_3$)—O—C(=O)—O-4-isopropylphenyl | |
| 389 | —CH(CH$_3$)—O—C(=O)—O-4-propylphenyl | |
| 390 | —CH(CH$_3$)—O—C(=O)—O-4-t-butylphenyl | |
| 391 | —CH(CH$_3$)—O—C(=O)—O-4-methoxyphenyl | |
| 392 | —CH(CH$_3$)—O—C(=O)—O-4-ethoxyphenyl | |
| 393 | —CH(CH$_3$)—O—C(=O)—O-4-isopropyloxyphenyl | |
| 394 | —CH(CH$_3$)—O—C(=O)—O-4-propyloxyphenyl | |
| 395 | —CH(CH$_3$)—O—C(=O)—O-4-t-butoxyphenyl | |
| 396 | —CH(CH$_3$)—O—C(=O)—O-4-biphenyl | |
| 397 | CH$_2$—N(CH$_3$)$_2$ | |

TABLE 11-continued

[Structure: cyclic peptide with NMeArg-J, Gly-NH, Asp(O-R), connected via benzoyl-CH2-NH ring]

J = D-Abu

| Ex. No. | R | FABMS (M + H) |
|---|---|---|
| 398 | CH$_2$—N(CH$_2$—CH$_3$)$_2$ | |
| 399 | CH$_2$CH$_2$—N(CH$_3$)$_2$ | |
| 400 | CH$_2$—CH$_2$—N(CH$_2$CH$_3$)$_2$ | |
| 401 | CH$_2$—CH$_2$—N(azetidinyl) | |
| 402 | CH$_2$—CH$_2$—N(pyrrolidinyl) | |
| 403 | CH$_2$—CH$_2$—N(piperidinyl) | |
| 404 | —CH(CH$_3$)OC(=O)C(CH$_3$)$_2$OCH$_3$ | |
| 405 | [1,3-dioxol-2-one with ethyl and CH$_3$ substituents] | |
| 406 | [1,3-dioxol-2-one with ethyl and tBu substituents] | |
| 407 | [1,3-dioxol-2-one with ethyl and phenyl substituents] | |
| 408 | CH$_2$C(=O)OCH$_3$ | |
| 409 | CH$_2$C(=O)O-tBu | |

Specifically disclosed by the present invention are those compounds of Table 10 wherein D-Abu is replaced by a residue selected from: D-Val, D-Leu, D-Ala, Gly, D-Pro, D-norvaline, D-Ser, D-Lys, β-Ala, Pro, Phe, NMeGly, D-Nle, D-Phg, D-Ile, D-Phe, D-Tyr, Ala.

What is claimed is:

1. A compound of the formula (I):

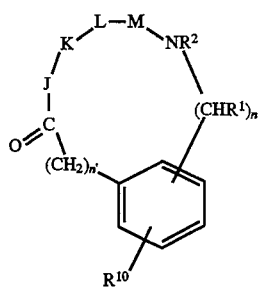

or a pharmaceutically acceptable salt form thereof wherein:

$R^1$ is H, $C_1$–$C_4$ alkyl, phenyl, benzyl or phenyl ($C_1$–$C_4$) alkyl;

$R^2$ is H or methyl;

$R^{10}$ is H, halogen, $C_1$–$C_8$ alkyl, phenyl or $C_1$–$C_4$ alkoxy;

n is 0–2;

n' is 0–1;

J is D-Ala, D-Val, D-Ile, D-Leu, D-Nle, D-phenylGly, D-Phe, D-Lys, D-Orn, D-Met, D-Pro, β-Ala, D-Tyr, D-Ser, NMeGly, D-cyclohexylGly, D-cyclohexylmethylGly, D-norvaline, D-2-aminobutyric acid, D-2-aminopentanoic acid, Gly, $N^\epsilon$-p-azidobenzoyl-D-Lys, $N^\epsilon$-p-benzoylbenzoyl-D-Lys, $N^\epsilon$-tryptophanyl-D-Lys, $N^\epsilon$-o-benzylbenzoyl-D-Lys, $N^\epsilon$-p-acetobenzoyl-D-Lys, $N^\epsilon$-dansyl-D-Lys, $N^\epsilon$-t-butoxycarbonylglycyl-D-Lys, $N^\epsilon$-glycyl-D-Lys, $N^\epsilon$-p-benzoylbenzoylglycyl-D-Lys, $N^\epsilon$-p-phenylbenzoyl-D-Lys, $N^\epsilon$-m-benzoylbenzoyl-D-Lys, or $N^\epsilon$-o-benzoylbenzoyl-D-Lys;

K is αNMeArg, $N^\delta,N^\alpha$-diMe-$N^\delta$-guanidinylOrn, $N^\alpha$-MeLys or $N^\epsilon,N^\alpha$-diMeLys;

L is Gly;

M is selected from Asp, β-MeAsp, NMeAsp,
Asp-(methylcarbonyloxymethyl ester),
Asp-(ethylcarbonyloxymethyl ester),
Asp-(t-butylcarbonyloxymethyl ester),
Asp-(cyclohexylcarbonyloxymethyl ester),
Asp-(1-(methylcarbonyloxy)ethyl ester),
Asp-(1-(ethylcarbonyloxy)ethyl ester),
Asp-(1-(t-butylcarbonyloxy)ethyl ester),
Asp-(1-(cyclohexylcarbonyloxy)ethyl ester),
Asp-(i-propyloxycarbonyloxymethyl ester),
Asp-(cyclohexylcarbonyloxymethyl ester),
Asp-(t-butyloxycarbonyloxymethyl ester),
Asp-(1-(i-propyloxycarbonyloxy)ethyl ester),
Asp-(1-(cyclohexyloxycarbonyloxy)ethyl ester),
Asp-(1-(t-butyloxycarbonyloxy)ethyl ester),
Asp-(dimethylaminoethyl ester),
Asp-(diethylaminoethyl ester),
Asp-((1,3-dioxa-5-methyl-cyclopenten-2-one-4-yl) methyl ester),
Asp-((5-(t-butyl)-1,3-dioxa-cyclopenten-2-one-4-yl) methyl ester),
Asp-((1,3-dioxa-5-phenyl-cyclopenten-2-one-4-yl) methyl ester), or
Asp-(1-(2-(2-methoxypropyl)carbonyloxy)ethyl ester).

2. A compound of formula (II):

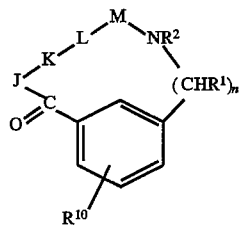

or a pharmaceutically acceptable salt thereof wherein:

$R^1$ is H, $C_1$–$C_4$ alkyl, phenyl, benzyl or phenyl($C_1$–$C_4$) alkyl;

$R^2$ is H or methyl;

$R^{10}$ is H, halogen, $C_1$–$C_8$ alkyl, phenyl or $C_1$–$C_4$ alkoxy;

alternatively, when $R^{10}$ is para to the carbonyl, $R^{10}$ and $R^1$ may be taken together to form —$CH_2$—$CH_2$—$CH_2$— thereby to form a six-membered fused ring;

n is 0–1;

J is D-Ala, D-Val, D-Ile, D-Leu, D-Nle, D-phenylGly, D-Phe, D-Lys, D-Orn, D-Met, D-Pro, β-Ala, D-Tyr, D-Ser, NMeGly, D-cyclohexylGly, D-cyclohexylmethylGly, D-norvaline, D-2-aminobutyric acid, D-2-aminopentanoic acid, $N^\epsilon$-p-azidobenzoyl-D-Lys, $N^\epsilon$-p-benzoylbenzoyl-D-Lys, $N^\epsilon$-tryptophanyl-D-Lys, $N^\epsilon$-o-benzylbenzoyl-D-Lys, $N^\epsilon$-p-acetobenzoyl-D-Lys, $N^\epsilon$-dansyl-D-Lys, $N^\epsilon$-t-butoxycarbonylglycyl-D-Lys, $N^\epsilon$-glycyl-D-Lys, $N^\epsilon$-p-benzoylbenzoylglycyl-D-Lys, $N^\epsilon$-p-phenylbenzoyl-D-Lys, $N^\epsilon$-m-benzoylbenzoyl-D-Lys, $N^\epsilon$-o-benzoylbenzoyl-D-Lys;

K is αNMeArg, $N^\delta$, $N^\alpha$-diMe-$N^\delta$-guanidinylOrn, $N^\alpha$-MeLys or $N^\epsilon,N^\alpha$-diMeLys;

L is Gly; and

M is Asp, β-MeAsp, NMeAsp,
Asp-(methylcarbonyloxymethyl ester),
Asp-(ethylcarbonyloxymethyl ester),
Asp-(t-butylcarbonyloxymethyl ester),
Asp-(cyclohexylcarbonyloxymethyl ester),
Asp-(1-(methylcarbonyloxy)ethyl ester),
Asp-(1-(ethylcarbonyloxy)ethyl ester),
Asp-(1-(t-butylcarbonyloxy)ethyl ester),
Asp-(1-(cyclohexylcarbonyloxy)ethyl ester),
Asp-(i-propyloxycarbonyloxymethyl ester),
Asp-(cyclohexylcarbonyloxymethyl ester),
Asp-(t-butyloxycarbonyloxymethyl ester),
Asp-(1-(i-propyloxycarbonyloxy)ethyl ester),
Asp-(1-(cyclohexyloxycarbonyloxy)ethyl ester), Asp-(1-(t-butyloxycarbonyloxy)ethyl ester),
Asp-(dimethylaminoethyl ester),
Asp-(diethylaminoethyl ester),
Asp-((1,3-dioxa-5-methyl-cyclopenten-2-one-4-yl) methyl ester),
Asp-((5-(t-butyl)-1,3-dioxa-cyclopenten-2-one-4-yl) methyl ester),
Asp-((1,3-dioxa-5-phenyl-cyclopenten-2-one-4-yl) methyl ester), or
Asp-(1-(2-(2-methoxypropyl)carbonyloxy)ethyl ester).

3. A compound of claim 2, or a pharmaceutically acceptable salt thereof, wherein:

$R^1$ is H, $C_1$–$C_4$ alkyl, phenyl, benzyl or phenyl($C_1$–$C_4$) alkyl;

$R^2$ is H or methyl;

$R^{10}$ is H, halogen, $C_1$–$C_8$ alkyl, phenyl or $C_1$–$C_4$ alkoxy; alternatively, when $R^{10}$ is para to the carbonyl, $R^{10}$ and $R^1$ may be taken together to form —$CH_2$—$CH_2$—$CH_2$— thereby to form a six-membered fused ring;

n is 1;

J is D-Ala, D-Val, D-Ile, D-Leu, D-Nle, D-phenylGly, D-Phe, D-Lys, D-Orn, D-Met, D-Pro, β-Ala, D-Tyr, D-Ser, NMeGly, D-cyclohexylGly, D-cyclohexylmethylGly, D-norvaline, D-2-aminobutyric acid, $N^\epsilon$-p-azidobenzoyl-D-Lys, $N^\epsilon$-p-benzoylbenzoyl-D-Lys, $N^\epsilon$-tryptophanyl-D-Lys, $N^\epsilon$-o-benzylbenzoyl-D-Lys, $N^\epsilon$-p-acetobenzoyl-D-Lys, $N^\epsilon$-dansyl-D-Lys, $N^\epsilon$-t-butoxycarbonylglycyl-D-Lys, $N^\epsilon$-glycyl-D-Lys, $N^\epsilon$-p-benzoylbenzoylglycyl-D-Lys, $N^\epsilon$-p-phenylbenzoyl-D-Lys, $N^\epsilon$-m-benzoylbenzoyl-D-Lys, or $N^\epsilon$-o-benzoylbenzoyl-D-Lys;

K is αNMeArg;

L is Gly; and

M is Asp, βMeAsp, NMeAsp,
Asp-(methylcarbonyloxymethyl ester),
Asp-(ethylcarbonyloxymethyl ester),
Asp-(t-butylcarbonyloxymethyl ester),
Asp-(cyclohexylcarbonyloxymethyl ester),
Asp-(1-(methylcarbonyloxy)ethyl ester),
Asp-(1-(ethylcarbonyloxy)ethyl ester),
Asp-(1-(t-butylcarbonyloxy)ethyl ester),
Asp-(1-(cyclohexylcarbonyloxy)ethyl ester),
Asp-(i-propyloxycarbonyloxymethyl ester),
Asp-(cyclohexylcarbonyloxymethyl ester),
Asp-(t-butyloxycarbonyloxymethyl ester),
Asp-(1-(i-propyloxycarbonyloxy)ethyl ester),
Asp-(1-(cyclohexyloxycarbonyloxy)ethyl ester),
Asp-(1-(t-butyloxycarbonyloxy)ethyl ester),
Asp-(dimethylaminoethyl ester),
Asp-(diethylaminoethyl ester),
Asp-((1,3-dioxa-5-methyl-cyclopenten-2-one-4-yl) methyl ester),
Asp-((5-(t-butyl)-1,3-dioxa-cyclopenten-2-one-4-yl) methyl ester),
Asp-((1,3-dioxa-5-phenyl-cyclopenten-2-one-4-yl) methyl ester), or
Asp-(1-(2-(2-methoxypropyl)carbonyloxy)ethyl ester).

4. A compound of claim 2, or a pharmaceutically acceptable salt thereof, wherein:

$R^1$ and $R^2$ are independently selected from H or methyl;
$R^{10}$ is H;
alternatively, when $R^{10}$ is para to the carbonyl, $R^{10}$ and $R^1$ may be taken together to form —$CH_2$—$CH_2$—$CH_2$— thereby to form a six-membered fused ring;

J is D-Val, D-2-aminobutyric acid, D-Leu, D-Ala, D-Pro, D-Ser, D-Lys, β-Ala, NMeGly, D-Nle, D-phenylGly, D-Ile, D-Phe or, D-Tyr;

K is αNMeArg;

L is Gly;

M is Asp; β-MeAsp, NMeAsp;
Asp-(methylcarbonyloxymethyl ester);
Asp-(ethylcarbonyloxymethyl ester);
Asp-(t-butylcarbonyloxymethyl ester);
Asp-(cyclohexylcarbonyloxymethyl ester);
Asp-(1-(methylcarbonyloxy)ethyl ester);
Asp-(1-(ethylcarbonyloxy)ethyl ester);
Asp-(1-(t-butylcarbonyloxy)ethyl ester);
Asp-(1-(cyclohexylcarbonyloxy)ethyl ester);
Asp-(i-propyloxycarbonyloxymethyl ester);
Asp-(cyclohexylcarbonyloxymethyl ester);
Asp-(t-butyloxycarbonyloxymethyl ester);
Asp-(1-(i-propyloxycarbonyloxy)ethyl ester);
Asp-(1-(cyclohexyloxycarbonyloxy)ethyl ester);
Asp-(1-(t-butyloxycarbonyloxy)ethyl ester);
Asp-(dimethylaminoethyl ester);
Asp-(diethylaminoethyl ester);
Asp-((1,3-dioxa-5-methyl-cyclopenten-2-one-4-yl) methyl ester);
Asp-((5-(t-butyl)-1,3-dioxa-cyclopenten-2-one-4-yl) methyl ester);
Asp-((1,3-dioxa-5-phenyl-cyclopenten-2-one-4-yl) methyl ester) OR;
Asp-(1-(2-(2-methoxypropyl)carbonyloxy)ethyl ester).

5. A compound of claim 1 of Formula (IV):

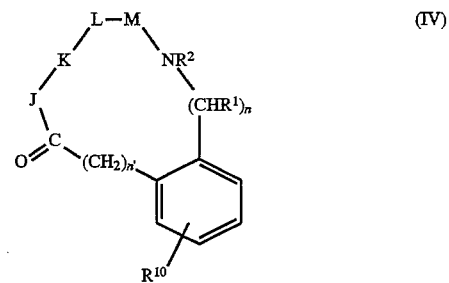

(IV)

or a pharmaceutically acceptable salt thereof, wherein:

$R^1$ and $R^2$ are independently selected from H or methyl;
$R^{10}$ is H, halogen, $C_1$–$C_8$ alkyl, phenyl or $C_1$–$C_4$ alkoxy;
n is 1;
n' is 1;
J is D-Val, D-2-aminobutyric acid, D-Leu, D-Ala, D-Pro, D-Ser, D-Lys, β-Ala, NMeGly, D-Nle, D-phenylGly, D-Ile, D-Phe or, D-Tyr;

K is αNMeArg;

L is Gly;

M is Asp; β-MeAsp; NMeAsp;
Asp-(methylcarbonyloxymethyl ester);
Asp-(ethylcarbonyloxymethyl ester);
Asp-(t-butylcarbonyloxymethyl ester);
Asp-(cyclohexylcarbonyloxymethyl ester);
Asp-(1-(methylcarbonyloxy)ethyl ester);
Asp-(1-(ethylcarbonyloxy)ethyl ester);
Asp-(1-(t-butylcarbonyloxy)ethyl ester);
Asp-(1-(cyclohexylcarbonyloxy)ethyl ester);
Asp-(i-propyloxycarbonyloxymethyl ester);
Asp-(cyclohexylcarbonyloxymethyl ester);
Asp-(t-butyloxycarbonyloxymethyl ester);
Asp-(1-(i-propyloxycarbonyloxy)ethyl ester);
Asp-(1-(cyclohexyloxycarbonyloxy)ethyl ester);
Asp-(1-(t-butyloxycarbonyloxy)ethyl ester);
Asp-(dimethylaminoethyl ester);
Asp-(diethylaminoethyl ester);

Asp-((1,3-dioxa-5-methyl-cyclopenten-2-one-4-yl) methyl ester);
Asp-((5-(t-butyl)-1,3-dioxa-cyclopenten-2-one-4-yl) methyl ester);
Asp-((1,3-dioxa-5-phenyl-cyclopenten-2-one-4-yl) methyl ester) or;
Asp-(1-(2-(2-methoxypropyl)carbonyloxy)ethyl ester).

6. A compound of claim 2 of formula (IIa):

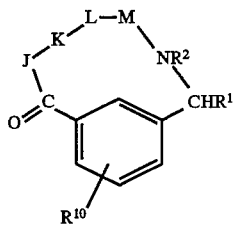

or a pharmaceutically acceptable salt thereof, which is selected from the group consisting of:

the compound of formula (IIa) wherein $R^1$, $R^2$ and $R^{10}$ are H; J is D-Val; K is NMeArg; L is Gly; and M is Asp;
the compound of formula (IIa) wherein $R^1$, $R^2$ and $R^{10}$ are H; J is D-2-aminobutyric acid; K is NMeArg; L is Gly; and M is Asp;
the compound of formula (IIa) wherein $R^1$, $R^2$ and $R^{10}$ are H; J is D-Leu; K is NMeArg; L is Gly; and M is Asp;
the compound of formula (IIa) wherein $R^1$, $R^2$ and $R^{10}$ are H; J is D-Ala; K is NMeArg; L is Gly; and M is Asp;
the compound of formula (IIa) wherein $R^1$, $R^2$ and $R^{10}$ are H; J is D-Pro; K is NMeArg; L is Gly; and M is Asp;
the compound of formula (IIa) wherein $R^1$, $R^2$ and $R^{10}$ are H; J is D-Lys; K is NMeArg; L is Gly; and M is Asp;
the compound of formula (IIa) wherein $R^1$ is methyl (isomer 1); $R^2$ and $R^{10}$ are H; J is D-Val; K is NMeArg; L is Gly; and M is Asp;
the compound of formula (IIa) wherein $R^1$ is methyl (isomer 2); $R^2$ and $R^{10}$ are H; J is D-Val; K is NMeArg; L is Gly; and M is Asp;
the compound of formula (IIa) wherein $R^1$ is phenyl (isomer 1); $R^2$ and $R^{10}$ are H; J is D-Val; K is NMeArg; L is Gly; and M is Asp;
the compound of formula (IIa) wherein $R^1$, $R^2$ and $R^{10}$ are H, J=D-Met, K=NMeArg, L=Gly, M=Asp;
the compound of formula (IIa) wherein $R^1$, $R^2$ and $R^{10}$ are H, J=D-2-aminobutyric acid, K=$N^\delta,N^\alpha$-diMe-$N^\delta$-guanidinylOrn, L=Gly, M=Asp;
the compound of formula (IIa) wherein $R^1$, $R^2$ and $R^{10}$ are H, J=D-2-aminobutyric acid, K=$N^\epsilon,N^\alpha$-diMeLys, L=Gly, M=Asp;
the compound of formula (IIa) wherein $R^1$, $R^2$ and $R^{10}$ are H, J is $N^\epsilon$-p-azidobenzoyl-D-Lys; K is NMeArg; L is Gly; and M is Asp;
the compound of formula (IIa) wherein $R^1$, $R^2$ and $R^{10}$ are H; J is $N^\epsilon$-p-benzoylbenzoyl-D-Lys; K is NMeArg; L is Gly; and M is Asp;
the compound of formula (IIa) wherein $R^1$, $R^2$ and $R^{10}$ are H; J is $N^\epsilon$-tryptophanyl-D-Lys; K is NMeArg; L is Gly; and M is Asp;
the compound of formula (IIa) wherein $R^1$, $R^2$ and $R^{10}$ are H; J is $N^\epsilon$-o-benzylbenzoyl-D-Lys; K is NMeArg; L is Gly; and M is Asp;
the compound of formula (IIa) wherein $R^1$, $R^2$ and $R^{10}$ are H; J is $N^\epsilon$-p-acetylbenzoyl-D-Lys; K is NMeArg; L is Gly; and M is Asp;
the compound of formula (IIa) wherein $R^1$, $R^2$ and $R^{10}$ are H; J is $N^\epsilon$-dansyl-D-Lys; K is NMeArg; L is Gly; and M is Asp;
the compound of formula (IIa) wherein $R^1$, $R^2$ and $R^{10}$ are H; J is $N^\epsilon$-glycyl-D-Lys; K is NMeArg; L is Gly; and M is Asp;
the compound of formula (IIa) wherein $R^1$, $R^2$ and $R^{10}$ are H; J is $N^\epsilon$-p-benzoylbenzoylglycyl-D-Lys; K is NMeArg; L is Gly; and M is Asp;
the compound of formula (IIa) wherein $R^1$, $R^2$ and $R^{10}$ are H; J is $N^\epsilon$-p-phenylbenzoyl-D-Lys; K is NMeArg; L is Gly; and M is Asp;
the compound of formula (IIa) wherein $R^1$, $R^2$ and $R^{10}$ are H; J is $N^\epsilon$-m-benzoylbenzoyl-D-Lys; K is NMeArg; L is Gly; and M is Asp;
the compound of formula (IIa) wherein $R^1$, $R^2$ and $R^{10}$ are H; J is $N^\epsilon$-o-benzoylbenzoyl-D-Lys; K is NMeArg; L is Gly; and M is Asp;
the compound of formula (IIa) wherein $R^1$, $R^2$ and $R^{10}$ are H; J is D-Nle; K is NMeArg; L is Gly; and M is Asp;
the compound of formula (IIa) wherein $R^1$, $R^2$ and $R^{10}$ are H; J is D-phenylGly; K is NMeArg; L is Gly; and M is Asp;
the compound of formula (IIa) wherein $R^1$, $R^2$ and $R^{10}$ are H; J is D-Phe; K is NMeArg; L is Gly; and M is Asp;
the compound of formula (IIa) wherein $R^1$, $R^2$ and $R^{10}$ are H; J is D-Ile; K is NMeArg; L is Gly; and M is Asp;
the compound of formula (IIa) wherein $R^1$ and $R^2$ are H; $R^{10}$ is 4-Cl; J is D-Val; K is NMeArg; L is Gly; and M is Asp;
the compound of formula (IIa) wherein $R^1$ and $R^2$ are H; $R^{10}$ is 4-I; J is D-Val; K is NMeArg; L is Gly; and M is Asp;
the compound of formula (IIa) wherein $R^1$ and $R^2$ are H; $R^{10}$ is 4-I; J is D-2-aminobutyric acid; K is NMeArg; L is Gly; and M is Asp;
the compound of formula (IIa) wherein $R^1$ and $R^2$ are H; $R^{10}$ is 4-Me; J is D-Val; K is NMeArg; L is Gly; and M is Asp;
the compound of formula (IIa) wherein $R^1$ and $R^2$ are H; $R^{10}$ is 6-Cl; J is D-Val; K is NMeArg; L is Gly; and M is Asp;
the compound of formula (IIa) wherein $R^1$ and $R^2$ are H; $R^{10}$ is 6-methoxy; J is D-Val; K is NMeArg; L is Gly; and M is Asp;
the compound of formula (IIa) wherein $R^1$ and $R^2$ are H; $R^{10}$ is 6-Me; J is D-Val; K is NMeArg; L is Gly; and M is Asp;
the compound of formula (IIa) wherein $R^1$ and $R^2$ are H; $R^{10}$ is 4-Cl; J is D-2-aminobutyric acid; K is NMeArg; L is Gly; and M is Asp;
the compound of formula (IIa) wherein $R^1$ and $R^2$ are H; $R^{10}$ is 4-I; J is D-2-aminobutyric acid; K is NMeArg; L is Gly; and M is Asp;
the compound of formula (IIa) wherein $R^1$ and $R^2$ are H; $R^{10}$ is 4-Me; J is D-2-aminobutyric acid; K is NMeArg; L is Gly; and M is Asp;
the compound of formula (IIa) wherein $R^1$, $R^2$ and $R^{10}$ are H; J is D-Tyr; K is NMeArg; L is Gly; and M is Asp;
the compound of formula (IIa) wherein $R^1$, $R^2$ and $R^{10}$ are H; J is D-Val; K is NMeArg; L is Gly; and M is D-MeAsp;
the compound of formula (IIa) wherein $R^1$ and $R^{10}$ are H; $R^2$ is $CH_3$; J is D-Val; K is NMeArg; L is Gly; and M is Asp;
the compound of formula (IIa) wherein $R^1$, $R^2$ and $R^{10}$ are H; J is D-cyclohexylGly; K is NMeArg; L is Gly; and M is Asp;
the compound of formula (IIa) wherein $R^1$, $R^2$ and $R^{10}$ are H; J is $N^\epsilon$-t-butoxyglycyl-D-Lys; K is NMeArg; L is Gly; and M is Asp;
the compound of formula (IIa) wherein $R^1$, $R^2$ and $R^{10}$ are H; J is D-Ser; K is NMeArg; L is Gly; and M is Asp;
the compound of formula (IIa) wherein $R^{10}$ is para to the carbonyl and $R^1$ and $R^{10}$ are taken together to form —$CH_2$—$CH_2$—$CH_2$—, $R^2$ is H; J is D-Val; K is NMeArg; L is Gly; and M is Asp and;
the compound of formula (IIa) wherein $R^{10}$ is para to the carbonyl and $R^1$ and $R^{10}$ are taken together to form —CH₂—CH₂—CH₂—, R² is H; J is D-Abu; K is NMe-Arg; L is Gly; and M is Asp.

7. A method for preventing thrombus formation which comprises administering to a host in need of such treatment a therapeutically effective amount of a compound of one of claims 1–5.

8. A method for lysing a blood clot which comprises administering to a host in need of such treatment a therapeutically effective amount of a compound of one of claims 1–5.

9. A pharmaceutical composition comprising a compound of one of claims 1–5 and a pharmaceutically acceptable carrier.

10. A compound of Formula (I):

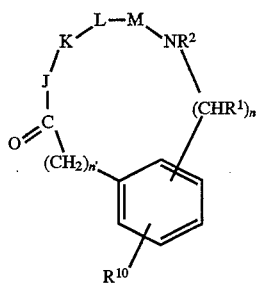

or a pharmaceutically acceptable salt form thereof wherein:

R¹ is H, C₁–C₄ alkyl, phenyl, benzyl or phenyl(C₁–C₄) alkyl;

R² is H or methyl;

R¹⁰ is H, halogen, C₁–C₈ alkyl, phenyl or C₁–C₄ alkoxy;

n is 0–2;

n' is 0–1;

J is Ala, Val, Ile, Leu, Nle, phenylGly, Phe, Lys, Orn, Met, Pro, β-Ala, Tyr, Ser, NMeGly, cyclohexylGly, cyclohexylmethylGly, norvaline, 2-aminobutyric acid, 2-aminopentanoic acid, Gly, Cys, S-benzyl-Cys, S-methyl-Cys, Asp, Glu, 2-amino-2-methylpropionic acid, His, 1-allo-isoleucine, Asn, Gln, Thr, Trp, or O-methyl-Tyr;

K is Arg, N^δ-Me-N^δ-guanidinylOrn, p-aminomethylPhe, p-guanidinylPhe, Lys or N^ε-MeLys;

L is Gly;

M is Asp, β-MeAsp, NMeAsp,
Asp-(methylcarbonyloxymethyl ester),
Asp-(ethylcarbonyloxymethyl ester),
Asp-(t-butylcarbonyloxymethyl ester),
Asp-(cyclohexylcarbonyloxymethyl ester),
Asp-(1-(methylcarbonyloxy)ethyl ester),
Asp-(1-(ethylcarbonyloxy)ethyl ester),
Asp-(1-(t-butylcarbonyloxy)ethyl ester),
Asp-(1-(cyclohexylcarbonyloxy)ethyl ester),
Asp-(i-propyloxycarbonyloxymethyl ester),
Asp-(cyclohexylcarbonyloxymethyl ester),
Asp-(t-butyloxycarbonyloxymethyl ester),
Asp-(1-(i-propyloxycarbonyloxy)ethyl ester),
Asp-(1-(cyclohexyloxycarbonyloxy)ethyl ester),
Asp-(1-(t-butyloxycarbonyloxy)ethyl ester),
Asp-(dimethylaminoethyl ester),
Asp-(diethylaminoethyl ester),
Asp-((1,3-dioxa-5-methyl-cyclopenten-2-one-4-yl) methyl ester),
Asp-((5-(t-butyl)-1,3-dioxa-cyclopenten-2-one-4-yl) methyl ester),
Asp-((1,3-dioxa-5-phenyl-cyclopenten-2-one-4-yl) methyl ester), or Asp-(1-(2-(2-methoxypropyl)carbonyloxy)ethyl ester).

11. A compound of claim 10 of Formula (II):

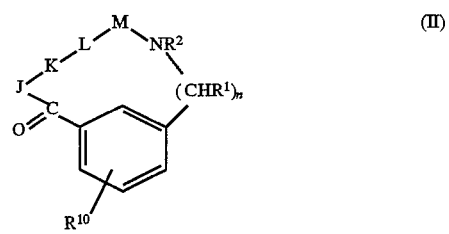

or a pharmaceutically acceptable salt thereof wherein:

R¹ is H, C₁–C₄ alkyl, phenyl, benzyl or phenyl(C₁–C₄) alkyl;

R² is H or methyl;

R¹⁰ is H, halogen, C₁–C₈ alkyl, phenyl or C₁–C₄ alkoxy;

alternatively, when R¹⁰ is para to the carbonyl, R¹⁰ and R¹ may be taken together to form —CH₂—CH₂—CH₂— thereby to form a six-membered fused ring;

n is 0–1;

J is Ala, Val, Ile, Leu, Nle, phenylGly, Phe, Lys, Orn, Met, Pro, β-Ala, Tyr, Ser, NMeGly, cyclohexylGly, cyclohexylmethylGly, norvaline, 2-aminobutyric acid, 2-aminopentanoic acid, Gly, N^ε-p-azidobenzoyl-Lys, Cys, S-benzyl-Cys, S-methyl-Cys, Asp, Glu, 2-amino-2-methylpropionic acid, His, 1-allo-isoleucine, Asn, Gln, Thr, Trp, or O-methyl-Tyr;

K is Arg, N^δ-Me-N^δ-guanidinylOrn, Lys or N^ε-MeLys;

L is Gly; and

M is Asp, β-MeAsp, or NMeAsp.

12. A compound of claim 11 wherein:

n is 1;

K is Arg;

J is Ala, Val, Ile, Leu, Pro, Ser, or Lys.

13. A compound of claim 11 of Formula (IIa):

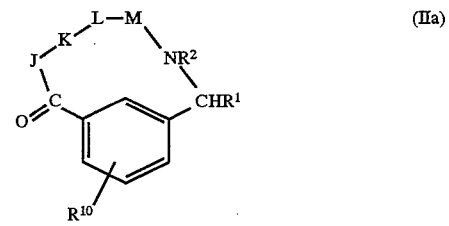

or a pharmaceutically acceptable salt thereof, which is selected from the group consisting of:

the compound of formula (IIa) wherein R¹, R² and R¹⁰ are H; J is Ala; K is Arg; L is Gly; and M is Asp;

the compound of formula (IIa) wherein R¹, R² and R¹⁰ are H; J is Val; K is Arg; L is Gly; and M is Asp;

the compound of formula (IIa) wherein R¹, R² and R¹⁰ are H; J is Ile; K is Arg; L is Gly; and M is Asp;

the compound of formula (IIa) wherein R¹, R² and R¹⁰ are H; J is Leu; K is Arg; L is Gly; and M is Asp;

the compound of formula (IIa) wherein R¹, R² and R¹⁰ are H; J is Pro; K is Arg; L is Gly; and M is Asp;

the compound of formula (IIa) wherein R¹, R² and R¹⁰ are H; J is Ser; K is Arg; L is Gly; and M is Asp;

the compound of formula (IIa) wherein R¹, R² and R¹⁰ are H; J is Lys; K is Arg; L is Gly; and M is Asp.

14. A pharmaceutical composition comprising a compound of claim 10 and a pharmaceutically acceptable carrier.

15. A pharmaceutical composition comprising a compound of claim 11 and a pharmaceutically acceptable carrier.

16. A pharmaceutical composition comprising a compound of claim 12 and a pharmaceutically acceptable carrier.

17. A pharmaceutical composition comprising a compound of claim 13 and a pharmaceutically acceptable carrier.

18. A method of treatment of arterial or venous thrombosis in a host comprising administering to a host in need prevention or treatment a therapeutically effective amount of a compound of claim 10.

19. A method of treatment of arterial or venous thrombosis in a host comprising administering to a host in need prevention or treatment a therapeutically effective amount of a compound of claim 11.

20. A method of treatment of arterial or venous thrombosis in a host comprising administering to a host in need prevention or treatment a therapeutically effective amount of a compound of claim 12.

21. A method of treatment of arterial or venous thrombosis in a host comprising administering to a host in need prevention or treatment a therapeutically effective amount of a compound of claim 13.

22. A pharmaceutical kit comprising a compound of claim 10 in pharmaceutical dosage unit form.

* * * * *

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
    ( A ) LENGTH: 4 amino acids
    ( B ) TYPE: amino acid
    ( C ) TOPOLOGY: circular ( i i ) MOLECULE TYPE: peptide ( v i ) ORIGINAL SOURCE: synthetic ( i x ) FEATURE:
    ( D ) OTHER INFORMATION: Example Number 1;
      GPIIb/IIIa inhibitor ( x i ) SEQUENCE DESCRIPTION: SEQ ID NO:1:

Gly Xaa Gly Asp
1

( 2 ) INFORMATION FOR SEQ ID NO:2:

( i ) SEQUENCE CHARACTERISTICS:
    ( A ) LENGTH: 4 amino acids
    ( B ) TYPE: amino acid
    ( C ) TOPOLOGY: circular ( i i ) MOLECULE TYPE: peptide ( v i ) ORIGINAL SOURCE: synthetic ( i x ) FEATURE:
    ( D ) OTHER INFORMATION: Example Number 2a;
      GPIIb/IIIa inhibitor ( x i ) SEQUENCE DESCRIPTION: SEQ ID NO:2:

Ala Xaa Gly Asp
1

( 2 ) INFORMATION FOR SEQ ID NO:3:

( i ) SEQUENCE CHARACTERISTICS:
    ( A ) LENGTH: 4 amino acids
    ( B ) TYPE: amino acid
    ( C ) TOPOLOGY: circular ( i i ) MOLECULE TYPE: peptide ( v i ) ORIGINAL SOURCE: synthetic ( i x ) FEATURE:
    ( D ) OTHER INFORMATION: Example Number 3a;
      GPIIb/IIIa inhibitor ( x i ) SEQUENCE DESCRIPTION: SEQ ID NO:3:

Xaa Xaa Gly Asp
1

( 2 ) INFORMATION FOR SEQ ID NO:4:

( i ) SEQUENCE CHARACTERISTICS:
    ( A ) LENGTH: 4 amino acids
    ( B ) TYPE: amino acid
    ( C ) TOPOLOGY: circular ( i i ) MOLECULE TYPE: peptide ( v i ) ORIGINAL SOURCE: synthetic ( i x ) FEATURE:
( D ) OTHER INFORMATION: Example Number 4a;
GPIIb/IIIa inhibitor ( x i ) SEQUENCE DESCRIPTION: SEQ ID NO:4:

Val Xaa Gly Asp
1

( 2 ) INFORMATION FOR SEQ ID NO:5:

( i ) SEQUENCE CHARACTERISTICS:
( A ) LENGTH: 4 amino acids
( B ) TYPE: amino acid
( C ) TOPOLOGY: circular ( i i ) MOLECULE TYPE: peptide ( v i ) ORIGINAL SOURCE: synthetic ( i x ) FEATURE:
( D ) OTHER INFORMATION: Example Number 5a;
GPIIb/IIIa inhibitor ( x i ) SEQUENCE DESCRIPTION: SEQ ID NO:5:

Leu Xaa Gly Asp
1

( 2 ) INFORMATION FOR SEQ ID NO:6:

( i ) SEQUENCE CHARACTERISTICS:
( A ) LENGTH: 4 amino acids
( B ) TYPE: amino acid
( C ) TOPOLOGY: circular ( i i ) MOLECULE TYPE: peptide ( v i ) ORIGINAL SOURCE: synthetic ( i x ) FEATURE:
( D ) OTHER INFORMATION: Example Number 6a;
GPIIb/IIIa inhibitor ( x i ) SEQUENCE DESCRIPTION: SEQ ID NO:6:

Xaa Xaa Gly Asp
1

( 2 ) INFORMATION FOR SEQ ID NO:7:

( i ) SEQUENCE CHARACTERISTICS:
( A ) LENGTH: 4 amino acids
( B ) TYPE: amino acid
( C ) TOPOLOGY: circular ( i i ) MOLECULE TYPE: peptide ( v i ) ORIGINAL SOURCE: synthetic ( i x ) FEATURE:
( D ) OTHER INFORMATION: Example Number 7a;
GPIIb/IIIa inhibitor ( x i ) SEQUENCE DESCRIPTION: SEQ ID NO:7:

Xaa Xaa Gly Asp
1

( 2 ) INFORMATION FOR SEQ ID NO:8:

( i ) SEQUENCE CHARACTERISTICS:
( A ) LENGTH: 4 amino acids
( B ) TYPE: amino acid (C) TOPOLOGY: circular (ii) MOLECULE TYPE: peptide (vi) ORIGINAL SOURCE: synthetic (ix) FEATURE:
(D) OTHER INFORMATION: Example Number 8a;
GPIIb/IIIa inhibitor (xi) SEQUENCE DESCRIPTION: SEQ ID NO:8:

Xaa Xaa Gly Asp
1

(2) INFORMATION FOR SEQ ID NO:9:

(i) SEQUENCE CHARACTERISTICS:
(A) LENGTH: 4 amino acids
(B) TYPE: amino acid
(C) TOPOLOGY: circular (ii) MOLECULE TYPE: peptide (vi) ORIGINAL SOURCE: synthetic (ix) FEATURE:
(D) OTHER INFORMATION: Example Number 9a;
GPIIb/IIIa inhibitor (xi) SEQUENCE DESCRIPTION: SEQ ID NO:9:

Xaa Xaa Gly Asp
1

(2) INFORMATION FOR SEQ ID NO:10:

(i) SEQUENCE CHARACTERISTICS:
(A) LENGTH: 4 amino acids
(B) TYPE: amino acid
(C) TOPOLOGY: circular (ii) MOLECULE TYPE: peptide (vi) ORIGINAL SOURCE: synthetic (ix) FEATURE:
(D) OTHER INFORMATION: Example Number 10a;
GPIIb/IIIa inhibitor (xi) SEQUENCE DESCRIPTION: SEQ ID NO:10:

Xaa Xaa Gly Asp
1

(2) INFORMATION FOR SEQ ID NO:11:

(i) SEQUENCE CHARACTERISTICS:
(A) LENGTH: 4 amino acids
(B) TYPE: amino acid
(C) TOPOLOGY: circular (ii) MOLECULE TYPE: peptide (vi) ORIGINAL SOURCE: synthetic (ix) FEATURE:
(D) OTHER INFORMATION: Example Number 11a;
GPIIb/IIIa inhibitor (xi) SEQUENCE DESCRIPTION: SEQ ID NO:11:

Xaa Xaa Gly Asp
1

(2) INFORMATION FOR SEQ ID NO:12:

( i ) SEQUENCE CHARACTERISTICS:
   ( A ) LENGTH: 4 amino acids
   ( B ) TYPE: amino acid
   ( C ) TOPOLOGY: circular ( i i ) MOLECULE TYPE: peptide ( v i ) ORIGINAL SOURCE: synthetic ( i x ) FEATURE:
   ( D ) OTHER INFORMATION: Example Number 12a;
      GPIIb/IIIa inhibitor ( x i ) SEQUENCE DESCRIPTION: SEQ ID NO:12:

Phe Xaa Gly Asp
1

( 2 ) INFORMATION FOR SEQ ID NO:13:

( i ) SEQUENCE CHARACTERISTICS:
      ( A ) LENGTH: 4 amino acids
      ( B ) TYPE: amino acid
      ( C ) TOPOLOGY: circular ( i i ) MOLECULE TYPE: peptide ( v i ) ORIGINAL SOURCE: synthetic ( i x ) FEATURE:
      ( D ) OTHER INFORMATION: Example Number 13a;
         GPIIb/IIIa inhibitor ( x i ) SEQUENCE DESCRIPTION: SEQ ID NO:13:

Ser Xaa Gly Asp
1

( 2 ) INFORMATION FOR SEQ ID NO:14:

( i ) SEQUENCE CHARACTERISTICS:
      ( A ) LENGTH: 4 amino acids
      ( B ) TYPE: amino acid
      ( C ) TOPOLOGY: circular ( i i ) MOLECULE TYPE: peptide ( v i ) ORIGINAL SOURCE: synthetic ( i x ) FEATURE:
      ( D ) OTHER INFORMATION: Example Number 13c;
         GPIIb/IIIa inhibitor ( x i ) SEQUENCE DESCRIPTION: SEQ ID NO:14:

Xaa Xaa Gly Asp
1

( 2 ) INFORMATION FOR SEQ ID NO:15:

( i ) SEQUENCE CHARACTERISTICS:
      ( A ) LENGTH: 4 amino acids
      ( B ) TYPE: amino acid
      ( C ) TOPOLOGY: circular ( i i ) MOLECULE TYPE: peptide ( v i ) ORIGINAL SOURCE: synthetic ( i x ) FEATURE:
      ( D ) OTHER INFORMATION: Example Number 13e;
         GPIIb/IIIa inhibitor ( x i ) SEQUENCE DESCRIPTION: SEQ ID NO:15:

```
Arg Xaa Gly Asp
1
```

( 2 ) INFORMATION FOR SEQ ID NO:16:

( i ) SEQUENCE CHARACTERISTICS:
        ( A ) LENGTH: 4 amino acids
        ( B ) TYPE: amino acid
        ( C ) TOPOLOGY: circular ( i i ) MOLECULE TYPE: peptide ( v i ) ORIGINAL SOURCE: synthetic ( i x ) FEATURE:
        ( D ) OTHER INFORMATION: Example Number 13g;
            GPIIb/IIIa inhibitor ( x i ) SEQUENCE DESCRIPTION: SEQ ID NO:16:

```
Lys Xaa Gly Asp
1
```

( 2 ) INFORMATION FOR SEQ ID NO:17:

( i ) SEQUENCE CHARACTERISTICS:
        ( A ) LENGTH: 4 amino acids
        ( B ) TYPE: amino acid
        ( C ) TOPOLOGY: circular ( i i ) MOLECULE TYPE: peptide ( v i ) ORIGINAL SOURCE: synthetic ( i x ) FEATURE:
        ( D ) OTHER INFORMATION: Example Number 13i;
            GPIIb/IIIa inhibitor ( x i ) SEQUENCE DESCRIPTION: SEQ ID NO:17:

```
Xaa Xaa Gly Asp
1
```

( 2 ) INFORMATION FOR SEQ ID NO:18:

( i ) SEQUENCE CHARACTERISTICS:
        ( A ) LENGTH: 4 amino acids
        ( B ) TYPE: amino acid
        ( C ) TOPOLOGY: circular ( i i ) MOLECULE TYPE: peptide ( v i ) ORIGINAL SOURCE: synthetic ( i x ) FEATURE:
        ( D ) OTHER INFORMATION: Example Number 13k;
            GPIIb/IIIa inhibitor ( x i ) SEQUENCE DESCRIPTION: SEQ ID NO:18:

```
Xaa Xaa Gly Asp
1
```

( 2 ) INFORMATION FOR SEQ ID NO:19:

( i ) SEQUENCE CHARACTERISTICS:
        ( A ) LENGTH: 4 amino acids
        ( B ) TYPE: amino acid
        ( C ) TOPOLOGY: circular ( i i ) MOLECULE TYPE: peptide ( v i ) ORIGINAL SOURCE: synthetic ( i x ) FEATURE:
        ( D ) OTHER INFORMATION: Example Number 13m;

GPIIb/IIIa inhibitor ( x i ) SEQUENCE DESCRIPTION: SEQ ID NO:19:

Xaa Xaa Gly Asp
1

( 2 ) INFORMATION FOR SEQ ID NO:20:

( i ) SEQUENCE CHARACTERISTICS:
        ( A ) LENGTH: 4 amino acids
        ( B ) TYPE: amino acid
        ( C ) TOPOLOGY: circular ( i i ) MOLECULE TYPE: peptide ( v i ) ORIGINAL SOURCE: synthetic ( i x ) FEATURE:
        ( D ) OTHER INFORMATION: Example Number 13o;
        GPIIb/IIIa inhibitor ( x i ) SEQUENCE DESCRIPTION: SEQ ID NO:20:

Xaa Xaa Gly Asp
1

( 2 ) INFORMATION FOR SEQ ID NO:21:

( i ) SEQUENCE CHARACTERISTICS:
        ( A ) LENGTH: 4 amino acids
        ( B ) TYPE: amino acid
        ( C ) TOPOLOGY: circular ( i i ) MOLECULE TYPE: peptide ( v i ) ORIGINAL SOURCE: synthetic ( i x ) FEATURE:
        ( D ) OTHER INFORMATION: Example Number 13q;
        GPIIb/IIIa inhibitor ( x i ) SEQUENCE DESCRIPTION: SEQ ID NO:21:

Xaa Xaa Gly Asp
1

( 2 ) INFORMATION FOR SEQ ID NO:22:

( i ) SEQUENCE CHARACTERISTICS:
        ( A ) LENGTH: 4 amino acids
        ( B ) TYPE: amino acid
        ( C ) TOPOLOGY: circular ( i i ) MOLECULE TYPE: peptide ( v i ) ORIGINAL SOURCE: synthetic ( i x ) FEATURE:
        ( D ) OTHER INFORMATION: Example Number 13s;
        GPIIb/IIIa inhibitor ( x i ) SEQUENCE DESCRIPTION: SEQ ID NO:22:

Ile Xaa Gly Asp
1

( 2 ) INFORMATION FOR SEQ ID NO:23:

( i ) SEQUENCE CHARACTERISTICS:
        ( A ) LENGTH: 4 amino acids
        ( B ) TYPE: amino acid
        ( C ) TOPOLOGY: circular ( i i ) MOLECULE TYPE: peptide (v i) ORIGINAL SOURCE: synthetic (i x) FEATURE:
(D) OTHER INFORMATION: Example Number 14a;
GPIIb/IIIa inhibitor (x i) SEQUENCE DESCRIPTION: SEQ ID NO:23:

Cys  Xaa  Gly  Asp
1

(2) INFORMATION FOR SEQ ID NO:24:

(i) SEQUENCE CHARACTERISTICS:
(A) LENGTH: 4 amino acids
(B) TYPE: amino acid
(C) TOPOLOGY: circular (i i) MOLECULE TYPE: peptide (v i) ORIGINAL SOURCE: synthetic (i x) FEATURE:
(D) OTHER INFORMATION: Example Number 15a;
GPIIb/IIIa inhibitor (x i) SEQUENCE DESCRIPTION: SEQ ID NO:24:

Xaa  Xaa  Gly  Asp
1

(2) INFORMATION FOR SEQ ID NO:25:

(i) SEQUENCE CHARACTERISTICS:
(A) LENGTH: 4 amino acids
(B) TYPE: amino acid
(C) TOPOLOGY: circular (i i) MOLECULE TYPE: peptide (v i) ORIGINAL SOURCE: synthetic (i x) FEATURE:
(D) OTHER INFORMATION: Example Number 16a;
GPIIb/IIIa inhibitor (x i) SEQUENCE DESCRIPTION: SEQ ID NO:25:

Xaa  Xaa  Gly  Asp
1

(2) INFORMATION FOR SEQ ID NO:26:

(i) SEQUENCE CHARACTERISTICS:
(A) LENGTH: 4 amino acids
(B) TYPE: amino acid
(C) TOPOLOGY: circular (i i) MOLECULE TYPE: peptide (v i) ORIGINAL SOURCE: synthetic (i x) FEATURE:
(D) OTHER INFORMATION: Example Number 17a;
GPIIb/IIIa inhibitor (x i) SEQUENCE DESCRIPTION: SEQ ID NO:26:

Met  Xaa  Gly  Asp
1

(2) INFORMATION FOR SEQ ID NO:27:

(i) SEQUENCE CHARACTERISTICS:
(A) LENGTH: 4 amino acids
(B) TYPE: amino acid (C) TOPOLOGY: circular (ii) MOLECULE TYPE: peptide (vi) ORIGINAL SOURCE: synthetic (ix) FEATURE:
    (D) OTHER INFORMATION: Example Number 18;
        GPIIb/IIIa inhibitor (xi) SEQUENCE DESCRIPTION: SEQ ID NO:27:

Xaa Xaa Gly Asp
1

(2) INFORMATION FOR SEQ ID NO:28:

(i) SEQUENCE CHARACTERISTICS:
    (A) LENGTH: 4 amino acids
    (B) TYPE: amino acid
    (C) TOPOLOGY: circular (ii) MOLECULE TYPE: peptide (vi) ORIGINAL SOURCE: synthetic (ix) FEATURE:
    (D) OTHER INFORMATION: Example Number 21a;
        GPIIb/IIIa inhibitor (xi) SEQUENCE DESCRIPTION: SEQ ID NO:28:

Xaa Xaa Gly Asp
1

(2) INFORMATION FOR SEQ ID NO:29:

(i) SEQUENCE CHARACTERISTICS:
    (A) LENGTH: 4 amino acids
    (B) TYPE: amino acid
    (C) TOPOLOGY: circular (ii) MOLECULE TYPE: peptide (vi) ORIGINAL SOURCE: synthetic (ix) FEATURE:
    (D) OTHER INFORMATION: Example Number 22a;
        GPIIb/IIIa inhibitor (xi) SEQUENCE DESCRIPTION: SEQ ID NO:29:

Xaa Xaa Gly Asp
1

(2) INFORMATION FOR SEQ ID NO:30:

(i) SEQUENCE CHARACTERISTICS:
    (A) LENGTH: 4 amino acids
    (B) TYPE: amino acid
    (C) TOPOLOGY: circular (ii) MOLECULE TYPE: peptide (vi) ORIGINAL SOURCE: synthetic (ix) FEATURE:
    (D) OTHER INFORMATION: Example Number 23c;
        GPIIb/IIIa inhibitor (xi) SEQUENCE DESCRIPTION: SEQ ID NO:30:

Xaa Xaa Gly Asp
1

(2) INFORMATION FOR SEQ ID NO:31:

( i ) SEQUENCE CHARACTERISTICS:
  ( A ) LENGTH: 4 amino acids
  ( B ) TYPE: amino acid
  ( C ) TOPOLOGY: circular ( i i ) MOLECULE TYPE: peptide ( v i ) ORIGINAL SOURCE: synthetic ( i x ) FEATURE:
  ( D ) OTHER INFORMATION: Example Number 23b;
    GPIIb/IIIa inhibitor ( x i ) SEQUENCE DESCRIPTION: SEQ ID NO:31:

Val Xaa Gly Asp
1

( 2 ) INFORMATION FOR SEQ ID NO:32:

( i ) SEQUENCE CHARACTERISTICS:
    ( A ) LENGTH: 4 amino acids
    ( B ) TYPE: amino acid
    ( C ) TOPOLOGY: circular ( i i ) MOLECULE TYPE: peptide ( v i ) ORIGINAL SOURCE: synthetic ( i x ) FEATURE:
    ( D ) OTHER INFORMATION: Example Number 24;
      GPIIb/IIIa inhibitor ( x i ) SEQUENCE DESCRIPTION: SEQ ID NO:32:

Pro Xaa Gly Asp
1

( 2 ) INFORMATION FOR SEQ ID NO:33:

( i ) SEQUENCE CHARACTERISTICS:
    ( A ) LENGTH: 4 amino acids
    ( B ) TYPE: amino acid
    ( C ) TOPOLOGY: circular ( i i ) MOLECULE TYPE: peptide ( v i ) ORIGINAL SOURCE: synthetic ( i x ) FEATURE:
    ( D ) OTHER INFORMATION: Example Number 28b;
      GPIIb/IIIa inhibitor ( x i ) SEQUENCE DESCRIPTION: SEQ ID NO:33:

Xaa Xaa Gly Asp
1

( 2 ) INFORMATION FOR SEQ ID NO:34:

( i ) SEQUENCE CHARACTERISTICS:
    ( A ) LENGTH: 4 amino acids
    ( B ) TYPE: amino acid
    ( C ) TOPOLOGY: circular ( i i ) MOLECULE TYPE: peptide ( v i ) ORIGINAL SOURCE: synthetic ( i x ) FEATURE:
    ( D ) OTHER INFORMATION: Example Number 28c;
      GPIIb/IIIa inhibitor ( x i ) SEQUENCE DESCRIPTION: SEQ ID NO:34:

Xaa Xaa Gly Asp
1

( 2 ) INFORMATION FOR SEQ ID NO:35:

( i ) SEQUENCE CHARACTERISTICS:
        ( A ) LENGTH: 4 amino acids
        ( B ) TYPE: amino acid
        ( C ) TOPOLOGY: circular ( i i ) MOLECULE TYPE: peptide ( v i ) ORIGINAL SOURCE: synthetic ( i x ) FEATURE:
        ( D ) OTHER INFORMATION: Example Number 28g;
        GPIIb/IIIa inhibitor ( x i ) SEQUENCE DESCRIPTION: SEQ ID NO:35:

Xaa Xaa Gly Asp
1

( 2 ) INFORMATION FOR SEQ ID NO:36:

( i ) SEQUENCE CHARACTERISTICS:
        ( A ) LENGTH: 4 amino acids
        ( B ) TYPE: amino acid
        ( C ) TOPOLOGY: circular ( i i ) MOLECULE TYPE: peptide ( v i ) ORIGINAL SOURCE: synthetic ( i x ) FEATURE:
        ( D ) OTHER INFORMATION: Example Number 29;
        GPIIb/IIIa inhibitor ( x i ) SEQUENCE DESCRIPTION: SEQ ID NO:36:

Gly Arg Gly Asp
1

( 2 ) INFORMATION FOR SEQ ID NO:37:

( i ) SEQUENCE CHARACTERISTICS:
        ( A ) LENGTH: 4 amino acids
        ( B ) TYPE: amino acid
        ( C ) TOPOLOGY: circular ( i i ) MOLECULE TYPE: peptide ( v i ) ORIGINAL SOURCE: synthetic ( i x ) FEATURE:
        ( D ) OTHER INFORMATION: Example Number 31;
        GPIIb/IIIa inhibitor ( x i ) SEQUENCE DESCRIPTION: SEQ ID NO:37:

Ala Arg Gly Asp
1

( 2 ) INFORMATION FOR SEQ ID NO:38:

( i ) SEQUENCE CHARACTERISTICS:
        ( A ) LENGTH: 4 amino acids
        ( B ) TYPE: amino acid
        ( C ) TOPOLOGY: circular ( i i ) MOLECULE TYPE: peptide ( v i ) ORIGINAL SOURCE: synthetic ( i x ) FEATURE:
        ( D ) OTHER INFORMATION: Example Number 32a;

GPIIb/IIIa inhibitor ( x i ) SEQUENCE DESCRIPTION: SEQ ID NO:38:

Val Arg Gly Asp
1

( 2 ) INFORMATION FOR SEQ ID NO:39:

( i ) SEQUENCE CHARACTERISTICS:
        ( A ) LENGTH: 4 amino acids
        ( B ) TYPE: amino acid
        ( C ) TOPOLOGY: circular ( i i ) MOLECULE TYPE: peptide ( v i ) ORIGINAL SOURCE: synthetic ( i x ) FEATURE:
        ( D ) OTHER INFORMATION: Example Number 33a;
        GPIIb/IIIa inhibitor ( x i ) SEQUENCE DESCRIPTION: SEQ ID NO:39:

Leu Arg Gly Asp
1

( 2 ) INFORMATION FOR SEQ ID NO:40:

( i ) SEQUENCE CHARACTERISTICS:
        ( A ) LENGTH: 4 amino acids
        ( B ) TYPE: amino acid
        ( C ) TOPOLOGY: circular ( i i ) MOLECULE TYPE: peptide ( v i ) ORIGINAL SOURCE: synthetic ( i x ) FEATURE:
        ( D ) OTHER INFORMATION: Example Number 34a;
        GPIIb/IIIa inhibitor ( x i ) SEQUENCE DESCRIPTION: SEQ ID NO:40:

Xaa Arg Gly Asp
1

( 2 ) INFORMATION FOR SEQ ID NO:41:

( i ) SEQUENCE CHARACTERISTICS:
        ( A ) LENGTH: 4 amino acids
        ( B ) TYPE: amino acid
        ( C ) TOPOLOGY: circular ( i i ) MOLECULE TYPE: peptide ( v i ) ORIGINAL SOURCE: synthetic ( i x ) FEATURE:
        ( D ) OTHER INFORMATION: Example Number 35a;
        GPIIb/IIIa inhibitor ( x i ) SEQUENCE DESCRIPTION: SEQ ID NO:41:

Ser Arg Gly Asp
1

( 2 ) INFORMATION FOR SEQ ID NO:42:

( i ) SEQUENCE CHARACTERISTICS:
        ( A ) LENGTH: 4 amino acids
        ( B ) TYPE: amino acid
        ( C ) TOPOLOGY: circular ( i i ) MOLECULE TYPE: peptide (vi) ORIGINAL SOURCE: synthetic (ix) FEATURE:
(D) OTHER INFORMATION: Example Number 37; GPIIb/IIIa inhibitor (xi) SEQUENCE DESCRIPTION: SEQ ID NO:42:

Phe Arg Gly Asp
 1